US007998695B2

(12) United States Patent
Nakamura et al.

(10) Patent No.: US 7,998,695 B2
(45) Date of Patent: Aug. 16, 2011

(54) METHOD OF DIAGNOSING BLADDER CANCER

(75) Inventors: Yusuke Nakamura, Bunkyo-ku (JP); Toyomasa Katagiri, Bunkyo-ku (JP); Shuichi Nakatsuru, Kawasaki (JP)

(73) Assignee: Oncotherapy Science, Inc., Kanagawa (JP)

( * ) Notice: Subject to any disclaimer, the term of this patent is extended or adjusted under 35 U.S.C. 154(b) by 468 days.

(21) Appl. No.: 11/815,850

(22) PCT Filed: Feb. 9, 2006

(86) PCT No.: PCT/JP2006/302684
§ 371 (c)(1),
(2), (4) Date: Nov. 20, 2008

(87) PCT Pub. No.: WO2006/085684
PCT Pub. Date: Aug. 17, 2006

(65) Prior Publication Data
US 2009/0175844 A1    Jul. 9, 2009

Related U.S. Application Data

(60) Provisional application No. 60/652,318, filed on Feb. 10, 2005, provisional application No. 60/703,225, filed on Jul. 27, 2005.

(51) Int. Cl.
*G01N 33/574* (2006.01)
*G01N 33/53* (2006.01)
*C12Q 1/68* (2006.01)
(52) U.S. Cl. .............................. 435/7.23; 435/6; 435/7.1
(58) Field of Classification Search .................... None
See application file for complete search history.

(56) References Cited

U.S. PATENT DOCUMENTS

| 7,001,999 B1 * | 2/2006 | Martelange et al. .......... 536/23.5 |
| 2004/0076955 A1 | 4/2004 | Mack et al. |
| 2004/0241726 A1 | 12/2004 | Liew |
| 2004/0253232 A1 | 12/2004 | Jakobovits et al. |
| 2010/0184088 A1 | 7/2010 | Nakatsuru |

FOREIGN PATENT DOCUMENTS

| WO | WO 01/22864 A2 | 4/2001 |
| WO | WO 01/53312 A1 | 7/2001 |
| WO | WO 01/53535 A2 | 7/2001 |
| WO | WO 02/31111 A2 | 4/2002 |
| WO | WO 03/083074 A2 | 10/2003 |
| WO | WO 2004/031413 A2 | 4/2004 |
| WO | WO 2004/112589 A2 | 12/2004 |
| WO | WO 2005/090603 A2 | 9/2005 |
| WO | WO 2008/047473 A1 | 4/2008 |

OTHER PUBLICATIONS

Tockman et al (Cancer Res., 1992, 52:2711s-2718s).*
Ardelt, Peter, et al., "Gene and Antisense Therapy of Bladder Cancer," Bladder Disease: Research Concepts and Clinical Application, *Adv. Exp Med Biol.*, 539 (Pt A), pp. 155-183 (2003).
Fuessel, Susanne, et al., "Systematic In Vitro Evaluation of Survivin Directed Antisense Oligodeoxynucleotides In Bladder Cancer Cells," *The Journal of Urology*, vol. 171, pp. 2471-2476 (Jun. 2004).
Modlich, Olga, et al., "Identifying Superficial, Muscle-Invasive, and Metastasizing Transitional Cell Carcinoma of the Bladder . . . " *Clinical Cancer Research*, vol. 10, pp. 3410-3421 (May 15, 2004).
Nicholson, Brian E., et al., "Profiling the Evolution of Human Metastic Bladder Cancer," *Cancer Research*, vol. 64, pp. 7813-7821 (Nov. 1, 2004).
Smith, Shannon D., et al., "Urine Detection of Survivin and Diagnosis of Bladder Cancer," *JAMA*, vol. 285(3), pp. 324-328 (Jan. 17, 2001).
Tyagi, Anil K., et al., "Silibinin down-regulates survivin protein and mRNA expression . . . " *Biochemical and Biophysical Res Commun.*, vol. 312, pp. 1178-1184 (Dec. 26, 2003).
GEO Accession Viewer, "Affymetrix GeneChip Human Genome U133 Plus 2.0 Array," Internet Article [Online], entire document, Available: http://www.ncbi.nlm.nih.gov/geo/query/acc.cgi?acc=GPL570 (Nov. 7, 2003).
Greenbaum, D., et al., "Comparing protein abundance and mRNA expression levels on a genomic scale," *Genome Biology*, vol. 4(9), pp. 117.1-117.8 (2003, Epub Aug. 29, 2003).
Greenbaum, D., et al., "Interrelating Different Types of Genomic Data, from Proteome to Secretome: 'Oming in on Function," *Genome Research*, vol. 11(9), pp. 1463-1468 (Sep. 2001).
Lu, P., et al,. "siRNA-mediated antitumorigenesis for drug target validation and therapeutics," *Current Opinion in Molecular Therapeutics*, vol. 5(3), pp. 225-234 (Jun. 2003).
Ota, T., et al., "Complete sequencing and characterization of 21,243 full-length human cDNAs," Nat. Genet., vol. 36(1), pp. 40-45 (Jan. 2004); Genbank Accession No. NM_017779:2004.10.28 (XP007907000), 3 pgs.
Sanchez-Carbayo, M., "Recent advances in bladder cancer diagnostics," *Clinical Biochemistry*, vol. 37(7), pp. 562-571 (Jul. 2004).
Tang, Y., et al., "FLJ20354 fis clone HEP15013," Accession No. ABP43909:2000.10.12 (XP007907002), 2 pgs. (Oct. 12, 2000).

(Continued)

*Primary Examiner* — Laura B Goddard
(74) *Attorney, Agent, or Firm* — Kilpatrick Townsend & Stockton LLP

(57) ABSTRACT

Objective methods for detecting and diagnosing bladder cancer (BLC) are described herein. In one embodiment, the diagnostic method involves determining the expression level of a BLC-associated gene that discriminates between BLC cells and normal cells. The present invention further provides means for predicting and preventing bladder cancer metastasis using BLC-associated genes having unique altered expression patterns in bladder cancer cells with lymph-node metastasis. Finally, the present invention provides methods of screening for therapeutic agents useful in the treatment of bladder cancer, methods of treating bladder cancer and method for vaccinating a subject against bladder cancer. In particular, the present application provides novel human genes C2093, B5860Ns and C6055s whose expression is markedly elevated in bladder cancers. The genes and polypeptides encoded by the genes can be used, for example, in the diagnosis of bladder cancers, as target molecules for developing drugs against the disease, and for attenuating cell growth of bladder cancer.

6 Claims, 22 Drawing Sheets

OTHER PUBLICATIONS

U.S. Appl. No. 12/377,024, which is a U.S. Nat'l Phase of PCT/JP2007/065992, filed Aug. 10, 2007, 221 pgs.

U.S. Appl. No. 12/666,253, filed Jun. 14, 2010, 72 pgs.

U.S. Appl. No. 12/673,432, which is a U.S. Nat'l Phase of PCT/JP2008/064437, filed Aug. 12, 2008, 83 pgs.

U.S. Appl. No. 12/673,434, which is a US National Stage (371) of PCT/JP2008/060837, 102 pgs.

U.S. Appl. No. 12/673,451, filed Feb. 2, 2010, 131 pgs.

U.S. Appl. No. 12/674,759, which is a US National Stage (371) of PCT/JP2008/065352, 233 pgs.

Sanchez-Carbayo, M., "Use of High-Throughput DNA Microarrays to Identify Biomarkers for Bladder Cancer," *Clinical Chemistry*, vol. 49(1), pp. 23-31 (Jan. 2003).

Suzuki, T., et al., "Expression of the Catalytic Subunit Associated with Telomerase Gene in Human Urinary Bladder Cancer," *J. Urol.*, vol. 162(6), pp. 2217-2220 (Dec. 1999).

U.S. Appl. No. 13/001,869, which is a US National Phase of PCT/JP2009/003009 filed Jun. 30, 2009, 63 pgs.

Netaffx, "HG-U133_PLUS_2:1555826_AT," Internet Article [Online] entire document, Available: http://www.affymetrix.com/analysis/index.affx (Jun. 22, 2006).

* cited by examiner

Fig. 1 a

| LMMID | 10 Clinical Samples | Normal Bladder (TC, Bulk) | Normal Vital organs (Heart, Lung, Liver, Kidney) |
|---|---|---|---|
| B5860N | | | |
| B0811 | | | |
| C2093 | | | |
| F6022 | | | |
| F7562 | | | |
| F4976 | | | |
| F6193 | | | |
| F7409 | | | |
| C6055 | | | |
| D5491 | | | |
| C5088 | | | |
| D7746 | | | |
| A0303 | | | |
| C6865 | | | |
| F0411 | | | |
| A8295 | | | |
| F4025 | | | |
| B2879N | | | |
| A0576N | | | |
| F6507 | | | |
| F1653 | | | |
| C2210 | | | |
| C7757 | | | |
| F5981 | | | |
| B9838 | | | |

Continuation of Fig. 1a
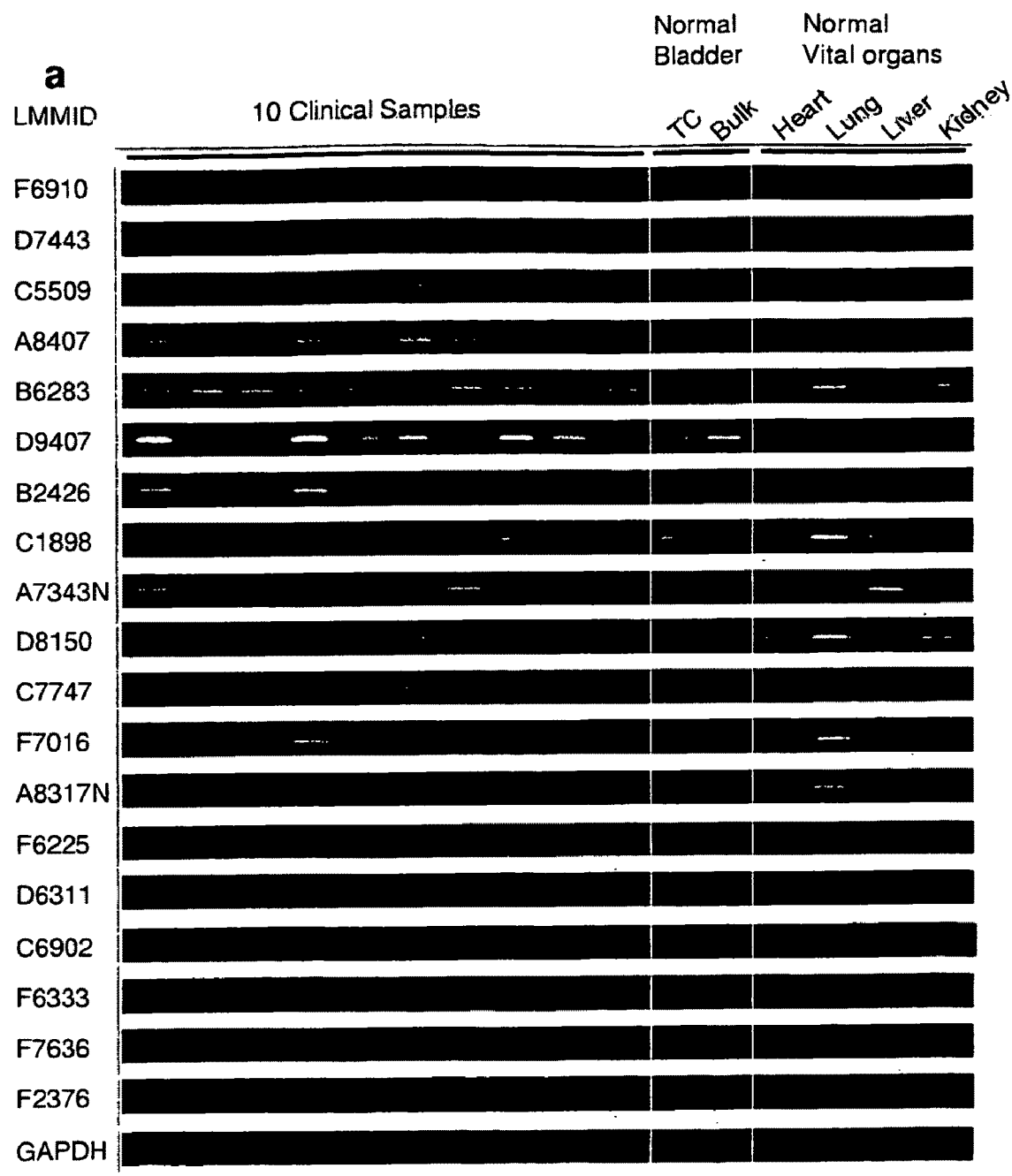

Fig. 1
b
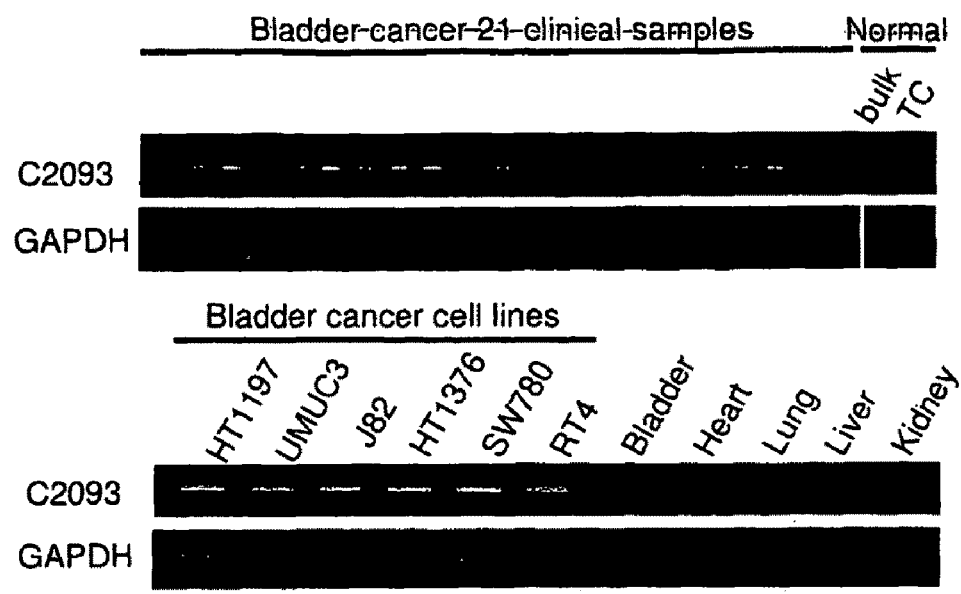
c
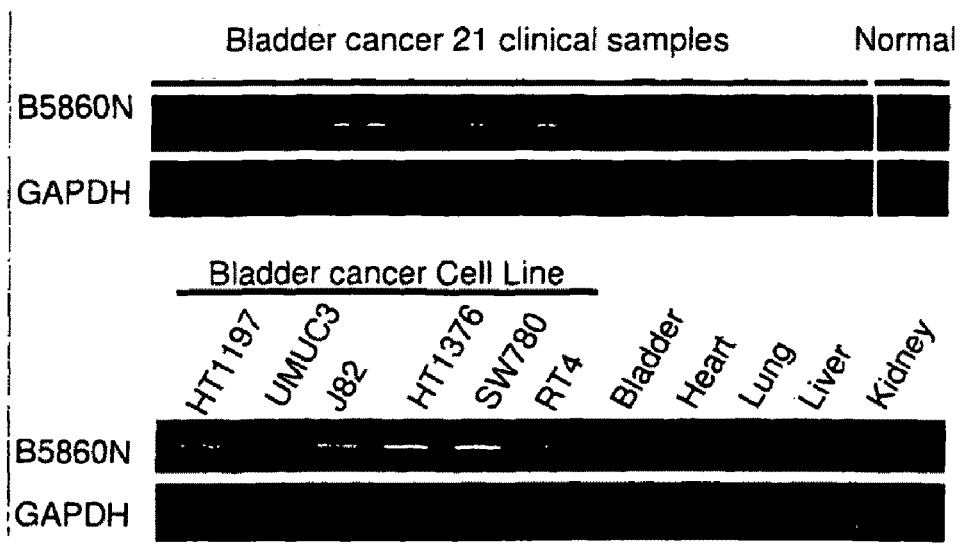

Fig. 2
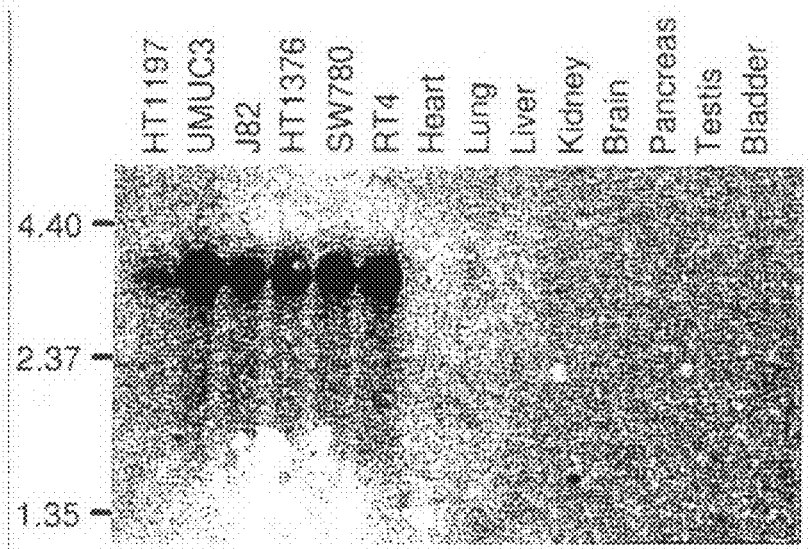
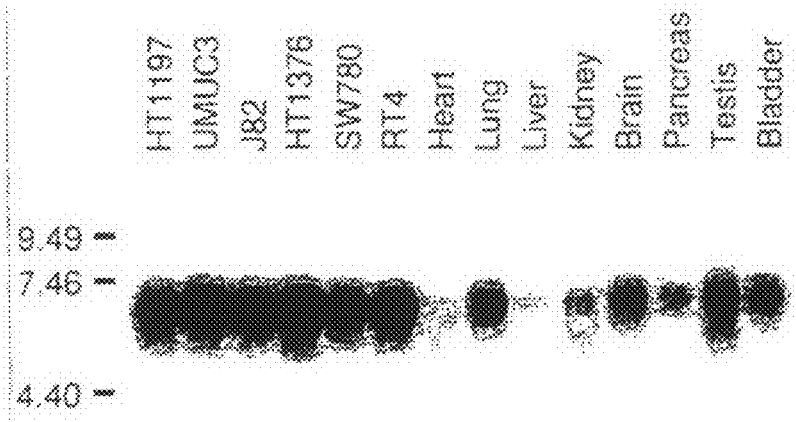

Fig. 2
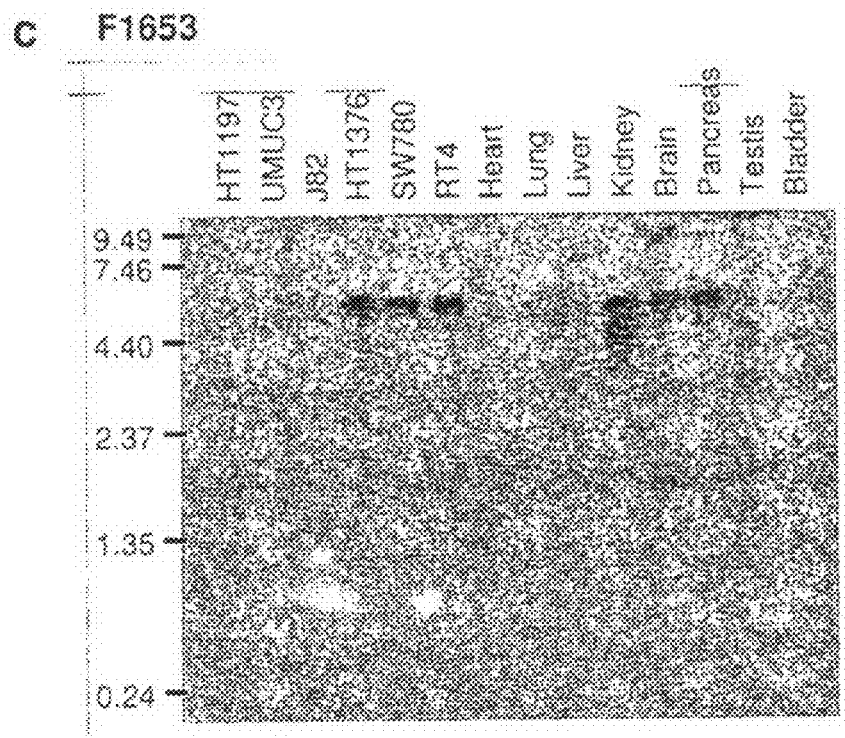
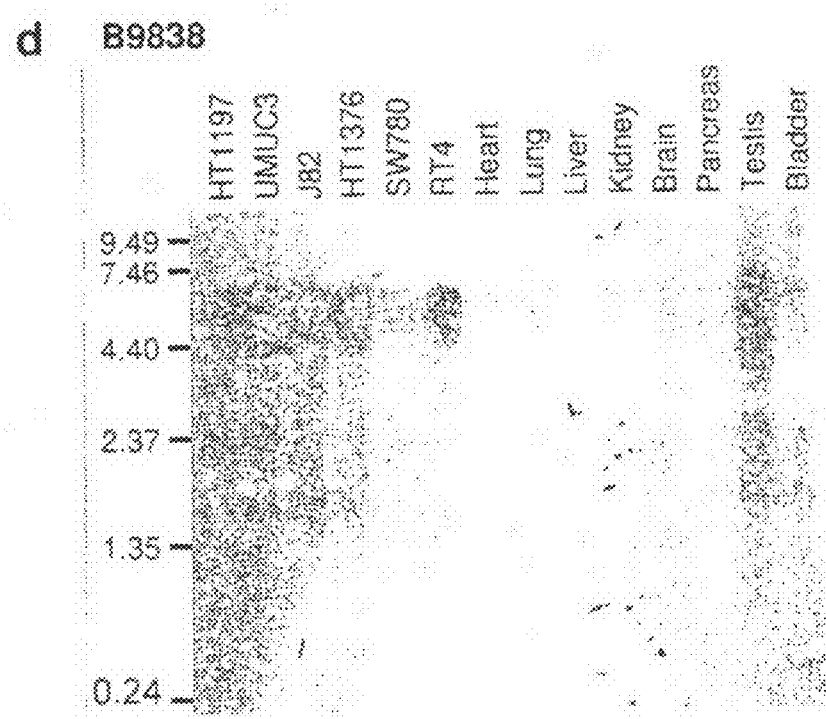

Cell : UMUC3 (Bladder cancer cell line)

Cell : UMUC3 (Bladder cancer cell line)

Fig. 4
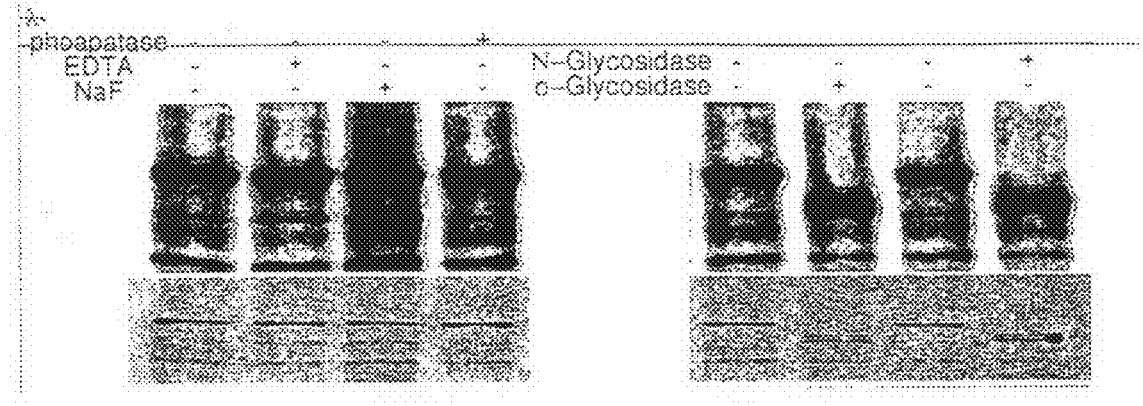
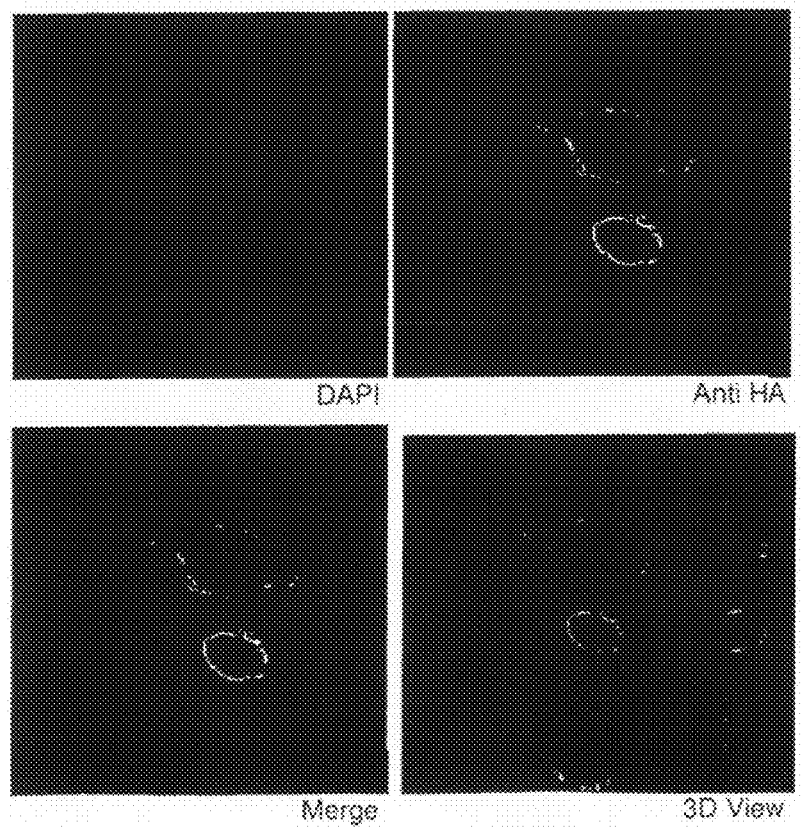

Fig. 5
Cell line: UMUC3
a
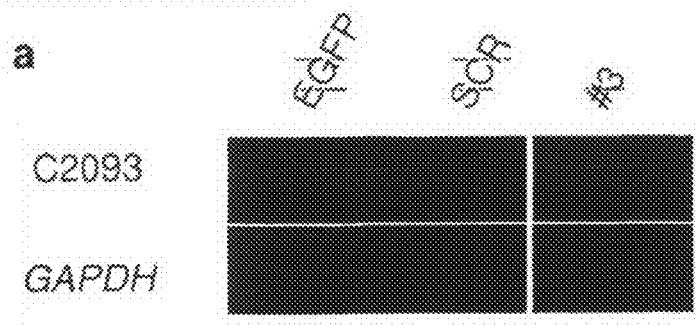
b
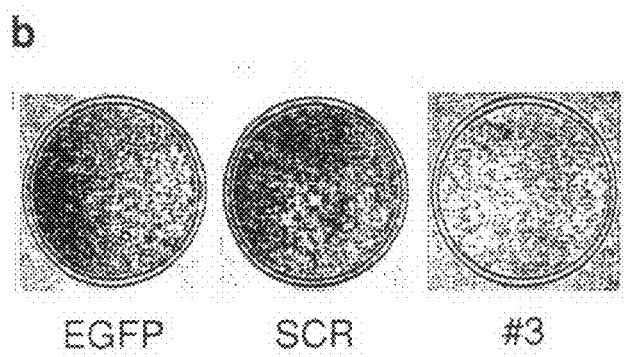
c
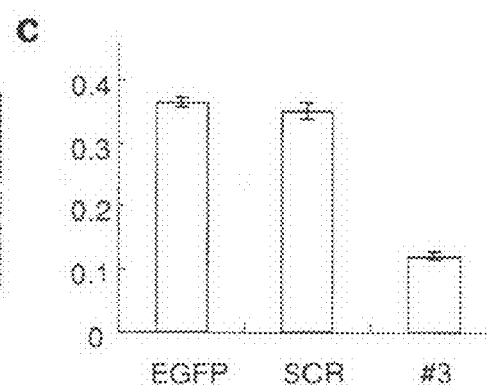
Cell line: J82
d
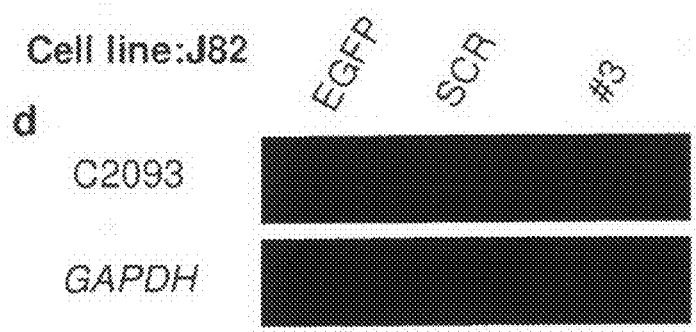
e
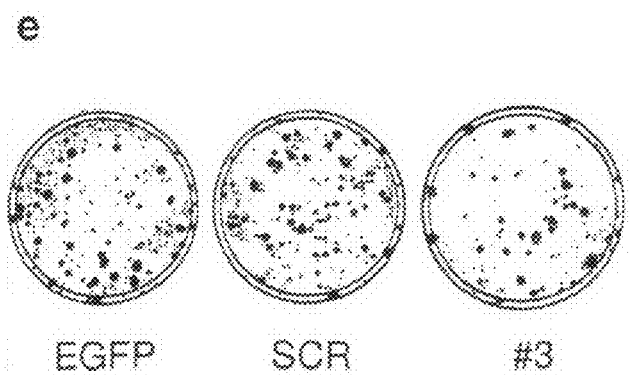
f
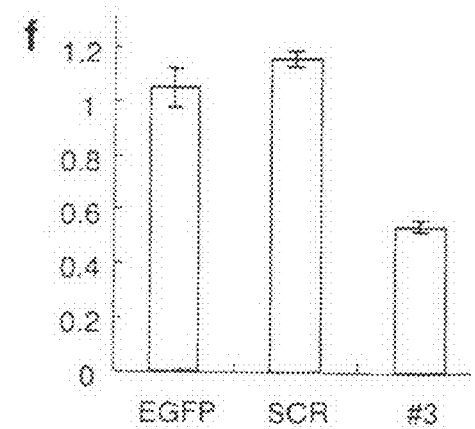

Fig. 6
Cell line: J82
a
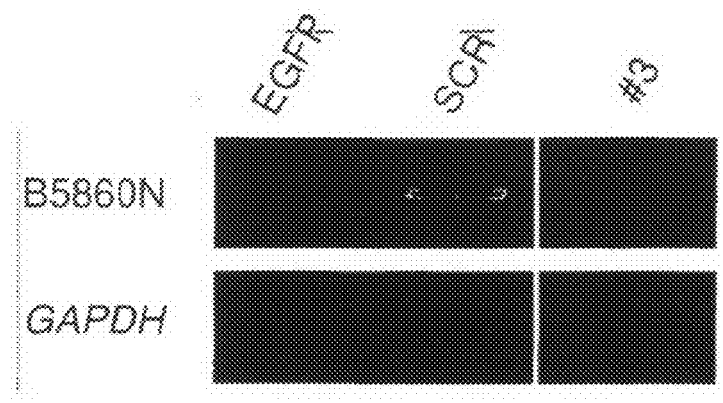
b
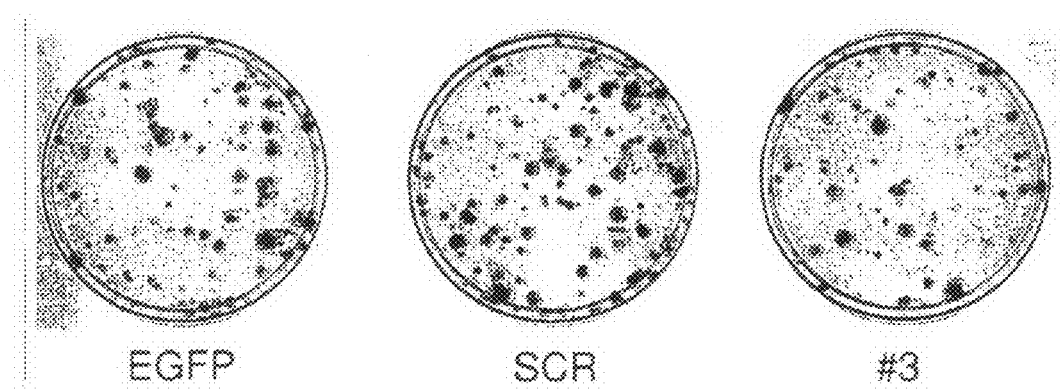
c
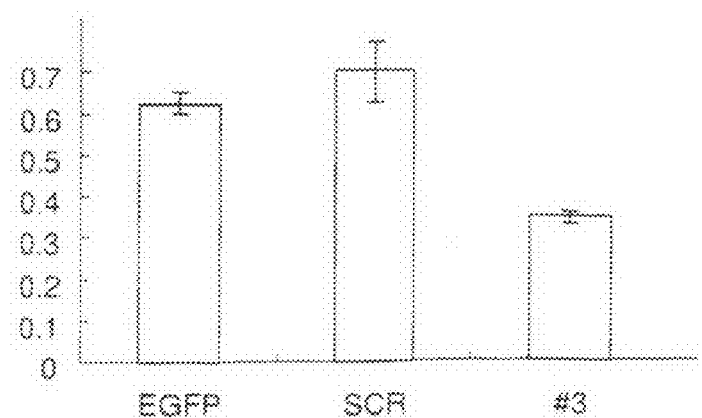

Fig. 9
a
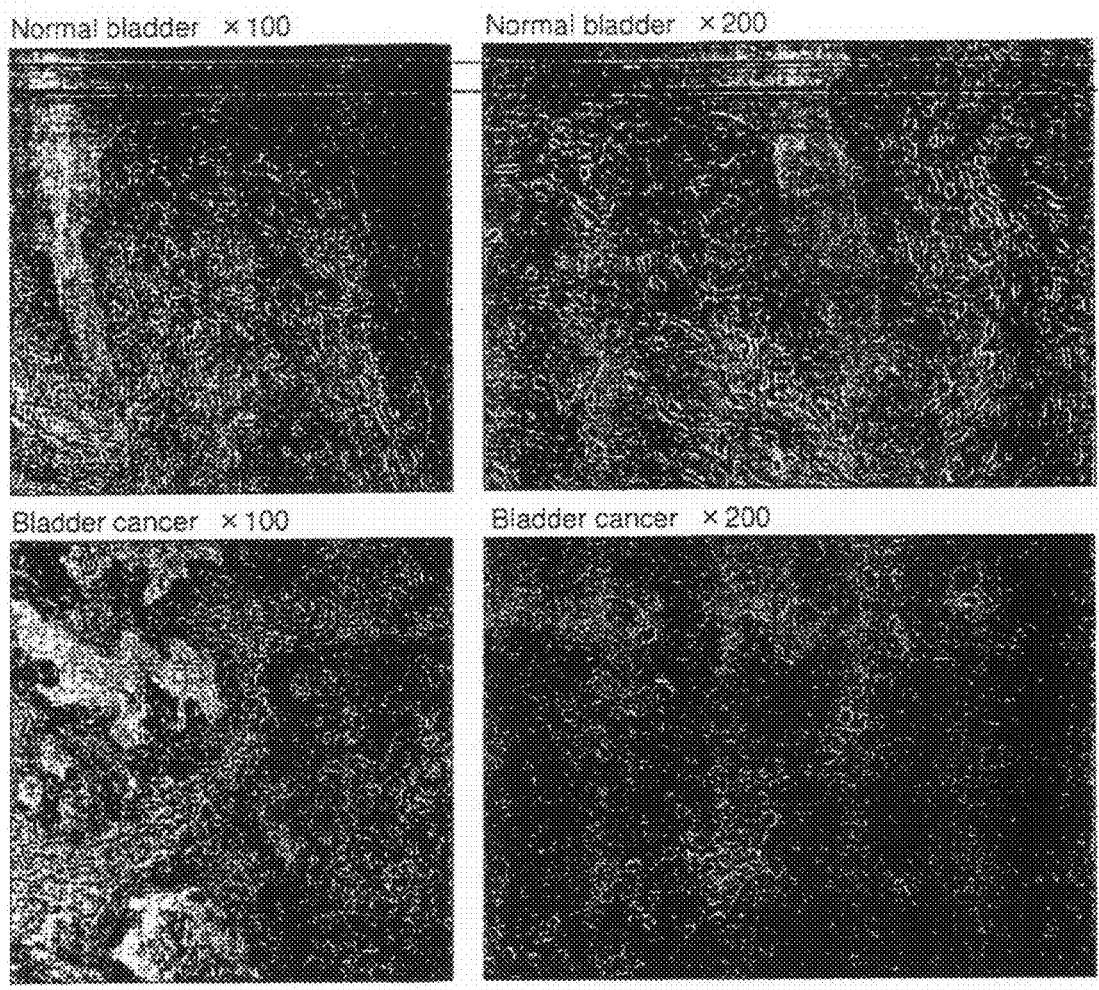
b
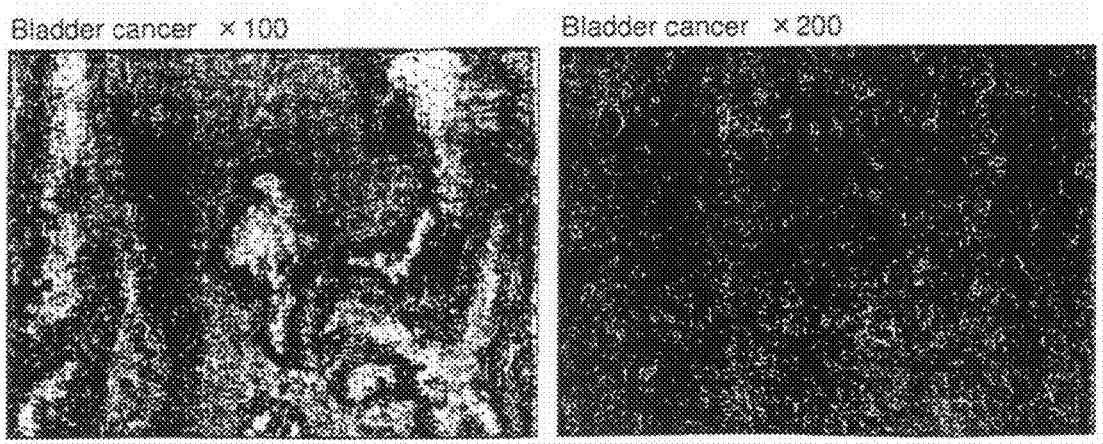

ive bladder cancer to treat micrometastases and

SEQUENCE LISTING

```
<160> NUMBER OF SEQ ID NOS: 151

<210> SEQ ID NO 1
<211> LENGTH: 6319
<212> TYPE: DNA
<213> ORGANISM: Homo sapiens
<220> FEATURE:
<221> NAME/KEY: CDS
<222> LOCATION: (73)..(5415)

<400> SEQUENCE: 1
attgtttgaa tttgaaaacg gtaacatcgc agtgctgctc gcgggtctgg ctagtcaggc         60
gaagtttgca ga atg gaa tct aat ttt aat caa gag gga gta cct cga cca        111
               Met Glu Ser Asn Phe Asn Gln Glu Gly Val Pro Arg Pro
                 1               5                  10 tct tat gtt ttt agt gct gac cca att gca agg cct tca gaa ata aat        159
Ser Tyr Val Phe Ser Ala Asp Pro Ile Ala Arg Pro Ser Glu Ile Asn
     15                  20                  25 ttc gat ggc att aag ctt gat ctg tct cat gaa ttt tcc tta gtt gct        207
Phe Asp Gly Ile Lys Leu Asp Leu Ser His Glu Phe Ser Leu Val Ala
 30                  35                  40                  45
```

| | | | | | | | | | | | | | | | |
|---|---|---|---|---|---|---|---|---|---|---|---|---|---|---|---|
| cca | aat | act | gag | gca | aac | agt | ttc | gaa | tct | aaa | gat | tat | ctc | cag | gtt | 255
| Pro | Asn | Thr | Glu | Ala | Asn | Ser | Phe | Glu | Ser | Lys | Asp | Tyr | Leu | Gln | Val
| | | | 50 | | | | 55 | | | | 60 | | | | tgt ctt cga ata aga cca ttt aca cag tca gaa aaa gaa ctt gag tct   303
Cys Leu Arg Ile Arg Pro Phe Thr Gln Ser Glu Lys Glu Leu Glu Ser
         65              70              75 gag ggc tgt gtg cat att ctg gat tca cag act gtt gtg ctg aaa gag   351
Glu Gly Cys Val His Ile Leu Asp Ser Gln Thr Val Val Leu Lys Glu
             80              85              90 cct caa tgc atc ctt ggt cgg tta agt gaa aaa agc tca ggg cag atg   399
Pro Gln Cys Ile Leu Gly Arg Leu Ser Glu Lys Ser Ser Gly Gln Met
 95             100             105 gca cag aaa ttc agt ttt tcc aag gtt ttt ggc cca gca act aca cag   447
Ala Gln Lys Phe Ser Phe Ser Lys Val Phe Gly Pro Ala Thr Thr Gln
110             115             120             125 aag gaa ttc ttt cag ggt tgc att atg caa cca gta aaa gac ctc ttg   495
Lys Glu Phe Phe Gln Gly Cys Ile Met Gln Pro Val Lys Asp Leu Leu
                130             135             140 aaa gga cag agt cgt ctg att ttt act tac ggg cta acc aat tca gga   543
Lys Gly Gln Ser Arg Leu Ile Phe Thr Tyr Gly Leu Thr Asn Ser Gly
             145             150             155 aaa aca tat aca ttt caa ggg aca gaa gaa aat att ggc att ctg cct   591
Lys Thr Tyr Thr Phe Gln Gly Thr Glu Glu Asn Ile Gly Ile Leu Pro
160             165             170 cga act ttg aat gta tta ttt gat agt ctt caa gaa aga ctg tat aca   639
Arg Thr Leu Asn Val Leu Phe Asp Ser Leu Gln Glu Arg Leu Tyr Thr
        175             180             185 aag atg aac ctt aaa cca cat aga tcc aga gaa tac tta agg tta tca   687
Lys Met Asn Leu Lys Pro His Arg Ser Arg Glu Tyr Leu Arg Leu Ser
190             195             200             205 tca gaa caa gag aaa gaa gaa att gct agc aaa agt gca ttg ctt cgg   735
Ser Glu Gln Glu Lys Glu Glu Ile Ala Ser Lys Ser Ala Leu Leu Arg
             210             215             220 caa att aaa gag gtt act gtg cat aat gat agt gat gat act ctt tat   783
Gln Ile Lys Glu Val Thr Val His Asn Asp Ser Asp Asp Thr Leu Tyr
         225             230             235 gga agt tta act aac tct ttg aat atc tca gag ttt gaa gaa tcc ata   831
Gly Ser Leu Thr Asn Ser Leu Asn Ile Ser Glu Phe Glu Glu Ser Ile
         240             245             250 aaa gat tat gaa caa gcc aac ttg aat atg gct aat agt ata aaa ttt   879
Lys Asp Tyr Glu Gln Ala Asn Leu Asn Met Ala Asn Ser Ile Lys Phe
255             260             265 tct gtg tgg gtt tct ttc ttt gaa att tac aat gaa tat att tat gac   927
Ser Val Trp Val Ser Phe Phe Glu Ile Tyr Asn Glu Tyr Ile Tyr Asp
270             275             280             285 tta ttt gtt cct gta tca tct aaa ttc caa aag aga aag atg ctg cgc   975
Leu Phe Val Pro Val Ser Ser Lys Phe Gln Lys Arg Lys Met Leu Arg
             290             295             300 ctt tcc caa gac gta aag ggc tat tct ttt ata aaa gat cta caa tgg   1023
Leu Ser Gln Asp Val Lys Gly Tyr Ser Phe Ile Lys Asp Leu Gln Trp
         305             310             315 att caa gta tct gat tcc aaa gaa gcc tat aga ctt tta aaa cta gga   1071
Ile Gln Val Ser Asp Ser Lys Glu Ala Tyr Arg Leu Leu Lys Leu Gly
         320             325             330 ata aag cac cag agt gtt gcc ttc aca aaa ttg aat aat gct tcc agt   1119
Ile Lys His Gln Ser Val Ala Phe Thr Lys Leu Asn Asn Ala Ser Ser
335             340             345 aga agt cac agc ata ttc act gtt aaa ata tta cag att gaa gat tct   1167
Arg Ser His Ser Ile Phe Thr Val Lys Ile Leu Gln Ile Glu Asp Ser
350             355             360             365

```
gaa atg tct cgt gta att cga gtc agt gaa tta tct tta tgt gat ctt      1215
Glu Met Ser Arg Val Ile Arg Val Ser Glu Leu Ser Leu Cys Asp Leu
        370                 375                 380 gct ggt tca gaa cga act atg aag aca cag aat gaa ggt gaa agg tta      1263
Ala Gly Ser Glu Arg Thr Met Lys Thr Gln Asn Glu Gly Glu Arg Leu
            385                 390                 395 aga gag act ggg aat atc aac act tct tta ttg act ctg gga aag tgt      1311
Arg Glu Thr Gly Asn Ile Asn Thr Ser Leu Leu Thr Leu Gly Lys Cys
                400                 405                 410 att aac gtc ttg aag aat agt gaa aag tca aag ttt caa cag cat gtg      1359
Ile Asn Val Leu Lys Asn Ser Glu Lys Ser Lys Phe Gln Gln His Val
                    415                 420                 425 cct ttc cgg gaa agt aaa ctg act cac tat ttt caa agt ttt ttt aat      1407
Pro Phe Arg Glu Ser Lys Leu Thr His Tyr Phe Gln Ser Phe Phe Asn
430                 435                 440                 445 ggt aaa ggg aaa att tgt atg att gtc aat atc agc caa tgt tat tta      1455
Gly Lys Gly Lys Ile Cys Met Ile Val Asn Ile Ser Gln Cys Tyr Leu
                450                 455                 460 gcc tat gat gaa aca ctc aat gta ttg aag ttc tcc gcc att gca caa      1503
Ala Tyr Asp Glu Thr Leu Asn Val Leu Lys Phe Ser Ala Ile Ala Gln
                    465                 470                 475 aaa gtt tgt gtc cca gac act tta aat tcc tct caa gag aaa tta ttt      1551
Lys Val Cys Val Pro Asp Thr Leu Asn Ser Ser Gln Glu Lys Leu Phe
                        480                 485                 490 gga cct gtc aaa tct tct caa gat gta tca cta gac agt aat tca aac      1599
Gly Pro Val Lys Ser Ser Gln Asp Val Ser Leu Asp Ser Asn Ser Asn
            495                 500                 505 agt aaa ata tta aat gta aaa aga gcc acc att tca tgg gaa aat agt      1647
Ser Lys Ile Leu Asn Val Lys Arg Ala Thr Ile Ser Trp Glu Asn Ser
510                 515                 520                 525 cta gaa gat ttg atg gaa gac gag gat ttg gtt gag gag cta gaa aac      1695
Leu Glu Asp Leu Met Glu Asp Glu Asp Leu Val Glu Glu Leu Glu Asn
                530                 535                 540 gct gaa gaa act caa aat gtg gaa act aaa ctt ctt gat gaa gat cta      1743
Ala Glu Glu Thr Gln Asn Val Glu Thr Lys Leu Leu Asp Glu Asp Leu
                    545                 550                 555 gat aaa aca tta gag gaa aat aag gct ttc att agc cac gag gag aaa      1791
Asp Lys Thr Leu Glu Glu Asn Lys Ala Phe Ile Ser His Glu Glu Lys
                        560                 565                 570 aga aaa ctg ttg gac tta ata gaa gac ttg aaa aaa aaa ctg ata aat      1839
Arg Lys Leu Leu Asp Leu Ile Glu Asp Leu Lys Lys Lys Leu Ile Asn
            575                 580                 585 gaa aaa aag gaa aaa tta acc ttg gaa ttt aaa att cga gaa gaa gtt      1887
Glu Lys Lys Glu Lys Leu Thr Leu Glu Phe Lys Ile Arg Glu Glu Val
590                 595                 600                 605 aca cag gag ttt act cag tat tgg gct caa cgg gaa gct gac ttt aag      1935
Thr Gln Glu Phe Thr Gln Tyr Trp Ala Gln Arg Glu Ala Asp Phe Lys
                610                 615                 620 gag act ctg ctt caa gaa cga gag ata tta gaa gaa aat gct gaa cgt      1983
Glu Thr Leu Leu Gln Glu Arg Glu Ile Leu Glu Glu Asn Ala Glu Arg
                    625                 630                 635 cgt ttg gct atc ttc aag gat ttg gtt ggt aaa tgt gac act cga gaa      2031
Arg Leu Ala Ile Phe Lys Asp Leu Val Gly Lys Cys Asp Thr Arg Glu
                        640                 645                 650 gaa gca gcg aaa gac att tgt gcc aca aaa gtt gaa act gaa gaa gct      2079
Glu Ala Ala Lys Asp Ile Cys Ala Thr Lys Val Glu Thr Glu Glu Ala
            655                 660                 665 act gct tgt tta gaa cta aag ttt aat caa att aaa gct gaa tta gct      2127
Thr Ala Cys Leu Glu Leu Lys Phe Asn Gln Ile Lys Ala Glu Leu Ala
670                 675                 680                 685
```

```
aaa acc aaa gga gaa tta atc aaa acc aaa gaa gag tta aaa aag aga    2175
Lys Thr Lys Gly Glu Leu Ile Lys Thr Lys Glu Glu Leu Lys Lys Arg
            690                 695                 700 gaa aat gaa tca gat tca ttg att caa gag ctt gag aca tct aat aag    2223
Glu Asn Glu Ser Asp Ser Leu Ile Gln Glu Leu Glu Thr Ser Asn Lys
        705                 710                 715 aaa ata att aca cag aat caa aga att aaa gaa ttg ata aat ata att    2271
Lys Ile Ile Thr Gln Asn Gln Arg Ile Lys Glu Leu Ile Asn Ile Ile
    720                 725                 730 gat caa aaa gaa gat act atc aac gaa ttt cag aac cta aag tct cat    2319
Asp Gln Lys Glu Asp Thr Ile Asn Glu Phe Gln Asn Leu Lys Ser His
735                 740                 745 atg gaa aac aca ttt aaa tgc aat gac aag gct gat aca tct tct tta    2367
Met Glu Asn Thr Phe Lys Cys Asn Asp Lys Ala Asp Thr Ser Ser Leu
750                 755                 760                 765 ata ata aac aat aaa ttg att tgt aat gaa aca gtt gaa gta cct aag    2415
Ile Ile Asn Asn Lys Leu Ile Cys Asn Glu Thr Val Glu Val Pro Lys
            770                 775                 780 gac agc aaa tct aaa atc tgt tca gaa aga aaa aga gta aat gaa aat    2463
Asp Ser Lys Ser Lys Ile Cys Ser Glu Arg Lys Arg Val Asn Glu Asn
        785                 790                 795 gaa ctt cag caa gat gaa cca cca gca aag aaa ggg tct atc cat gtt    2511
Glu Leu Gln Gln Asp Glu Pro Pro Ala Lys Lys Gly Ser Ile His Val
    800                 805                 810 agt tca gct atc act gaa gac caa aag aaa agt gaa gaa gtg cga ccg    2559
Ser Ser Ala Ile Thr Glu Asp Gln Lys Lys Ser Glu Glu Val Arg Pro
815                 820                 825 aac att gca gaa att gaa gac atc aga gtt tta caa gaa aat aat gaa    2607
Asn Ile Ala Glu Ile Glu Asp Ile Arg Val Leu Gln Glu Asn Asn Glu
830                 835                 840                 845 gga ctg aga gca ttt tta ctc act att gag aat gaa ctt aaa aat gaa    2655
Gly Leu Arg Ala Phe Leu Leu Thr Ile Glu Asn Glu Leu Lys Asn Glu
            850                 855                 860 aag gaa gaa aaa gca gaa tta aat aaa cag att gtt cat ttt cag cag    2703
Lys Glu Glu Lys Ala Glu Leu Asn Lys Gln Ile Val His Phe Gln Gln
        865                 870                 875 gaa ctt tct ctt tct gaa aaa aag aat tta act tta agt aaa gag gtc    2751
Glu Leu Ser Leu Ser Glu Lys Lys Asn Leu Thr Leu Ser Lys Glu Val
    880                 885                 890 caa caa att cag tca aat tat gat att gca att gct gaa tta cat gtg    2799
Gln Gln Ile Gln Ser Asn Tyr Asp Ile Ala Ile Ala Glu Leu His Val
895                 900                 905 cag aaa agt aaa aat caa gaa cag gag gaa aag atc atg aaa ttg tca    2847
Gln Lys Ser Lys Asn Gln Glu Gln Glu Glu Lys Ile Met Lys Leu Ser
910                 915                 920                 925 aat gag ata gaa act gct aca aga agc att aca aat aat gtt tca caa    2895
Asn Glu Ile Glu Thr Ala Thr Arg Ser Ile Thr Asn Asn Val Ser Gln
            930                 935                 940 ata aaa tta atg cac acg aaa ata gac gaa cta cgt act ctt gat tca    2943
Ile Lys Leu Met His Thr Lys Ile Asp Glu Leu Arg Thr Leu Asp Ser
        945                 950                 955 gtt tct cag att tca aac ata gat ttg ctc aat ctc agg gat ctg tca    2991
Val Ser Gln Ile Ser Asn Ile Asp Leu Leu Asn Leu Arg Asp Leu Ser
    960                 965                 970 aat ggt tct gag gag gat aat ttg cca aat aca cag tta gac ctt tta    3039
Asn Gly Ser Glu Glu Asp Asn Leu Pro Asn Thr Gln Leu Asp Leu Leu
975                 980                 985 ggt aat gat tat ttg gta agt aag caa gtt aaa  gaa tat cga att caa   3087
Gly Asn Asp Tyr Leu Val Ser Lys Gln Val Lys  Glu Tyr Arg Ile Gln
990                 995                 1000                1005
```

-continued

| | | |
|---|---|---|
| gaa ccc aat agg gaa aat tct ttc cac tct agt att gaa gct att<br>Glu Pro Asn Arg Glu Asn Ser Phe His Ser Ser Ile Glu Ala Ile<br>1010                    1015                   1020 | 3132 | |
| tgg gaa gaa tgt aaa gag att gtg aag gcc tct tcc aaa aaa agt<br>Trp Glu Glu Cys Lys Glu Ile Val Lys Ala Ser Ser Lys Lys Ser<br>1025                    1030                   1035 | 3177 | |
| cat cag att gag gaa ctg gaa caa caa att gaa aaa ttg cag gca<br>His Gln Ile Glu Glu Leu Glu Gln Gln Ile Glu Lys Leu Gln Ala<br>1040                    1045                   1050 | 3222 | |
| gaa gta aaa ggc tat aag gat gaa aac aat aga cta aag gag aag<br>Glu Val Lys Gly Tyr Lys Asp Glu Asn Asn Arg Leu Lys Glu Lys<br>1055                    1060                   1065 | 3267 | |
| gag cat aaa aac caa gat gac cta cta aaa gaa aaa gaa act ctt<br>Glu His Lys Asn Gln Asp Asp Leu Leu Lys Glu Lys Glu Thr Leu<br>1070                    1075                   1080 | 3312 | |
| ata cag cag ctg aaa gaa gaa ttg caa gaa aaa aat gtt act ctt<br>Ile Gln Gln Leu Lys Glu Glu Leu Gln Glu Lys Asn Val Thr Leu<br>1085                    1090                   1095 | 3357 | |
| gat gtt caa ata cag cat gta gtt gaa gga aag aga gcg ctt tca<br>Asp Val Gln Ile Gln His Val Val Glu Gly Lys Arg Ala Leu Ser<br>1100                    1105                   1110 | 3402 | |
| gaa ctt aca caa ggt gtt act tgc tat aag gca aaa ata aag gaa<br>Glu Leu Thr Gln Gly Val Thr Cys Tyr Lys Ala Lys Ile Lys Glu<br>1115                    1120                   1125 | 3447 | |
| ctt gaa aca att tta gag act cag aaa gtt gaa tgt agt cat tca<br>Leu Glu Thr Ile Leu Glu Thr Gln Lys Val Glu Cys Ser His Ser<br>1130                    1135                   1140 | 3492 | |
| gcc aag tta gaa caa gac att ttg gaa aag gaa tct atc atc tta<br>Ala Lys Leu Glu Gln Asp Ile Leu Glu Lys Glu Ser Ile Ile Leu<br>1145                    1150                   1155 | 3537 | |
| aag cta gaa aga aat ttg aag gaa ttt caa gaa cat ctt cag gat<br>Lys Leu Glu Arg Asn Leu Lys Glu Phe Gln Glu His Leu Gln Asp<br>1160                    1165                   1170 | 3582 | |
| tct gtc aaa aac acc aaa gat tta aat gta aag gaa ctc aag ctg<br>Ser Val Lys Asn Thr Lys Asp Leu Asn Val Lys Glu Leu Lys Leu<br>1175                    1180                   1185 | 3627 | |
| aaa gaa gaa atc aca cag tta aca aat aat ttg caa gat atg aaa<br>Lys Glu Glu Ile Thr Gln Leu Thr Asn Asn Leu Gln Asp Met Lys<br>1190                    1195                   1200 | 3672 | |
| cat tta ctt caa tta aaa gaa gaa gaa gaa acc aac agg caa<br>His Leu Leu Gln Leu Lys Glu Glu Glu Glu Thr Asn Arg Gln<br>1205                    1210                   1215 | 3717 | |
| gaa aca gaa aaa ttg aaa gag gaa ctc tct gca agc tct gct cgt<br>Glu Thr Glu Lys Leu Lys Glu Glu Leu Ser Ala Ser Ser Ala Arg<br>1220                    1225                   1230 | 3762 | |
| acc cag aat ctg aaa gca gat ctt cag agg aag gaa gaa gat tat<br>Thr Gln Asn Leu Lys Ala Asp Leu Gln Arg Lys Glu Glu Asp Tyr<br>1235                    1240                   1245 | 3807 | |
| gct gac ctg aaa gag aaa ctg act gat gcc aaa aag cag att aag<br>Ala Asp Leu Lys Glu Lys Leu Thr Asp Ala Lys Lys Gln Ile Lys<br>1250                    1255                   1260 | 3852 | |
| caa gta cag aaa gag gta tct gta atg cgt gat gag gat aaa tta<br>Gln Val Gln Lys Glu Val Ser Val Met Arg Asp Glu Asp Lys Leu<br>1265                    1270                   1275 | 3897 | |
| ctg agg att aaa att aat gaa ctg gag aaa aag aaa aac cag tgt<br>Leu Arg Ile Lys Ile Asn Glu Leu Glu Lys Lys Lys Asn Gln Cys<br>1280                    1285                   1290 | 3942 | |
| tct cag gaa tta gat atg aaa cag cga acc att cag caa ctc aag<br>Ser Gln Glu Leu Asp Met Lys Gln Arg Thr Ile Gln Gln Leu Lys<br>1295                    1300                   1305 | 3987 | |

```
                                                            -continued
gag cag tta aat aat cag aaa gtg gaa gaa gct ata caa cag tat      4032
Glu Gln Leu Asn Asn Gln Lys Val Glu Glu Ala Ile Gln Gln Tyr
            1310                1315                1320 gag aga gca tgc aaa gat cta aat gtt aaa gag aaa ata att gaa      4077
Glu Arg Ala Cys Lys Asp Leu Asn Val Lys Glu Lys Ile Ile Glu
        1325                1330                1335 gac atg cga atg aca cta gaa gaa cag gaa caa act cag gta gaa      4122
Asp Met Arg Met Thr Leu Glu Glu Gln Glu Gln Thr Gln Val Glu
        1340                1345                1350 cag gat caa gtg ctt gag gct aaa tta gag gaa gtt gaa agg ctg      4167
Gln Asp Gln Val Leu Glu Ala Lys Leu Glu Glu Val Glu Arg Leu
        1355                1360                1365 gcc aca gaa ttg gaa aaa tgg aag gaa aaa tgc aat gat ttg gaa      4212
Ala Thr Glu Leu Glu Lys Trp Lys Glu Lys Cys Asn Asp Leu Glu
        1370                1375                1380 acc aaa aac aat caa agg tca aat aaa gaa cat gag aac aac aca      4257
Thr Lys Asn Asn Gln Arg Ser Asn Lys Glu His Glu Asn Asn Thr
        1385                1390                1395 gat gtg ctt gga aag ctc act aat ctt caa gat gag tta cag gag      4302
Asp Val Leu Gly Lys Leu Thr Asn Leu Gln Asp Glu Leu Gln Glu
        1400                1405                1410 tct gaa cag aaa tat aat gct gat aga aag aaa tgg tta gaa gaa      4347
Ser Glu Gln Lys Tyr Asn Ala Asp Arg Lys Lys Trp Leu Glu Glu
        1415                1420                1425 aaa atg atg ctt atc act caa gcg aaa gaa gca gag aat ata cga      4392
Lys Met Met Leu Ile Thr Gln Ala Lys Glu Ala Glu Asn Ile Arg
        1430                1435                1440 aat aaa gag atg aaa aaa tat gct gag gac agg gag cgt ttt ttt      4437
Asn Lys Glu Met Lys Lys Tyr Ala Glu Asp Arg Glu Arg Phe Phe
        1445                1450                1455 aag caa cag aat gaa atg gaa ata ctg aca gcc cag ctg aca gag      4482
Lys Gln Gln Asn Glu Met Glu Ile Leu Thr Ala Gln Leu Thr Glu
        1460                1465                1470 aaa gat agt gac ctt caa aag tgg cga gaa gaa cga gat caa ctg      4527
Lys Asp Ser Asp Leu Gln Lys Trp Arg Glu Glu Arg Asp Gln Leu
        1475                1480                1485 gtt gca gct tta gaa ata cag cta aaa gca ctg ata tcc agt aat      4572
Val Ala Ala Leu Glu Ile Gln Leu Lys Ala Leu Ile Ser Ser Asn
        1490                1495                1500 gta cag aaa gat aat gaa att gaa caa cta aaa agg atc ata tca      4617
Val Gln Lys Asp Asn Glu Ile Glu Gln Leu Lys Arg Ile Ile Ser
        1505                1510                1515 gag act tct aaa ata gaa aca caa atc atg gat atc aag ccc aaa      4662
Glu Thr Ser Lys Ile Glu Thr Gln Ile Met Asp Ile Lys Pro Lys
        1520                1525                1530 cgt att agt tca gca gat cct gac aaa ctt caa act gaa cct cta      4707
Arg Ile Ser Ser Ala Asp Pro Asp Lys Leu Gln Thr Glu Pro Leu
        1535                1540                1545 tcg aca agt ttt gaa att tcc aga aat aaa ata gag gat gga tct      4752
Ser Thr Ser Phe Glu Ile Ser Arg Asn Lys Ile Glu Asp Gly Ser
        1550                1555                1560 gta gtc ctt gac tct tgt gaa gtg tca aca gaa aat gat caa agc      4797
Val Val Leu Asp Ser Cys Glu Val Ser Thr Glu Asn Asp Gln Ser
        1565                1570                1575 act cga ttt cca aaa cct gag tta gag att caa ttt aca cct tta      4842
Thr Arg Phe Pro Lys Pro Glu Leu Glu Ile Gln Phe Thr Pro Leu
        1580                1585                1590 cag cca aac aaa atg gca gtg aaa cac cct ggt tgt acc aca cca      4887
Gln Pro Asn Lys Met Ala Val Lys His Pro Gly Cys Thr Thr Pro
        1595                1600                1605
```

```
gtg aca gtt aag att ccc aag gct cgg aag agg aag agt aat gaa       4932
Val Thr Val Lys Ile Pro Lys Ala Arg Lys Arg Lys Ser Asn Glu
            1610                1615                1620 atg gag gag gac ttg gtg aaa tgt gaa aat aag aag aat gct aca       4977
Met Glu Glu Asp Leu Val Lys Cys Glu Asn Lys Lys Asn Ala Thr
        1625                1630                1635 ccc aga act aat ttg aaa ttt cct att tca gat gat aga aat tct       5022
Pro Arg Thr Asn Leu Lys Phe Pro Ile Ser Asp Asp Arg Asn Ser
        1640                1645                1650 tct gtc aaa aag gaa caa aag gtt gcc ata cgt cca tca tct aag       5067
Ser Val Lys Lys Glu Gln Lys Val Ala Ile Arg Pro Ser Ser Lys
        1655                1660                1665 aaa aca tat tct tta cgg agt cag gca tcc ata att ggt gta aac       5112
Lys Thr Tyr Ser Leu Arg Ser Gln Ala Ser Ile Ile Gly Val Asn
        1670                1675                1680 ctg gcc act aag aaa aaa gaa gga aca cta cag aaa ttt gga gac       5157
Leu Ala Thr Lys Lys Lys Glu Gly Thr Leu Gln Lys Phe Gly Asp
        1685                1690                1695 ttc tta caa cat tct ccc tca att ctt caa tca aaa gca aag aag       5202
Phe Leu Gln His Ser Pro Ser Ile Leu Gln Ser Lys Ala Lys Lys
        1700                1705                1710 ata att gaa aca atg agc tct tca aag ctc tca aat gta gaa gca       5247
Ile Ile Glu Thr Met Ser Ser Ser Lys Leu Ser Asn Val Glu Ala
        1715                1720                1725 agt aaa gaa aat gtg tct caa cca aaa cga gcc aaa cgg aaa tta       5292
Ser Lys Glu Asn Val Ser Gln Pro Lys Arg Ala Lys Arg Lys Leu
        1730                1735                1740 tac aca agt gaa att tca tct cct att gat ata tca ggc caa gtg       5337
Tyr Thr Ser Glu Ile Ser Ser Pro Ile Asp Ile Ser Gly Gln Val
        1745                1750                1755 att tta atg gac cag aaa atg aag gag agt gat cac cag att atc       5382
Ile Leu Met Asp Gln Lys Met Lys Glu Ser Asp His Gln Ile Ile
        1760                1765                1770 aaa cga cga ctt cga aca aaa aca gcc aaa taa atcacttatg            5425
Lys Arg Arg Leu Arg Thr Lys Thr Ala Lys
        1775                1780 gaaatgttta ataaaattt tatagtcata gtcattggaa cttgcatcct gtattgtaaa  5485
tataaatgta tatattatgc attaaatcac tctgcatata gattgctgtt ttatacatag 5545 tataatttta attcaataaa tgagtcaaaa tttgtatatt tttataaggc tttttttaaa 5605 tagcttcttt caaactgtat ttccctatta tctcagacat tggatcagtg aagatcctag 5665 gaaagaggct gttattctca tttatttgc tatacaggat gtaataggtc aggtatttgg  5725
tttacttata tttaacaatg tcttatgaat tttttttact ttatctgtta tacaactgat 5785 tttacatatc tgtttggatt atagctagga tttggagaat aagtgtgtac agatcacaaa 5845 acatgtatat acattattta gaaaagatct caagtcttta attagaatgt ctcacttatt 5905 ttgtaaacat tttgtgggta catagtacat gtatatattt acggggtatg tgagatgttt 5965 tgacacaggc atgcaatgtg aaatacgtgt atcatggaga atgaggtatc catcccctca 6025 agcattttc ctttgaatta cagataatcc aattacattc tttagatcat ttaaaaatat  6085
acaagtaagt tattattgat tatagtcact ctattgtgct atcagatagt agatcattct 6145 ttttatctta tttgtttttg tacccattaa ccatccccac ctcccctgc aaccgtcagt  6205 acccttacca gccactggta accattcttc tactctgtat gcccatgagg tcaattgatt 6265 ttatttttag atcccataaa taatgagaa catgcagtct ttgtcaaaaa aaaa         6319
```

-continued

```
<210> SEQ ID NO 2
<211> LENGTH: 1780
<212> TYPE: PRT
<213> ORGANISM: Homo sapiens

<400> SEQUENCE: 2

Met Glu Ser Asn Phe Asn Gln Glu Gly Val Pro Arg Pro Ser Tyr Val
1               5                   10                  15

Phe Ser Ala Asp Pro Ile Ala Arg Pro Ser Glu Ile Asn Phe Asp Gly
            20                  25                  30

Ile Lys Leu Asp Leu Ser His Glu Phe Ser Leu Val Ala Pro Asn Thr
            35                  40                  45

Glu Ala Asn Ser Phe Glu Ser Lys Asp Tyr Leu Gln Val Cys Leu Arg
    50                  55                  60

Ile Arg Pro Phe Thr Gln Ser Glu Lys Glu Leu Glu Ser Glu Gly Cys
65                  70                  75                  80

Val His Ile Leu Asp Ser Gln Thr Val Val Leu Lys Glu Pro Gln Cys
                85                  90                  95

Ile Leu Gly Arg Leu Ser Glu Lys Ser Ser Gly Gln Met Ala Gln Lys
            100                 105                 110

Phe Ser Phe Ser Lys Val Phe Gly Pro Ala Thr Thr Gln Lys Glu Phe
        115                 120                 125

Phe Gln Gly Cys Ile Met Gln Pro Val Lys Asp Leu Leu Lys Gly Gln
    130                 135                 140

Ser Arg Leu Ile Phe Thr Tyr Gly Leu Thr Asn Ser Gly Lys Thr Tyr
145                 150                 155                 160

Thr Phe Gln Gly Thr Glu Asn Ile Gly Ile Leu Pro Arg Thr Leu
                165                 170                 175

Asn Val Leu Phe Asp Ser Leu Gln Glu Arg Leu Tyr Thr Lys Met Asn
            180                 185                 190

Leu Lys Pro His Arg Ser Arg Glu Tyr Leu Arg Leu Ser Ser Glu Gln
        195                 200                 205

Glu Lys Glu Glu Ile Ala Ser Lys Ser Ala Leu Leu Arg Gln Ile Lys
    210                 215                 220

Glu Val Thr Val His Asn Asp Ser Asp Thr Leu Tyr Gly Ser Leu
225                 230                 235                 240

Thr Asn Ser Leu Asn Ile Ser Glu Phe Glu Glu Ser Ile Lys Asp Tyr
                245                 250                 255

Glu Gln Ala Asn Leu Asn Met Ala Asn Ser Ile Lys Phe Ser Val Trp
            260                 265                 270

Val Ser Phe Phe Glu Ile Tyr Asn Glu Tyr Ile Tyr Asp Leu Phe Val
        275                 280                 285

Pro Val Ser Ser Lys Phe Gln Lys Arg Lys Met Leu Arg Leu Ser Gln
    290                 295                 300

Asp Val Lys Gly Tyr Ser Phe Ile Lys Asp Leu Gln Trp Ile Gln Val
305                 310                 315                 320

Ser Asp Ser Lys Glu Ala Tyr Arg Leu Leu Lys Leu Gly Ile Lys His
                325                 330                 335

Gln Ser Val Ala Phe Thr Lys Leu Asn Asn Ala Ser Arg Ser His
            340                 345                 350

Ser Ile Phe Thr Val Lys Ile Leu Gln Ile Glu Asp Ser Glu Met Ser
        355                 360                 365

Arg Val Ile Arg Val Ser Glu Leu Ser Leu Cys Asp Leu Ala Gly Ser
    370                 375                 380
```

```
Glu Arg Thr Met Lys Thr Gln Asn Glu Gly Glu Arg Leu Arg Glu Thr
385                 390                 395                 400

Gly Asn Ile Asn Thr Ser Leu Leu Thr Leu Gly Lys Cys Ile Asn Val
            405                 410                 415

Leu Lys Asn Ser Glu Lys Ser Lys Phe Gln Gln His Val Pro Phe Arg
        420                 425                 430

Glu Ser Lys Leu Thr His Tyr Phe Gln Ser Phe Phe Asn Gly Lys Gly
    435                 440                 445

Lys Ile Cys Met Ile Val Asn Ile Ser Gln Cys Tyr Leu Ala Tyr Asp
450                 455                 460

Glu Thr Leu Asn Val Leu Lys Phe Ser Ala Ile Ala Gln Lys Val Cys
465                 470                 475                 480

Val Pro Asp Thr Leu Asn Ser Ser Gln Glu Lys Leu Phe Gly Pro Val
            485                 490                 495

Lys Ser Ser Gln Asp Val Ser Leu Asp Ser Asn Ser Asn Ser Lys Ile
        500                 505                 510

Leu Asn Val Lys Arg Ala Thr Ile Ser Trp Glu Asn Ser Leu Glu Asp
    515                 520                 525

Leu Met Glu Asp Glu Asp Leu Val Glu Glu Leu Glu Asn Ala Glu Glu
530                 535                 540

Thr Gln Asn Val Glu Thr Lys Leu Leu Asp Glu Asp Leu Asp Lys Thr
545                 550                 555                 560

Leu Glu Glu Asn Lys Ala Phe Ile Ser His Glu Glu Lys Arg Lys Leu
            565                 570                 575

Leu Asp Leu Ile Glu Asp Leu Lys Lys Lys Leu Ile Asn Glu Lys Lys
        580                 585                 590

Glu Lys Leu Thr Leu Glu Phe Lys Ile Arg Glu Glu Val Thr Gln Glu
    595                 600                 605

Phe Thr Gln Tyr Trp Ala Gln Arg Glu Ala Asp Phe Lys Glu Thr Leu
610                 615                 620

Leu Gln Glu Arg Glu Ile Leu Glu Glu Asn Ala Glu Arg Arg Leu Ala
625                 630                 635                 640

Ile Phe Lys Asp Leu Val Gly Lys Cys Asp Thr Arg Glu Glu Ala Ala
            645                 650                 655

Lys Asp Ile Cys Ala Thr Lys Val Glu Thr Glu Glu Ala Thr Ala Cys
        660                 665                 670

Leu Glu Leu Lys Phe Asn Gln Ile Lys Ala Glu Leu Ala Lys Thr Lys
    675                 680                 685

Gly Glu Leu Ile Lys Thr Lys Glu Glu Leu Lys Lys Arg Glu Asn Glu
690                 695                 700

Ser Asp Ser Leu Ile Gln Glu Leu Glu Thr Ser Asn Lys Lys Ile Ile
705                 710                 715                 720

Thr Gln Asn Gln Arg Ile Lys Glu Leu Ile Asn Ile Asp Gln Lys
            725                 730                 735

Glu Asp Thr Ile Asn Glu Phe Gln Asn Leu Lys Ser His Met Glu Asn
        740                 745                 750

Thr Phe Lys Cys Asn Asp Lys Ala Asp Thr Ser Ser Leu Ile Ile Asn
    755                 760                 765

Asn Lys Leu Ile Cys Asn Glu Thr Val Glu Val Pro Lys Asp Ser Lys
770                 775                 780

Ser Lys Ile Cys Ser Glu Arg Lys Arg Val Asn Glu Asn Glu Leu Gln
785                 790                 795                 800

Gln Asp Glu Pro Pro Ala Lys Lys Gly Ser Ile His Val Ser Ser Ala
            805                 810                 815
```

-continued

Ile Thr Glu Asp Gln Lys Lys Ser Glu Glu Val Arg Pro Asn Ile Ala
            820                 825                 830

Glu Ile Glu Asp Ile Arg Val Leu Gln Glu Asn Asn Glu Gly Leu Arg
            835                 840                 845

Ala Phe Leu Leu Thr Ile Glu Asn Glu Leu Lys Asn Glu Lys Glu Glu
850                 855                 860

Lys Ala Glu Leu Asn Lys Gln Ile Val His Phe Gln Gln Glu Leu Ser
865                 870                 875                 880

Leu Ser Glu Lys Lys Asn Leu Thr Leu Ser Lys Glu Val Gln Gln Ile
                885                 890                 895

Gln Ser Asn Tyr Asp Ile Ala Ile Ala Glu Leu His Val Gln Lys Ser
            900                 905                 910

Lys Asn Gln Glu Gln Glu Glu Lys Ile Met Lys Leu Ser Asn Glu Ile
            915                 920                 925

Glu Thr Ala Thr Arg Ser Ile Thr Asn Asn Val Ser Gln Ile Lys Leu
            930                 935                 940

Met His Thr Lys Ile Asp Glu Leu Arg Thr Leu Asp Ser Val Ser Gln
945                 950                 955                 960

Ile Ser Asn Ile Asp Leu Leu Asn Leu Arg Asp Leu Ser Asn Gly Ser
            965                 970                 975

Glu Glu Asp Asn Leu Pro Asn Thr Gln Leu Asp Leu Leu Gly Asn Asp
            980                 985                 990

Tyr Leu Val Ser Lys Gln Val Lys Glu Tyr Arg Ile Gln Glu Pro Asn
            995                 1000                1005

Arg Glu Asn Ser Phe His Ser Ser Ile Glu Ala Ile Trp Glu Glu
    1010                1015                1020

Cys Lys Glu Ile Val Lys Ala Ser Ser Lys Lys Ser His Gln Ile
    1025                1030                1035

Glu Glu Leu Glu Gln Gln Ile Glu Lys Leu Gln Ala Glu Val Lys
    1040                1045                1050

Gly Tyr Lys Asp Glu Asn Asn Arg Leu Lys Glu Lys Glu His Lys
    1055                1060                1065

Asn Gln Asp Asp Leu Leu Lys Glu Lys Glu Thr Leu Ile Gln Gln
    1070                1075                1080

Leu Lys Glu Glu Leu Gln Glu Lys Asn Val Thr Leu Asp Val Gln
    1085                1090                1095

Ile Gln His Val Val Glu Gly Lys Arg Ala Leu Ser Glu Leu Thr
    1100                1105                1110

Gln Gly Val Thr Cys Tyr Lys Ala Lys Ile Lys Glu Leu Glu Thr
    1115                1120                1125

Ile Leu Glu Thr Gln Lys Val Glu Cys Ser His Ser Ala Lys Leu
    1130                1135                1140

Glu Gln Asp Ile Leu Glu Lys Glu Ser Ile Ile Leu Lys Leu Glu
    1145                1150                1155

Arg Asn Leu Lys Glu Phe Gln Glu His Leu Gln Asp Ser Val Lys
    1160                1165                1170

Asn Thr Lys Asp Leu Asn Val Lys Glu Leu Lys Leu Lys Glu Glu
    1175                1180                1185

Ile Thr Gln Leu Thr Asn Asn Leu Gln Asp Met Lys His Leu Leu
    1190                1195                1200

Gln Leu Lys Glu Glu Glu Glu Thr Asn Arg Gln Glu Thr Glu
    1205                1210                1215

Lys Leu Lys Glu Glu Leu Ser Ala Ser Ser Ala Arg Thr Gln Asn
    1220                1225                1230

-continued

Leu Lys Ala Asp Leu Gln Arg Lys Glu Glu Asp Tyr Ala Asp Leu
1235                1240                1245

Lys Glu Lys Leu Thr Asp Ala Lys Lys Gln Ile Lys Gln Val Gln
1250                1255                1260

Lys Glu Val Ser Val Met Arg Asp Glu Asp Lys Leu Leu Arg Ile
1265                1270                1275

Lys Ile Asn Glu Leu Glu Lys Lys Asn Gln Cys Ser Gln Glu
1280                1285                1290

Leu Asp Met Lys Gln Arg Thr Ile Gln Gln Leu Lys Glu Gln Leu
1295                1300                1305

Asn Asn Gln Lys Val Glu Glu Ala Ile Gln Gln Tyr Glu Arg Ala
1310                1315                1320

Cys Lys Asp Leu Asn Val Lys Glu Lys Ile Ile Glu Asp Met Arg
1325                1330                1335

Met Thr Leu Glu Glu Gln Glu Gln Thr Gln Val Glu Gln Asp Gln
1340                1345                1350

Val Leu Glu Ala Lys Leu Glu Glu Val Glu Arg Leu Ala Thr Glu
1355                1360                1365

Leu Glu Lys Trp Lys Glu Lys Cys Asn Asp Leu Glu Thr Lys Asn
1370                1375                1380

Asn Gln Arg Ser Asn Lys Glu His Glu Asn Asn Thr Asp Val Leu
1385                1390                1395

Gly Lys Leu Thr Asn Leu Gln Asp Glu Leu Gln Glu Ser Glu Gln
1400                1405                1410

Lys Tyr Asn Ala Asp Arg Lys Lys Trp Leu Glu Glu Lys Met Met
1415                1420                1425

Leu Ile Thr Gln Ala Lys Glu Ala Glu Asn Ile Arg Asn Lys Glu
1430                1435                1440

Met Lys Lys Tyr Ala Glu Asp Arg Glu Arg Phe Phe Lys Gln Gln
1445                1450                1455

Asn Glu Met Glu Ile Leu Thr Ala Gln Leu Thr Glu Lys Asp Ser
1460                1465                1470

Asp Leu Gln Lys Trp Arg Glu Glu Arg Asp Gln Leu Val Ala Ala
1475                1480                1485

Leu Glu Ile Gln Leu Lys Ala Leu Ile Ser Ser Asn Val Gln Lys
1490                1495                1500

Asp Asn Glu Ile Glu Gln Leu Lys Arg Ile Ile Ser Glu Thr Ser
1505                1510                1515

Lys Ile Glu Thr Gln Ile Met Asp Ile Lys Pro Lys Arg Ile Ser
1520                1525                1530

Ser Ala Asp Pro Asp Lys Leu Gln Thr Glu Pro Leu Ser Thr Ser
1535                1540                1545

Phe Glu Ile Ser Arg Asn Lys Ile Glu Asp Gly Ser Val Val Leu
1550                1555                1560

Asp Ser Cys Glu Val Ser Thr Glu Asn Asp Gln Ser Thr Arg Phe
1565                1570                1575

Pro Lys Pro Glu Leu Glu Ile Gln Phe Thr Pro Leu Gln Pro Asn
1580                1585                1590

Lys Met Ala Val Lys His Pro Gly Cys Thr Thr Pro Val Thr Val
1595                1600                1605

Lys Ile Pro Lys Ala Arg Lys Arg Lys Ser Asn Glu Met Glu Glu
1610                1615                1620

Asp Leu Val Lys Cys Glu Asn Lys Lys Asn Ala Thr Pro Arg Thr
1625                1630                1635

```
Asn Leu Lys Phe Pro Ile Ser Asp Asp Arg Asn Ser Ser Val Lys
    1640                1645                1650

Lys Glu Gln Lys Val Ala Ile Arg Pro Ser Ser Lys Lys Thr Tyr
1655                1660                1665

Ser Leu Arg Ser Gln Ala Ser Ile Ile Gly Val Asn Leu Ala Thr
    1670                1675                1680

Lys Lys Lys Glu Gly Thr Leu Gln Lys Phe Gly Asp Phe Leu Gln
1685                1690                1695

His Ser Pro Ser Ile Leu Gln Ser Lys Ala Lys Lys Ile Ile Glu
    1700                1705                1710

Thr Met Ser Ser Ser Lys Leu Ser Asn Val Glu Ala Ser Lys Glu
1715                1720                1725

Asn Val Ser Gln Pro Lys Arg Ala Lys Arg Lys Leu Tyr Thr Ser
    1730                1735                1740

Glu Ile Ser Ser Pro Ile Asp Ile Ser Gly Gln Val Ile Leu Met
1745                1750                1755

Asp Gln Lys Met Lys Glu Ser Asp His Gln Ile Ile Lys Arg Arg
    1760                1765                1770

Leu Arg Thr Lys Thr Ala Lys
1775                1780

<210> SEQ ID NO 3
<211> LENGTH: 5318
<212> TYPE: DNA
<213> ORGANISM: Homo sapiens
<220> FEATURE:
<221> NAME/KEY: CDS
<222> LOCATION: (79)..(2511)

<400> SEQUENCE: 3
gagactcgcc actgccgcgg ccgctgggcc tgagtgtcgc cttcgccgcc atggacgcca        60
ccgggcgctg acagacct atg gag agt cag ggt gtg cct ccc ggg cct tat       111
                    Met Glu Ser Gln Gly Val Pro Pro Gly Pro Tyr
                      1               5                  10 cgg gcc acc aag ctg tgg aat gaa gtt acc aca tct ttt cga gca gga       159
Arg Ala Thr Lys Leu Trp Asn Glu Val Thr Thr Ser Phe Arg Ala Gly
         15                  20                  25 atg cct cta aga aaa cac aga caa cac ttt aaa aaa tat ggc aat tgt       207
Met Pro Leu Arg Lys His Arg Gln His Phe Lys Lys Tyr Gly Asn Cys
             30                  35                  40 ttc aca gca gga gaa gca gtg gat tgg ctt tat gac cta tta aga aat       255
Phe Thr Ala Gly Glu Ala Val Asp Trp Leu Tyr Asp Leu Leu Arg Asn
         45                  50                  55 aat agc aat ttt ggt cct gaa gtt aca agg caa cag act atc caa ctg       303
Asn Ser Asn Phe Gly Pro Glu Val Thr Arg Gln Gln Thr Ile Gln Leu
60                  65                  70                  75 ttg agg aaa ttt ctt aag aat cat gta att gaa gat atc aaa ggg agg       351
Leu Arg Lys Phe Leu Lys Asn His Val Ile Glu Asp Ile Lys Gly Arg
                 80                  85                  90 tgg gga tca gaa aat gtt gat gat aac aac cag ctc ttc aga ttt cct       399
Trp Gly Ser Glu Asn Val Asp Asp Asn Asn Gln Leu Phe Arg Phe Pro
             95                 100                 105 gca act tcg cca ctt aaa act cta cca cga agg tat cca gaa ttg aga       447
Ala Thr Ser Pro Leu Lys Thr Leu Pro Arg Arg Tyr Pro Glu Leu Arg
         110                 115                 120 aaa aac aac ata gag aac ttt tcc aaa gat aaa gat agc att ttt aaa       495
Lys Asn Asn Ile Glu Asn Phe Ser Lys Asp Lys Asp Ser Ile Phe Lys
     125                 130                 135
```

-continued

| | | |
|---|---|---|
| tta cga aac tta tct cgt aga act cct aaa agg cat gga tta cat tta<br>Leu Arg Asn Leu Ser Arg Arg Thr Pro Lys Arg His Gly Leu His Leu<br>140                   145                   150                   155 | 543 |
| tct cag gaa aat ggc gag aaa ata aag cat gaa ata atc aat gaa gat<br>Ser Gln Glu Asn Gly Glu Lys Ile Lys His Glu Ile Ile Asn Glu Asp<br>                   160                   165                   170 | 591 |
| caa gaa aat gca att gat aat aga gaa cta agc cag gaa gat gtt gaa<br>Gln Glu Asn Ala Ile Asp Asn Arg Glu Leu Ser Gln Glu Asp Val Glu<br>               175                   180                   185 | 639 |
| gaa gtt tgg aga tat gtt att ctg atc tac ctg caa acc att tta ggt<br>Glu Val Trp Arg Tyr Val Ile Leu Ile Tyr Leu Gln Thr Ile Leu Gly<br>190                   195                   200 | 687 |
| gtg cca tcc cta gaa gaa gtc ata aat cca aaa caa gta att ccc caa<br>Val Pro Ser Leu Glu Glu Val Ile Asn Pro Lys Gln Val Ile Pro Gln<br>205                   210                   215 | 735 |
| tat ata atg tac aac atg gcc aat aca agt aaa cgt gga gta gtt ata<br>Tyr Ile Met Tyr Asn Met Ala Asn Thr Ser Lys Arg Gly Val Val Ile<br>220                   225                   230                   235 | 783 |
| cta caa aac aaa tca gat gac ctc cct cac tgg gta tta tct gcc atg<br>Leu Gln Asn Lys Ser Asp Asp Leu Pro His Trp Val Leu Ser Ala Met<br>               240                   245                   250 | 831 |
| aag tgc cta gca aat tgg cca aga agc aat gat atg aat aat cca act<br>Lys Cys Leu Ala Asn Trp Pro Arg Ser Asn Asp Met Asn Asn Pro Thr<br>                   255                   260                   265 | 879 |
| tat gtt gga ttt gaa cga gat gta ttc aga aca atc gca gat tat ttt<br>Tyr Val Gly Phe Glu Arg Asp Val Phe Arg Thr Ile Ala Asp Tyr Phe<br>270                   275                   280 | 927 |
| cta gat ctc cct gaa cct cta ctt act ttt gaa tat tac gaa tta ttt<br>Leu Asp Leu Pro Glu Pro Leu Leu Thr Phe Glu Tyr Tyr Glu Leu Phe<br>285                   290                   295 | 975 |
| gta aac att ttg gtt gtt tgt ggc tac atc aca gtt tca gat aga tcc<br>Val Asn Ile Leu Val Val Cys Gly Tyr Ile Thr Val Ser Asp Arg Ser<br>300                   305                   310                   315 | 1023 |
| agt ggg ata cat aaa att caa gat gat cca cag tct tca aaa ttc ctt<br>Ser Gly Ile His Lys Ile Gln Asp Asp Pro Gln Ser Ser Lys Phe Leu<br>               320                   325                   330 | 1071 |
| cac tta aac aat ttg aat tcc ttc aaa tca act gag tgc ctt ctt ctc<br>His Leu Asn Asn Leu Asn Ser Phe Lys Ser Thr Glu Cys Leu Leu Leu<br>                   335                   340                   345 | 1119 |
| agt ctg ctt cat aga gaa aaa aac aaa gaa gaa tca gat tct act gag<br>Ser Leu Leu His Arg Glu Lys Asn Lys Glu Glu Ser Asp Ser Thr Glu<br>350                   355                   360 | 1167 |
| aga cta cag ata agc aat cca gga ttt caa gaa aga tgt gct aag aaa<br>Arg Leu Gln Ile Ser Asn Pro Gly Phe Gln Glu Arg Cys Ala Lys Lys<br>365                   370                   375 | 1215 |
| atg cag cta gtt aat tta aga aac aga aga gtg agt gct aat gac ata<br>Met Gln Leu Val Asn Leu Arg Asn Arg Arg Val Ser Ala Asn Asp Ile<br>380                   385                   390                   395 | 1263 |
| atg gga gga agt tgt cat aat tta ata ggg tta agt aat atg cat gat<br>Met Gly Gly Ser Cys His Asn Leu Ile Gly Leu Ser Asn Met His Asp<br>               400                   405                   410 | 1311 |
| cta tcc tct aac agc aaa cca agg tgc tgt tct ttg gaa gga att gta<br>Leu Ser Ser Asn Ser Lys Pro Arg Cys Cys Ser Leu Glu Gly Ile Val<br>                   415                   420                   425 | 1359 |
| gat gtg cca ggg aat tca agt aaa gag gca tcc agt gtc ttt cat caa<br>Asp Val Pro Gly Asn Ser Ser Lys Glu Ala Ser Ser Val Phe His Gln<br>               430                   435                   440 | 1407 |
| tct ttt ccg aac ata gaa gga caa aat aat aaa ctg ttt tta gag tct<br>Ser Phe Pro Asn Ile Glu Gly Gln Asn Asn Lys Leu Phe Leu Glu Ser<br>445                   450                   455 | 1455 |

| | | | | | | | | | | | | | | | |
|---|---|---|---|---|---|---|---|---|---|---|---|---|---|---|---|
| aag | ccc | aaa | cag | gaa | ttc | ctg | ttg | aat | ctt | cat | tca | gag | gaa | aat | att | 1503 |
| Lys | Pro | Lys | Gln | Glu | Phe | Leu | Leu | Asn | Leu | His | Ser | Glu | Glu | Asn | Ile |
| 460 | | | | 465 | | | | | 470 | | | | | 475 | |

| caa | aag | cca | ttc | agt | gct | ggt | ttt | aag | aga | acc | tct | act | ttg | act | gtt | 1551 |
|---|---|---|---|---|---|---|---|---|---|---|---|---|---|---|---|---|
| Gln | Lys | Pro | Phe | Ser | Ala | Gly | Phe | Lys | Arg | Thr | Ser | Thr | Leu | Thr | Val |
| | | | 480 | | | | | 485 | | | | | 490 | | |

| caa | gac | caa | gag | gag | ttg | tgt | aat | ggg | aaa | tgc | aag | tca | aaa | cag | ctt | 1599 |
|---|---|---|---|---|---|---|---|---|---|---|---|---|---|---|---|---|
| Gln | Asp | Gln | Glu | Glu | Leu | Cys | Asn | Gly | Lys | Cys | Lys | Ser | Lys | Gln | Leu |
| | | | 495 | | | | | 500 | | | | | 505 | | |

| tgt | agg | tct | cag | agt | ttg | ctt | tta | aga | agt | agt | aca | aga | agg | aat | agt | 1647 |
|---|---|---|---|---|---|---|---|---|---|---|---|---|---|---|---|---|
| Cys | Arg | Ser | Gln | Ser | Leu | Leu | Leu | Arg | Ser | Ser | Thr | Arg | Arg | Asn | Ser |
| | | 510 | | | | | 515 | | | | | 520 | | | |

| tat | atc | aat | aca | cca | gtg | gct | gaa | att | atc | atg | aaa | cca | aat | gtt | gga | 1695 |
|---|---|---|---|---|---|---|---|---|---|---|---|---|---|---|---|---|
| Tyr | Ile | Asn | Thr | Pro | Val | Ala | Glu | Ile | Ile | Met | Lys | Pro | Asn | Val | Gly |
| | 525 | | | | | 530 | | | | | 535 | | | | |

| caa | ggc | agc | aca | agt | gtg | caa | aca | gct | atg | gaa | agt | gaa | ctc | gga | gag | 1743 |
|---|---|---|---|---|---|---|---|---|---|---|---|---|---|---|---|---|
| Gln | Gly | Ser | Thr | Ser | Val | Gln | Thr | Ala | Met | Glu | Ser | Glu | Leu | Gly | Glu |
| 540 | | | | | 545 | | | | | 550 | | | | | 555 |

| tct | agt | gcc | aca | atc | aat | aaa | aga | ctc | tgc | aaa | agt | aca | ata | gaa | ctt | 1791 |
|---|---|---|---|---|---|---|---|---|---|---|---|---|---|---|---|---|
| Ser | Ser | Ala | Thr | Ile | Asn | Lys | Arg | Leu | Cys | Lys | Ser | Thr | Ile | Glu | Leu |
| | | | | 560 | | | | | 565 | | | | | 570 | |

| tca | gaa | aat | tct | tta | ctt | cca | gct | tct | tct | atg | ttg | act | ggc | aca | caa | 1839 |
|---|---|---|---|---|---|---|---|---|---|---|---|---|---|---|---|---|
| Ser | Glu | Asn | Ser | Leu | Leu | Pro | Ala | Ser | Ser | Met | Leu | Thr | Gly | Thr | Gln |
| | | | 575 | | | | | 580 | | | | | 585 | | |

| agc | ttg | ctg | caa | cct | cat | tta | gag | agg | gtt | gcc | atc | gat | gct | cta | cag | 1887 |
|---|---|---|---|---|---|---|---|---|---|---|---|---|---|---|---|---|
| Ser | Leu | Leu | Gln | Pro | His | Leu | Glu | Arg | Val | Ala | Ile | Asp | Ala | Leu | Gln |
| | | 590 | | | | | 595 | | | | | 600 | | | |

| tta | tgt | tgt | ttg | tta | ctt | ccc | cca | cca | aat | cgt | aga | aag | ctt | caa | ctt | 1935 |
|---|---|---|---|---|---|---|---|---|---|---|---|---|---|---|---|---|
| Leu | Cys | Cys | Leu | Leu | Leu | Pro | Pro | Pro | Asn | Arg | Arg | Lys | Leu | Gln | Leu |
| | 605 | | | | | 610 | | | | | 615 | | | | |

| tta | atg | cgt | atg | att | tcc | cga | atg | agt | caa | aat | gtt | gat | atg | ccc | aaa | 1983 |
|---|---|---|---|---|---|---|---|---|---|---|---|---|---|---|---|---|
| Leu | Met | Arg | Met | Ile | Ser | Arg | Met | Ser | Gln | Asn | Val | Asp | Met | Pro | Lys |
| 620 | | | | | 625 | | | | | 630 | | | | | 635 |

| ctt | cat | gat | gca | atg | ggt | acg | agg | tca | ctg | atg | ata | cat | acc | ttt | tct | 2031 |
|---|---|---|---|---|---|---|---|---|---|---|---|---|---|---|---|---|
| Leu | His | Asp | Ala | Met | Gly | Thr | Arg | Ser | Leu | Met | Ile | His | Thr | Phe | Ser |
| | | | | 640 | | | | | 645 | | | | | 650 | |

| cga | tgt | gtg | tta | tgc | tgt | gct | gaa | gaa | gtg | gat | ctt | gat | gag | ctt | ctt | 2079 |
|---|---|---|---|---|---|---|---|---|---|---|---|---|---|---|---|---|
| Arg | Cys | Val | Leu | Cys | Cys | Ala | Glu | Glu | Val | Asp | Leu | Asp | Glu | Leu | Leu |
| | | | 655 | | | | | 660 | | | | | 665 | | |

| gct | gga | aga | tta | gtt | tct | ttc | tta | atg | gat | cat | cat | cag | gaa | att | ctt | 2127 |
|---|---|---|---|---|---|---|---|---|---|---|---|---|---|---|---|---|
| Ala | Gly | Arg | Leu | Val | Ser | Phe | Leu | Met | Asp | His | His | Gln | Glu | Ile | Leu |
| | | 670 | | | | | 675 | | | | | 680 | | | |

| caa | gta | ccc | tct | tac | tta | cag | act | gca | gtg | gaa | aaa | cat | ctt | gac | tac | 2175 |
|---|---|---|---|---|---|---|---|---|---|---|---|---|---|---|---|---|
| Gln | Val | Pro | Ser | Tyr | Leu | Gln | Thr | Ala | Val | Glu | Lys | His | Leu | Asp | Tyr |
| | 685 | | | | | 690 | | | | | 695 | | | | |

| tta | aaa | aag | gga | cat | att | gaa | aat | cct | gga | gat | gga | cta | ttt | gct | cct | 2223 |
|---|---|---|---|---|---|---|---|---|---|---|---|---|---|---|---|---|
| Leu | Lys | Lys | Gly | His | Ile | Glu | Asn | Pro | Gly | Asp | Gly | Leu | Phe | Ala | Pro |
| 700 | | | | | 705 | | | | | 710 | | | | | 715 |

| ttg | cca | act | tac | tca | tac | tgt | aag | cag | att | agt | gct | cag | gag | ttt | gat | 2271 |
|---|---|---|---|---|---|---|---|---|---|---|---|---|---|---|---|---|
| Leu | Pro | Thr | Tyr | Ser | Tyr | Cys | Lys | Gln | Ile | Ser | Ala | Gln | Glu | Phe | Asp |
| | | | 720 | | | | | 725 | | | | | 730 | | |

| gag | caa | aaa | gtt | tct | acc | tct | caa | gct | gca | att | gca | gaa | ctt | tta | gaa | 2319 |
|---|---|---|---|---|---|---|---|---|---|---|---|---|---|---|---|---|
| Glu | Gln | Lys | Val | Ser | Thr | Ser | Gln | Ala | Ala | Ile | Ala | Glu | Leu | Leu | Glu |
| | | | 735 | | | | | 740 | | | | | 745 | | |

| aat | att | att | aaa | aac | agg | agt | tta | cct | cta | aag | gag | aaa | aga | aaa | aaa | 2367 |
|---|---|---|---|---|---|---|---|---|---|---|---|---|---|---|---|---|
| Asn | Ile | Ile | Lys | Asn | Arg | Ser | Leu | Pro | Leu | Lys | Glu | Lys | Arg | Lys | Lys |
| | | 750 | | | | | 755 | | | | | 760 | | | |

| cta | aaa | cag | ttt | cag | aag | gaa | tat | cct | ttg | ata | tat | cag | aaa | aga | ttt | 2415 |
|---|---|---|---|---|---|---|---|---|---|---|---|---|---|---|---|---|
| Leu | Lys | Gln | Phe | Gln | Lys | Glu | Tyr | Pro | Leu | Ile | Tyr | Gln | Lys | Arg | Phe |
| 765 | | | | | 770 | | | | | 775 | | | | | |

```
cca acc acg gag agt gaa gca gca ctt ttt ggt gac aaa cct aca atc     2463
Pro Thr Thr Glu Ser Glu Ala Ala Leu Phe Gly Asp Lys Pro Thr Ile
780             785                 790                 795 aag caa cca atg ctg att tta aga aaa cca aag ttc cgt agt cta aga     2511
Lys Gln Pro Met Leu Ile Leu Arg Lys Pro Lys Phe Arg Ser Leu Arg
                800                 805                 810 taactaactg aattaaaaat tatgtaatac ttgtggaact ttgataaatg aagccatatc   2571
tgagaatgta gctactcaaa aggaagtctg tcattaataa ggtatttcta aataaacaca   2631
ttatgtaagg aagtgccaaa atagttatca atgtgagact cttaggaaac taactagatc   2691
tcaattgaga gcacataaca atagatgata ccaaatactt tttgttttta acacagctat   2751
ccagtaaggc tatcatgatg tgtgctaaaa ttttatttac ttgaattttg aaaactgagc   2811
tgtgttaggg attaaactat aattctgttc ttaaaagaaa atttatctgc aaatgtgcaa   2871
gttctgagat attagctaat gaattagttg tttggggtta cttcttttgtt tctaagtata  2931 agaatgtgaa gaatatttga aaactcaatg aaataattct cagctgccaa atgttgcact   2991
cttttatata ttcttttttcc acttttgatc tatttatata tatgtatgtg ttttttaaaat 3051 atgtgtatat tttatcagat ttggttttgc cttaaatatt atccccaatt gcttcagtca   3111
ttcatttgtt cagtatatat attttgaatt ctagttttca taatctatta gaagatgggg   3171
atataaaaga agtataaggc aatcatatat tcattcaaaa gatatttatt tagcaactgc   3231
tatgtgcctt tcgttgttcc agatatgcag agacaatgat aaataaaaca tataatctct   3291
tccataaggt atttattttt taatcaaggg agatacacct atcagatgtt taaaataaca   3351
acactaccca ctgaaatcag ggcatataga atcattcagc taaagagtga cttctatgat   3411
gatggaacag gtctctaagc tagtggtttt caaactggta cacattagac tcacccgagg   3471
aattttaaaa cagcctatat gcccagggcc taacttacac taattaaatc tgaattttgg   3531
ggatgttgta tagggattag tattttttttt aatctaggtg attccaatat tcagccaact   3591
gtgagaatca atggcctaaa tgcttttat aaacattttt ataagtgtca agataatggc    3651
acattgactt tatttttca ttggaagaaa atgcctgcca agtataaatg actctcatct    3711
taaaacaagg ttcttcaggt ttctgcttga ttgacttggt acaaacttga agcaagttgc   3771
cttctaattt ttactccaag attgtttcat atctattcct taagtgtaaa gaaatatata   3831
atgcatggtt tgtaataaaa tcttaatgtt taatgactgt tctcatttct caatgtaatt   3891
tcatactgtt tctctataaa atgatagtat tccatttaac attactgatt tttattaaaa   3951
acctggacag aaaattataa attataaata tgactttatc ctggctataa aattattgaa   4011
ccaaaatgaa ttcttttctaa ggcatttgaa tactaaaacg tttattgttt atagatatgt   4071
aaaatgtgga ttatgttgca aattgagatt aaaattattt ggggttttgt aacaatataa   4131
ttttgctttt gtattataga caaatatata aataataaag gcaggcaact ttcatttgca   4191
ctaatgtaca tgcaattgag attacaaaat acatggtaca atgctttaat aacaaactct   4251
gccagtcagg tttgaatcct actgtgctat taactagcta gtaaactcag acaagttact   4311
taacttctct aagccccagt tttgttatct ataaaatgaa tattataata gtacctcttt   4371
ttaggattgc gaggattaag caggataatg catgtaaagt gttagcacag tgtctcacat   4431
agaataagca ctctataaat atttttactag aatcacctag gattatagca ctagaagaga  4491
tcttagcaaa aatgtggtcc tttctgttgc tttggacaga catgaaccaa aacaaaatta   4551
cggacaattg atgagcctta ttaactatct tttcattatg agacaaaggt tctgattatg   4611
cctactggtt gaaattttttt aatctagtca agaaggaaaa tttgatgagg aaggaaggaa  4671
```

```
tggatatctt cagaagggct tcgcctaagc tggaacatgg atagattcca ttctaacata    4731
aagatcttta agttcaaata tagatgagtt gactggtaga tttggtggta gttgctttct    4791
cgggatataa gaagcaaaat caactgctac aagtaaagag gggatgggga aggtgttgca    4851
catttaaaga gagaaagtgt gaaaaagcct aattgtggga atgcacaggt ttcaccagat    4911
cagatgatgt ctggttattc tgtaaattat agttcttatc ccagaaatta ctgcctccac    4971
catccctaat atcttctaat tggtatcata taatgaccca ctcttcttat gttatccaaa    5031
cagttatgtg gcatttagta atggaatgta catggaattt cccactgact tacctttctg    5091
tccttgggaa gcttaaactc tgaatcttct catctgtaaa atgtgaatta aagtatctac    5151
ctaactgagt tgtgattgta gtgaaagaaa ggcaatatat ttaaatcttg aatttagcaa    5211
gcccacgctc gatttttatg tccttcctc ttgccttgta ttgagtttaa gatctctact    5271
gattaaaact cttttgctat caaaaaaaaa aaaaaaaaa aaaaaa              5318
```

<210> SEQ ID NO 4
<211> LENGTH: 811
<212> TYPE: PRT
<213> ORGANISM: Homo sapiens

<400> SEQUENCE: 4

```
Met Glu Ser Gln Gly Val Pro Pro Gly Pro Tyr Arg Ala Thr Lys Leu
1               5                   10                  15

Trp Asn Glu Val Thr Thr Ser Phe Arg Ala Gly Met Pro Leu Arg Lys
            20                  25                  30

His Arg Gln His Phe Lys Lys Tyr Gly Asn Cys Phe Thr Ala Gly Glu
        35                  40                  45

Ala Val Asp Trp Leu Tyr Asp Leu Leu Arg Asn Asn Ser Asn Phe Gly
    50                  55                  60

Pro Glu Val Thr Arg Gln Gln Thr Ile Gln Leu Leu Arg Lys Phe Leu
65                  70                  75                  80

Lys Asn His Val Ile Glu Asp Ile Lys Gly Arg Trp Gly Ser Glu Asn
                85                  90                  95

Val Asp Asp Asn Asn Gln Leu Phe Arg Phe Pro Ala Thr Ser Pro Leu
            100                 105                 110

Lys Thr Leu Pro Arg Arg Tyr Pro Glu Leu Arg Lys Asn Asn Ile Glu
        115                 120                 125

Asn Phe Ser Lys Asp Lys Asp Ser Ile Phe Lys Leu Arg Asn Leu Ser
    130                 135                 140

Arg Arg Thr Pro Lys Arg His Gly Leu His Leu Ser Gln Glu Asn Gly
145                 150                 155                 160

Glu Lys Ile Lys His Glu Ile Ile Asn Glu Asp Gln Glu Asn Ala Ile
                165                 170                 175

Asp Asn Arg Glu Leu Ser Gln Glu Asp Val Glu Glu Val Trp Arg Tyr
            180                 185                 190

Val Ile Leu Ile Tyr Leu Gln Thr Ile Leu Gly Val Pro Ser Leu Glu
        195                 200                 205

Glu Val Ile Asn Pro Lys Gln Val Ile Pro Gln Tyr Ile Met Tyr Asn
    210                 215                 220

Met Ala Asn Thr Ser Lys Arg Gly Val Val Ile Leu Gln Asn Lys Ser
225                 230                 235                 240

Asp Asp Leu Pro His Trp Val Leu Ser Ala Met Lys Cys Leu Ala Asn
                245                 250                 255

Trp Pro Arg Ser Asn Asp Met Asn Asn Pro Thr Tyr Val Gly Phe Glu
            260                 265                 270
```

-continued

Arg Asp Val Phe Arg Thr Ile Ala Asp Tyr Phe Leu Asp Leu Pro Glu
    275                 280                 285

Pro Leu Leu Thr Phe Glu Tyr Tyr Glu Leu Phe Val Asn Ile Leu Val
290                 295                 300

Val Cys Gly Tyr Ile Thr Val Ser Asp Arg Ser Ser Gly Ile His Lys
305                 310                 315                 320

Ile Gln Asp Asp Pro Gln Ser Ser Lys Phe Leu His Leu Asn Asn Leu
                325                 330                 335

Asn Ser Phe Lys Ser Thr Glu Cys Leu Leu Leu Ser Leu Leu His Arg
                340                 345                 350

Glu Lys Asn Lys Glu Glu Ser Asp Ser Thr Glu Arg Leu Gln Ile Ser
            355                 360                 365

Asn Pro Gly Phe Gln Glu Arg Cys Ala Lys Lys Met Gln Leu Val Asn
370                 375                 380

Leu Arg Asn Arg Arg Val Ser Ala Asn Asp Ile Met Gly Gly Ser Cys
385                 390                 395                 400

His Asn Leu Ile Gly Leu Ser Asn Met His Asp Leu Ser Ser Asn Ser
                405                 410                 415

Lys Pro Arg Cys Cys Ser Leu Glu Gly Ile Val Asp Val Pro Gly Asn
                420                 425                 430

Ser Ser Lys Glu Ala Ser Ser Val Phe His Gln Ser Phe Pro Asn Ile
            435                 440                 445

Glu Gly Gln Asn Asn Lys Leu Phe Leu Glu Ser Lys Pro Lys Gln Glu
450                 455                 460

Phe Leu Leu Asn Leu His Ser Glu Glu Asn Ile Gln Lys Pro Phe Ser
465                 470                 475                 480

Ala Gly Phe Lys Arg Thr Ser Thr Leu Thr Val Gln Asp Gln Glu Glu
                485                 490                 495

Leu Cys Asn Gly Lys Cys Lys Ser Lys Gln Leu Cys Arg Ser Gln Ser
                500                 505                 510

Leu Leu Leu Arg Ser Ser Thr Arg Arg Asn Ser Tyr Ile Asn Thr Pro
            515                 520                 525

Val Ala Glu Ile Ile Met Lys Pro Asn Val Gly Gln Gly Ser Thr Ser
530                 535                 540

Val Gln Thr Ala Met Glu Ser Glu Leu Gly Glu Ser Ser Ala Thr Ile
545                 550                 555                 560

Asn Lys Arg Leu Cys Lys Ser Thr Ile Glu Leu Ser Glu Asn Ser Leu
                565                 570                 575

Leu Pro Ala Ser Ser Met Leu Thr Gly Thr Gln Ser Leu Leu Gln Pro
                580                 585                 590

His Leu Glu Arg Val Ala Ile Asp Ala Leu Gln Leu Cys Cys Leu Leu
            595                 600                 605

Leu Pro Pro Pro Asn Arg Arg Lys Leu Gln Leu Leu Met Arg Met Ile
610                 615                 620

Ser Arg Met Ser Gln Asn Val Asp Met Pro Lys Leu His Asp Ala Met
625                 630                 635                 640

Gly Thr Arg Ser Leu Met Ile His Thr Phe Ser Arg Cys Val Leu Cys
                645                 650                 655

Cys Ala Glu Glu Val Asp Leu Asp Glu Leu Leu Ala Gly Arg Leu Val
                660                 665                 670

Ser Phe Leu Met Asp His His Gln Glu Ile Leu Gln Val Pro Ser Tyr
            675                 680                 685

Leu Gln Thr Ala Val Glu Lys His Leu Asp Tyr Leu Lys Lys Gly His
690                 695                 700

```
Ile Glu Asn Pro Gly Asp Gly Leu Phe Ala Pro Leu Pro Thr Tyr Ser
705                 710                 715                 720

Tyr Cys Lys Gln Ile Ser Ala Gln Glu Phe Asp Glu Gln Lys Val Ser
            725                 730                 735

Thr Ser Gln Ala Ala Ile Ala Glu Leu Leu Glu Asn Ile Ile Lys Asn
        740                 745                 750

Arg Ser Leu Pro Leu Lys Glu Lys Arg Lys Lys Leu Lys Gln Phe Gln
    755                 760                 765

Lys Glu Tyr Pro Leu Ile Tyr Gln Lys Arg Phe Pro Thr Thr Glu Ser
770                 775                 780

Glu Ala Ala Leu Phe Gly Asp Lys Pro Thr Ile Lys Gln Pro Met Leu
785                 790                 795                 800

Ile Leu Arg Lys Pro Lys Phe Arg Ser Leu Arg
                805                 810

<210> SEQ ID NO 5
<211> LENGTH: 4466
<212> TYPE: DNA
<213> ORGANISM: Homo sapiens
<220> FEATURE:
<221> NAME/KEY: CDS
<222> LOCATION: (79)..(1659)

<400> SEQUENCE: 5
gagactcgcc actgccgcgg ccgctgggcc tgagtgtcgc cttcgccgcc atggacgcca        60
ccgggcgctg acagacct atg gag agt cag ggt gtg cct ccc ggg cct tat       111
                    Met Glu Ser Gln Gly Val Pro Pro Gly Pro Tyr
                     1               5                  10 cgg gcc acc aag ctg tgg aat gaa gtt acc aca tct ttt cga gca gga       159
Arg Ala Thr Lys Leu Trp Asn Glu Val Thr Thr Ser Phe Arg Ala Gly
             15                  20                  25 atg cct cta aga aaa cac aga caa cac ttt aaa aaa tat ggc aat tgt       207
Met Pro Leu Arg Lys His Arg Gln His Phe Lys Lys Tyr Gly Asn Cys
         30                  35                  40 ttc aca gca gga gaa gca gtg gat tgg ctt tat gac cta tta aga aat       255
Phe Thr Ala Gly Glu Ala Val Asp Trp Leu Tyr Asp Leu Leu Arg Asn
     45                  50                  55 aat agc aat ttt ggt cct gaa gtt aca agg caa cag act atc caa ctg       303
Asn Ser Asn Phe Gly Pro Glu Val Thr Arg Gln Gln Thr Ile Gln Leu
60                  65                  70                  75 ttg agg aaa ttt ctt aag aat cat gta att gaa gat atc aaa ggg agg       351
Leu Arg Lys Phe Leu Lys Asn His Val Ile Glu Asp Ile Lys Gly Arg
                 80                  85                  90 tgg gga tca gaa aat gtt gat gat aac aac cag ctc ttc aga ttt cct       399
Trp Gly Ser Glu Asn Val Asp Asp Asn Asn Gln Leu Phe Arg Phe Pro
             95                 100                 105 gca act tcg cca ctt aaa act cta cca cga agg tat cca gaa ttg aga       447
Ala Thr Ser Pro Leu Lys Thr Leu Pro Arg Arg Tyr Pro Glu Leu Arg
         110                 115                 120 aaa aac aac ata gag aac ttt tcc aaa gat aaa gat agc att ttt aaa       495
Lys Asn Asn Ile Glu Asn Phe Ser Lys Asp Lys Asp Ser Ile Phe Lys
     125                 130                 135 tta cga aac tta tct cgt aga act cct aaa agg cat gga tta cat tta       543
Leu Arg Asn Leu Ser Arg Arg Thr Pro Lys Arg His Gly Leu His Leu
140                 145                 150                 155 tct cag gaa aat ggc gag aaa ata aag cat gaa ata atc aat gaa gat       591
Ser Gln Glu Asn Gly Glu Lys Ile Lys His Glu Ile Ile Asn Glu Asp
                160                 165                 170
```

-continued

| | | |
|---|---|---|
| caa gaa aat gca att gat aat aga gaa cta agc cag gaa gat gtt gaa<br>Gln Glu Asn Ala Ile Asp Asn Arg Glu Leu Ser Gln Glu Asp Val Glu<br>175 180 185 | 639 | |
| gaa gtt tgg aga tat gtt att ctg atc tac ctg caa acc att tta ggt<br>Glu Val Trp Arg Tyr Val Ile Leu Ile Tyr Leu Gln Thr Ile Leu Gly<br>190 195 200 | 687 | |
| gtg cca tcc cta gaa gaa gtc ata aat cca aaa caa gta att ccc caa<br>Val Pro Ser Leu Glu Glu Val Ile Asn Pro Lys Gln Val Ile Pro Gln<br>205 210 215 | 735 | |
| tat ata atg tac aac atg gcc aat aca agt aaa cgt gga gta gtt ata<br>Tyr Ile Met Tyr Asn Met Ala Asn Thr Ser Lys Arg Gly Val Val Ile<br>220 225 230 235 | 783 | |
| cta caa aac aaa tca gat gac ctc cct cac tgg gta tta tct gcc atg<br>Leu Gln Asn Lys Ser Asp Asp Leu Pro His Trp Val Leu Ser Ala Met<br>240 245 250 | 831 | |
| aag tgc cta gca aat tgg cca aga agc aat gat atg aat aat cca act<br>Lys Cys Leu Ala Asn Trp Pro Arg Ser Asn Asp Met Asn Asn Pro Thr<br>255 260 265 | 879 | |
| tat gtt gga ttt gaa cga gat gta ttc aga aca atc gca gat tat ttt<br>Tyr Val Gly Phe Glu Arg Asp Val Phe Arg Thr Ile Ala Asp Tyr Phe<br>270 275 280 | 927 | |
| cta gat ctc cct gaa cct cta ctt act ttt gaa tat tac gaa tta ttt<br>Leu Asp Leu Pro Glu Pro Leu Leu Thr Phe Glu Tyr Tyr Glu Leu Phe<br>285 290 295 | 975 | |
| gta aac att ttg ggc ttg ctg caa cct cat tta gag agg gtt gcc atc<br>Val Asn Ile Leu Gly Leu Leu Gln Pro His Leu Glu Arg Val Ala Ile<br>300 305 310 315 | 1023 | |
| gat gct cta cag tta tgt tgt ttg tta ctt ccc cca cca aat cgt aga<br>Asp Ala Leu Gln Leu Cys Cys Leu Leu Leu Pro Pro Pro Asn Arg Arg<br>320 325 330 | 1071 | |
| aag ctt caa ctt tta atg cgt atg att tcc cga atg agt caa aat gtt<br>Lys Leu Gln Leu Leu Met Arg Met Ile Ser Arg Met Ser Gln Asn Val<br>335 340 345 | 1119 | |
| gat atg ccc aaa ctt cat gat gca atg ggt acg agg tca ctg atg ata<br>Asp Met Pro Lys Leu His Asp Ala Met Gly Thr Arg Ser Leu Met Ile<br>350 355 360 | 1167 | |
| cat acc ttt tct cga tgt gtg tta tgc tgt gct gaa gaa gtg gat ctt<br>His Thr Phe Ser Arg Cys Val Leu Cys Cys Ala Glu Glu Val Asp Leu<br>365 370 375 | 1215 | |
| gat gag ctt ctt gct gga aga tta gtt tct ttc tta atg gat cat cat<br>Asp Glu Leu Leu Ala Gly Arg Leu Val Ser Phe Leu Met Asp His His<br>380 385 390 395 | 1263 | |
| cag gaa att ctt caa gta ccc tct tac tta cag act gca gtg gaa aaa<br>Gln Glu Ile Leu Gln Val Pro Ser Tyr Leu Gln Thr Ala Val Glu Lys<br>400 405 410 | 1311 | |
| cat ctt gac tac tta aaa aag gga cat att gaa aat cct gga gat gga<br>His Leu Asp Tyr Leu Lys Lys Gly His Ile Glu Asn Pro Gly Asp Gly<br>415 420 425 | 1359 | |
| cta ttt gct cct ttg cca act tac tca tac tgt aag cag att agt gct<br>Leu Phe Ala Pro Leu Pro Thr Tyr Ser Tyr Cys Lys Gln Ile Ser Ala<br>430 435 440 | 1407 | |
| cag gag ttt gat gag caa aaa gtt tct acc tct caa gct gca att gca<br>Gln Glu Phe Asp Glu Gln Lys Val Ser Thr Ser Gln Ala Ala Ile Ala<br>445 450 455 | 1455 | |
| gaa ctt tta gaa aat att att aaa aac agg agt tta cct cta aag gag<br>Glu Leu Leu Glu Asn Ile Ile Lys Asn Arg Ser Leu Pro Leu Lys Glu<br>460 465 470 475 | 1503 | |
| aaa aga aaa aaa cta aaa cag ttt cag aag gaa tat cct ttg ata tat<br>Lys Arg Lys Lys Leu Lys Gln Phe Gln Lys Glu Tyr Pro Leu Ile Tyr<br>480 485 490 | 1551 | |

```
cag aaa aga ttt cca acc acg gag agt gaa gca gca ctt ttt ggt gac    1599
Gln Lys Arg Phe Pro Thr Thr Glu Ser Glu Ala Ala Leu Phe Gly Asp
            495                 500                 505 aaa cct aca atc aag caa cca atg ctg att tta aga aaa cca aag ttc    1647
Lys Pro Thr Ile Lys Gln Pro Met Leu Ile Leu Arg Lys Pro Lys Phe
            510                 515                 520 cgt agt cta aga taactaactg aattaaaaat tatgtaatac ttgtggaact        1699
Arg Ser Leu Arg
    525 ttgataaatg aagccatatc tgagaatgta gctactcaaa aggaagtctg tcattaataa  1759
ggtatttcta aataaacaca ttatgtaagg aagtgccaaa atagttatca atgtgagact  1819
cttaggaaac taactagatc tcaattgaga gcacataaca atagatgata ccaaatactt  1879
tttgttttta acacagctat ccagtaaggc tatcatgatg tgtgctaaaa ttttatttac  1939
ttgaattttg aaaactgagc tgtgttaggg attaaactat aattctgttc ttaaaagaaa  1999
atttatctgc aaatgtgcaa gttctgagat attagctaat gaattagttg tttggggtta  2059
cttctttgtt tctaagtata agaatgtgaa gaatatttga aaactcaatg aaataattct  2119
cagctgccaa atgttgcact cttttatata ttcttttttcc acttttgatc tatttatata  2179
tatgtatgtg tttttaaaat atgtgtatat tttatcagat ttggttttgc cttaaatatt  2239
atccccaatt gcttcagtca ttcatttgtt cagtatatat attttgaatt ctagttttca  2299
taatctatta gaagatgggg atataaaaga agtataaggc aatcatatat tcattcaaaa  2359
gatatttatt tagcaactgc tatgtgcctt tcgttgttcc agatatgcag agacaatgat  2419
aaataaaaca tataatctct tccataaggt atttattttt taatcaaggg agatacacct  2479
atcagatgtt taaataaaca acactaccca ctgaaatcag ggcatataga atcattcagc  2539
taaagagtga cttctatgat gatggaacag gtctctaagc tagtggtttt caaactggta  2599
cacattagac tcacccgagg aattttaaaa cagcctatat gcccagggcc taacttacac  2659
taattaaatc tgaattttgg ggatgttgta tagggattag tatttttttt aatctaggtg  2719
attccaatat tcagccaact gtgagaatca atggcctaaa tgctttttat aaacattttt  2779
ataagtgtca agataatggc acattgactt tattttttca ttggaagaaa atgcctgcca  2839
agtataaatg actctcatct taaaacaagg ttcttcaggt ttctgcttga ttgacttggt  2899
acaaacttga agcaagttgc cttctaattt ttactccaag attgtttcat atctattcct  2959
taagtgtaaa gaaatatata atgcatggtt tgtaataaaa tcttaatgtt taatgactgt  3019
tctcatttct caatgtaatt tcatactgtt tctctataaa atgatagtat tccatttaac  3079
attactgatt tttattaaaa acctggacag aaaattataa attataaata tgactttatc  3139
ctggctataa aattattgaa ccaaaatgaa ttctttctaa ggcatttgaa tactaaaacg  3199
tttattgttt atagatatgt aaaatgtgga ttatgttgca aattgagatt aaaattattt  3259
ggggttttgt aacaatataa ttttgctttt gtattataga caaatatata aataataaag  3319
gcaggcaact ttcatttgca ctaatgtaca tgcaattgag attacaaaat acatggtaca  3379
atgctttaat aacaaactct gccagtcagg tttgaatcct actgtgctat taactagcta  3439
gtaaactcag acaagttact taacttctct aagccccagt tttgttatct ataaaatgaa  3499
tattataata gtacctcttt ttaggattgc gaggattaag caggataatg catgtaaagt  3559
gttagcacag tgtctcacat agaataagca ctctataaat attttactag aatcacctag  3619
gattatagca ctagaagaga tcttagcaaa aatgtggtcc tttctgttgc tttggacaga  3679
catgaaccaa aacaaaatta cggacaattg atgagcctta ttaactatct tttcattatg  3739
```

```
agacaaaggt tctgattatg cctactggtt gaaattttt aatctagtca agaaggaaaa    3799
tttgatgagg aaggaaggaa tggatatctt cagaagggct tcgcctaagc tggaacatgg    3859
atagattcca ttctaacata aagatcttta agttcaaata tagatgagtt gactggtaga    3919
tttggtggta gttgctttct cgggatataa gaagcaaaat caactgctac aagtaaagag    3979
gggatgggga aggtgttgca catttaaaga gagaaagtgt gaaaaagcct aattgtggga    4039
atgcacaggt tcaccagat cagatgatgt ctggttattc tgtaaattat agttcttatc    4099
ccagaaatta ctgcctccac catccctaat atcttctaat tggtatcata taatgaccca    4159
ctcttcttat gttatccaaa cagttatgtg gcatttagta atggaatgta catggaattt    4219
cccactgact tacctttctg tccttgggaa gcttaaactc tgaatcttct catctgtaaa    4279
atgtgaatta agtatctac ctaactgagt tgtgattgta gtgaaagaaa ggcaatatat    4339
ttaaatcttg aatttagcaa gcccacgctc gattttatg tcctttcctc ttgccttgta    4399
ttgagtttaa gatctctact gattaaaact cttttgctat caaaaaaaaa aaaaaaaaaa    4459
aaaaaaa                                                              4466
```

<210> SEQ ID NO 6
<211> LENGTH: 527
<212> TYPE: PRT
<213> ORGANISM: Homo sapiens

<400> SEQUENCE: 6

```
Met Glu Ser Gln Gly Val Pro Pro Gly Pro Tyr Arg Ala Thr Lys Leu
1               5                   10                  15

Trp Asn Glu Val Thr Thr Ser Phe Arg Ala Gly Met Pro Leu Arg Lys
                20                  25                  30

His Arg Gln His Phe Lys Lys Tyr Gly Asn Cys Phe Thr Ala Gly Glu
            35                  40                  45

Ala Val Asp Trp Leu Tyr Asp Leu Leu Arg Asn Asn Ser Asn Phe Gly
        50                  55                  60

Pro Glu Val Thr Arg Gln Gln Thr Ile Gln Leu Leu Arg Lys Phe Leu
65                  70                  75                  80

Lys Asn His Val Ile Glu Asp Ile Lys Gly Arg Trp Gly Ser Glu Asn
                85                  90                  95

Val Asp Asp Asn Asn Gln Leu Phe Arg Phe Pro Ala Thr Ser Pro Leu
            100                 105                 110

Lys Thr Leu Pro Arg Arg Tyr Pro Glu Leu Arg Lys Asn Asn Ile Glu
        115                 120                 125

Asn Phe Ser Lys Asp Lys Asp Ser Ile Phe Lys Leu Arg Asn Leu Ser
    130                 135                 140

Arg Arg Thr Pro Lys Arg His Gly Leu His Leu Ser Gln Glu Asn Gly
145                 150                 155                 160

Glu Lys Ile Lys His Glu Ile Ile Asn Glu Asp Gln Glu Asn Ala Ile
                165                 170                 175

Asp Asn Arg Glu Leu Ser Gln Glu Asp Val Glu Glu Val Trp Arg Tyr
            180                 185                 190

Val Ile Leu Ile Tyr Leu Gln Thr Ile Leu Gly Val Pro Ser Leu Glu
        195                 200                 205

Glu Val Ile Asn Pro Lys Gln Val Ile Pro Gln Tyr Ile Met Tyr Asn
    210                 215                 220

Met Ala Asn Thr Ser Lys Arg Gly Val Val Ile Leu Gln Asn Lys Ser
225                 230                 235                 240
```

-continued

Asp Asp Leu Pro His Trp Val Leu Ser Ala Met Lys Cys Leu Ala Asn
            245                 250                 255

Trp Pro Arg Ser Asn Asp Met Asn Asn Pro Thr Tyr Val Gly Phe Glu
            260                 265                 270

Arg Asp Val Phe Arg Thr Ile Ala Asp Tyr Phe Leu Asp Leu Pro Glu
            275                 280                 285

Pro Leu Leu Thr Phe Glu Tyr Tyr Glu Leu Phe Val Asn Ile Leu Gly
            290                 295                 300

Leu Leu Gln Pro His Leu Glu Arg Val Ala Ile Asp Ala Leu Gln Leu
305                 310                 315                 320

Cys Cys Leu Leu Leu Pro Pro Asn Arg Arg Lys Leu Gln Leu Leu
            325                 330                 335

Met Arg Met Ile Ser Arg Met Ser Gln Asn Val Asp Met Pro Lys Leu
            340                 345                 350

His Asp Ala Met Gly Thr Arg Ser Leu Met Ile His Thr Phe Ser Arg
            355                 360                 365

Cys Val Leu Cys Cys Ala Glu Val Asp Leu Asp Glu Leu Leu Ala
            370                 375                 380

Gly Arg Leu Val Ser Phe Leu Met Asp His His Gln Glu Ile Leu Gln
385                 390                 395                 400

Val Pro Ser Tyr Leu Gln Thr Ala Val Glu Lys His Leu Asp Tyr Leu
            405                 410                 415

Lys Lys Gly His Ile Glu Asn Pro Gly Asp Gly Leu Phe Ala Pro Leu
            420                 425                 430

Pro Thr Tyr Ser Tyr Cys Lys Gln Ile Ser Ala Gln Glu Phe Asp Glu
            435                 440                 445

Gln Lys Val Ser Thr Ser Gln Ala Ala Ile Ala Glu Leu Leu Glu Asn
            450                 455                 460

Ile Ile Lys Asn Arg Ser Leu Pro Leu Lys Glu Lys Arg Lys Lys Leu
465                 470                 475                 480

Lys Gln Phe Gln Lys Glu Tyr Pro Leu Ile Tyr Gln Lys Arg Phe Pro
            485                 490                 495

Thr Thr Glu Ser Glu Ala Ala Leu Phe Gly Asp Lys Pro Thr Ile Lys
            500                 505                 510

Gln Pro Met Leu Ile Leu Arg Lys Pro Lys Phe Arg Ser Leu Arg
            515                 520                 525

<210> SEQ ID NO 7
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 7
cgaccacttt gtcaagctca                                               20

<210> SEQ ID NO 8
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 8
ggttgagcac agggtacttt att                                           23

```
<210> SEQ ID NO 9
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 9
tgctggttca gaacgaacta tg                                              22

<210> SEQ ID NO 10
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 10
tcctcgtggc taatgaaagc                                                 20

<210> SEQ ID NO 11
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 11
gctacaagta aagaggggat gg                                              22

<210> SEQ ID NO 12
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 12
ggacagaaag gtaagtcagt ggg                                             23

<210> SEQ ID NO 13
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 13
aggcaggcaa ctttcatttg                                                 20

<210> SEQ ID NO 14
<211> LENGTH: 26
<212> TYPE: DNA
<213> ORGANISM: Artificial
<220> FEATURE:
<223> OTHER INFORMATION: An artificially synthesized primer for RT-PCR

<400> SEQUENCE: 14
cattttctga tccccacctc cctttg                                          26

<210> SEQ ID NO 15
<211> LENGTH: 23
<212> TYPE: DNA
<213> ORGANISM: Artificial
<220> FEATURE:
<223> OTHER INFORMATION: An artificially synthesized primer for RT-PCR
```

```
<400> SEQUENCE: 15
agaggggatg gggaaggtgt tgc                                              23

<210> SEQ ID NO 16
<211> LENGTH: 42
<212> TYPE: DNA
<213> ORGANISM: Artificial
<220> FEATURE:
<223> OTHER INFORMATION: An artificially synthesized primer for RT-PCR

<400> SEQUENCE: 16
ataagaatgc ggccgcaatg gaatctaatt ttaatcaaga gg                         42

<210> SEQ ID NO 17
<211> LENGTH: 35
<212> TYPE: DNA
<213> ORGANISM: Artificial
<220> FEATURE:
<223> OTHER INFORMATION: An artificially synthesized primer for RT-PCR

<400> SEQUENCE: 17
ataagaatgc ggccgctttg gctgttttg ttcga                                  35

<210> SEQ ID NO 18
<211> LENGTH: 36
<212> TYPE: DNA
<213> ORGANISM: Artificial
<220> FEATURE:
<223> OTHER INFORMATION: An artificially synthesized primer for RT-PCR

<400> SEQUENCE: 18
ataagaatgc ggccgctatg gagagtcagg gtgtgc                                36

<210> SEQ ID NO 19
<211> LENGTH: 31
<212> TYPE: DNA
<213> ORGANISM: Artificial
<220> FEATURE:
<223> OTHER INFORMATION: An artificially synthesized primer for RT-PCR

<400> SEQUENCE: 19
ccgctcgagt cttagactac ggaactttgg t                                     31

<210> SEQ ID NO 20
<211> LENGTH: 25
<212> TYPE: DNA
<213> ORGANISM: Artificial
<220> FEATURE:
<223> OTHER INFORMATION: An artificially synthesized primer for RT-PCR

<400> SEQUENCE: 20
ggaattcatg gagagtcagg gtgtg                                            25

<210> SEQ ID NO 21
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 21
gtgaagaagt gcgaccgaa                                                   19
```

```
<210> SEQ ID NO 22
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 22
caccgtgaag aagtgcgacc gaattcaaga gattcggtcg cacttcttca c          51

<210> SEQ ID NO 23
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 23
aaaagtgaag aagtgcgacc gaatctcttg aattcggtcg cacttcttca c          51

<210> SEQ ID NO 24
<211> LENGTH: 47
<212> TYPE: DNA
<213> ORGANISM: Artificial
<220> FEATURE:
<223> OTHER INFORMATION: siRNA hairpin design

<400> SEQUENCE: 24
gtgaagaagt gcgaccgaat tcaagagatt cggtcgcact tcttcac              47

<210> SEQ ID NO 25
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 25
ccaaagttcc gtagtctaa                                              19

<210> SEQ ID NO 26
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 26
caccccaaag ttccgtagtc taattcaaga gattagacta cggaactttg g          51

<210> SEQ ID NO 27
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 27
aaaaccaaag ttccgtagtc taatctcttg aattagacta cggaactttg g          51
```

<210> SEQ ID NO 28
<211> LENGTH: 47
<212> TYPE: DNA
<213> ORGANISM: Artificial
<220> FEATURE:
<223> OTHER INFORMATION: siRNA hairpin design

<400> SEQUENCE: 28
ccaaagttcc gtagtctaat tcaagagatt agactacgga actttgg                    47

<210> SEQ ID NO 29
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 29
gaagcagcac gacttcttc                                                   19

<210> SEQ ID NO 30
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 30
caccgaagca gcacgacttc ttcttcaaga gagaagaagt cgtgctgctt c               51

<210> SEQ ID NO 31
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 31
aaaagaagca gcacgacttc ttctctcttg aagaagaagt cgtgctgctt c               51

<210> SEQ ID NO 32
<211> LENGTH: 47
<212> TYPE: DNA
<213> ORGANISM: Artificial
<220> FEATURE:
<223> OTHER INFORMATION: siRNA hairpin design

<400> SEQUENCE: 32
gaagcagcac gacttcttct tcaagagaga agaagtcgtg ctgcttc                    47

<210> SEQ ID NO 33
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 33
gcgcgctttg taggattcg                                                   19

<210> SEQ ID NO 34
<211> LENGTH: 51
<212> TYPE: DNA
<213> ORGANISM: Artificial

```
<220> FEATURE:
<223> OTHER INFORMATION: An artificially synthesized oligonucleotide for
      siRNA

<400> SEQUENCE: 34
caccgcgcgc tttgtaggat tcgttcaaga gacgaatcct acaaagcgcg c          51

<210> SEQ ID NO 35
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 35
aaaagcgcgc tttgtaggat tcgtctcttg aacgaatcct acaaagcgcg c          51

<210> SEQ ID NO 36
<211> LENGTH: 47
<212> TYPE: DNA
<213> ORGANISM: Artificial
<220> FEATURE:
<223> OTHER INFORMATION: siRNA hairpin design

<400> SEQUENCE: 36
gcgcgctttg taggattcgt tcaagagacg aatcctacaa agcgcgc              47

<210> SEQ ID NO 37
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 37
attgtgggaa tgcacaggtt                                            20

<210> SEQ ID NO 38
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 38
gatgtacata tgaggatttc ccg                                        23

<210> SEQ ID NO 39
<211> LENGTH: 24
<212> TYPE: DNA
<213> ORGANISM: Artificial
<220> FEATURE:
<223> OTHER INFORMATION: An artificially synthesized primer for RT-PCR

<400> SEQUENCE: 39
gtcagtgcac ataattccaa tagc                                       24

<210> SEQ ID NO 40
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 40
ttctagctcc tcaaccaaat cct                                        23
```

```
<210> SEQ ID NO 41
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 41
ccgggaaagt aaactgactc ac                                                  22

<210> SEQ ID NO 42
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 42
tctcttgagg gctgctttgt                                                     20

<210> SEQ ID NO 43
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 43
tcatccactg aaatacctgg ctt                                                 23

<210> SEQ ID NO 44
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 44
tggccatatc agttccaaca                                                     20

<210> SEQ ID NO 45
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 45
ctttggcata gcagcctgaa ct                                                  22

<210> SEQ ID NO 46
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 46
ggagaatgag ctggatcagg                                                     20

<210> SEQ ID NO 47
<211> LENGTH: 22
<212> TYPE: DNA
<213> ORGANISM: Artificial
<220> FEATURE:
<223> OTHER INFORMATION: An artificially synthesized primer for RT-PCR
```

```
<400> SEQUENCE: 47
atgctgcaat tcccaaatct ct                                              22

<210> SEQ ID NO 48
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 48
aactcattgt gtggctgtgc                                                 20

<210> SEQ ID NO 49
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 49
catcacaatc ctgggaattc ag                                              22

<210> SEQ ID NO 50
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 50
tcctgagggc catttactca                                                 20

<210> SEQ ID NO 51
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 51
tgcatccagt agctattcag caa                                             23

<210> SEQ ID NO 52
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 52
tccagttggt tactcagtgt ttg                                             23

<210> SEQ ID NO 53
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 53
ctgtcatgtg ctcatgtgag ttt                                             23
```

```
<210> SEQ ID NO 54
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 54
cgtcgacaat ataaacaggg act                                              23

<210> SEQ ID NO 55
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 55
cgagcacaag ataatttttc cc                                               22

<210> SEQ ID NO 56
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 56
gcaagtcagt gcctagatgg ata                                              23

<210> SEQ ID NO 57
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 57
aaaaattgag tgtgtctcgg tg                                               22

<210> SEQ ID NO 58
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 58
tacagagagg atgggattgt gtt                                              23

<210> SEQ ID NO 59
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 59
cctagcagtt gttagaggca gaa                                              23

<210> SEQ ID NO 60
<211> LENGTH: 24
<212> TYPE: DNA
<213> ORGANISM: Artificial
<220> FEATURE:
<223> OTHER INFORMATION: An artificially synthesized primer for RT-PCR
```

```
<400> SEQUENCE: 60 gggctttttaa tttgtgaact tctg                                          24

<210> SEQ ID NO 61
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 61
tgaaatagtc tggccatttg ac                                             22

<210> SEQ ID NO 62
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 62
gtcccagaca acagaagtta cca                                            23

<210> SEQ ID NO 63
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 63
aatttcctca gagctcacat acg                                            23

<210> SEQ ID NO 64
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 64
tttatattgt gccatgcagt cc                                             22

<210> SEQ ID NO 65
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 65
accaggatca cagagagctt ga                                             22

<210> SEQ ID NO 66
<211> LENGTH: 26
<212> TYPE: DNA
<213> ORGANISM: Artificial
<220> FEATURE:
<223> OTHER INFORMATION: An artificially synthesized primer for RT-PCR

<400> SEQUENCE: 66
tcagagtgag gactcattta tcattt                                         26
```

```
<210> SEQ ID NO 67
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 67
cacagggcag gttttgattt at                                          22

<210> SEQ ID NO 68
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 68
ccccttcagt gagcctcata                                             20

<210> SEQ ID NO 69
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 69
tgaaattgac ctggtagagc ctt                                         23

<210> SEQ ID NO 70
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 70
tgtgttttct tttggcacca t                                           21

<210> SEQ ID NO 71
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 71
ttactcctgg caagctgtga g                                           21

<210> SEQ ID NO 72
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 72
atatcagcat cacggcacaa                                             20

<210> SEQ ID NO 73
<211> LENGTH: 23
<212> TYPE: DNA
<213> ORGANISM: Artificial
<220> FEATURE:
<223> OTHER INFORMATION: An artificially synthesized primer for RT-PCR
```

```
<400> SEQUENCE: 73
gtatgatgta gctgaggtcc gtg                                              23

<210> SEQ ID NO 74
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 74
tgctggctaa ctaaagaaga tgc                                              23

<210> SEQ ID NO 75
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 75
aaatgaggcc attctgttga ga                                               22

<210> SEQ ID NO 76
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 76
tgagattctg gagagtgaat gc                                               22

<210> SEQ ID NO 77
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 77
tcagatgttg tagcagggac ttt                                              23

<210> SEQ ID NO 78
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 78
catttcttta tagttgcctc ccc                                              23

<210> SEQ ID NO 79
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 79
ttttgggtca gcactgacaa t                                                21
```

```
<210> SEQ ID NO 80
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 80
gtcttggagg agcagattcc a                                              21

<210> SEQ ID NO 81
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 81
ctacaattta tttccgagtc ccc                                            23

<210> SEQ ID NO 82
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 82
cctcaaggcc attgatgtaa a                                              21

<210> SEQ ID NO 83
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 83
atggtaacca catgacccac tg                                             22

<210> SEQ ID NO 84
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 84
agataaatca tgacaaggtc ccc                                            23

<210> SEQ ID NO 85
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 85
gccttttgct tcttctgtct tct                                            23

<210> SEQ ID NO 86
<211> LENGTH: 20
<212> TYPE: DNA
<213> ORGANISM: Artificial
<220> FEATURE:
<223> OTHER INFORMATION: An artificially synthesized primer for RT-PCR
```

```
<400> SEQUENCE: 86
ttggtgtagc accacactgg                                                   20

<210> SEQ ID NO 87
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 87
gcatgactca gggaagggta tt                                                22

<210> SEQ ID NO 88
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 88
aatggcatga tcttgtgtga ag                                                22

<210> SEQ ID NO 89
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 89
agatcactgt gggtcttaag caa                                               23

<210> SEQ ID NO 90
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 90
tctacaccac agaaagcaag tca                                               23

<210> SEQ ID NO 91
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 91
tacctgagga aattcccgtt act                                               23

<210> SEQ ID NO 92
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 92
atagggataa tggcctccaa ttc                                               23
```

```
<210> SEQ ID NO 93
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 93
ctcgcaccta ataatctggt ctc                                              23

<210> SEQ ID NO 94
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 94
tgtgtctcat ctgtgaactg ctt                                              23

<210> SEQ ID NO 95
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 95
ttcgtgttac ggtatatcct gct                                              23

<210> SEQ ID NO 96
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 96
ccctaaagag tgagttttcc aca                                              23

<210> SEQ ID NO 97
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 97
aaaggtattt tcctgcagta gcc                                              23

<210> SEQ ID NO 98
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 98
gggccagtat gtgtaactga cat                                              23

<210> SEQ ID NO 99
<211> LENGTH: 23
<212> TYPE: DNA
<213> ORGANISM: Artificial
<220> FEATURE:
<223> OTHER INFORMATION: An artificially synthesized primer for RT-PCR
```

<400> SEQUENCE: 99
tcagacatct gctgactaca gga					23

<210> SEQ ID NO 100
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 100
caacgagagc aaaactccaa tac					23

<210> SEQ ID NO 101
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 101
atagggtttt gcagtaggga gag					23

<210> SEQ ID NO 102
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 102
cacatggtga ccacagtgca t					21

<210> SEQ ID NO 103
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 103
agagggtgag ggctttcatc t					21

<210> SEQ ID NO 104
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 104
cttgctattg tcaggttttg gtg					23

<210> SEQ ID NO 105
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 105
cactgcattt actgcttttg ga					22

```
<210> SEQ ID NO 106
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 106
aggagaggga gaaatcttag caa                                              23

<210> SEQ ID NO 107
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 107
ccagttgtat gccaacatac tca                                              23

<210> SEQ ID NO 108
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 108
caggattcca aatgtcagtg ag                                               22

<210> SEQ ID NO 109
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 109
cctgccattg tctttcaggt tt                                               22

<210> SEQ ID NO 110
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 110
cctatcacag acggaaatcc c                                                21

<210> SEQ ID NO 111
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 111
tagggcagtt tcctgtgttc ct                                               22

<210> SEQ ID NO 112
<211> LENGTH: 20
<212> TYPE: DNA
<213> ORGANISM: Artificial
<220> FEATURE:
<223> OTHER INFORMATION: An artificially synthesized primer for RT-PCR
```

```
<400> SEQUENCE: 112
tgctctgtac atgcctctgc                                            20

<210> SEQ ID NO 113
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 113
gcacccagaa ggacttgcta tt                                         22

<210> SEQ ID NO 114
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 114
cttcagagtg ggttggaaaa at                                         22

<210> SEQ ID NO 115
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 115
tagtgtgtaa tgcgatcctg tga                                        23

<210> SEQ ID NO 116
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 116
cactgtggca agattgctct                                            20

<210> SEQ ID NO 117
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 117
tacatcacag ccttgttctt tcc                                        23

<210> SEQ ID NO 118
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 118
aagcggtcca cagtccaata                                            20
```

```
<210> SEQ ID NO 119
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 119
tcacattgga ggatagctgg aa                                              22

<210> SEQ ID NO 120
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 120
gaagtttcct gaggctccaa                                                 20

<210> SEQ ID NO 121
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 121
gcccacaaga gaaggtagag ga                                              22

<210> SEQ ID NO 122
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 122
tcctctgtcg gtagctgtca                                                 20

<210> SEQ ID NO 123
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 123
acccttcatg tttctagggc tg                                              22

<210> SEQ ID NO 124
<211> LENGTH: 22
<212> TYPE: DNA
<213> ORGANISM: Artificial
<220> FEATURE:
<223> OTHER INFORMATION: An artificially synthesized primer for RT-PCR

<400> SEQUENCE: 124
gtccctcatg ccatcacagt at                                              22

<210> SEQ ID NO 125
<211> LENGTH: 20
<212> TYPE: DNA
<213> ORGANISM: Artificial
<220> FEATURE:
<223> OTHER INFORMATION: An artificially synthesized primer for RT-PCR
```

<400> SEQUENCE: 125
agcagaggct gagcaaagag								20

<210> SEQ ID NO 126
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 126
ccccagtttc tggaatgcta								20

<210> SEQ ID NO 127
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 127
agcggagttc ataagccaaa								20

<210> SEQ ID NO 128
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 128
tcaagggaca atggtgtgac								20

<210> SEQ ID NO 129
<211> LENGTH: 3851
<212> TYPE: DNA
<213> ORGANISM: Homo sapiens
<220> FEATURE:
<221> NAME/KEY: CDS
<222> LOCATION: (228)..(2252)

<400> SEQUENCE: 129

```
cagtttgatc tcagactgct gtgctagcaa tcagcgagac tccatgggcg taggaccctc      60
tgagccaggt gtgggatata atctcgtcgt gcgccgtttt ttaagccggt cggaaaagcg     120
cagtatttgg gtgggagtga cccgattttc caggtgatcc aaggacatat gacccagatt     180
tcaaggggcc tgttgccaac aggagttgta cagatgttct gtgctgt atg atc ttc      236
                                                    Met Ile Phe
                                                      1 cta ctg tgt att att ggc tac att gtt tta gga ctt gtg gcc tgg gta      284
Leu Leu Cys Ile Ile Gly Tyr Ile Val Leu Gly Leu Val Ala Trp Val
        5                  10                  15 cat ggg gac ccc aga aga gca gcc tat cct aca gac agc cag ggc cac      332
His Gly Asp Pro Arg Arg Ala Ala Tyr Pro Thr Asp Ser Gln Gly His
 20                  25                  30                  35 ttt tgt ggc cag aag ggc act ccc aat gag aac aag acc att ttg ttt      380
Phe Cys Gly Gln Lys Gly Thr Pro Asn Glu Asn Lys Thr Ile Leu Phe
                 40                  45                  50 tac ttt aac ctg tta cgc tgt acc agt ccc tcc gtg ttg cta aac cta      428
Tyr Phe Asn Leu Leu Arg Cys Thr Ser Pro Ser Val Leu Leu Asn Leu
             55                  60                  65 cag tgc cct acc aca cag atc tgt gtc tcc aag tgc cca gaa aaa ttt      476
Gln Cys Pro Thr Thr Gln Ile Cys Val Ser Lys Cys Pro Glu Lys Phe
         70                  75                  80
```

```
tta acc tat gtg gaa atg caa ctt ttg tac aca aaa gac aaa agc tac      524
Leu Thr Tyr Val Glu Met Gln Leu Leu Tyr Thr Lys Asp Lys Ser Tyr
    85                  90                  95 tgg gaa gac tac cgt cag ttc tgt aag acc act gct aag cct gtg aag      572
Trp Glu Asp Tyr Arg Gln Phe Cys Lys Thr Thr Ala Lys Pro Val Lys
100                 105                 110                 115 tct ctc aca cag ctt tta ctg gat gat gat tgt cca aca gcg att ttt      620
Ser Leu Thr Gln Leu Leu Leu Asp Asp Asp Cys Pro Thr Ala Ile Phe
                    120                 125                 130 ccc agc aaa cct ttt ctc cag aga tgt ttc cct gac ttc tct acc aaa      668
Pro Ser Lys Pro Phe Leu Gln Arg Cys Phe Pro Asp Phe Ser Thr Lys
            135                 140                 145 aat ggc act tta aca ata gga agt aag atg atg ttt caa gat gga aat      716
Asn Gly Thr Leu Thr Ile Gly Ser Lys Met Met Phe Gln Asp Gly Asn
        150                 155                 160 gga ggg aca aga agt gtt gta gaa ctc ggg att gct gca aat ggt atc      764
Gly Gly Thr Arg Ser Val Val Glu Leu Gly Ile Ala Ala Asn Gly Ile
    165                 170                 175 aat aaa ctt ctt gat gca aag tca ctt gga ttg aaa gtg ttt gaa gac      812
Asn Lys Leu Leu Asp Ala Lys Ser Leu Gly Leu Lys Val Phe Glu Asp
180                 185                 190                 195 tat gca aga act tgg tat tgg att ctc att ggc ctg acg att gcc atg      860
Tyr Ala Arg Thr Trp Tyr Trp Ile Leu Ile Gly Leu Thr Ile Ala Met
                    200                 205                 210 gtc ctt agt tgg ata ttt ttg ata ctt ctg agg ttc ata gct gga tgc      908
Val Leu Ser Trp Ile Phe Leu Ile Leu Leu Arg Phe Ile Ala Gly Cys
            215                 220                 225 ctc ttc tgg gtc ttc atg att ggt gtg att gga att ata ggt tat gga      956
Leu Phe Trp Val Phe Met Ile Gly Val Ile Gly Ile Ile Gly Tyr Gly
        230                 235                 240 ata tgg cac tgt tac cag cag tac acc aat ctt cag gaa cgc cca agt     1004
Ile Trp His Cys Tyr Gln Gln Tyr Thr Asn Leu Gln Glu Arg Pro Ser
    245                 250                 255 tct gta tta act atc tat gac atc ggg att cag act aac ata agc atg     1052
Ser Val Leu Thr Ile Tyr Asp Ile Gly Ile Gln Thr Asn Ile Ser Met
260                 265                 270                 275 tac ttt gaa ctg caa caa aca tgg ttc aca ttt atg ata ata ctc tgc     1100
Tyr Phe Glu Leu Gln Gln Thr Trp Phe Thr Phe Met Ile Ile Leu Cys
                    280                 285                 290 atc att gaa gtg att gtc atc ctc atg ctg atc ttc ctc agg aat cga     1148
Ile Ile Glu Val Ile Val Ile Leu Met Leu Ile Phe Leu Arg Asn Arg
            295                 300                 305 atc cga gtc gcc att atc ctg ctg aag gaa gga agc aaa gcc att gga     1196
Ile Arg Val Ala Ile Ile Leu Leu Lys Glu Gly Ser Lys Ala Ile Gly
        310                 315                 320 tat gtt cct agt aca tta gtc tat cca gct tta act ttc att ttg ctc     1244
Tyr Val Pro Ser Thr Leu Val Tyr Pro Ala Leu Thr Phe Ile Leu Leu
    325                 330                 335 tca atc tgc att tgc tac tgg gtc gtg aca gca gtt ttc ttg gcg aca     1292
Ser Ile Cys Ile Cys Tyr Trp Val Val Thr Ala Val Phe Leu Ala Thr
340                 345                 350                 355 tcg ggg gta cct gta tac aaa gtc ata gct cca ggg ggg cat tgt ata     1340
Ser Gly Val Pro Val Tyr Lys Val Ile Ala Pro Gly Gly His Cys Ile
                    360                 365                 370 cat gaa aat caa acc tgt gac cca gag att ttt aat aca act gaa att     1388
His Glu Asn Gln Thr Cys Asp Pro Glu Ile Phe Asn Thr Thr Glu Ile
            375                 380                 385 gcc aaa gct tgc cct ggg gct ctg tgt aac ttt gct ttc tat ggt gga     1436
Ala Lys Ala Cys Pro Gly Ala Leu Cys Asn Phe Ala Phe Tyr Gly Gly
        390                 395                 400
```

```
aag agc ttg tac cat cag tac atc cct acc ttc cat gta tac aac tta    1484
Lys Ser Leu Tyr His Gln Tyr Ile Pro Thr Phe His Val Tyr Asn Leu
    405                 410                 415 ttt gtc ttt ctc tgg ctt ata aac ttc gtc att gca tta ggt cag tgc    1532
Phe Val Phe Leu Trp Leu Ile Asn Phe Val Ile Ala Leu Gly Gln Cys
420                 425                 430                 435 gcc ctt gct ggt gca ttc gct act tat tac tgg gcc atg aaa aaa cct    1580
Ala Leu Ala Gly Ala Phe Ala Thr Tyr Tyr Trp Ala Met Lys Lys Pro
                440                 445                 450 gat gac atc cca cga tat cca ctt ttt act gca ttt gga cga gcc ata    1628
Asp Asp Ile Pro Arg Tyr Pro Leu Phe Thr Ala Phe Gly Arg Ala Ile
            455                 460                 465 cga tat cac aca gga tcc cta gca ttt gga tct tta att att gca tta    1676
Arg Tyr His Thr Gly Ser Leu Ala Phe Gly Ser Leu Ile Ile Ala Leu
        470                 475                 480 att caa atg ttt aaa att gta cta gaa tac ttg gac cac cgt ctt aaa    1724
Ile Gln Met Phe Lys Ile Val Leu Glu Tyr Leu Asp His Arg Leu Lys
    485                 490                 495 cgt acc cag aac aca ttg tct aaa ttc cta cag tgc tgc ctg aga tgc    1772
Arg Thr Gln Asn Thr Leu Ser Lys Phe Leu Gln Cys Cys Leu Arg Cys
500                 505                 510                 515 tgc ttc tgg tgt ttg gaa aat gca ata aag ttt tta aac aga aat gcc    1820
Cys Phe Trp Cys Leu Glu Asn Ala Ile Lys Phe Leu Asn Arg Asn Ala
                520                 525                 530 tat att atg att gca ata tat ggc aga aac ttc tgc agg tca gca aaa    1868
Tyr Ile Met Ile Ala Ile Tyr Gly Arg Asn Phe Cys Arg Ser Ala Lys
            535                 540                 545 gat gct ttc aat ctg ctg atg aga aat gtt ttg aaa gtt gca gtt aca    1916
Asp Ala Phe Asn Leu Leu Met Arg Asn Val Leu Lys Val Ala Val Thr
        550                 555                 560 gat gaa gtt aca tac ttt gta tta ttc ctg ggg aaa ctt cta gtt gct    1964
Asp Glu Val Thr Tyr Phe Val Leu Phe Leu Gly Lys Leu Leu Val Ala
    565                 570                 575 gga agt ata ggt gtt ctg gcc ttc cta ttc ttc aca caa aga ctg cca    2012
Gly Ser Ile Gly Val Leu Ala Phe Leu Phe Phe Thr Gln Arg Leu Pro
580                 585                 590                 595 gtg att gca caa gga cca gca tct tta aat tac tac tgg gta cct ttg    2060
Val Ile Ala Gln Gly Pro Ala Ser Leu Asn Tyr Tyr Trp Val Pro Leu
                600                 605                 610 ctg aca gtc att ttt ggg tct tac ctg att gca cat ggg ttc ttc agc    2108
Leu Thr Val Ile Phe Gly Ser Tyr Leu Ile Ala His Gly Phe Phe Ser
            615                 620                 625 gtc tat gca atg tgt gtt gaa aca att ttc atc tgc ttc ttg gaa gat    2156
Val Tyr Ala Met Cys Val Glu Thr Ile Phe Ile Cys Phe Leu Glu Asp
        630                 635                 640 tta gaa aga aat gat ggt tct act gca aga cct tat tat gtg agt caa    2204
Leu Glu Arg Asn Asp Gly Ser Thr Ala Arg Pro Tyr Tyr Val Ser Gln
    645                 650                 655 cct ttg ctg aag att ttc cag gag gaa aat cca caa act agg aag cag    2252
Pro Leu Leu Lys Ile Phe Gln Glu Glu Asn Pro Gln Thr Arg Lys Gln
660                 665                 670                 675 tagaagagca aactggtcgt cctacagctg tgtgttacct tttctccatc tgctgtgtct    2312
gtgcaacatt tgtttcataa gtgctttgtg tttagcaaca ctgtattcac gaccttgttg    2372
gcttgcattt gcatgtttta taccaaagct tatactgtac tatgtgaagc catcagaagt    2432
cgcaagggaa ttgttaataa cataaaacat ttttatacta agatcatttg ttttgtaatt    2492 cgttttaaa gagtggcttg gatgtttga aatactact gaatatgtta atattctttt    2552
aaatcttaga ttgaaaaatg atacattact taaattgata gctcctaata tattttaaa    2612
```

```
attacaacta aaagaagact tcttctgcag ggaaaattgg tcagcaaagt gaaattaaaa    2672
attttaaagt ttttcccact ctcgttggac agtaaatcag tgaaaggact gccccagttg    2732
agagtttgct ctctttaagt atagaatgtt tcctcttaaa caaattgcca atcatccagc    2792
ctttactact tagccctctg acaaagtgcc ttactggcta tttaatatta cccagctttt    2852
atgggcaagt ttacaaacat tgttttttaa aaaattaaaa cctgcaatgt tcgtgatta    2912 aaacaagtct tattgcattt gtttcactct tagctcactg attggaaaac atttgtcatt    2972
ttgctctgtt tgatatcctc actattatgg aatacattgt gcagctaaac aatttcccctt   3032 gcgcctagtg acattcatg aatgtgtact acacgcaaga agaaacaaac cccgaaagaa    3092
cacttgttgg atttctttgt tttttttttt actaaaagag aagttttaaa atgaaatgtt    3152
ttctatagta gatctttgaa aatacaatag gtataatact gcatttctca gtgttttaca    3212
aagatcagaa agagaaactt ctaggaattg caaagggaaa ctttactcct cgaaagggtg    3272
ctcacagatg tcatgtactg aatagctccc ttttaaatga tcatttattt tcatcaaagc    3332
ctgttctata tatgccactt catttctaa cttttggtat gaaaaaatca gtttacttac    3392
agtatgttaa ttgtattgta ctactataaa caggaacata atttccaatt cagttttaaa   3452
taattttacc agtactacta acttttaagg aaattaattc agttggttac tcagtgtttg    3512
ttacagaaag agtccagaaa agtattcacc ctaagagaat gtcaatcata taatgataat    3572
ttgtgaaagc tttgagaatc aatcatcagt aagttactat cagtttataa aatattatca    3632
catttgttta aatgtgactt tagatacttt tatgccaaaa ataaactcac atgagcacat    3692
gacagtctga gctctataat cagtgtgctt ctgctgtgca gaaatgttag aaacgtattg    3752
tctaaatatc tttgataatt aaaatgttta atatttaatg aaatttgttg ttacttgttt    3812
taaatctttt ttctttaat aaagatttaa ataagaaat                           3851
```

<210> SEQ ID NO 130
<211> LENGTH: 675
<212> TYPE: PRT
<213> ORGANISM: Homo sapiens

<400> SEQUENCE: 130

```
Met Ile Phe Leu Leu Cys Ile Ile Gly Tyr Ile Val Leu Gly Leu Val
1               5                   10                  15

Ala Trp Val His Gly Asp Pro Arg Ala Ala Tyr Pro Thr Asp Ser
            20                  25                  30

Gln Gly His Phe Cys Gly Gln Lys Gly Thr Pro Asn Glu Asn Lys Thr
        35                  40                  45

Ile Leu Phe Tyr Phe Asn Leu Leu Arg Cys Thr Ser Pro Ser Val Leu
    50                  55                  60

Leu Asn Leu Gln Cys Pro Thr Thr Gln Ile Cys Val Ser Lys Cys Pro
65                  70                  75                  80

Glu Lys Phe Leu Thr Tyr Val Glu Met Gln Leu Leu Tyr Thr Lys Asp
                85                  90                  95

Lys Ser Tyr Trp Glu Asp Tyr Arg Gln Phe Cys Lys Thr Thr Ala Lys
            100                 105                 110

Pro Val Lys Ser Leu Thr Gln Leu Leu Leu Asp Asp Cys Pro Thr
        115                 120                 125

Ala Ile Phe Pro Ser Lys Pro Phe Leu Gln Arg Cys Phe Pro Asp Phe
    130                 135                 140

Ser Thr Lys Asn Gly Thr Leu Thr Ile Gly Ser Lys Met Met Phe Gln
145                 150                 155                 160
```

```
Asp Gly Asn Gly Gly Thr Arg Ser Val Val Glu Leu Gly Ile Ala Ala
                165                 170                 175

Asn Gly Ile Asn Lys Leu Leu Asp Ala Lys Ser Leu Gly Leu Lys Val
            180                 185                 190

Phe Glu Asp Tyr Ala Arg Thr Trp Tyr Trp Ile Leu Ile Gly Leu Thr
        195                 200                 205

Ile Ala Met Val Leu Ser Trp Ile Phe Leu Ile Leu Leu Arg Phe Ile
    210                 215                 220

Ala Gly Cys Leu Phe Trp Val Phe Met Ile Gly Val Ile Gly Ile Ile
225                 230                 235                 240

Gly Tyr Gly Ile Trp His Cys Tyr Gln Gln Tyr Thr Asn Leu Gln Glu
                245                 250                 255

Arg Pro Ser Ser Val Leu Thr Ile Tyr Asp Ile Gly Ile Gln Thr Asn
            260                 265                 270

Ile Ser Met Tyr Phe Glu Leu Gln Gln Thr Trp Phe Thr Phe Met Ile
        275                 280                 285

Ile Leu Cys Ile Ile Glu Val Ile Val Ile Leu Met Leu Ile Phe Leu
    290                 295                 300

Arg Asn Arg Ile Arg Val Ala Ile Ile Leu Leu Lys Glu Gly Ser Lys
305                 310                 315                 320

Ala Ile Gly Tyr Val Pro Ser Thr Leu Val Tyr Pro Ala Leu Thr Phe
                325                 330                 335

Ile Leu Leu Ser Ile Cys Ile Cys Tyr Trp Val Val Thr Ala Val Phe
            340                 345                 350

Leu Ala Thr Ser Gly Val Pro Val Tyr Lys Val Ile Ala Pro Gly Gly
        355                 360                 365

His Cys Ile His Glu Asn Gln Thr Cys Asp Pro Glu Ile Phe Asn Thr
    370                 375                 380

Thr Glu Ile Ala Lys Ala Cys Pro Gly Ala Leu Cys Asn Phe Ala Phe
385                 390                 395                 400

Tyr Gly Gly Lys Ser Leu Tyr His Gln Tyr Ile Pro Thr Phe His Val
                405                 410                 415

Tyr Asn Leu Phe Val Phe Leu Trp Leu Ile Asn Phe Val Ile Ala Leu
            420                 425                 430

Gly Gln Cys Ala Leu Ala Gly Ala Phe Ala Thr Tyr Tyr Trp Ala Met
        435                 440                 445

Lys Lys Pro Asp Asp Ile Pro Arg Tyr Pro Leu Phe Thr Ala Phe Gly
    450                 455                 460

Arg Ala Ile Arg Tyr His Thr Gly Ser Leu Ala Phe Gly Ser Leu Ile
465                 470                 475                 480

Ile Ala Leu Ile Gln Met Phe Lys Ile Val Leu Glu Tyr Leu Asp His
                485                 490                 495

Arg Leu Lys Arg Thr Gln Asn Thr Leu Ser Lys Phe Leu Gln Cys Cys
            500                 505                 510

Leu Arg Cys Cys Phe Trp Cys Leu Glu Asn Ala Ile Lys Phe Leu Asn
        515                 520                 525

Arg Asn Ala Tyr Ile Met Ile Ala Ile Tyr Gly Arg Asn Phe Cys Arg
    530                 535                 540

Ser Ala Lys Asp Ala Phe Asn Leu Leu Met Arg Asn Val Leu Lys Val
545                 550                 555                 560

Ala Val Thr Asp Glu Val Thr Tyr Phe Val Leu Phe Leu Gly Lys Leu
                565                 570                 575

Leu Val Ala Gly Ser Ile Gly Val Leu Ala Phe Leu Phe Phe Thr Gln
            580                 585                 590
```

```
                    Arg Leu Pro Val Ile Ala Gln Gly Pro Ala Ser Leu Asn Tyr Tyr Trp
                        595                 600                 605

Val Pro Leu Leu Thr Val Ile Phe Gly Ser Tyr Leu Ile Ala His Gly
                        610                 615                 620

Phe Phe Ser Val Tyr Ala Met Cys Val Glu Thr Ile Phe Ile Cys Phe
                    625                 630                 635                 640

Leu Glu Asp Leu Glu Arg Asn Asp Gly Ser Thr Ala Arg Pro Tyr Tyr
                                645                 650                 655

Val Ser Gln Pro Leu Leu Lys Ile Phe Gln Glu Asn Pro Gln Thr
                                660                 665                 670

Arg Lys Gln
                            675

<210> SEQ ID NO 131
<211> LENGTH: 3819
<212> TYPE: DNA
<213> ORGANISM: Homo sapiens
<220> FEATURE:
<221> NAME/KEY: CDS
<222> LOCATION: (196)..(2220)

<400> SEQUENCE: 131
agatgaaccc ggtacctcag atggaaatgc agaaatcacc catcttctgt gtcactcacg     60
ctgggagctg tagacaggag ctgttcctat tcggccatct tggctcctcc acgattcagt    120
ggtgatccaa ggacatatga cccagatttc aaggggcctg ttgccaacag agttgtaca     180 gatgttctgt gctgt atg atc ttc cta ctg tgt att att ggc tac att gtt     231
                Met Ile Phe Leu Leu Cys Ile Ile Gly Tyr Ile Val
                  1               5                  10 tta gga ctt gtg gcc tgg gta cat ggg gac ccc aga aga gca gcc tat     279
Leu Gly Leu Val Ala Trp Val His Gly Asp Pro Arg Arg Ala Ala Tyr
             15                  20                  25 cct aca gac agc cag ggc cac ttt tgt ggc cag aag ggc act ccc aat     327
Pro Thr Asp Ser Gln Gly His Phe Cys Gly Gln Lys Gly Thr Pro Asn
         30                  35                  40 gag aac aag acc att ttg ttt tac ttt aac ctg tta cgc tgt acc agt     375
Glu Asn Lys Thr Ile Leu Phe Tyr Phe Asn Leu Leu Arg Cys Thr Ser
 45                  50                  55                  60 ccc tcc gtg ttg cta aac cta cag tgc cct acc aca cag atc tgt gtc     423
Pro Ser Val Leu Leu Asn Leu Gln Cys Pro Thr Thr Gln Ile Cys Val
                 65                  70                  75 tcc aag tgc cca gaa aaa ttt tta acc tat gtg gaa atg caa ctt ttg     471
Ser Lys Cys Pro Glu Lys Phe Leu Thr Tyr Val Glu Met Gln Leu Leu
             80                  85                  90 tac aca aaa gac aaa agc tac tgg gaa gac tac cgt cag ttc tgt aag     519
Tyr Thr Lys Asp Lys Ser Tyr Trp Glu Asp Tyr Arg Gln Phe Cys Lys
         95                 100                 105 acc act gct aag cct gtg aag tct ctc aca cag ctt tta ctg gat gat     567
Thr Thr Ala Lys Pro Val Lys Ser Leu Thr Gln Leu Leu Leu Asp Asp
    110                 115                 120 gat tgt cca aca gcg att ttt ccc agc aaa cct ttt ctc cag aga tgt     615
Asp Cys Pro Thr Ala Ile Phe Pro Ser Lys Pro Phe Leu Gln Arg Cys
125                 130                 135                 140 ttc cct gac ttc tct acc aaa aat ggc act tta aca ata gga agt aag     663
Phe Pro Asp Phe Ser Thr Lys Asn Gly Thr Leu Thr Ile Gly Ser Lys
                145                 150                 155 atg atg ttt caa gat gga aat gga ggg aca aga agt gtt gta gaa ctc     711
Met Met Phe Gln Asp Gly Asn Gly Gly Thr Arg Ser Val Val Glu Leu
            160                 165                 170
```

```
                                          -continued
ggg att gct gca aat ggt atc aat aaa ctt ctt gat gca aag tca ctt    759
Gly Ile Ala Ala Asn Gly Ile Asn Lys Leu Leu Asp Ala Lys Ser Leu
        175                 180                 185 gga ttg aaa gtg ttt gaa gac tat gca aga act tgg tat tgg att ctc    807
Gly Leu Lys Val Phe Glu Asp Tyr Ala Arg Thr Trp Tyr Trp Ile Leu
190                 195                 200 att ggc ctg acg att gcc atg gtc ctt agt tgg ata ttt ttg ata ctt    855
Ile Gly Leu Thr Ile Ala Met Val Leu Ser Trp Ile Phe Leu Ile Leu
205                 210                 215                 220 ctg agg ttc ata gct gga tgc ctc ttc tgg gtc ttc atg att ggt gtg    903
Leu Arg Phe Ile Ala Gly Cys Leu Phe Trp Val Phe Met Ile Gly Val
                225                 230                 235 att gga att ata ggt tat gga ata tgg cac tgt tac cag cag tac acc    951
Ile Gly Ile Ile Gly Tyr Gly Ile Trp His Cys Tyr Gln Gln Tyr Thr
        240                 245                 250 aat ctt cag gaa cgc cca agt tct gta tta act atc tat gac atc ggg    999
Asn Leu Gln Glu Arg Pro Ser Ser Val Leu Thr Ile Tyr Asp Ile Gly
                255                 260                 265 att cag act aac ata agc atg tac ttt gaa ctg caa caa aca tgg ttc   1047
Ile Gln Thr Asn Ile Ser Met Tyr Phe Glu Leu Gln Gln Thr Trp Phe
270                 275                 280 aca ttt atg ata ata ctc tgc atc att gaa gtg att gtc atc ctc atg   1095
Thr Phe Met Ile Ile Leu Cys Ile Ile Glu Val Ile Val Ile Leu Met
285                 290                 295                 300 ctg atc ttc ctc agg aat cga atc cga gtc gcc att atc ctg ctg aag   1143
Leu Ile Phe Leu Arg Asn Arg Ile Arg Val Ala Ile Ile Leu Leu Lys
                305                 310                 315 gaa gga agc aaa gcc att gga tat gtt cct agt aca tta gtc tat cca   1191
Glu Gly Ser Lys Ala Ile Gly Tyr Val Pro Ser Thr Leu Val Tyr Pro
        320                 325                 330 gct tta act ttc att ttg ctc tca atc tgc att tgc tac tgg gtc gtg   1239
Ala Leu Thr Phe Ile Leu Leu Ser Ile Cys Ile Cys Tyr Trp Val Val
                335                 340                 345 aca gca gtt ttc ttg gcg aca tcg ggg gta cct gta tac aaa gtc ata   1287
Thr Ala Val Phe Leu Ala Thr Ser Gly Val Pro Val Tyr Lys Val Ile
350                 355                 360 gct cca ggg ggg cat tgt ata cat gaa aat caa acc tgt gac cca gag   1335
Ala Pro Gly Gly His Cys Ile His Glu Asn Gln Thr Cys Asp Pro Glu
365                 370                 375                 380 att ttt aat aca act gaa att gcc aaa gct tgc cct ggg gct ctg tgt   1383
Ile Phe Asn Thr Thr Glu Ile Ala Lys Ala Cys Pro Gly Ala Leu Cys
                385                 390                 395 aac ttt gct ttc tat ggt gga aag agc ttg tac cat cag tac atc cct   1431
Asn Phe Ala Phe Tyr Gly Gly Lys Ser Leu Tyr His Gln Tyr Ile Pro
        400                 405                 410 acc ttc cat gta tac aac tta ttt gtc ttt ctc tgg ctt ata aac ttc   1479
Thr Phe His Val Tyr Asn Leu Phe Val Phe Leu Trp Leu Ile Asn Phe
                415                 420                 425 gtc att gca tta ggt cag tgc gcc ctt gct ggt gca ttc gct act tat   1527
Val Ile Ala Leu Gly Gln Cys Ala Leu Ala Gly Ala Phe Ala Thr Tyr
430                 435                 440 tac tgg gcc atg aaa aaa cct gat gac atc cca cga tat cca ctt ttt   1575
Tyr Trp Ala Met Lys Lys Pro Asp Asp Ile Pro Arg Tyr Pro Leu Phe
445                 450                 455                 460 act gca ttt gga cga gcc ata cga tat cac aca gga tcc cta gca ttt   1623
Thr Ala Phe Gly Arg Ala Ile Arg Tyr His Thr Gly Ser Leu Ala Phe
                465                 470                 475 gga tct tta att att gca tta att caa atg ttt aaa att gta cta gaa   1671
Gly Ser Leu Ile Ile Ala Leu Ile Gln Met Phe Lys Ile Val Leu Glu
        480                 485                 490
```

```
tac ttg gac cac cgt ctt aaa cgt acc cag aac aca ttg tct aaa ttc      1719
Tyr Leu Asp His Arg Leu Lys Arg Thr Gln Asn Thr Leu Ser Lys Phe
            495                 500                 505 cta cag tgc tgc ctg aga tgc tgc ttc tgg tgt ttg gaa aat gca ata      1767
Leu Gln Cys Cys Leu Arg Cys Cys Phe Trp Cys Leu Glu Asn Ala Ile
510                 515                 520 aag ttt tta aac aga aat gcc tat att atg att gca ata tat ggc aga      1815
Lys Phe Leu Asn Arg Asn Ala Tyr Ile Met Ile Ala Ile Tyr Gly Arg
525                 530                 535                 540 aac ttc tgc agg tca gca aaa gat gct ttc aat ctg ctg atg aga aat      1863
Asn Phe Cys Arg Ser Ala Lys Asp Ala Phe Asn Leu Leu Met Arg Asn
                545                 550                 555 gtt ttg aaa gtt gca gtt aca gat gaa gtt aca tac ttt gta tta ttc      1911
Val Leu Lys Val Ala Val Thr Asp Glu Val Thr Tyr Phe Val Leu Phe
            560                 565                 570 ctg ggg aaa ctt cta gtt gct gga agt ata ggt gtt ctg gcc ttc cta      1959
Leu Gly Lys Leu Leu Val Ala Gly Ser Ile Gly Val Leu Ala Phe Leu
            575                 580                 585 ttc ttc aca caa aga ctg cca gtg att gca caa gga cca gca tct tta      2007
Phe Phe Thr Gln Arg Leu Pro Val Ile Ala Gln Gly Pro Ala Ser Leu
590                 595                 600 aat tac tac tgg gta cct ttg ctg aca gtc att ttt ggg tct tac ctg      2055
Asn Tyr Tyr Trp Val Pro Leu Leu Thr Val Ile Phe Gly Ser Tyr Leu
605                 610                 615                 620 att gca cat ggg ttc ttc agc gtc tat gca atg tgt gtt gaa aca att      2103
Ile Ala His Gly Phe Phe Ser Val Tyr Ala Met Cys Val Glu Thr Ile
                625                 630                 635 ttc atc tgc ttc ttg gaa gat tta gaa aga aat gat ggt tct act gca      2151
Phe Ile Cys Phe Leu Glu Asp Leu Glu Arg Asn Asp Gly Ser Thr Ala
            640                 645                 650 aga cct tat tat gtg agt caa cct ttg ctg aag att ttc cag gag gaa      2199
Arg Pro Tyr Tyr Val Ser Gln Pro Leu Leu Lys Ile Phe Gln Glu Glu
            655                 660                 665 aat cca caa act agg aag cag tagaagagca aactggtcgt cctacagctg         2250
Asn Pro Gln Thr Arg Lys Gln
670                 675 tgtgttacct tttctccatc tgctgtgtct gtgcaacatt tgtttcataa gtgctttgtg    2310
tttagcaaca ctgtattcac gaccttgttg gcttgcattt gcatgtttta taccaaagct   2370
tatactgtac tatgtgaagc catcagaagt cgcaagggaa ttgttaataa cataaaacat   2430
ttttatacta agatcatttg ttttgtaatt cgttttttaaa gagtggcttg gatgttttga   2490
aaatactact gaatatgtta atattctttt aaatcttaga ttgaaaaatg atacattact   2550
taaattgata gctcctaata tattttttaaa attacaacta aaagaagact tcttctgcag   2610
ggaaaattgg tcagcaaagt gaaattaaaa attttaaagt ttttcccact ctcgttggac   2670
agtaaatcag tgaaaggact gccccagttg agagtttgct ctctttaagt atagaatgtt   2730
tcctcttaaa caaattgcca atcatccagc ctttactact tagccctctg acaaagtgcc   2790
ttactggcta tttaatatta cccagctttt atgggcaagt ttacaaacat tgttttttaa   2850
aaaattaaaa cctgcaatgt ttcgtgatta aaacaagtct tattgcattt gtttcactct   2910
tagctcactg attggaaaac atttgtcatt ttgctctgtt tgatatcctc actattatgg   2970
aatacattgt gcagctaaac aatttccctt gcgcctagtg gacattcatg aatgtgtact   3030
acacgcaaga agaaacaaac cccgaaagaa cacttgttgg atttctttgt ttttttttt   3090 actaaaagag aagttttaaa atgaaatgtt ttctatagta gatctttgaa aatacaaatag  3150 gtataatact gcatttctca gtgttttaca aagatcagaa agagaaactt ctaggaattg   3210
```

-continued

```
caaagggaaa ctttactcct cgaaagggtg ctcacagatg tcatgtactg aatagctccc    3270 tttttaaatga tcatttattt tcatcaaagc ctgttctata tatgccactt cattttctaa    3330
cttttggtat gaaaaaatca gtttacttac agtatgttaa ttgtattgta ctactataaa    3390
caggaacata atttccaatt cagttttaaa taatttttacc agtactacta acttttaagg    3450
aaattaattc agttggttac tcagtgtttg ttacagaaag agtccagaaa agtattcacc    3510
ctaagagaat gtcaatcata taatgataat ttgtgaaagc tttgagaatc aatcatcagt    3570
aagttactat cagtttataa aatattatca catttgttta aatgtgactt tagatacttt    3630
tatgccaaaa ataaactcac atgagcacat gacagtctga gctctataat cagtgtgctt    3690
ctgctgtgca gaaatgttag aaacgtattg tctaaatatc tttgataatt aaaatgttta    3750
atatttaatg aaatttgttg ttacttgttt taaatctttt ttcttttaat aaagatttaa    3810
ataagaaat                                                            3819
```

<210> SEQ ID NO 132
<211> LENGTH: 675
<212> TYPE: PRT
<213> ORGANISM: Homo sapiens

<400> SEQUENCE: 132

```
Met Ile Phe Leu Leu Cys Ile Ile Gly Tyr Ile Val Leu Gly Leu Val
1               5                   10                  15

Ala Trp Val His Gly Asp Pro Arg Arg Ala Ala Tyr Pro Thr Asp Ser
            20                  25                  30

Gln Gly His Phe Cys Gly Gln Lys Gly Thr Pro Asn Glu Asn Lys Thr
        35                  40                  45

Ile Leu Phe Tyr Phe Asn Leu Leu Arg Cys Thr Ser Pro Ser Val Leu
    50                  55                  60

Leu Asn Leu Gln Cys Pro Thr Thr Gln Ile Cys Val Ser Lys Cys Pro
65                  70                  75                  80

Glu Lys Phe Leu Thr Tyr Val Glu Met Gln Leu Leu Tyr Thr Lys Asp
                85                  90                  95

Lys Ser Tyr Trp Glu Asp Tyr Arg Gln Phe Cys Lys Thr Thr Ala Lys
            100                 105                 110

Pro Val Lys Ser Leu Thr Gln Leu Leu Leu Asp Asp Cys Pro Thr
        115                 120                 125

Ala Ile Phe Pro Ser Lys Pro Phe Leu Gln Arg Cys Phe Pro Asp Phe
    130                 135                 140

Ser Thr Lys Asn Gly Thr Leu Thr Ile Gly Ser Lys Met Met Phe Gln
145                 150                 155                 160

Asp Gly Asn Gly Gly Thr Arg Ser Val Val Glu Leu Gly Ile Ala Ala
                165                 170                 175

Asn Gly Ile Asn Lys Leu Leu Asp Ala Lys Ser Leu Gly Leu Lys Val
            180                 185                 190

Phe Glu Asp Tyr Ala Arg Thr Trp Tyr Trp Ile Leu Ile Gly Leu Thr
        195                 200                 205

Ile Ala Met Val Leu Ser Trp Ile Phe Leu Ile Leu Leu Arg Phe Ile
    210                 215                 220

Ala Gly Cys Leu Phe Trp Val Phe Met Ile Gly Val Ile Gly Ile Ile
225                 230                 235                 240

Gly Tyr Gly Ile Trp His Cys Tyr Gln Gln Tyr Thr Asn Leu Gln Glu
                245                 250                 255
```

```
Arg Pro Ser Ser Val Leu Thr Ile Tyr Asp Ile Gly Ile Gln Thr Asn
            260                 265                 270

Ile Ser Met Tyr Phe Glu Leu Gln Gln Thr Trp Phe Thr Phe Met Ile
        275                 280                 285

Ile Leu Cys Ile Ile Glu Val Ile Val Ile Leu Met Leu Ile Phe Leu
        290                 295                 300

Arg Asn Arg Ile Arg Val Ala Ile Ile Leu Lys Glu Gly Ser Lys
305                 310                 315                 320

Ala Ile Gly Tyr Val Pro Ser Thr Leu Val Tyr Pro Ala Leu Thr Phe
                325                 330                 335

Ile Leu Leu Ser Ile Cys Ile Cys Tyr Trp Val Val Thr Ala Val Phe
            340                 345                 350

Leu Ala Thr Ser Gly Val Pro Val Tyr Lys Val Ile Ala Pro Gly Gly
            355                 360                 365

His Cys Ile His Glu Asn Gln Thr Cys Asp Pro Glu Ile Phe Asn Thr
        370                 375                 380

Thr Glu Ile Ala Lys Ala Cys Pro Gly Ala Leu Cys Asn Phe Ala Phe
385                 390                 395                 400

Tyr Gly Gly Lys Ser Leu Tyr His Gln Tyr Ile Pro Thr Phe His Val
                405                 410                 415

Tyr Asn Leu Phe Val Phe Leu Trp Leu Ile Asn Phe Val Ile Ala Leu
            420                 425                 430

Gly Gln Cys Ala Leu Ala Gly Ala Phe Ala Thr Tyr Tyr Trp Ala Met
        435                 440                 445

Lys Lys Pro Asp Asp Ile Pro Arg Tyr Pro Leu Phe Thr Ala Phe Gly
450                 455                 460

Arg Ala Ile Arg Tyr His Thr Gly Ser Leu Ala Phe Gly Ser Leu Ile
465                 470                 475                 480

Ile Ala Leu Ile Gln Met Phe Lys Ile Val Leu Glu Tyr Leu Asp His
                485                 490                 495

Arg Leu Lys Arg Thr Gln Asn Thr Leu Ser Lys Phe Leu Gln Cys Cys
            500                 505                 510

Leu Arg Cys Cys Phe Trp Cys Leu Glu Asn Ala Ile Lys Phe Leu Asn
            515                 520                 525

Arg Asn Ala Tyr Ile Met Ile Ala Ile Tyr Gly Arg Asn Phe Cys Arg
530                 535                 540

Ser Ala Lys Asp Ala Phe Asn Leu Leu Met Arg Asn Val Leu Lys Val
545                 550                 555                 560

Ala Val Thr Asp Glu Val Thr Tyr Phe Val Leu Phe Leu Gly Lys Leu
                565                 570                 575

Leu Val Ala Gly Ser Ile Gly Val Leu Ala Phe Leu Phe Thr Gln
            580                 585                 590

Arg Leu Pro Val Ile Ala Gln Gly Pro Ala Ser Leu Asn Tyr Tyr Trp
        595                 600                 605

Val Pro Leu Leu Thr Val Ile Phe Gly Ser Tyr Leu Ile Ala His Gly
610                 615                 620

Phe Phe Ser Val Tyr Ala Met Cys Val Glu Thr Ile Phe Ile Cys Phe
625                 630                 635                 640

Leu Glu Asp Leu Glu Arg Asn Asp Gly Ser Thr Ala Arg Pro Tyr Tyr
                645                 650                 655

Val Ser Gln Pro Leu Leu Lys Ile Phe Gln Glu Asn Pro Gln Thr
            660                 665                 670

Arg Lys Gln
    675
```

```
<210> SEQ ID NO 133
<211> LENGTH: 2302
<212> TYPE: DNA
<213> ORGANISM: Homo sapiens
<220> FEATURE:
<221> NAME/KEY: CDS
<222> LOCATION: (118)..(2277)

<400> SEQUENCE: 133
gggaggttca gtgttgatgg agttattgaa gaaatgatgg agtaagagac tcttttctaa      60
gcaactcaag tttgcagtga ttcaggccta cttctgaaga gacagccttt tatctca       117 atg aat gac aca gaa aaa cca gca gat act ccc tct gag gaa gag gac       165
Met Asn Asp Thr Glu Lys Pro Ala Asp Thr Pro Ser Glu Glu Glu Asp
1               5                   10                  15 ttt ggt gat cca agg aca tat gac cca gat ttc aag ggg cct gtt gcc       213
Phe Gly Asp Pro Arg Thr Tyr Asp Pro Asp Phe Lys Gly Pro Val Ala
                20                  25                  30 aac agg agt tgt aca gat gtt ctg tgc tgt atg atc ttc cta ctg tgt       261
Asn Arg Ser Cys Thr Asp Val Leu Cys Cys Met Ile Phe Leu Leu Cys
            35                  40                  45 att att ggc tac att gtt tta gga ctt gtg gcc tgg gta cat ggg gac       309
Ile Ile Gly Tyr Ile Val Leu Gly Leu Val Ala Trp Val His Gly Asp
        50                  55                  60 ccc aga aga gca gcc tat cct aca gac agc cag ggc cac ttt tgt ggc       357
Pro Arg Arg Ala Ala Tyr Pro Thr Asp Ser Gln Gly His Phe Cys Gly
65                  70                  75                  80 cag aag ggc act ccc aat gag aac aag acc att ttg ttt tac ttt aac       405
Gln Lys Gly Thr Pro Asn Glu Asn Lys Thr Ile Leu Phe Tyr Phe Asn
                85                  90                  95 ctg tta cgc tgt acc agt ccc tcc gta ttg cta aac cta cag tgc cct       453
Leu Leu Arg Cys Thr Ser Pro Ser Val Leu Leu Asn Leu Gln Cys Pro
                100                 105                 110 acc aca cag atc tgt gtc tcc aag tgc cca gaa aaa ttt tta acc tat       501
Thr Thr Gln Ile Cys Val Ser Lys Cys Pro Glu Lys Phe Leu Thr Tyr
            115                 120                 125 gtg gaa atg caa ctt ttg tac aca aaa gac aaa agc tac tgg gaa gac       549
Val Glu Met Gln Leu Leu Tyr Thr Lys Asp Lys Ser Tyr Trp Glu Asp
130                 135                 140 tac cgt cag ttc tgt aag acc act gct aag cct gtg aag tct ctc aca       597
Tyr Arg Gln Phe Cys Lys Thr Thr Ala Lys Pro Val Lys Ser Leu Thr
145                 150                 155                 160 cag ctt tta ctg gat gat gat tgt cca aca gcg att ttt ccc agc aaa       645
Gln Leu Leu Leu Asp Asp Asp Cys Pro Thr Ala Ile Phe Pro Ser Lys
                165                 170                 175 cct ttt ctc cag aga tgt ttc cct gac ttc tct acc aaa aat ggc act       693
Pro Phe Leu Gln Arg Cys Phe Pro Asp Phe Ser Thr Lys Asn Gly Thr
                180                 185                 190 tta aca ata gga agt aag atg atg ttt caa gat gga aat gga ggg aca       741
Leu Thr Ile Gly Ser Lys Met Met Phe Gln Asp Gly Asn Gly Gly Thr
            195                 200                 205 aga agt gtt gta gaa ctc ggg att gct gca aat ggt atc aat aaa ctt       789
Arg Ser Val Val Glu Leu Gly Ile Ala Ala Asn Gly Ile Asn Lys Leu
        210                 215                 220 ctt gat gca aag tca ctt gga ttg aaa gtg ttt gaa gac tat gca aga       837
Leu Asp Ala Lys Ser Leu Gly Leu Lys Val Phe Glu Asp Tyr Ala Arg
225                 230                 235                 240 act tgg tat tgg att ctc att ggc ctg acg att gcc atg gtc ctt agt       885
Thr Trp Tyr Trp Ile Leu Ile Gly Leu Thr Ile Ala Met Val Leu Ser
                245                 250                 255
```

```
tgg ata ttt ttg ata ctt ctg agg ttc ata gct gga tgc ctc ttc tgg      933
Trp Ile Phe Leu Ile Leu Leu Arg Phe Ile Ala Gly Cys Leu Phe Trp
            260             265             270 gtc ttc atg att ggt gtg att gga att ata ggt tat gga ata tgg cac      981
Val Phe Met Ile Gly Val Ile Gly Ile Ile Gly Tyr Gly Ile Trp His
            275             280             285 tgt tac cag cag tac acc aat ctt cag gaa cgc cca agt tct gta tta     1029
Cys Tyr Gln Gln Tyr Thr Asn Leu Gln Glu Arg Pro Ser Ser Val Leu
            290             295             300 act atc tat gac atc ggg att cag act aac ata agc atg tac ttt gaa     1077
Thr Ile Tyr Asp Ile Gly Ile Gln Thr Asn Ile Ser Met Tyr Phe Glu
305             310             315             320 ctg caa caa aca tgg ttc aca ttt atg ata ata ctc tgc atc att gaa     1125
Leu Gln Gln Thr Trp Phe Thr Phe Met Ile Ile Leu Cys Ile Ile Glu
                325             330             335 gtg att gtc atc ctc atg ctg atc ttc ctc agg aat cga atc cga gtc     1173
Val Ile Val Ile Leu Met Leu Ile Phe Leu Arg Asn Arg Ile Arg Val
            340             345             350 gcc att atc ctg ctg aag gaa gga agc aaa gcc att gga tat gtt cct     1221
Ala Ile Ile Leu Leu Lys Glu Gly Ser Lys Ala Ile Gly Tyr Val Pro
            355             360             365 agt aca tta gtc tat cca gct tta act ttc att ttg ctc tca atc tgc     1269
Ser Thr Leu Val Tyr Pro Ala Leu Thr Phe Ile Leu Leu Ser Ile Cys
370             375             380 att tgc tac tgg gtc gtg aca gca gtt ttc ttg gcg aca tcg ggg gta     1317
Ile Cys Tyr Trp Val Val Thr Ala Val Phe Leu Ala Thr Ser Gly Val
385             390             395             400 cct gta tac aaa gtc ata gct cca ggg ggg cat tgt ata cat gaa aat     1365
Pro Val Tyr Lys Val Ile Ala Pro Gly Gly His Cys Ile His Glu Asn
            405             410             415 caa acc tgt gac cca gag att ttt aat aca act gaa att gcc aaa gct     1413
Gln Thr Cys Asp Pro Glu Ile Phe Asn Thr Thr Glu Ile Ala Lys Ala
            420             425             430 tgc cct ggg gct ctg tgt aac ttt gct ttc tat ggt gga aag agc ttg     1461
Cys Pro Gly Ala Leu Cys Asn Phe Ala Phe Tyr Gly Gly Lys Ser Leu
            435             440             445 tac cat cag tac atc cct acc ttc cat gta tac aac tta ttt gtc ttt     1509
Tyr His Gln Tyr Ile Pro Thr Phe His Val Tyr Asn Leu Phe Val Phe
450             455             460 ctc tgg ctt ata aac ttc gtc att gca tta ggt cag tgc gcc ctt gct     1557
Leu Trp Leu Ile Asn Phe Val Ile Ala Leu Gly Gln Cys Ala Leu Ala
465             470             475             480 ggt gca ttc gct act tat tac tgg gcc atg aaa aaa cct gat gac atc     1605
Gly Ala Phe Ala Thr Tyr Tyr Trp Ala Met Lys Lys Pro Asp Asp Ile
            485             490             495 cca cga tat cca ctt ttt act gca ttt gga cga gcc ata cga tat cac     1653
Pro Arg Tyr Pro Leu Phe Thr Ala Phe Gly Arg Ala Ile Arg Tyr His
            500             505             510 aca gga tcc cta gca ttt gga tct tta att att gca tta att caa atg     1701
Thr Gly Ser Leu Ala Phe Gly Ser Leu Ile Ile Ala Leu Ile Gln Met
            515             520             525 ttt aaa att gta cta gaa tac ttg gac cac cgt ctt aaa cgt acc cag     1749
Phe Lys Ile Val Leu Glu Tyr Leu Asp His Arg Leu Lys Arg Thr Gln
530             535             540 aac aca ttg tct aaa ttc cta cag tgc tgc ctg aga tgc tgc ttc tgg     1797
Asn Thr Leu Ser Lys Phe Leu Gln Cys Cys Leu Arg Cys Cys Phe Trp
545             550             555             560 tgt ttg gaa aat gca ata aag ttt tta aac aga aat gcc tat att atg     1845
Cys Leu Glu Asn Ala Ile Lys Phe Leu Asn Arg Asn Ala Tyr Ile Met
                565             570             575
```

-continued

```
att gca ata tat ggc aga aac ttc tgc agg tca gca aaa gat gct ttc    1893
Ile Ala Ile Tyr Gly Arg Asn Phe Cys Arg Ser Ala Lys Asp Ala Phe
        580                 585                 590 aat ctg ctg atg aga aat gtt ttg aaa gtt gca gtt aca gat gaa gtt    1941
Asn Leu Leu Met Arg Asn Val Leu Lys Val Ala Val Thr Asp Glu Val
            595                 600                 605 aca tac ttt gta tta ttc ctg ggg aaa ctt cta gtt gct gga agt ata    1989
Thr Tyr Phe Val Leu Phe Leu Gly Lys Leu Leu Val Ala Gly Ser Ile
        610                 615                 620 ggt gtt ctg gcc ttc cta ttc ttc aca caa aga ctg cca gtg att gca    2037
Gly Val Leu Ala Phe Leu Phe Phe Thr Gln Arg Leu Pro Val Ile Ala
625                 630                 635                 640 caa gga cca gca tct tta tat tac tac tgg gta cct ttg ctg aca gtc    2085
Gln Gly Pro Ala Ser Leu Tyr Tyr Tyr Trp Val Pro Leu Leu Thr Val
                645                 650                 655 att ttt ggg tct tac ctg att gca cat ggg ttc ttc agc gtc tat gca    2133
Ile Phe Gly Ser Tyr Leu Ile Ala His Gly Phe Phe Ser Val Tyr Ala
            660                 665                 670 atg tgt gtt gaa aca att ttc atc tgc ttc tgt gaa gat ctg gaa aga    2181
Met Cys Val Glu Thr Ile Phe Ile Cys Phe Cys Glu Asp Leu Glu Arg
        675                 680                 685 aat gat gga tcc aca gaa aaa ccc tac ttc gta acc cct aac ctg cat    2229
Asn Asp Gly Ser Thr Glu Lys Pro Tyr Phe Val Thr Pro Asn Leu His
690                 695                 700 gga att ctg atc aag aag caa cta gtt ccc cag aag cag aaa gag tag    2277
Gly Ile Leu Ile Lys Lys Gln Leu Val Pro Gln Lys Gln Lys Glu
705                 710                 715 aaaagctcca aaaaaaaaaa aaaaa                                        2302

<210> SEQ ID NO 134
<211> LENGTH: 719
<212> TYPE: PRT
<213> ORGANISM: Homo sapiens

<400> SEQUENCE: 134

Met Asn Asp Thr Glu Lys Pro Ala Asp Thr Pro Ser Glu Glu Glu Asp
1               5                   10                  15

Phe Gly Asp Pro Arg Thr Tyr Asp Pro Asp Phe Lys Gly Pro Val Ala
            20                  25                  30

Asn Arg Ser Cys Thr Asp Val Leu Cys Cys Met Ile Phe Leu Leu Cys
        35                  40                  45

Ile Ile Gly Tyr Ile Val Leu Gly Leu Val Ala Trp Val His Gly Asp
    50                  55                  60

Pro Arg Arg Ala Ala Tyr Pro Thr Asp Ser Gln Gly His Phe Cys Gly
65                  70                  75                  80

Gln Lys Gly Thr Pro Asn Glu Asn Lys Thr Ile Leu Phe Tyr Phe Asn
                85                  90                  95

Leu Leu Arg Cys Thr Ser Pro Ser Val Leu Leu Asn Leu Gln Cys Pro
            100                 105                 110

Thr Thr Gln Ile Cys Val Ser Lys Cys Pro Glu Lys Phe Leu Thr Tyr
        115                 120                 125

Val Glu Met Gln Leu Leu Tyr Thr Lys Asp Lys Ser Tyr Trp Glu Asp
    130                 135                 140

Tyr Arg Gln Phe Cys Lys Thr Ala Lys Pro Val Lys Ser Leu Thr
145                 150                 155                 160

Gln Leu Leu Leu Asp Asp Asp Cys Pro Thr Ala Ile Phe Pro Ser Lys
                165                 170                 175
```

-continued

```
Pro Phe Leu Gln Arg Cys Phe Pro Asp Phe Ser Thr Lys Asn Gly Thr
            180                 185                 190

Leu Thr Ile Gly Ser Lys Met Met Phe Gln Asp Gly Asn Gly Gly Thr
            195                 200                 205

Arg Ser Val Val Glu Leu Gly Ile Ala Ala Asn Gly Ile Asn Lys Leu
            210                 215                 220

Leu Asp Ala Lys Ser Leu Gly Leu Lys Val Phe Glu Asp Tyr Ala Arg
225                 230                 235                 240

Thr Trp Tyr Trp Ile Leu Ile Gly Leu Thr Ile Ala Met Val Leu Ser
                        245                 250                 255

Trp Ile Phe Leu Ile Leu Leu Arg Phe Ile Ala Gly Cys Leu Phe Trp
                260                 265                 270

Val Phe Met Ile Gly Val Ile Gly Ile Ile Gly Tyr Gly Ile Trp His
            275                 280                 285

Cys Tyr Gln Gln Tyr Thr Asn Leu Gln Glu Arg Pro Ser Ser Val Leu
            290                 295                 300

Thr Ile Tyr Asp Ile Gly Ile Gln Thr Asn Ile Ser Met Tyr Phe Glu
305                 310                 315                 320

Leu Gln Gln Thr Trp Phe Thr Phe Met Ile Ile Leu Cys Ile Ile Glu
                        325                 330                 335

Val Ile Val Ile Leu Met Leu Ile Phe Leu Arg Asn Arg Ile Arg Val
                340                 345                 350

Ala Ile Ile Leu Leu Lys Glu Gly Ser Lys Ala Ile Gly Tyr Val Pro
            355                 360                 365

Ser Thr Leu Val Tyr Pro Ala Leu Thr Phe Ile Leu Leu Ser Ile Cys
            370                 375                 380

Ile Cys Tyr Trp Val Val Thr Ala Val Phe Leu Ala Thr Ser Gly Val
385                 390                 395                 400

Pro Val Tyr Lys Val Ile Ala Pro Gly Gly His Cys Ile His Glu Asn
                        405                 410                 415

Gln Thr Cys Asp Pro Glu Ile Phe Asn Thr Thr Glu Ile Ala Lys Ala
                420                 425                 430

Cys Pro Gly Ala Leu Cys Asn Phe Ala Phe Tyr Gly Lys Ser Leu
            435                 440                 445

Tyr His Gln Tyr Ile Pro Thr Phe His Val Tyr Asn Leu Phe Val Phe
            450                 455                 460

Leu Trp Leu Ile Asn Phe Val Ile Ala Leu Gly Gln Cys Ala Leu Ala
465                 470                 475                 480

Gly Ala Phe Ala Thr Tyr Tyr Trp Ala Met Lys Lys Pro Asp Asp Ile
                        485                 490                 495

Pro Arg Tyr Pro Leu Phe Thr Ala Phe Gly Arg Ala Ile Arg Tyr His
                500                 505                 510

Thr Gly Ser Leu Ala Phe Gly Ser Leu Ile Ile Ala Leu Ile Gln Met
            515                 520                 525

Phe Lys Ile Val Leu Glu Tyr Leu Asp His Arg Leu Lys Arg Thr Gln
            530                 535                 540

Asn Thr Leu Ser Lys Phe Leu Gln Cys Cys Leu Arg Cys Cys Phe Trp
545                 550                 555                 560

Cys Leu Glu Asn Ala Ile Lys Phe Leu Asn Arg Asn Ala Tyr Ile Met
                        565                 570                 575

Ile Ala Ile Tyr Gly Arg Asn Phe Cys Arg Ser Ala Lys Asp Ala Phe
                580                 585                 590

Asn Leu Leu Met Arg Asn Val Leu Lys Val Ala Val Thr Asp Glu Val
            595                 600                 605
```

```
Thr Tyr Phe Val Leu Phe Leu Gly Lys Leu Leu Val Ala Gly Ser Ile
    610             615                 620

Gly Val Leu Ala Phe Leu Phe Phe Thr Gln Arg Leu Pro Val Ile Ala
625             630             635                 640

Gln Gly Pro Ala Ser Leu Tyr Tyr Tyr Trp Val Pro Leu Leu Thr Val
                645             650                 655

Ile Phe Gly Ser Tyr Leu Ile Ala His Gly Phe Phe Ser Val Tyr Ala
            660             665                 670

Met Cys Val Glu Thr Ile Phe Ile Cys Phe Cys Glu Asp Leu Glu Arg
        675             680             685

Asn Asp Gly Ser Thr Glu Lys Pro Tyr Phe Val Thr Pro Asn Leu His
    690             695                 700

Gly Ile Leu Ile Lys Lys Gln Leu Val Pro Gln Lys Gln Lys Glu
705             710             715
```

<210> SEQ ID NO 135
<211> LENGTH: 3947
<212> TYPE: DNA
<213> ORGANISM: Homo sapiens
<220> FEATURE:
<221> NAME/KEY: CDS
<222> LOCATION: (588)..(2348)

<400> SEQUENCE: 135

```
agtgttgatg gagttattga agaaatgatg gagtaagaga ctctttctta agcaactcaa      60
gtttgcagtg attcaggcct acttctgaag agacagcctt ttatctcaat gaatgacaca     120
gaaaaaccag cagatactcc ctctgaggaa gaggactttg gtgatccaag acatatgac     180 ccagatttca aggggcctgt tgccaacaga ctaaactggg aactccgtga gagaaagcat     240
ctcatctgtg tggttcacca acgtttcata gcatctgcca cagtatccgg cacaaaatag     300
gagttgtaca gatgttctgt gctgtatgat cttcctactg tattattggc tacattgttt     360
taggacttgt ggcctgggta catggggacc ccagaagagc agcctatcct acagacagcc     420
agggccactt ttgtggccag aagggcactc ccaatgagaa caagaccatt ttgtttttact    480 ttaacctgtt acgctgtacc agcccctccg tattgctaaa cctacagtgc cctaccacac     540
agatctgtgt ctccaagtgc ccagaaaaat ttttaaccta tgtggaa atg caa ctt       596
                                                   Met Gln Leu
                                                   1 ttg tac aca aaa gac aaa agc tac tgg gaa gac tac cgt cag ttc tgt      644
Leu Tyr Thr Lys Asp Lys Ser Tyr Trp Glu Asp Tyr Arg Gln Phe Cys
  5                  10                  15 aag acc act gct aag cct gtg aag tct ctc aca cag ctt tta ctg gat      692
Lys Thr Thr Ala Lys Pro Val Lys Ser Leu Thr Gln Leu Leu Leu Asp
20                  25                  30                  35 gat gat tgt cca aca gcg att ttt ccc agc aaa cct ttt ctc cag aga      740
Asp Asp Cys Pro Thr Ala Ile Phe Pro Ser Lys Pro Phe Leu Gln Arg
                40                  45                  50 tgt ttc cct gac ttc tct acc aaa aat ggc act tta aca ata gga agt      788
Cys Phe Pro Asp Phe Ser Thr Lys Asn Gly Thr Leu Thr Ile Gly Ser
            55                  60                  65 aag atg atg ttt caa gat gga aat gga ggg aca aga agt gtt gta gaa      836
Lys Met Met Phe Gln Asp Gly Asn Gly Gly Thr Arg Ser Val Val Glu
        70                  75                  80 ctc ggg att gct gca aat ggt atc aat aaa ctt ctt gat gca aag tca      884
Leu Gly Ile Ala Ala Asn Gly Ile Asn Lys Leu Leu Asp Ala Lys Ser
    85                  90                  95
```

-continued

| | | |
|---|---|---|
| ctt gga ttg aaa gtg ttt gaa gac tat gca aga act tgg tat tgg att<br>Leu Gly Leu Lys Val Phe Glu Asp Tyr Ala Arg Thr Trp Tyr Trp Ile<br>100                    105                    110                    115 | 932 |
| ctc att ggc ctg acg att gcc atg gtc ctt agt tgg ata ttt ttg ata<br>Leu Ile Gly Leu Thr Ile Ala Met Val Leu Ser Trp Ile Phe Leu Ile<br>                  120                    125                    130 | 980 |
| ctt ctg agg ttc ata gct gga tgc ctc ttc tgg gtc ttc atg att ggt<br>Leu Leu Arg Phe Ile Ala Gly Cys Leu Phe Trp Val Phe Met Ile Gly<br>                  135                    140                    145 | 1028 |
| gtg att gga att ata ggt tat gga ata tgg cac tgt tac cag cag tac<br>Val Ile Gly Ile Ile Gly Tyr Gly Ile Trp His Cys Tyr Gln Gln Tyr<br>            150                    155                    160 | 1076 |
| acc aat ctt cag gaa cgc cca agt tcc gta tta act atc tat gac atc<br>Thr Asn Leu Gln Glu Arg Pro Ser Ser Val Leu Thr Ile Tyr Asp Ile<br>     165                    170                    175 | 1124 |
| ggg att cag act aac ata agc atg tac ttt gaa ctg caa caa aca tgg<br>Gly Ile Gln Thr Asn Ile Ser Met Tyr Phe Glu Leu Gln Gln Thr Trp<br>180                    185                    190                    195 | 1172 |
| ttc aca ttt atg ata ata ctc tgc atc att gaa gtg att gtc atc ctc<br>Phe Thr Phe Met Ile Ile Leu Cys Ile Ile Glu Val Ile Val Ile Leu<br>                  200                    205                    210 | 1220 |
| atg ctg atc ttc ctc agg aat cga atc cga gtc gcc att atc ctg ctg<br>Met Leu Ile Phe Leu Arg Asn Arg Ile Arg Val Ala Ile Ile Leu Leu<br>                215                    220                    225 | 1268 |
| aag gaa gga agc aaa gcc att gga tat gtt cct agt aca tta gtc tat<br>Lys Glu Gly Ser Lys Ala Ile Gly Tyr Val Pro Ser Thr Leu Val Tyr<br>          230                    235                    240 | 1316 |
| cca gct tta act ttc att ttg ctc tca atc tgc att tgc tac tgg gtc<br>Pro Ala Leu Thr Phe Ile Leu Leu Ser Ile Cys Ile Cys Tyr Trp Val<br>245                    250                    255 | 1364 |
| gtg aca gca gtt ttc ttg gcg aca tcg ggg gta cct gta tac aaa gtc<br>Val Thr Ala Val Phe Leu Ala Thr Ser Gly Val Pro Val Tyr Lys Val<br>260                    265                    270                    275 | 1412 |
| ata gct cca ggg ggg cat tgt ata cat gaa aat caa acc tgt gac cca<br>Ile Ala Pro Gly Gly His Cys Ile His Glu Asn Gln Thr Cys Asp Pro<br>                  280                    285                    290 | 1460 |
| gag aat ttt aat aca act gaa att gcc aaa gct tgc cct ggg gct ctg<br>Glu Asn Phe Asn Thr Thr Glu Ile Ala Lys Ala Cys Pro Gly Ala Leu<br>          295                    300                    305 | 1508 |
| tgt aac ttt gct ttc tat ggt gga aag agc ttg tac cat cag tac atc<br>Cys Asn Phe Ala Phe Tyr Gly Gly Lys Ser Leu Tyr His Gln Tyr Ile<br>                  310                    315                    320 | 1556 |
| cct acc ttc cat gta tac aac tta ttt gtc ttt ctc tgg ctt ata aac<br>Pro Thr Phe His Val Tyr Asn Leu Phe Val Phe Leu Trp Leu Ile Asn<br>325                    330                    335 | 1604 |
| ttc gtc att gca tta ggt cag tgc gcc ctt gct ggt gca ttc gct act<br>Phe Val Ile Ala Leu Gly Gln Cys Ala Leu Ala Gly Ala Phe Ala Thr<br>340                    345                    350                    355 | 1652 |
| tat tac tgg gcc atg aaa aaa cct gat gac atc cca cga tat cca ctt<br>Tyr Tyr Trp Ala Met Lys Lys Pro Asp Asp Ile Pro Arg Tyr Pro Leu<br>                  360                    365                    370 | 1700 |
| ttt act gca ttt gga cga gcc ata cga tat cac aca gga tcc cta gca<br>Phe Thr Ala Phe Gly Arg Ala Ile Arg Tyr His Thr Gly Ser Leu Ala<br>                375                    380                    385 | 1748 |
| ttt gga tct tta att att gca tta att caa atg ttt aaa att gta cta<br>Phe Gly Ser Leu Ile Ile Ala Leu Ile Gln Met Phe Lys Ile Val Leu<br>          390                    395                    400 | 1796 |
| gaa tac ttg gac cac cgt ctt aaa cgt acc cag aac aca ttg tct aaa<br>Glu Tyr Leu Asp His Arg Leu Lys Arg Thr Gln Asn Thr Leu Ser Lys<br>405                    410                    415 | 1844 |

```
ttc cta cag tgc tgc ctg aga tgc tgc ttc tgg tgt ttg gaa aat gca    1892
Phe Leu Gln Cys Cys Leu Arg Cys Cys Phe Trp Cys Leu Glu Asn Ala
420                 425                 430                 435 ata aag ttt tta aac aga aat gcc tat att atg att gca ata tat ggc    1940
Ile Lys Phe Leu Asn Arg Asn Ala Tyr Ile Met Ile Ala Ile Tyr Gly
                440                 445                 450 aga aac ttc tgc agg tca gca aaa gat gct ttc aat ctg ctg atg aga    1988
Arg Asn Phe Cys Arg Ser Ala Lys Asp Ala Phe Asn Leu Leu Met Arg
            455                 460                 465 aat gtt ttg aaa gtt gca gtt aca gat gaa gtt aca tac ttt gta tta    2036
Asn Val Leu Lys Val Ala Val Thr Asp Glu Val Thr Tyr Phe Val Leu
        470                 475                 480 ttc ctg ggg aaa ctt cta gtt gct gga agt ata ggt gtt ctg gcc ttc    2084
Phe Leu Gly Lys Leu Leu Val Ala Gly Ser Ile Gly Val Leu Ala Phe
    485                 490                 495 cta ttc ttc aca caa aga ctg cca gtg att gca caa gga cca gca tct    2132
Leu Phe Phe Thr Gln Arg Leu Pro Val Ile Ala Gln Gly Pro Ala Ser
500                 505                 510                 515 tta aat tac tac tgg gta cct ttg ctg aca gtc att ttt ggg tct tac    2180
Leu Asn Tyr Tyr Trp Val Pro Leu Leu Thr Val Ile Phe Gly Ser Tyr
                520                 525                 530 ctg att gca cat ggg ttc ttc agc gtc tat gca atg tgt gtt gaa aca    2228
Leu Ile Ala His Gly Phe Phe Ser Val Tyr Ala Met Cys Val Glu Thr
            535                 540                 545 att ttc atc tgc ttc ttg gaa gat tta gaa aga aat gat ggt tct act    2276
Ile Phe Ile Cys Phe Leu Glu Asp Leu Glu Arg Asn Asp Gly Ser Thr
        550                 555                 560 gca aga cct tat tat gtg agt caa cct ttg ctg aag att ttc cag gag    2324
Ala Arg Pro Tyr Tyr Val Ser Gln Pro Leu Leu Lys Ile Phe Gln Glu
    565                 570                 575 gaa aat cca caa act agg aag cag tagaagagca aactggtcgt cctacagctg   2378
Glu Asn Pro Gln Thr Arg Lys Gln
580                 585 tgtgttacct tttctccatc tgctgtgtct gtgcaacatt tgtttcataa gtgctttgtg   2438
tttagcaaca ctgtattcac gaccttgttg gcttgcattt gcatgtttta taccaaagct   2498
tatactgtac tatgtgaagc catcagaagt cgcaagggaa ttgttaataa cataaaacat   2558
ttttatacta agatcatttg ttttgtaatt cgttttttaaa gagtggcttg gatgttttga   2618
aaatactact gaatatgtta atattctttt aaatcttaga ttgaaaaatg atacattact   2678
taaattgata gctcctaata tattttttaaa attacaacta aaagaagact tcttctgcag   2738
ggaaaattgg tcagcaaagt gaaattaaaa attttaaagt ttttcccact ctcgttggac    2798
agtaaatcag tgaaaggact gccccagttg agagtttgct ctctttaagt atagaatgtt   2858
tcctcttaaa caaattgcca atcatccagc ctttactact tagccctctg acaaagtgcc   2918
ttactggcta tttaatatta cccagctttt atgggcaagt ttacaaacat tgttttttaa   2978
aaaattaaaa cctgcaatgt ttcgtgatta aaacaagtct tattgcattt gtttcactct   3038
tagctcactg attggaaaac atttgtcatt ttgctctgtt tgatatcctc actattatgg   3098
aatacattgt gcagctaaac aatttcccctt gcgcctagtg gacattcatg aatgtgtact   3158
acacgcaaga agaaacaaac cccgaaagaa cacttgttgg atttctttgt ttttttttt    3218 actaaaagag aagttttaaa atgaaatgtt ttctatagta gatctttgaa aatacaatag   3278
gtataatact gcatttctca gtgtttttaca aagatcagaa agagaaactt ctaggaattg   3338
caaagggaaa ctttactcct cgaaagggtg ctcacagatg tcatgtactg aatagctccc   3398 tttttaaatga tcatttattt tcatcaaagc ctgttctata tatgccactt cattttctaa   3458
```

-continued

```
cttttggtat gaaaaaatca gtttacttac agtatgttaa ttgtattgta ctactataaa    3518
caggaacata atttccaatt cagttttaaa taatttttacc agtactacta acttttaagg    3578
aaattaattc agttggttac tcagtgtttg ttacagaaag agtccagaaa agtattcacc    3638
ctaagagaat gtcaatcata taatgataat ttgtgaaagc tttgagaatc aatcatcagt    3698
aagttactat cagtttataa aatattatca catttgttta aatgtgactt tagatacttt    3758
tatgccaaaa ataaactcac atgagcacat gacagtctga gctctataat cagtgtgctt    3818
ctgctgtgca gaaatgttag aaacgtattg tctaaatatc tttgataatt aaaatgttta    3878
atatttaatg aaatttgttg ttacttgttt taaatctttt ttcttttaat aaagatttaa    3938
ataagaaat                                                             3947
```

<210> SEQ ID NO 136
<211> LENGTH: 587
<212> TYPE: PRT
<213> ORGANISM: Homo sapiens

<400> SEQUENCE: 136

```
Met Gln Leu Leu Tyr Thr Lys Asp Lys Ser Tyr Trp Glu Asp Tyr Arg
1               5                   10                  15

Gln Phe Cys Lys Thr Thr Ala Lys Pro Val Lys Ser Leu Thr Gln Leu
            20                  25                  30

Leu Leu Asp Asp Asp Cys Pro Thr Ala Ile Phe Pro Ser Lys Pro Phe
        35                  40                  45

Leu Gln Arg Cys Phe Pro Asp Phe Ser Thr Lys Asn Gly Thr Leu Thr
    50                  55                  60

Ile Gly Ser Lys Met Met Phe Gln Asp Gly Asn Gly Gly Thr Arg Ser
65                  70                  75                  80

Val Val Glu Leu Gly Ile Ala Ala Asn Gly Ile Asn Lys Leu Leu Asp
                85                  90                  95

Ala Lys Ser Leu Gly Leu Lys Val Phe Glu Asp Tyr Ala Arg Thr Trp
            100                 105                 110

Tyr Trp Ile Leu Ile Gly Leu Thr Ile Ala Met Val Leu Ser Trp Ile
        115                 120                 125

Phe Leu Ile Leu Leu Arg Phe Ile Ala Gly Cys Leu Phe Trp Val Phe
    130                 135                 140

Met Ile Gly Val Ile Gly Ile Ile Gly Tyr Gly Ile Trp His Cys Tyr
145                 150                 155                 160

Gln Gln Tyr Thr Asn Leu Gln Glu Arg Pro Ser Ser Val Leu Thr Ile
                165                 170                 175

Tyr Asp Ile Gly Ile Gln Thr Asn Ile Ser Met Tyr Phe Glu Leu Gln
            180                 185                 190

Gln Thr Trp Phe Thr Phe Met Ile Ile Leu Cys Ile Ile Glu Val Ile
        195                 200                 205

Val Ile Leu Met Leu Ile Phe Leu Arg Asn Arg Ile Arg Val Ala Ile
    210                 215                 220

Ile Leu Leu Lys Glu Gly Ser Lys Ala Ile Gly Tyr Val Pro Ser Thr
225                 230                 235                 240

Leu Val Tyr Pro Ala Leu Thr Phe Ile Leu Ser Ile Cys Ile Cys
                245                 250                 255

Tyr Trp Val Val Thr Ala Val Phe Leu Ala Thr Ser Gly Val Pro Val
            260                 265                 270

Tyr Lys Val Ile Ala Pro Gly Gly His Cys Ile His Glu Asn Gln Thr
        275                 280                 285
```

```
Cys Asp Pro Glu Asn Phe Asn Thr Thr Glu Ile Ala Lys Ala Cys Pro
        290                 295                 300

Gly Ala Leu Cys Asn Phe Ala Phe Tyr Gly Gly Lys Ser Leu Tyr His
305                 310                 315                 320

Gln Tyr Ile Pro Thr Phe His Val Tyr Asn Leu Phe Val Phe Leu Trp
                325                 330                 335

Leu Ile Asn Phe Val Ile Ala Leu Gly Gln Cys Ala Leu Ala Gly Ala
            340                 345                 350

Phe Ala Thr Tyr Tyr Trp Ala Met Lys Lys Pro Asp Asp Ile Pro Arg
        355                 360                 365

Tyr Pro Leu Phe Thr Ala Phe Gly Arg Ala Ile Arg Tyr His Thr Gly
370                 375                 380

Ser Leu Ala Phe Gly Ser Leu Ile Ile Ala Leu Ile Gln Met Phe Lys
385                 390                 395                 400

Ile Val Leu Glu Tyr Leu Asp His Arg Leu Lys Arg Thr Gln Asn Thr
                405                 410                 415

Leu Ser Lys Phe Leu Gln Cys Cys Leu Arg Cys Cys Phe Trp Cys Leu
            420                 425                 430

Glu Asn Ala Ile Lys Phe Leu Asn Arg Asn Ala Tyr Ile Met Ile Ala
        435                 440                 445

Ile Tyr Gly Arg Asn Phe Cys Arg Ser Ala Lys Asp Ala Phe Asn Leu
450                 455                 460

Leu Met Arg Asn Val Leu Lys Val Ala Val Thr Asp Glu Val Thr Tyr
465                 470                 475                 480

Phe Val Leu Phe Leu Gly Lys Leu Leu Val Ala Gly Ser Ile Gly Val
                485                 490                 495

Leu Ala Phe Leu Phe Phe Thr Gln Arg Leu Pro Val Ile Ala Gln Gly
            500                 505                 510

Pro Ala Ser Leu Asn Tyr Tyr Trp Val Pro Leu Leu Thr Val Ile Phe
        515                 520                 525

Gly Ser Tyr Leu Ile Ala His Gly Phe Phe Ser Val Tyr Ala Met Cys
                530                 535                 540

Val Glu Thr Ile Phe Ile Cys Phe Leu Glu Asp Leu Glu Arg Asn Asp
545                 550                 555                 560

Gly Ser Thr Ala Arg Pro Tyr Tyr Val Ser Gln Pro Leu Leu Lys Ile
                565                 570                 575

Phe Gln Glu Glu Asn Pro Gln Thr Arg Lys Gln
                580                 585

<210> SEQ ID NO 137
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 137
ccccagttga gagtttgctc                                                  20

<210> SEQ ID NO 138
<211> LENGTH: 21
<212> TYPE: DNA
<213> ORGANISM: Artificial
<220> FEATURE:
<223> OTHER INFORMATION: An artificially synthesized primer for RT-PCR

<400> SEQUENCE: 138
tgacatcggg attcagacta a                                                21
```

```
<210> SEQ ID NO 139
<211> LENGTH: 20
<212> TYPE: DNA
<213> ORGANISM: Artificial
<220> FEATURE:
<223> OTHER INFORMATION: An artificially synthesized primer for RT-PCR

<400> SEQUENCE: 139
aaagatgctg gtccttgtgc                                                      20

<210> SEQ ID NO 140
<211> LENGTH: 26
<212> TYPE: DNA
<213> ORGANISM: Artificial
<220> FEATURE:
<223> OTHER INFORMATION: An artificially synthesized primer for RT-PCR

<400> SEQUENCE: 140
gatccaaatg ctagggatcc tgtgtg                                               26

<210> SEQ ID NO 141
<211> LENGTH: 27
<212> TYPE: DNA
<213> ORGANISM: Artificial
<220> FEATURE:
<223> OTHER INFORMATION: An artificially synthesized primer for RT-PCR

<400> SEQUENCE: 141
cctgtgtgat atcgtatggc tcgtcca                                              27

<210> SEQ ID NO 142
<211> LENGTH: 34
<212> TYPE: DNA
<213> ORGANISM: Artificial
<220> FEATURE:
<223> OTHER INFORMATION: An artificially synthesized primer for PCR

<400> SEQUENCE: 142
agaattcatg atcttcctac tgtgtattat tggc                                      34

<210> SEQ ID NO 143
<211> LENGTH: 33
<212> TYPE: DNA
<213> ORGANISM: Artificial
<220> FEATURE:
<223> OTHER INFORMATION: An artificially synthesized primer for PCR

<400> SEQUENCE: 143
tatctcgagc tgcttcctag tttgtggatt ttc                                       33

<210> SEQ ID NO 144
<211> LENGTH: 19
<212> TYPE: DNA
<213> ORGANISM: Artificial
<220> FEATURE:
<223> OTHER INFORMATION: An artificially synthesized target sequence for
      siRNA

<400> SEQUENCE: 144
gttgcagtta cagatgaag                                                       19

<210> SEQ ID NO 145
<211> LENGTH: 51
<212> TYPE: DNA
<213> ORGANISM: Artificial
<220> FEATURE:
<223> OTHER INFORMATION: An artificially synthesized oligonucleotide for
      siRNA
```

<400> SEQUENCE: 145
caccgttgca gttacagatg aagttcaaga gacttcatct gtaactgcaa c    51

<210> SEQ ID NO 146
<211> LENGTH: 51
<212> TYPE: DNA
<213> ORGANISM: Artificial
<220> FEATURE:
<223> OTHER INFORMATION: An artificially synthesized oligonucleotide for
      siRNA

<400> SEQUENCE: 146
aaaagttgca gttacagatg aagtctcttg aacttcatct gtaactgcaa c    51

<210> SEQ ID NO 147
<211> LENGTH: 47
<212> TYPE: DNA
<213> ORGANISM: Artificial
<220> FEATURE:
<223> OTHER INFORMATION: siRNA hairpin design

<400> SEQUENCE: 147
gttgcagtta cagatgaagt tcaagagact tcatctgtaa ctgcaac    47

<210> SEQ ID NO 148
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 148
catccacgaa actaccttca act    23

<210> SEQ ID NO 149
<211> LENGTH: 23
<212> TYPE: DNA
<213> ORGANISM: Artificial
<220> FEATURE:
<223> OTHER INFORMATION: An artificially synthesized primer for RT-PCR

<400> SEQUENCE: 149
tctccttaga gagaagtggg gtg    23

<210> SEQ ID NO 150
<211> LENGTH: 169
<212> TYPE: PRT
<213> ORGANISM: Artificial
<220> FEATURE:
<223> OTHER INFORMATION: An artificially synthesized antigen polypeptide

<400> SEQUENCE: 150

Lys Ala Arg Lys Arg Lys Ser Asn Glu Met Glu Glu Asp Leu Val Lys
1               5                   10                  15

Cys Glu Asn Lys Lys Asn Ala Thr Pro Arg Thr Asn Leu Lys Phe Pro
                20                  25                  30

Ile Ser Asp Asp Arg Asn Ser Ser Val Lys Lys Glu Gln Lys Val Ala
            35                  40                  45

Ile Arg Pro Ser Ser Lys Lys Thr Tyr Ser Leu Arg Ser Gln Ala Ser
        50                  55                  60

Ile Ile Gly Val Asn Leu Ala Thr Lys Lys Lys Glu Gly Thr Leu Gln
65                  70                  75                  80

Lys Phe Gly Asp Phe Leu Gln His Ser Pro Ser Ile Leu Gln Ser Lys
                85                  90                  95

```
Ala Lys Lys Ile Ile Glu Thr Met Ser Ser Lys Leu Ser Asn Val
                100                 105                 110

Glu Ala Ser Lys Glu Asn Val Ser Gln Pro Lys Arg Ala Lys Arg Lys
            115                 120                 125

Leu Tyr Thr Ser Glu Ile Ser Ser Pro Ile Asp Ile Ser Gly Gln Val
130                 135                 140

Ile Leu Met Asp Gln Lys Met Lys Glu Ser Asp His Gln Ile Ile Lys
145                 150                 155                 160

Arg Arg Leu Arg Thr Lys Thr Ala Lys
                165

<210> SEQ ID NO 151
<211> LENGTH: 191
<212> TYPE: PRT
<213> ORGANISM: Artificial
<220> FEATURE:
<223> OTHER INFORMATION: An artificially synthesized antigen polypeptide

<400> SEQUENCE: 151

Met Arg Met Ile Ser Arg Met Ser Gln Asn Val Asp Met Pro Lys Leu
1               5                   10                  15

His Asp Ala Met Gly Thr Arg Ser Leu Met Ile His Thr Phe Ser Arg
            20                  25                  30

Cys Val Leu Cys Cys Ala Glu Glu Val Asp Leu Asp Glu Leu Leu Ala
            35                  40                  45

Gly Arg Leu Val Ser Phe Leu Met Asp His His Gln Glu Ile Leu Gln
        50                  55                  60

Val Pro Ser Tyr Leu Gln Thr Ala Val Glu Lys His Leu Asp Tyr Leu
65                  70                  75                  80

Lys Lys Gly His Ile Glu Asn Pro Gly Asp Gly Leu Phe Ala Pro Leu
                85                  90                  95

Pro Thr Tyr Ser Tyr Cys Lys Gln Ile Ser Ala Gln Glu Phe Asp Glu
            100                 105                 110

Gln Lys Val Ser Thr Ser Gln Ala Ala Ile Ala Glu Leu Leu Glu Asn
            115                 120                 125

Ile Ile Lys Asn Arg Ser Leu Pro Leu Lys Glu Lys Arg Lys Lys Leu
        130                 135                 140

Lys Gln Phe Gln Lys Glu Tyr Pro Leu Ile Tyr Gln Lys Arg Phe Pro
145                 150                 155                 160

Thr Thr Glu Ser Glu Ala Ala Leu Phe Gly Asp Lys Pro Thr Ile Lys
                165                 170                 175

Gln Pro Met Leu Ile Leu Arg Lys Pro Lys Phe Arg Ser Leu Arg
                180                 185                 190
```

METHOD OF DIAGNOSING BLADDER CANCER This application is a U.S. National Stage of PCT/JP2006/302684, filed Feb. 9, 2006, which claims the benefit of U.S. Provisional Application Ser. No. 60/652,318 filed Feb. 10, 2005 and U.S. Provisional Application Ser. No. 60/703,225 filed Jul. 27, 2005, all the contents of which are hereby incorporated by reference in their entirety.

FIELD OF THE INVENTION

The present invention relates to methods of detecting and diagnosing bladder cancer as well as methods of treating and preventing bladder cancer and bladder cancer metastasis. The present invention also relates to genes and polypeptides associated with bladder cancers.

BACKGROUND OF THE INVENTION

Bladder cancer is the second most common genitourinary tumor in human populations, with an incidence of approximately 261,000 new cases each year worldwide; about a third of those are likely to be invasive or metastatic disease at the time of diagnosis (Parkin D M, et al., (1999) CA Cancer J Clin; 49:33-64). Although radical cystectomy is considered the "gold standard" for treatment of patients with localized but muscle-invasive bladder cancer, about 50% of such patients develop metastases within two years after cystectomy and subsequently die of the disease (Sternberg Conn., (1995) Ann Oncol; 6:113-26).

Neoadjuvant chemotherapy is usually prescribed for muscle-invasive bladder cancer to treat micrometastases and to improve resectability of larger neoplasms (Fagg S L, et al., (1984) Br J Urol; 56:296-300, Raghavan D, et al., (1984) Med J Aust; 140:276-8). Regimens involving methotrexate, vinblastine, doxorubicin, and cisplatin (M-VAC), followed by radical cystectomy, are more likely to eliminate residual cancer than radical cystectomy alone, and, as such, improve survival among patients with locally advanced bladder cancer ((2003) Lancet; 361:1927-34, Grossman H B, et al., (2003) N Engl J Med; 349:859-66). In some clinical trials, down-staging with drugs prior to surgery was shown to have significant survival benefits (Grossman H B, et al., (2003) N Engl J Med; 349:859-66, Splinter T A, et al., (1992) J Urol; 147:606-8); moreover, patients who respond to neoadjuvant chemotherapy may preserve bladder function and enjoy an improved quality of life. However, since no method yet exists for predicting the response of an individual patient to chemotherapies, such as M-VAC, some patients will suffer from adverse reactions to the drugs without achieving any benefit in terms of positive effects, often losing the opportunity for additional therapy when their physical condition deteriorates. Hence, it is of critical importance to identify molecular targets for the development of novel drugs for bladder cancer patients. Some recent studies have demonstrated that gene expression information generated by cDNA microarray analysis in human tumors can provide molecular phenotyping that identifies distinct tumor classifications not evident by traditional histopathological method (Armstrong, S. A, et al., (2002) Nat Genet, 30: 41-47; Golub, T. R, et al., (1999) Science, 286: 531-537; Hofmann, W. K et al., (2002) Lancet, 359: 481-486). Moreover, several studies have demonstrated the effectiveness of this method for identifying novel cancer-related genes. The promise of such information lies in the potential to improve clinical strategies with neoplastic disease.

SUMMARY OF THE INVENTION

Hence, in the study reported here, we identified novel molecular targets using genome-wide information obtained from 33 invasive bladder cancer cases on a cDNA microarray consisting of 27,648 transcribed elements in combination with laser microbeam microdissection (LMM) of the tumors to obtain pure populations of cancer cells for analysis. These results suggest that such information may lead ultimately to our goal of "personalized therapy".

To characterize the detailed molecular mechanisms associated with bladder cancers, with a view toward development of novel therapeutic targets, the present inventors analyzed gene-expression profiles of 33 cancer cells using a cDNA microarray representing 27,648 genes coupled with laser microbeam microdissection (LMM). By comparing expression patterns between cancer cells from diagnostic bladder cancer patients and normal human bladder cells (used as universal control), 394 genes that were commonly up-regulated in bladder cancer cells were identified. Of those genes, 288 represent functionally characterized genes that were up-regulated in bladder cancer cells; however, the functions of the remaining 106 (including 51 ESTs) genes are currently unknown. In addition, 1272 genes were identified as being commonly down-regulated in bladder cancer cells. Of these, 1026 represent functionally characterized genes that were down-regulated in bladder cancer cells; however, the functions of the remaining 246 (including 119 ESTs) are currently unknown. The genes contained in the semi-quantitative RT-PCR experiments of representative 44 up-regulated genes supported the results of our microarray analysis. Accordingly, the data herein will provide useful information for finding candidate genes whose products may serve as molecular targets for treatment of bladder cancers.

The present invention is based on the discovery of a pattern of gene expression that correlates with bladder cancer (BLC). Genes that are differentially expressed in bladder cancer are collectively referred to herein as "BLC nucleic acids" or "BLC polynucleotides" and the corresponding encoded polypeptides are referred to as "BLC polypeptides" or "BLC proteins."

Through the expression profiles of bladder cancers, the present inventors identified two specific genes, labeled C2093, B5860N and C6055, respectively, that were significantly overexpressed in bladder cancer cells. Furthermore, the present inventors isolated a novel transcriptional variant of the B5860N and C6055 gene. It was further demonstrated that the treatment of bladder cancer cells with siRNA effectively inhibited expression of C2093, B5860N and C6055 and suppressed cell/tumor growth of bladder cancer. These findings suggest that C2093, B5860N and C6055 play key roles in tumor cell growth, and, therefore, represent promising targets for the development of anti-cancer drugs.

The full-length mRNA sequence of C2093 contained 6319 nucleotides (SEQ ID NO: 1), encoding a polypeptide of 1780 amino acids (SEQ ID NO: 2). The B5860N gene has two different transcriptional variants, consisting of 12 and 11 exons and corresponding to B5860N V1 (SEQ ID NO.3, encoding SEQ ID NO.4) and B5860N V2 (SEQ ID NO.5, encoding SEQ ID NO.6), respectively (FIG. 3b). There were alternative variations in exon 8 of V1; however, the remaining exons were common to both variants. The V2 variant does not have exon 8 of the V1, but does generate the same stop codon within last exon. The full-length cDNA sequences of the B5860NV1 and B5860NV2 variants consist of 5318 and 4466 nucleotides, respectively. The ORF of these variants start within each exon 1. The V1 and V2 transcripts ultimately encode polypeptides of 812 and 528 amino acids, respectively. Accordingly, the term "BS860Ns" as used herein, refers to either or both of transcripts of B5860NV1 and B5860NV2. Namely, in the context of the present invention, it was revealed that the B5860N gene may be expressed as at least two transcript variants. To further confirm the expression pattern of each variant in bladder cancer cell lines and normal human tissues, including bladder, heart, lung, liver, kidney, brain, and pancreas, the present inventors performed northern blot analysis. As a result, it was discovered that both variants were highly overexpressed in bladder cancer cells; however, expression in normal human tissues was either absent or undetectable (FIG. 2f, lower panel). In particular, the V2 transcript was expressed exclusively in testis. The C6055 gene has four different splicing variants consisting of 24, 25, 22 and 22 exons, corresponding to MGC34032 (GeneBank Accession No.NM_152697, SEQ ID NO: 133 encoding a polypeptide of SEQ ID NO: 134), Genbank Accession No.AK128063 (SEQ ID NO: 135 encoding a polypeptide of SEQ ID NO: 136, C6055V1 (SEQ ID NO: 129 encoding a polypeptide of SEQ ID NO: 130) and C6055V2 (SEQ ID NO: 131 encoding a polypeptide of SEQ ID NO: 132), respectively (FIG. 3c). There were alternative variations in exon 1, 2, 3 and 24 of MGC34032, and the other remaining exons were common among four transcripts. C6055V1 and C6055V2 transcripts have no exon 1, 2 and 3 of MGC34032, generating same stop codon within last exon. Moreover, C6055V1, C6055V2 and Genbank Accession No.AK128063 transcripts have a different exon 24 of MGC34032. Genbank Accession No.AK128063 has a new exon as an exon 4a. In particular, the ORF of C6055V1 and C6055V2 transcripts start at within each exon 4, indicating C6055V1 and C6055V2 transcripts have same ORF. The full-length cDNA sequences of MGC34032, Genbank Accession No.AK128063, C6055V1 and C6055V2 transcripts consist of 2302, 3947, 3851, and 3819 nucleotides, respectively. Eventually, MGC34032, Genbank Accession No.AK128063, C6055V1 and C6055V2 transcripts encode 719, 587, 675 and 675 amino acids, respectively. Accordingly, the term "C6055s" as used herein, refers to one or more of transcripts of MGC34032, Genbank Accession No.AK128063, C6055V1 and C6055V2. Namely, in the context of the present invention, it was revealed that the C6055 gene may be expressed as at least four transcript variants. To further confirm the expression pattern of each variant in bladder cancer cell lines and normal human tissues including bladder, heart, lung, liver, kidney, brain, testis, pancreas, we performed northern blot analysis. As a result, approximately 3.9 kb transcripts were highly overexpressed in some bladder cancer cells (HT-1376, SW780 and RT4), but no or undetectable expression in normal human tissues (FIG. 2g). In addition, 7.5 kb transcript was specifically expressed only in HT1376 cells, but we have not yet identified the entire mRNA sequence of this transcript. Furthermore, when we performed northern blot analysis using the common region among these transcripts as a probe, we detected 2.3 kb transcript exclusively in normal testis, corresponding to MGC34032 (FIG. 2h). Therefore, we further perform functional analysis for C6055V1 gene product.

Many anticancer drugs are not only toxic to cancer cells but also to normally growing cells. However, since the normal expression of C2093, B5860Ns and C6055s is restricted to the testis, agents that suppress the expression of C2093, B5860Ns and C6055s may not adversely affect other organs, and thus may be conveniently used for treating or preventing bladder cancer.

Thus, the present invention provides a novel transcriptional variant, B5860NV1, which serves as a candidate for a diagnostic marker for bladder cancer as well as a promising potential target for developing new strategies for bladder cancer diagnosis and effective anti-cancer agents. Furthermore, the present invention provides a polypeptide encoded by this gene, as well as methods for the production and use of the same. More specifically, the present invention provides a novel human polypeptide, B5860NV1, or a functional equivalent thereof, the expression of which is elevated in bladder cancer cells.

In a preferred embodiment, the B5860NV1 polypeptide includes an 811 amino acid (SEQ ID NO: 4) protein encoded by the open reading frame of SEQ ID NO: 3. The present application also provides an isolated protein encoded from at least a portion of the B5860NV1 polynucleotide sequence, or polynucleotide sequences that are at least 15%, more preferably at least 25%, complementary to the sequence set forth in SEQ ID NO: 3, to the extent that they encode a B5860NV1 protein or a functional equivalent thereof. Examples of such polynucleotides are degenerates and allelic mutants of B5860NV1 encoded by the sequence of SEQ ID NO: 3.

As used herein, an isolated gene is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule, such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide.

Accordingly, in one aspect, the invention provides an isolated polynucleotide that encodes a polypeptide described herein or a fragment thereof. Preferably, the isolated polynucleotide includes a nucleotide sequence that is at least 60% identical to the nucleotide sequence shown in SEQ ID NO: 3. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence shown in SEQ ID NO: 3. In the case of an isolated polynucleotide which is longer than or equivalent in length to the reference sequence, e.g., SEQ ID NO: 3, the comparison is made with the full length of the reference sequence. Where the isolated polynucleotide is shorter than the reference sequence, e.g., shorter than SEQ ID NO: 3, the comparison is made to a segment of the reference sequence of the same length (excluding any loop required by the homology calculation).

The present invention also provides a method of producing a protein by transfecting or transforming a host cell with a polynucleotide sequence encoding the B5860NV1 protein, and expressing the polynucleotide sequence. In addition, the present invention provides vectors comprising a nucleotide sequence encoding the B5860NV1 protein, and host cells harboring a polynucleotide encoding the B5860NV1 protein. Such vectors and host cells may be used for producing the B5860NV1 protein.

A binding agent that specifically recognizes the B5860NV1 protein is also provided by the present application. For example, a binding agent may be an antibody raised against a B5860NV1 protein. Alternatively, a binding agent may be a ligand specific for the protein, or a synthetic polypeptide that specifically binds the protein (see e.g., WO2004/044011). An antisense polynucleotide (e.g., antisense DNA), ribozyme, and siRNA (small interfering RNA) of the B5860NV1 gene are also provided.

Accordingly, the present invention provides a method of diagnosing or determining a predisposition to bladder cancer in a subject by determining an expression level of a BLC-associated gene in a patient-derived biological sample, such as tissue sample. The term "BLC-associated gene" refers to a gene that is characterized by an expression level which differs in a BLC cell as compared to a normal cell. A normal cell is one obtained from bladder tissue. In the context of the present invention, a BLC-associated gene is a gene listed in Tables 4-5 (i.e., genes of BLC Nos. 1-1666). An alteration, e.g., an increase or decrease in the level of expression of a gene as compared to a normal control level of the gene, indicates that the subject suffers from or is at risk of developing BLC.

In the context of the present invention, the phrase "control level" refers to a protein expression level detected in a control sample and includes both a normal control level and a bladder cancer control level. A control level can be a single expression pattern derived from a single reference population or a value derived from a plurality of expression patterns. For example, the control level can be obtained from a database of expression patterns from previously tested cells. A "normal control level" refers to a level of gene expression detected in a normal, healthy individual or in a population of individuals known not to be suffering from bladder cancer. A normal individual is one with no clinical symptoms of bladder cancer. On the other hand, a "BLC control level" refers to an expression profile of BLC-associated genes found in a population suffering from BLC.

An increase in the expression level of one or more BLC-associated genes listed in Table 4 (i.e., the over-expressed or up-regulated genes of BLC Nos. 1-394) detected in a test sample as compared to a normal control level indicates that the subject (from which the sample was obtained) suffers from or is at risk of developing BLC. In contrast, a decrease in the expression level of one or more BLC-associated genes listed in Table 5 (i.e., the under-expressed or down-regulated genes of BLC Nos. 395-1666) detected in a test sample compared to a normal control level indicates said subject suffers from or is at risk of developing BLC.

Alternatively, expression of a panel of BLC-associated genes in a sample can be compared to a BLC control level of the same panel of genes. A similarity between sample expression and BLC control expression indicates that the subject (from which the sample was obtained) suffers from or is at risk of developing BLC.

According to the present invention, a gene expression level is deemed "altered" when expression of the gene is increased or decreased by at least 10%, preferably at least 25%, more preferably 50% or more as compared to the control level. Alternatively, an expression level is deemed "increased" or "decreased" when gene expression is increased or decreased by at least 0.1, at least 0.2, at least 1, at least 2, at least 5, or at least 10 or more fold as compared to a control level. Expression is determined by detecting hybridization, e.g., on an array, of a BLC-associated gene probe to a gene transcript of the patient-derived tissue sample.

In the context of the present invention, the patient-derived tissue sample may be any tissue obtained from a test subject, e.g., a patient known to or suspected of having BLC. For example, the tissue may contain an epithelial cell. More particularly, the tissue may be an epithelial cell from a bladder ductal carcinoma.

The present invention further provides a method for the diagnosis of bladder cancer which includes the step of determining an expression level of a C2093, B5860Ns or C6055s gene in a biological sample from a subject, comparing the expression level of the gene with that in a normal sample, and defining that a high expression level of the C2093, B5860Ns or C6055s gene in the sample indicates that the subject suffers from or is at risk of developing bladder cancer.

The present invention also provides a BLC reference expression profile, comprising a gene expression level of two or more of BLC-associated genes listed in Tables 4-5. Alternatively, the BLC reference expression profile may comprise the levels of expression of two or more of the BLC-associated genes listed in Table 4, or the BLC-associated genes listed in Table 5.

The present invention further provides methods of identifying an agent that inhibits or enhances the expression or activity of a BLC-associated gene, e.g. a BLC-associated gene listed in Tables 4-5, by contacting a test cell expressing a BLC-associated gene with a test compound and determining the expression level of the BLC-associated gene or the activity of its gene product. The test cell may be an epithelial cell, such as an epithelial cell obtained from a bladder carcinoma A decrease in the expression level of an up-regulated BLC-associated gene or the activity of its gene product as compared to a normal control level or activity of the gene or gene product indicates that the test agent is an inhibitor of the BLC-associated gene and may be used to reduce a symptom of BLC, e.g. the expression of one or more BLC-associated genes listed in Table 4. Alternatively, an increase in the expression level of a down-regulated BLC-associated gene or the activity of its gene product as compared to a normal control level or activity of the gene or gene product indicates that the test agent is an enhancer of expression or function of the BLC-associated gene and may be used to reduce a symptom of BLC, e.g., the under-expression of one or more BLC-associated genes listed in Table 5.

Further, a method of screening for a compound for treating or preventing bladder cancer is provided by the present invention. The method includes contacting a C2093, B5860Ns or C6055s polypeptide with test compounds, and selecting test compounds that bind to or that alter the biological activity of the C2093, B5860Ns or C6055s polypeptide.

The present invention further provides a method of screening for a compound for treating or preventing bladder cancer, wherein the method includes contacting a test compound with a cell expressing a C2093, B5860Ns or C6055s polypeptide or introduced with a vector comprising a transcriptional regulatory region of C2093, B5860Ns or C6055s upstream of a reporter gene, and selecting the test compound that suppresses the expression level or activity of the C2093, B5860Ns or C6055s polypeptide or a reporter gene product.

The present invention also provides a kit comprising a detection reagent which binds to one or more BLC nucleic acids or BLC polypeptides. Also provided is an array of nucleic acids that binds to one or more BLC nucleic acids.

Therapeutic methods of the present invention include a method of treating or preventing BLC in a subject, including the step of administering to the subject an antisense composition. In the context of the present invention, the antisense composition reduces the expression of the specific target gene. For example, the antisense composition may contain a nucleotide which is complementary to a BLC-associated gene sequence selected from the group consisting of the upregulated BLC-associated genes listed in Table 4. Alternatively, the present method may include the steps of administering to a subject a small interfering RNA (siRNA) composition. In the context of the present invention, the siRNA composition reduces the expression of a BLC nucleic acid selected from the group consisting of the BLC-associated genes listed in Table 4. In yet another method, the treatment or prevention of BLC in a subject may be carried out by administering to a subject a ribozyme composition. In the context of the present invention, the nucleic acid-specific ribozyme composition reduces the expression of a BLC nucleic acid selected from the group consisting of the BLC-associated genes listed in Table 4. Thus, in the present invention, the BLC-associated genes listed in Table 4 are preferred therapeutic targets for bladder cancer. Other therapeutic methods include those in which a subject is administered a compound that increases the expression of one or more of the down-regulated BLC-associated genes listed in Table 5 or the activity of a polypeptide encoded by one or more of the BLC-associated genes listed in Table 5.

The present invention further provides methods for treating or preventing bladder cancer using the pharmaceutical composition provided by the present invention. In addition, the present invention provides methods for treating or preventing cancer, which comprise the step of administering a C2093, B5860Ns or C6055s polypeptide. It is expected that antitumor immunity will be induced by the administration of a C2093, B5860Ns or C6055s polypeptide. Thus, the present invention also provides a method for inducing anti-tumor immunity, which method comprises the step of administering a C2093, B5860Ns or C6055s polypeptide, as well as pharmaceutical compositions for treating or preventing cancer comprising a C2093, B5860Ns or C6055s polypeptide.

The present invention also includes vaccines and vaccination methods. For example, a method of treating or preventing BLC in a subject may involve administering to the subject a vaccine containing a polypeptide encoded by a nucleic acid selected from the group consisting of the BLC-associated genes listed in Table 4 or an immunologically active fragment of such a polypeptide. In the context of the present invention, an immunologically active fragment is a polypeptide that is shorter in length than the full-length naturally-occurring protein, yet which induces an immune response analogous to that induced by the full-length protein. For example, an immunologically active fragment should be at least 8 residues in length and capable of stimulating an immune cell, such as a T cell or a B cell. Immune cell stimulation can be measured by detecting cell proliferation, elaboration of cytokines (e.g., IL-2), or production of an antibody.

The present application also provides a pharmaceutical composition for treating or preventing bladder cancer. The pharmaceutical composition may be, for example, an anticancer agent. The pharmaceutical composition can comprise at least a portion of antisense S-oligonucleotides, siRNA molecules or ribozymes against the C2093, B5860Ns or C6055s polynucleotide sequences shown and described in SEQ ID NOs: 1, 3, 5, 129, 131, 133 and 135 respectively. A suitable siRNA targets a sequence of SEQ ID NO: 21, 25 or 144. Thus, an siRNA of the invention comprises a nucleotide sequence selected from SEQ ID NO: 21, 25 or 144. This may be preferably selected as targets for treating or preventing bladder cancer according to the present invention. The pharmaceutical compositions may be also those comprising the compounds selected by the present methods of screening for compounds for treating or preventing cell proliferative diseases, such as bladder cancer.

The course of action of the pharmaceutical composition is desirably to inhibit growth of the cancerous cells, such as bladder cancer cells. The pharmaceutical composition may be applied to mammals, including humans and domesticated mammals. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein below. All publications, patent applications, patents, and other references mentioned herein are incorporated by reference herein in their entirety. In case of conflict, the present specification, including definitions, will control. In addition, the materials, methods, and examples are illustrative only and not intended to be limiting.

One advantage of the methods described herein is that the disease is identified prior to detection of overt clinical symptoms of bladder cancer. Other features and advantages of the invention will become more fully apparent when the following detailed description is read in conjunction with the accompanying figures and examples, as well as the claims appended hereto.

BRIEF DESCRIPTION OF THE DRAWINGS

FIG. 1a is a photograph of a DNA agarose gel showing expression of representative 44 genes and GAPDH examined by semi-quantitative RT-PCR using cDNA prepared from amplified RNA. The first 10 lanes show the expression level of the genes in different bladder cancer patients. The next 2 lanes show the expression level of the genes in bladder from a normal individual; normal transitional cells and bulk. The last 4 lanes show the expression level of the genes in a normal human tissues; Heart, Lung, Liver and Kidney. (b) C2093 and (c) B5860N in tumor cells from 21 bladder cancer patients (1001, 1009, 1010, 1012, 1013, 1014, 1015, 1016, 1017, 1018, 1019, 1020, 1021, 1022, 1023, 1024, 2003, 2014, 3001, 5001, 5002) (upper and middle panel), bladder cancer cell lines (HT1197, UMUC3, J82, HT1376, SW780 and RT4) (lower panel), and normal human tissues (normal bulk; normal bladder, TC; microdissected transitional cells, heart, lung, liver, kidney).

FIG. 5 depicts the growth-inhibitory effects of small-interfering RNAs (siRNAs) designed to reduce the expression of C2093 in bladder cancer cells. (a) Semi-quantitative RT-PCR showing suppression of endogenous expression of C2093 in bladder cancer cell line, UMUC3 cells. GAPDH was used as an internal control. EGFP; EGFP sequence and SCR; scramble sequence as control (see Materials and Methods) (b) Colony-formation assay demonstrating a decrease in the numbers of colonies by knockdown of C2093 in UMUC3 cells. (c) MTT assay demonstrating a decrease in the numbers of colonies by knockdown of C2093 in UMUC3 cells. (d) Semi-quantitative RT-PCR showing suppression of endogenous expression of C2093 in bladder cancer cell line, J82 cells. GAPDH was used as an internal control. (e) Colony-formation assay demonstrating a decrease in the numbers of colonies by knockdown of C2093 in J82 cells. (f) MTT assay demonstrating a decrease in the numbers of colonies by knockdown of C2093 in J82 cells.

FIG. 6 depicts the growth-inhibitory effects of small-interfering RNAs (siRNAs) designed to reduce the expression of B5860N in bladder cancer cells. (a) Semi-quantitative RT-PCR showing suppression of endogenous expression of B5860N in bladder cancer cell line, J82 cells. GAPDH was used as an internal control. EGFP; EGFP sequence and SCR; scramble sequence as controls (see Materials and Methods). (b) Colony-formation assay demonstrating a decrease in the numbers of colonies by knockdown of B5860N in J82 cells. (c) MTT assay demonstrating a decrease in the numbers of colonies by knockdown of B5860N in J82 cells.

FIG. 9 (a) Expression of C2093 in bladder cancer tissue sections (right panel x200; left panel X100), (b) Expression of B5860N in bladder cancer tissue sections (right panel x200; left panel X100), normal bladder tissues (bottom panel).

DETAILED DESCRIPTION OF THE INVENTION

Figure 2:
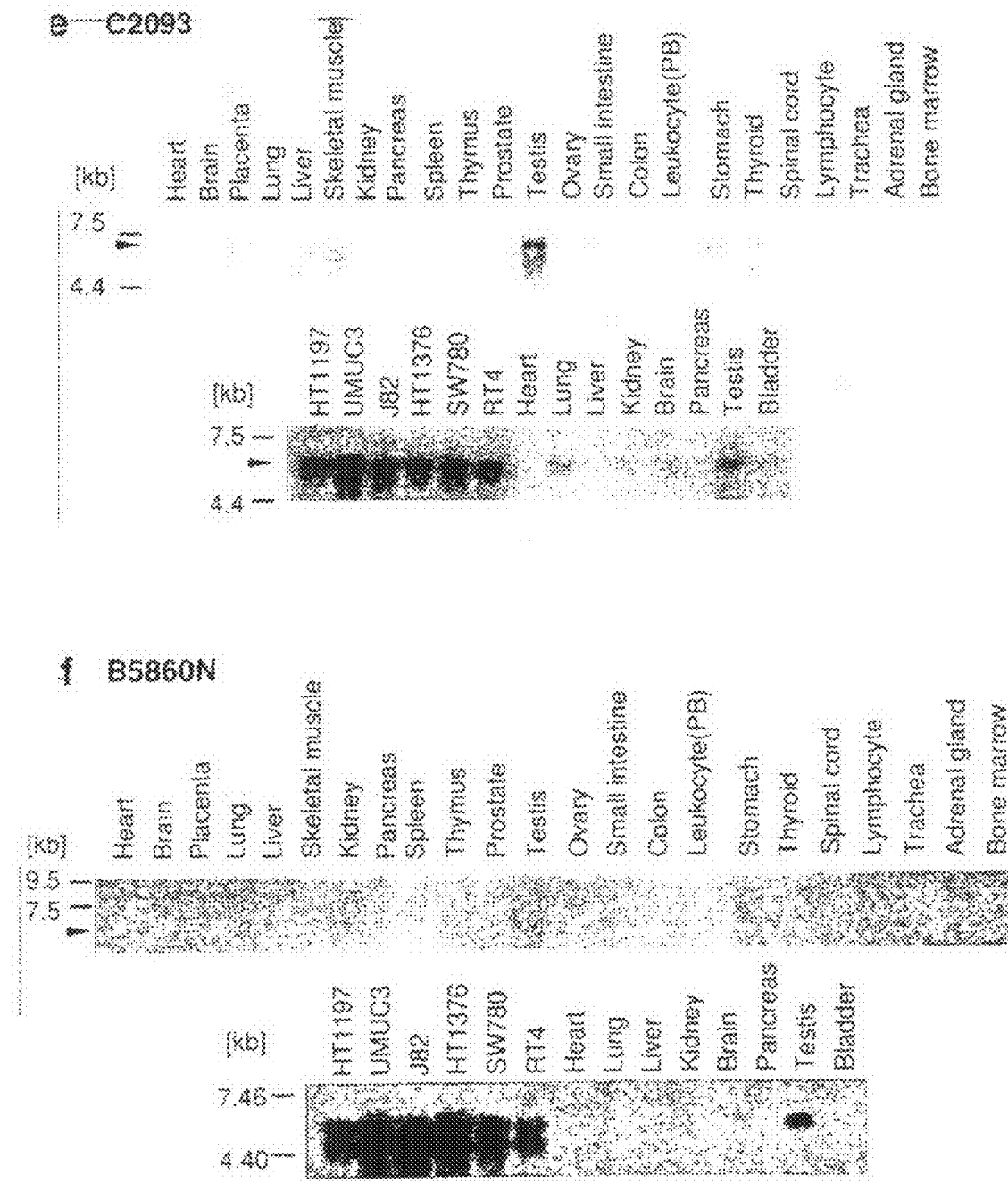
FIG. 2 depicts the results of Northern blot analysis with bladder cancer cell lines and normal human tissues including normal bladder using A0576N(a), C5509(b), F1653(c), B9838(d), C2093(e), B5860N(f), C6055(g,h) DNA fragment as each probe.
Figure 2:
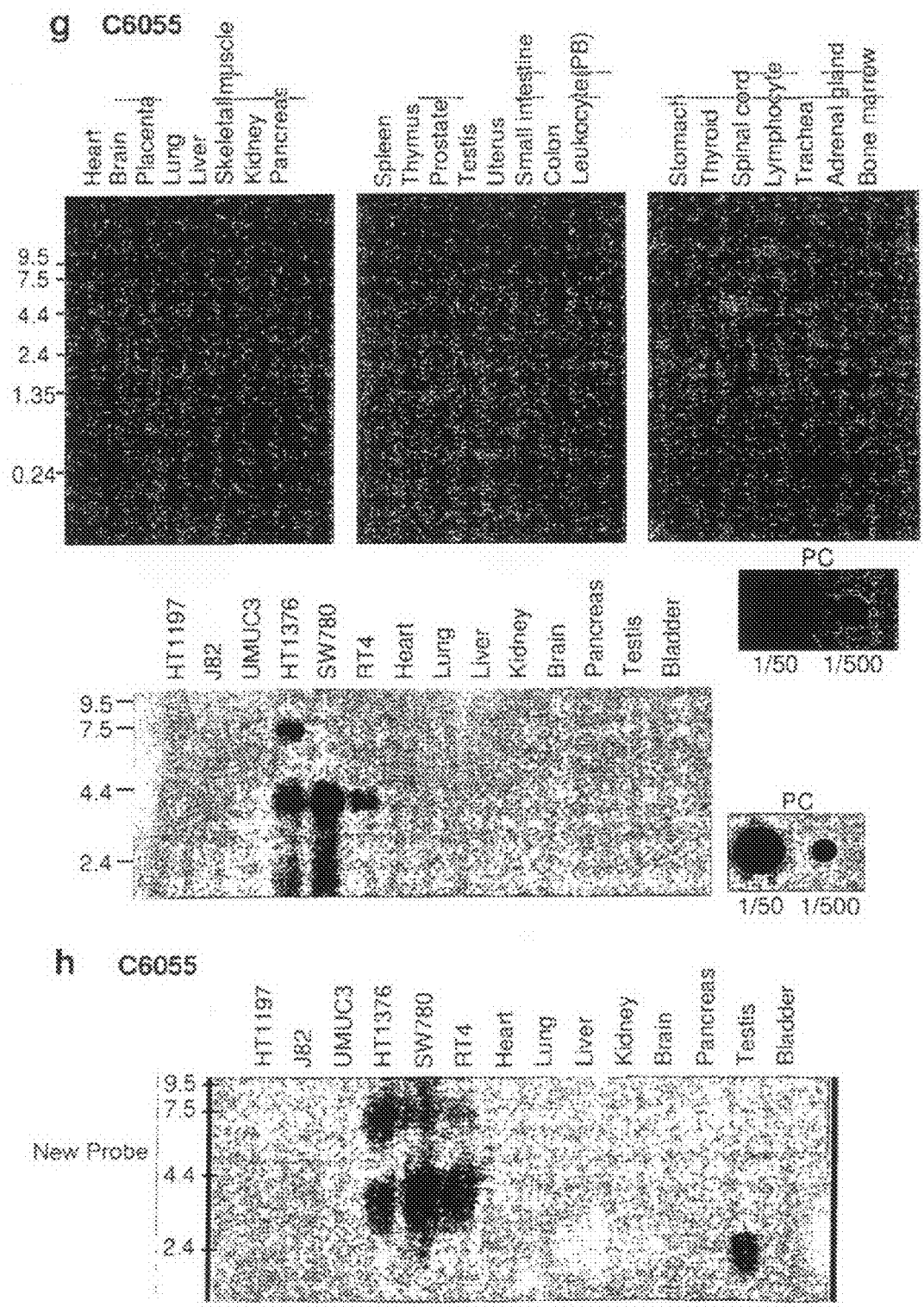

The words "a", "an" and "the" as used herein mean "at least one" unless otherwise specifically indicated.

Generally bladder cancer cells exist as a solid mass having a highly inflammatory reaction and containing various cellular components. Therefore, previous published microarray data are likely to reflect heterogenous profiles.

With these issues in view, the present inventors prepared purified populations of bladder cancer cells by a method of laser-microbeam microdissection (LMM), and analyzed genome-wide gene-expression profiles of 33 BLCs, using a cDNA microarray representing 27,648 genes. These data not only should provide important information about bladder carcinogenesis, but should also facilitate the identification of candidate genes whose products may serve as diagnostic markers and/or as molecular targets for the treatment of patients with bladder cancer and provide clinically relevant information.

The present invention is based, in part, on the discovery of changes in expression patterns of multiple nucleic acids between epithelial cells and carcinomas of patients with BLC. The differences in gene expression were identified using a comprehensive cDNA microarray system.

The gene-expression profiles of cancer cells from 33 BLCs were analyzed using a cDNA microarray representing 27,648 genes coupled with laser microdissection. By comparing expression patterns between cancer cells from patients diagnosed with BLC and normal ductal epithelial cells purely selected with Laser Microdissection, 394 genes (shown in Table 4) were identified as commonly up-regulated in BLC cells. Similarly, 1272 genes (shown in Table 5) were also identified as being commonly down-regulated in BLC cells. In addition, selection was made of candidate molecular markers having the potential to detect cancer-related proteins in serum or sputum of patients, and some potential targets for development of signal-suppressing strategies in human BLC were discovered. Among them, Tables 4 and 5 provide a list of genes whose expression is altered between BLC and normal tissue.

The differentially expressed genes identified herein find diagnostic utility as markers of BLC and as BLC gene targets, the expression of which may be altered to treat or alleviate a symptom of BLC. The genes whose expression level is modulated (i.e., increased or decreased) in BLC patients are summarized in Tables 4-5 and are collectively referred to herein as "BLC-associated genes", "BLC nucleic acids" or "BLC polynucleotides" and the corresponding encoded polypeptides are referred to as "BLC polypeptides" or "BLC proteins." Unless otherwise indicated, the term "BLC" refers to any of the sequences disclosed herein (e.g., BLC-associated genes listed in Tables 4-5). Genes that have been previously described are presented along with a database accession number.

By measuring the expression of the various genes in a sample of cells, BLC can be diagnosed. Similarly, measuring the expression of these genes in response to various agents can identify agents for treating BLC.

The present invention involves determining (e.g., measuring) the expression of at least one, and up to all, of the BLC-associated genes listed in Tables 4-5. Using sequence information provided by the GenBank™ database entries for known sequences, the BLC-associated genes can be detected and measured using techniques well known to one of ordinary skill in the art. For example, sequences within the sequence database entries corresponding to BLC-associated genes can be used to construct probes for detecting RNA sequences corresponding to BLC-associated genes in, e.g., Northern blot hybridization analyses. Probes typically include at least 10, at least 20, at least 50, at least 100, or at least 200 nucleotides of a reference sequence. As another example, the sequences can be used to construct primers for specifically amplifying one or more BLC nucleic acid in, e.g., amplification-based detection methods, such as reverse-transcription based polymerase chain reaction.

Expression level of one or more of BLC-associated gene in a test cell population, e.g., a patient-derived tissues sample, is then compared to the expression level(s) of the same gene(s) in a reference population. The reference cell population includes one or more cells for which the compared parameter is known, i.e., bladder ductal carcinoma cells (e.g., BLC cells) or normal bladder ductal epithelial cells (e.g., non-BLC cells).

Whether or not a pattern of gene expression in a test cell population as compared to a reference cell population indicates BLC or a predisposition thereto depends upon the composition of the reference cell population. For example, if the reference cell population is composed of non-BLC cells, a similarity in gene expression pattern between the test cell population and the reference cell population indicates that the test cell population is non-BLC. Conversely, if the reference cell population is made up of BLC cells, a similarity in gene expression profile between the test cell population and the reference cell population indicates that the test cell population includes BLC cells.

A level of expression of a BLC marker gene in a test cell population is considered "altered" if it varies from the expression level of the corresponding BLC marker gene in a reference cell population by more than 1.1, more than 1.5, more than 2.0, more than 5.0, or more than 10.0 fold.

Differential gene expression between a test cell population and a reference cell population can be normalized to a control nucleic acid, e.g. a housekeeping gene. For example, a control nucleic acid is one which is known not to differ depending on the cancerous or non-cancerous state of the cell. The expression level of a control nucleic acid can be used to normalize signal levels in the test and reference populations. Exemplary control genes include, but are not limited to, e.g., β-actin, glyceraldehyde 3-phosphate dehydrogenase and ribosomal protein P1.

The test cell population can be compared to multiple reference cell populations. Each of the multiple reference populations may differ in the known parameter. Thus, a test cell population may be compared to a first reference cell population known to contain, e.g., BLC cells, as well as a second reference population known to contain, e.g., non-BLC cells (e.g., normal cells). The test cell may be included in a tissue type or cell sample from a subject known to contain, or suspected of containing, BLC cells.

The test cell is preferably obtained from a bodily tissue or a bodily fluid, e.g., biological fluid (such as blood; sputum or urine, for example). For example, the test cell may be purified from bladder tissue. Preferably, the test cell population comprises an epithelial cell. The epithelial cell is preferably from a tissue known to be or suspected to be a bladder ductal carcinoma.

Cells in the reference cell population should be derived from a tissue type similar to that of the test cell. Optionally, the reference cell population is a cell line, e.g. a BLC cell line (i.e., a positive control) or a normal non-BLC cell line (i.e., a negative control). Alternatively, the control cell population may be derived from a database of molecular information derived from cells for which the assayed parameter or condition is known.

The subject is preferably a mammal. Exemplary mammals include, but are not limited to, e.g., a human, non-human primate, mouse, rat, dog, cat, horse, or cow.

Expression of the genes disclosed herein can be determined at the protein or nucleic acid level, using methods known in the art. For example, Northern hybridization analysis, using probes which specifically recognize one or more of these nucleic acid sequences, can be used to determine gene expression. Alternatively, gene expression may be measured using reverse-transcription-based PCR assays, e.g., using primers specific for the differentially expressed gene sequences. Expression may also be determined at the protein level, i.e., by measuring the level of a polypeptide encoded by a gene described herein, or the biological activity thereof. Such methods are well known in the art and include, but are not limited to, e.g., immunoassays that utilize antibodies to proteins encoded by the genes. The biological activities of the proteins encoded by the genes are generally well known.

To disclose the mechanism of bladder cancer and identify novel diagnostic markers and/or drug targets for the treatment and/or prevention of these tumors, the present inventors analyzed the expression profiles of genes in bladder cancer using a genome-wide cDNA microarray combined with laser microbeam microdissection. As a result, C2093, B5860N and C6055 specifically over-expressed in bladder cancer cells were identified. Furthermore, suppression of the expression of C2093, B5860N or C6055 gene with small interfering RNAs (siRNAs) resulted in a significant growth-inhibition of cancerous cells. These findings suggest that C2093, B5860N and/or C6055 render oncogenic activities to cancer cells, and that inhibition of the activity of one or more of these proteins could be a promising strategy for the treatment and prevention of proliferative diseases such as bladder cancers.

B5860N:

According to the present invention, a cDNA with a similar sequence was identified and encode variants of B5860N. The cDNA of the longer variant consists of 5318 nucleotides and contains an open reading frame of 2436 nucleotides (SEQ ID NO: 3). The open reading frame of known B5860N consists of 1584 nucleotide and encodes a 527 amino acid-protein (GeneBank Accession Number NM_017779). Therefore, the longer variant, consisting of 5318 nucleotide, is novel to the instant invention. Furthermore, the known sequence of the B5860N cDNA encoding the 527 amino acid-protein consists of 3338 nucleotides. However, in the present invention, a full length cDNA of B5860N consisting of 4466 nucleotide was isolated. The nucleotide sequence of this shorter variant comprises a novel sequence of 3'-UTR as compared with the known nucleotide sequence, although both of the amino acid sequences encoded thereby were identical. In the present specification, the transcripts of the shorter variant, encoding the known 527 amino acid-protein, and the longer variant, encoding the novel 811 amino acid-protein, are described herein as B5860NV2 and B5860NV1, respectively. The nucleotide sequence of B5860NV1 and B5860NV2, and amino acid sequence encoded thereby are set forth in the following SEQ ID NOs.

|  | nucleotide sequence | amino acid sequence |
|---|---|---|
| B5860NV1 | SEQ ID NO: 3 | SEQ ID NO: 4 |
| B5860NV2 | SEQ ID NO: 5 | SEQ ID NO: 6 |

Thus, the present invention provides substantially pure polypeptides encoded by the longer variant B5860NV1, including polypeptides comprising the amino acid sequence of SEQ ID NO: 4, as well as functional equivalents thereof, to the extent that they encode a B5860NV1 protein. Examples of polypeptides functionally equivalent to B5860NV1 include, for example, homologous proteins of other organisms corresponding to the human B5860NV1 protein, as well as mutants of human B5860NV1 proteins.

Figure 3:
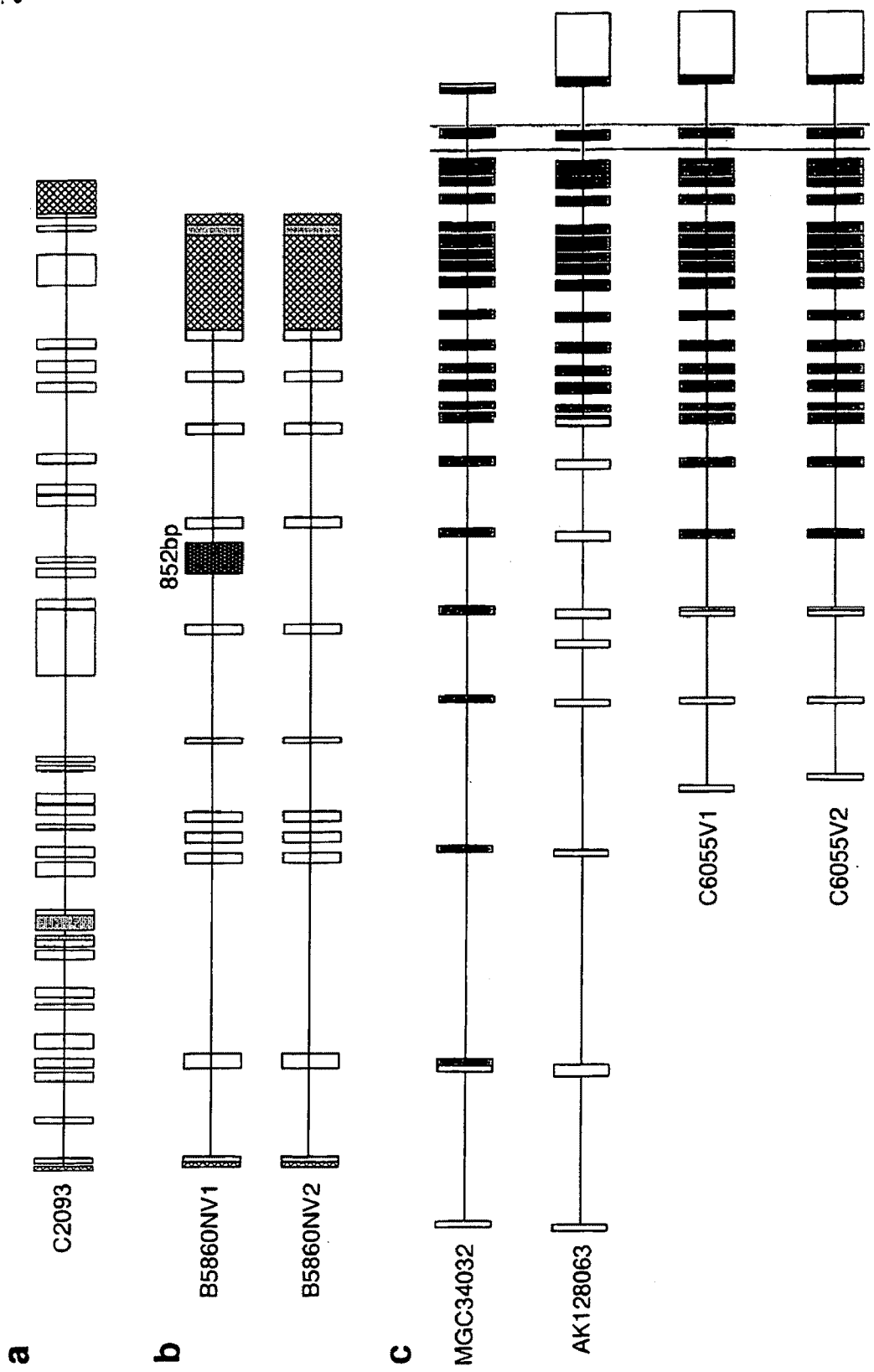
FIG. 3 shows Genomic structure of (a) C2093, (b) B5860N and (c) C6055. B5860N has two different variants, designated V1 and V2. C6055 has four different variants, designed MGC34032, Genbank Accession No.AK128063, C6055V1 and C6055V2.

C6055:

According to the present invention, a cDNA with a similar sequence was identified and encode variants of C6055. According to the database from NCBI, C6055 consists of 24 exons, designated MGC34032, located on the chromosome 1p31.3. Because C6055 is not included within last exon (exon24) of MGC34032 on database, we performed RT-PCR as EST-walking, and 5'RACE and 3'RACE experiments using bladder cancer cell line, SW780, as a template to obtain the entire cDNA sequence of C6055 (see Materials and Methods). As a result, we found two novel transcripts, C6055V1 and C6055V2. Eventually, this gene has four different splicing variants consisting of 24, 25, 22 and 22 exons, corresponding to MGC34032, Genbank Accession No.AK128063, C6055V1 and C6055V2, respectively (FIG. 3c). There were alternative splicing in exon 1, 2, 3, 4 and 24 of MGC34032, and the other remaining exons were common among four transcripts. C6055V1 and C6055V2 transcripts have no exon 1, 2 and 3 of MGC34032, generating same stop codon within last exon. In particular, the ORF of C6055V1 and C6055V2 transcripts start at within each exon 4, indicating C6055V1 and C6055V2 transcripts have same ORF. The full-length cDNA sequences of MGC34032, Genbank Accession No.AK128063, C6055V1 and C6055V2 transcripts consist of 2302, 3947, 3851, and 3819 nucleotides, respectively. Eventually, MGC34032, Genbank Accession No.AK128063, C6055V1 and C6055V2 transcripts encode 719, 587, 675 and 675 amino acids, respectively. The nucleotide sequence of C6055V1 and C6055V2, and amino acid sequence encoded thereby are set forth in the following SEQ ID NOs.

|  | nucleotide sequence | amino acid sequence |
| --- | --- | --- |
| C6055V1 | SEQ ID NO: 129 | SEQ ID NO: 130 |
| C6055V2 | SEQ ID NO: 131 | SEQ ID NO: 132 |

Thus, the present invention provides substantially pure polypeptides encoded by the longer variant C6055V1 or C6055V2, including polypeptides comprising the amino acid sequence of SEQ ID NO: 130 or SEQ ID NO: 132, as well as functional equivalents thereof, to the extent that they encode a Genbank Accession No.AK128063 protein. Examples of polypeptides functionally equivalent to C6055V1 or C6055V2 include, for example, homologous proteins of other organisms corresponding to the human C6055V1 or C6055V2 protein, as well as mutants of human C6055V1 or C6055V2 proteins.

In the present invention, the term "functionally equivalent" means that the subject polypeptide has the activity to promote cell proliferation like the B5860NV1 protein and to confer oncogenic activity to cancer cells. Whether the subject polypeptide has a cell proliferation activity or not can be judged by introducing the DNA encoding the subject polypeptide into a cell, expressing the respective polypeptide and detecting promotion of proliferation of the cells or increase in colony forming activity. Such cells include, for example, NIH3T3, COS7 and HEK293.

Methods for preparing polypeptides functionally equivalent to a given protein are well known by a person skilled in the art and include known methods of introducing mutations into the protein. For example, one skilled in the art can prepare polypeptides functionally equivalent to the human B5860NV1 protein by introducing an appropriate mutation in the amino acid sequence of this protein by site-directed mutagenesis (Hashimoto-Gotoh et al., (1995) Gene 152:271-5; Zoller and Smith, (1983) Methods Enzymol 100: 468-500; Kramer et al., (1984) Nucleic Acids Res. 12:9441-56; Kramer and Fritz, (1987) Methods Enzymol 154: 350-67; Kunkel, (1985) Proc Natl Acad Sci USA 82: 488-92; Kunkel, (1991) Methods Enzymol; 204:125-39). Amino acid mutations can occur in nature, too. The polypeptide of the present invention includes those proteins having the amino acid sequences of the human B5860NV1 protein in which one or more amino acids are mutated, provided the resulting mutated polypeptides are functionally equivalent to the human B5860NV1 protein. In the present invention, the number of mutation is generally no more than 35%, preferably no more than 30%, even more preferably no more than 25%, 20%, 10%, 5%, 2% or 1% of all amino acids. Specifically, the number of amino acids to be mutated in such a mutant is generally 200 or 100 amino acids or less, typically 10 amino acids or less, preferably 6 amino acids or less, and more preferably 3 amino acids or less.

Mutated or modified proteins, proteins having amino acid sequences modified by substituting, deleting, inserting and/or adding one or more amino acid residues of a certain amino acid sequence, have been known to retain the original biological activity (Mark et al., (1984) Proc Natl Acad Sci USA 81: 5662-6; Zoller and Smith, (1982) Nucleic Acids Res 10:6487-500; Dalbadie-McFarland et al., (1982) Proc Natl Acad Sci USA 79: 6409-13). To that end, the amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a polypeptide in which one or more amino acids residues are added to the amino acid sequence of human B5860NV1 protein is a fusion protein containing the human B5860NV1 protein. Fusion proteins, fusions of the human B5860NV1 protein and other peptides or proteins, are included in the present invention. Fusion proteins can be made by techniques well known to a person skilled in the art, such as by linking the DNA encoding the human B5860NV1 protein of the invention with DNA encoding other peptides or proteins, so that the frames match, inserting the fusion DNA into an expression vector and expressing it in a host. There is no restriction as to the peptides or proteins that may be fused to the protein of the present invention.

Known peptides that can be used as peptides that are fused to a protein of the present invention include, for example, FLAG (Hopp et al., (1988) Biotechnology 6: 1204-10), 6×His containing six H is (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment and the like. Examples of proteins that may be fused to a protein of the invention include GST (glutathione-S-transferase), Influenza agglutinin (HA), immunoglobulin constant region, β-galactosidase, MBP (maltose-binding protein) and such.

Fusion proteins can be prepared by fusing commercially available DNA, encoding the fusion peptides or proteins discussed above, with a DNA encoding a polypeptide of the present invention and expressing the fused DNA prepared.

Alternatively, functionally equivalent polypeptides may be isolated using methods known in the art, for example, using a hybridization technique (Sambrook et al., (1989) Molecular Cloning 2nd ed. 9.47-9.58, Cold Spring Harbor Lab. Press).

One skilled in the art can readily isolate a DNA having high homology with a whole or part of the DNA sequence encoding the human B5860NV1 protein (i.e., SEQ ID NO: 3), and isolate functionally equivalent polypeptides to the human B5860NV1 protein from the isolated DNA. The polypeptides of the present invention include those that are encoded by DNA that hybridize with a whole or part of the DNA sequence encoding the human B5860NV1 protein and are functionally equivalent to the human B5860NV1 protein. These polypeptides include mammalian homologues corresponding to the human-derived protein (for example, a polypeptide encoded by a monkey, rat, rabbit and bovine gene). In isolating a cDNA highly homologous to the DNA encoding the human B5860NV1 protein from animals, it is particularly preferable to use tissues from testis or bladder cancer tissue.

The condition of hybridization for isolating a DNA encoding a polypeptide functionally equivalent to the human B5860NV1 protein can be routinely selected by a person skilled in the art. For example, hybridization may be performed by conducting pre-hybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringency condition. A low stringency condition is, for example, 42° C., 2×SSC, 0.1% SDS, or preferably 50° C., 2×SSC, 0.1% SDS. More preferably, high stringency conditions are used. A high stringency condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human B5860NV1 protein, using a primer synthesized based on the sequence information of the protein encoding DNA (SEQ ID NO: 3).

Polypeptides that are functionally equivalent to the human B5860NV1 protein, encoded by the DNA isolated through the above hybridization techniques or gene amplification techniques, normally have a high homology to the amino acid sequence of the human B5860NV1 protein. As used herein, the term "high homology" typically refers to a homology of 40% or higher, preferably 60% or higher, more preferably 80% or higher, even more preferably 85%, 90%, 93%, 95%, 98%, 99% or higher between a polypeptide sequence or a polynucleotide sequence and a reference sequence. Percent homology (also referred to as percent identity) is typically determined between two optimally aligned sequences. Methods of aligning sequences for comparison are well-known in the art. Optimal alignment of sequences and comparison can be conducted, e.g., using the algorithm in "Wilbur and Lipman, (1983) Proc Natl Acad Sci USA 80: 726-30".

A polypeptide of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human B5860NV1 protein of the present invention, it is within the scope of the present invention.

The polypeptides of the present invention can be prepared as recombinant proteins or natural proteins, using methods well known to those skilled in the art. A recombinant protein can be prepared, for example, by inserting a DNA, which encodes a polypeptide of the present invention (for example, the DNA comprising the nucleotide sequence of SEQ ID NO: 3), into an appropriate expression vector, introducing the vector into an appropriate host cell, obtaining the extract, and purifying the polypeptide by subjecting the extract to chromatography, e.g., ion exchange chromatography, reverse phase chromatography, gel filtration or affinity chromatography utilizing a column to which antibodies against the protein of the present invention is fixed or by combining more than one of aforementioned columns.

In addition, when the polypeptide of the present invention is expressed within host cells (for example, animal cells and E. coli) as a fusion protein with glutathione-S-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines or FLAG, it can be detected and purified using antibodies to c-myc, His or FLAG, respectively.

After purifying the fusion protein, it is also possible to exclude regions other than the objective polypeptide by cutting the fusion protein with thrombin or factor-Xa as required.

A natural protein can be isolated by methods known to a person skilled in the art, for example, by contacting the affinity column, in which antibodies binding to the B5860NV1 protein described below are bound, with the extract of tissues or cells expressing the polypeptide of the present invention. The antibodies can be polyclonal antibodies or monoclonal antibodies.

The present invention also encompasses partial peptides of the polypeptides of the present invention. Preferably, the partial peptides of the present invention comprise an amino acid sequence selected from positions 304 to 588 of the amino acid sequence of SEQ ID NO: 4, or a part thereof. The amino acid sequence extending between positions 304 and 588 is a B5860NV1-specific region, as compared to B5860NV2. The partial peptide has an amino acid sequence specific to the polypeptide of the present invention and consists of at least 7 amino acids, preferably 8 amino acids or more, and more preferably 9 amino acids or more. The partial peptide can be used, for example, for preparing antibodies against the polypeptide of the present invention, screening for a compound that binds to the polypeptide of the present invention, and screening for inhibitors of the polypeptide of the present invention.

A partial peptide of the invention can be produced by genetic engineering, by known methods of peptide synthesis or by digesting the polypeptide of the invention with an appropriate peptidase. For peptide synthesis, for example, solid phase synthesis or liquid phase synthesis may be used.

The present invention further provides polynucleotides that encode such B5860NV1 polypeptides described above. The polynucleotides of the present invention can be used for the in vivo or in vitro production of a polypeptide of the present invention as described above, or can be applied to gene therapy for diseases attributed to genetic abnormality in the gene encoding the protein of the present invention. Any form of the polynucleotide of the present invention can be used, so long as it encodes a polypeptide of the present invention, including mRNA, RNA, cDNA, genomic DNA, chemically synthesized polynucleotides. The polynucleotide of the present invention includes a DNA comprising a given nucleotide sequences as well as its degenerate sequences, so long as the resulting DNA encodes a polypeptide of the present invention.

A polynucleotide of the present invention can be prepared by methods known to a person skilled in the art. For example, a polynucleotide of the present invention can be prepared by: preparing a cDNA library from cells which express a polypeptide of the present invention, and conducting hybridization using a partial sequence of the DNA of the present invention (for example, SEQ ID NO: 3) as a probe. A cDNA library can be prepared, for example, by the method described in Sambrook et al., (1989) Molecular Cloning, Cold Spring Harbor Laboratory Press; alternatively, commercially available cDNA libraries may be used. A cDNA library can be also prepared by: extracting RNAs from cells expressing the polypeptide of the present invention, synthesizing oligo DNAs based on the sequence of the DNA of the present invention (for example, SEQ ID NO: 3), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained. Moreover, by screening the genomic DNA library using the obtained cDNA or parts thereof as a probe, the genomic DNA can be isolated.

More specifically, mRNAs may first be prepared from a cell, tissue or organ (e.g., testis) or bladder cancer cell line in which the object polypeptide of the invention is expressed. Known methods can be used to isolate mRNAs; for instance, total RNA may be prepared by guanidine ultracentrifugation (Chirgwin et al., (1979) Biochemistry 18:5294-9) or AGPC method (Chomczynski and Sacchi, (1987) Anal Biochem 162:156-9). In addition, mRNA may be purified from total RNA using mRNA Purification Kit (Pharmacia) and such. Alternatively, mRNA may be directly purified by QuickPrep mRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., (1988) Proc Natl Acad Sci USA 85: 8998-9002; Belyavsky et al., (1989) Nucleic Acids Res 17: 2919-32), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform *E. coli* and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., (1981) Nucleic Acids Res 9: 43-74). The sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA or TAG).

Specifically, the polynucleotide of the present invention encompasses the DNA comprising the nucleotide sequence of SEQ ID NO: 3.

Furthermore, the present invention provides a polynucleotide that hybridizes under stringent conditions with a polynucleotide having a nucleotide sequence of SEQ ID NO: 3, and encodes a polypeptide functionally equivalent to the B5860NV1 protein of the invention described above. One skilled in the art may appropriately choose the appropriately stringent conditions. For example, low stringency condition can be used. More preferably, high stringency condition can be used. These conditions are the same as that described above. The hybridizing DNA above is preferably a cDNA or a chromosomal DNA.

The present invention also provides a polynucleotide which is complementary to the polynucleotide encoding human B5860NV1 protein (SEQ ID NO: 3) or the complementary strand thereof, and which comprises at least 15 nucleotides, wherein the polynucleotide hybridizes with the nucleotide sequence extending between positions 988 and 1842 of SEQ ID NO:3. The polynucleotide of the present invention is preferably a polynucleotide which specifically hybridizes with the DNA encoding the B5860NV1 polypeptide of the present invention. The term "specifically hybridize" as used herein, means that significant cross-hybridization does not occur with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the polypeptide of the invention or its complementary strand. Moreover, such polynucleotide can be utilized for the preparation of DNA chip.

Vectors and Host Cells

The present invention also provides a vector and host cell into which a polynucleotide of the present invention is introduced. A vector of the present invention is useful to keep a polynucleotide, especially a DNA, of the present invention in host cell, to express the polypeptide of the present invention, or to administer the polynucleotide of the present invention for gene therapy.

When *E. coli* is the host cell and the vector is amplified and produced in a large amount in *E. coli* (e.g., JM109, DH5α, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, the M13-series vectors, pUC-series vectors, pBR322, pBluescript, pCR-Script, etc. can be used. In addition, pGEM-T, pDIRECT and pT7 can also be used for subcloning and extracting cDNA as well as the vectors described above. When a vector is used to produce a protein of the present invention, an expression vector is especially useful. For example, an expression vector to be expressed in *E. coli* should have the above characteristics to be amplified in *E. coli*. When *E. coli*, such as JM109, DH5α, HB101 or XL1 Blue, are used as a host cell, the vector should have a promoter, for example, lacZ promoter (Ward et al., (1989) Nature 341: 544-6; (1992) FASEB J 6: 2422-7), araB promoter (Better et al., (1988) Science 240: 1041-3), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the *E. coli* is the pelB signal sequence (Lei et al., (1987) J Bacteriol 169:

4379-83.). Means for introducing of the vectors into the target host cells include, for example, the calcium chloride method, and the electroporation method.

In addition to *E. coli*, for example, expression vectors derived from mammals (for example, pcDNA3 (Invitrogen) and pEF-BOS (Mizushima S and Nagata S, (1990) Nucleic Acids Res 18(17): 5322), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., (1979) Nature 277: 108), the MMLV-LTR promoter, the EF1α promoter (Mizushima et al., (1990) Nucleic Acids Res 18: 5322), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Producing Polypeptides

In addition, the present invention provides methods for producing a polypeptide of the present invention. The polypeptides may be prepared by culturing a host cell which harbors an expression vector comprising a gene encoding the polypeptide. According to needs, methods may be used to express a gene stably and, at the same time, to amplify the copy number of the gene in cells. For example, a vector comprising the complementary DHFR gene (e.g., pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells and purified as a substantially pure homogeneous polypeptide. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., (1996) Cold Spring Harbor Laboratory Press). These chromatographies may be performed by liquid chromatography, such as HPLC and FPLC. Thus, the present invention provides for highly purified polypeptides prepared by the above methods.

A polypeptide of the present invention may be optionally modified or partially deleted by treating it with an appropriate protein modification enzyme before and/or after purification. Useful protein modification enzymes include, but are not limited to, trypsin, chymotrypsin, lysylendopeptidase, protein kinase, glucosidase and so on.

Diagnosing Bladder Cancer:

In the context of the present invention, BLC is diagnosed by measuring the expression level of one or more BLC nucleic acids from a test population of cells, (i.e., a patient-derived biological sample). Preferably, the test cell population contains an epithelial cell, e.g., a cell obtained from bladder tissue. Gene expression can also be measured from blood or other bodily fluids such as urine. Other biological samples can be used for measuring protein levels. For example, the protein level in blood or serum derived from a subject to be diagnosed can be measured by immunoassay or other conventional biological assay.

Expression of one or more BLC-associated genes, e.g., genes listed in Tables 4-5, is determined in the test cell or biological sample and compared to the normal control expression level associated with the one or more BLC-associated gene(s) assayed. A normal control level is an expression profile of a BLC-associated gene typically found in a population known not to be suffering from BLC. An alteration (e.g., an increase or decrease) in the level of expression in the patient-derived tissue sample of one or more BLC-associated genes indicates that the subject is suffering from or is at risk of developing BLC. For example, an increase in the expression of one or more up-regulated BLC-associated genes listed in Table 4 in the test population as compared to the normal control level indicates that the subject is suffering from or is at risk of developing BLC. Conversely, a decrease in expression of one or more down-regulated BLC-associated genes listed in Table 5 in the test population as compared to the normal control level indicates that the subject is suffering from or is at risk of developing BLC.

Alteration of one or more of the BLC-associated genes in the test population as compared to the normal control level indicates that the subject suffers from or is at risk of developing BLC. For example, alteration of at least 1%, at least 5%, at least 25%, at least 50%, at least 60%, at least 80%, or at least 90% or more of the panel of BLC-associated genes (genes listed in Tables 4-5) indicates that the subject suffers from or is at risk of developing BLC.

Moreover, the present invention provides a method for diagnosing cell proliferative disease such as bladder cancer using the expression level of the genes of the present invention as a diagnostic marker. This diagnostic method comprises the steps of: (a) detecting the expression level of one or more of C2093, B5860Ns and C6055s gene; and (b) relating an elevation of the expression level to bladder cancer. In the context of the present invention, the transcript of the B5860N gene includes B5860NV1 and B5860NV2. In the context of the present invention, the transcript of the C6055 gene includes MGC34032, Genbank Accession No.AK128063, C6055V1 and C6055V2. The expression levels of the C2093, B5860Ns or C6055s gene in a biological sample can be estimated by quantifying mRNA corresponding to or protein encoded by the C2093, B5860Ns or C6055s gene. Quantification methods for mRNA are known to those skilled in the art. For example, the levels of mRNAs corresponding to the C2093, B5860Ns or C6055s gene can be estimated by Northern blotting or RT-PCR. Since the full-length nucleotide sequences of the C2093 gene is shown in SEQ ID NO: 1. Alternatively, the full-length nucleotide sequences of two variant forms of B5860N gene transcripts are also shown in SEQ ID NO: 3 and 5. Alternatively, the full-length nucleotide sequences of four variant forms of C6055 gene transcripts are also shown in SEQ ID NO: 129, 131, 133 and 135. Accordingly, anyone skilled in the art can design the nucleotide sequences for probes or primers to quantify the C2093, B5860N or C6055 gene.

Also, the expression level of the C2093, B5860Ns or C6055s gene can be analyzed based on the activity or quantity of protein encoded by the gene. A method for determining the quantity of the C2093, B5860N or C6055 protein is shown in below. For example, immunoassay methods are useful for the determination of the proteins in biological materials. Any biological materials can be used as the biological sample for the determination of the protein or its activity, so long as the marker gene (i.e, the C2093, B5860Ns or C6055s gene) is expressed in the sample of a bladder cancer patient. For example, in the context of the present invention, bladder tissue is a preferred biological sample. However, bodily fluids, such as blood and urine, may be also analyzed. On the other hand, a suitable method can be selected for the determination of the activity of a protein encoded by the C2093, B5860Ns or C6055s gene according to the activity of a protein to be analyzed.

Expression levels of the C2093, B5860Ns or C6055s gene in a biological sample are estimated and compared with those in a normal sample (e.g., a sample derived from a non-diseased subject). When such a comparison shows that the expression level of the target gene is higher than those in the normal sample, the subject is judged to be affected with bladder cancer. The expression level of the C2093, B5860Ns or C6055s gene in the biological samples from a normal subject and subject to be diagnosed may be determined at the same time. Alternatively, normal ranges of the expression levels can be determined by a statistical method based on the results obtained by analyzing the expression level of the gene in samples previously collected from a control group. A result obtained by comparing the sample of a subject is compared with the normal range; when the result does not fall within the normal range, the subject is judged to be affected with or is at risk of developing bladder cancer.

In the present invention, a diagnostic agent for diagnosing cell proliferative disease, such as bladder cancer, is also provided. The diagnostic agent of the present invention comprises a compound that binds to C2093, B5860Ns or C6055s gene transcript or polypeptide encoded thereby. Preferably, an oligonucleotide that hybridizes to the polynucleotide comprising the nucleotide sequence selected from the group consisting of SEQ ID NOs: 1, 3, 5, 129, 131, 133 and 135, or an antibody that binds to the polypeptide consisting of amino acid sequence selected from the group consisting of SEQ ID NOs: 2, 4, 6, 130, 132, 134 and 136 may be used as such a compound.

Identifying Agents that Inhibit or Enhance BLC-Associated Gene Expression:

An agent that inhibits the expression of a BLC-associated gene or the activity of its gene product can be identified by contacting a test cell population expressing a BLC-associated up-regulated gene with a test agent and then determining the expression level of the BLC-associated gene or the activity of its gene product. A decrease in the level of expression of the BLC-associated gene or in the level of activity of its gene product in the presence of the agent as compared to the expression or activity level in the absence of the test agent indicates that the agent is an inhibitor of a BLC-associated up-regulated gene and useful in inhibiting BLC.

Alternatively, an agent that enhances the expression of a BLC-associated down-regulated gene or the activity of its gene product can be identified by contacting a test cell population expressing a BLC-associated gene with a test agent and then determining the expression level or activity of the BLC-associated down-regulated gene. An increase in the level of expression of the BLC-associated gene or in the level of activity of its gene product as compared to the expression or activity level in the absence of the test agent indicates that the test agent augments expression of the BLC-associated down-regulated gene or the activity of its gene product.

The test cell population may be any cell expressing the BLC-associated genes. For example, the test cell population may contain an epithelial cell, such as a cell derived from bladder tissue. Furthermore, the test cell may be an immortalized cell line derived from a carcinoma cell. Alternatively, the test cell may be a cell which has been transfected with a BLC-associated gene or which has been transfected with a regulatory sequence (e.g., a promoter sequence) from a BLC-associated gene operably linked to a reporter gene.

Assessing Efficacy of Treatment of BLC in a Subject:

The differentially expressed BLC-associated genes identified herein also allow for the course of treatment of BLC to be monitored. In this method, a test cell population is provided from a subject undergoing treatment for BLC. If desired, test cell populations are obtained from the subject at various time points, for example, before, during, and/or after treatment. Expression of one or more of the BLC-associated genes in the cell population is then determined and compared to a reference cell population which includes cells whose BLC state is known. In the context of the present invention, the reference cells should have not been exposed to the treatment of interest.

If the reference cell population contains no BLC cells, a similarity in the expression of a BLC-associated gene in the test cell population and the reference cell population indicates that the treatment of interest is efficacious. However, a difference in the expression of a BLC-associated gene in the test population and a normal control reference cell population indicates a less favorable clinical outcome or prognosis. Similarly, if the reference cell population contains BLC cells, a difference between the expression of a BLC-associated gene in the test cell population and the reference cell population indicates that the treatment of interest is efficacious, while a similarity in the expression of a BLC-associated gene in the test population and a bladder cancer control reference cell population indicates a less favorable clinical outcome or prognosis.

Additionally, the expression level of one or more BLC-associated genes determined in a subject-derived biological sample obtained after treatment (i.e., post-treatment levels) can be compared to the expression level of the one or more BLC-associated genes determined in a subject-derived biological sample obtained prior to treatment onset (i.e., pre-treatment levels). If the BLC-associated gene is an up-regulated gene, a decrease in the expression level in a post-treatment sample indicates that the treatment of interest is efficacious while an increase or maintenance in the expression level in the post-treatment sample indicates a less favorable clinical outcome or prognosis. Conversely, if the BLC-associated gene is an down-regulated gene, an increase in the expression level in a post-treatment sample may indicate that the treatment of interest is efficacious while an decrease or maintenance in the expression level in the post-treatment sample indicates a less favorable clinical outcome or prognosis.

As used herein, the term "efficacious" indicates that the treatment leads to a reduction in the expression of a pathologically up-regulated gene, an increase in the expression of a pathologically down-regulated gene or a decrease in size, prevalence, or metastatic potential of bladder ductal carcinoma in a subject. When a treatment of interest is applied prophylactically, the term "efficacious" means that the treatment retards or prevents a bladder tumor from forming or retards, prevents, or alleviates a symptom of clinical BLC. Assessment of bladder tumors can be made using standard clinical protocols. In addition, efficaciousness can be determined in association with any known method for diagnosing or treating BLC. BLC can be diagnosed, for example, by identifying symptomatic anomalies, e.g., weight loss, abdominal pain, back pain, anorexia, nausea, vomiting and generalized malaise, weakness, and jaundice.

The present method of diagnosing bladder cancer may be applied for assessing the efficacy of treatment of bladder cancer in a subject. According to the method, a biological sample, such as a test cell population, is obtained from a subject undergoing treatment for bladder cancer. The method for assessment can be conducted according to conventional methods of diagnosing bladder cancer.

If desired, biological samples are obtained from the subject at various time points before, during or after the treatment. The expression level of the C2093, B5860Ns or C6055s gene, in the biological sample is then determined and compared to a control level derived, for example, from a reference cell population which includes cells whose state of bladder cancer (i.e., cancerous cell or non-cancerous cell) is known. The control level is determined in a biological sample that has not been exposed to the treatment. If the control level is derived from a biological sample which contains no cancerous cell, a similarity between the expression level in the subject-derived biological sample and the control level indicates that the treatment is efficacious. A difference between the expression level of the C2093, B5860Ns or C6055s gene in the subject-derived biological sample and the control level indicates a less favorable clinical outcome or prognosis.

The term "efficacious" refers that the treatment leads to a reduction in the expression of a pathologically up-regulated gene (e.g., the C2093, B5860Ns and C6055s gene) or a decrease in size, prevalence or proliferating potential of bladder cancer cells in a subject. When a treatment is applied prophylactically, "efficacious" indicates that the treatment retards or prevents occurrence of bladder cancer. The assessment of bladder cancer can be made using standard clinical protocols. Furthermore, the efficaciousness of a treatment may be determined in association with any known method for diagnosing or treating bladder cancer. Moreover, the present method of diagnosing bladder cancer may also be applied for assessing the prognosis of a subject with bladder cancer by comparing the expression level of the C2093, B5860Ns or C6055s gene in a patient-derived biological sample, such as test cell population, to a control level. Alternatively, the expression level of the C2093, B5860Ns or C6055s gene in a biological sample derived from patients may be measured over a spectrum of disease stages to assess the prognosis of the patient.

An increase in the expression level of the C2093, B5860Ns or C6055s gene as compared to a normal control level indicates less favorable prognosis. A similarity in the expression level of the C2093, B5860Ns or C6055s gene compared to a normal control level indicates a more favorable prognosis for the patient.

Selecting a Therapeutic Agent for Treating BLC that is Appropriate for a Particular Individual:

Differences in the genetic makeup of individuals can result in differences in their relative abilities to metabolize various drugs. An agent that is metabolized in a subject to act as an anti-BLC agent can manifest itself by inducing a change in a gene expression pattern in the subject's cells from that characteristic of a cancerous state to a gene expression pattern characteristic of a non-cancerous state. Accordingly, the differentially expressed BLC-associated genes disclosed herein allow for a putative therapeutic or prophylactic inhibitor of BLC to be tested in a test cell population from a selected subject in order to determine if the agent is a suitable inhibitor of BLC in the subject.

To identify an inhibitor of BLC that is appropriate for a specific subject, a test cell population from the subject is exposed to a therapeutic agent, and the expression of one or more of BLC-associated genes listed in Table 4-5 is determined.

In the context of the method of the present invention, the test cell population contains a BLC cell expressing a BLC-associated gene. Preferably, the test cell is an epithelial cell. For example, a test cell population may be incubated in the presence of a candidate agent and the pattern of gene expression of the test cell population may be measured and compared to one or more reference profiles, e.g., a BLC reference expression profile or a non-BLC reference expression profile.

A decrease in expression of one or more of the BLC-associated genes listed in Table 4 or an increase in expression of one or more of the BLC-associated genes listed in Table 5 in a test cell population relative to a reference cell population containing BLC indicates that the agent has therapeutic potential.

In the context of the present invention, the test agent can be any compound or composition. Exemplary test agents include, but are not limited to, immunomodulatory agents.

Screening Assays for Identifying Therapeutic Agents:

The differentially expressed BLC-associated genes disclosed herein can also be used to identify candidate therapeutic agents for treating BLC. The method of the present invention involves screening a candidate therapeutic agent to determine if it can convert an expression profile of one or more BLC-associated genes listed in Tables 4-5 characteristic of a BLC state to a gene expression pattern characteristic of a non-BLC state.

In the instant method, a cell is exposed to a test agent or a plurality of test agents (sequentially or in combination) and the expression of one or more of the BLC-associated genes listed in Tables 4-5 in the cell is measured. The expression profile of the BLC-associated gene(s) assayed in the test population is compared to expression level of the same BLC-associated gene(s) in a reference cell population that is not exposed to the test agent.

An agent capable of stimulating the expression of an under-expressed gene or suppressing the expression of an over-expressed genes has potential clinical benefit. Such agents may be further tested for the ability to prevent bladder ductal carcinomal growth in animals or test subjects.

In a further embodiment, the present invention provides methods for screening candidate agents which act on the potential targets in the treatment of BLC. As discussed in detail above, by controlling the expression levels of marker genes or the activities of their gene products, one can control the onset and progression of BLC. Thus, candidate agents, which act on the potential targets in the treatment of BLC, can be identified through screening methods that use such expression levels and activities as indices of the cancerous or non-cancerous state. In the context of the present invention, such screening may comprise, for example, the following steps:
  a) contacting a test compound with a polypeptide encoded by a polynucleotide selected from the group consisting of the genes listed in Table 4 or 5;
  b) detecting the binding activity between the polypeptide and the test compound; and
  c) selecting the test compound that binds to the polypeptide.

Alternatively, the screening method of the present invention may comprise the following steps:
  a) contacting a candidate compound with a cell expressing one or more marker genes, wherein the one or more marker genes are selected from the group consisting of the genes listed in Table 4 or 5; and
  b) selecting the candidate compound that reduces the expression level of one or more marker genes selected from the group consisting of the genes listed in Table 4, or elevates the expression level of one or more marker genes selected from the group consisting of the genes listed in Table 5.

Cells expressing a marker gene include, for example, cell lines established from BLC; such cells can be used for the above screening of the present invention.

Alternatively, the screening method of the present invention may comprise the following steps:
  a) contacting a test compound with a polypeptide encoded by a polynucleotide selected from the group consisting of the genes listed in Table 4 or 5;
  b) detecting the biological activity of the polypeptide of step (a); and
  c) selecting a compound that suppresses the biological activity of the polypeptide encoded by the polynucleotide selected from the group consisting of the genes listed in Table 4 as compared to the biological activity detected in the absence of the test compound, or enhances the biological activity of the polypeptide encoded by the polynucleotide selected from the group consisting of the genes listed in Table 5 as compared to the biological activity detected in the absence of the test compound.

A protein for use in the screening method of the present invention can be obtained as a recombinant protein using the nucleotide sequence of the marker gene. Based on the information regarding the marker gene and its encoded protein, one skilled in the art can select any biological activity of the protein as an index for screening and any suitable measurement method to assay for the selected biological activity.

Alternatively, the screening method of the present invention may comprise the following steps:
  a) contacting a candidate compound with a cell into which a vector, comprising the transcriptional regulatory region of one or more marker genes and a reporter gene that is expressed under the control of the transcriptional regulatory region, has been introduced, wherein the one or more marker genes are selected from the group consisting of the genes listed in Table 4 or 5;
  b) measuring the expression or activity of said reporter gene; and
  c) selecting the candidate compound that reduces the expression level or activity of said reporter gene when said marker gene is an up-regulated marker gene selected from the group consisting of the genes listed in Table 4, or that enhances the expression level or activity of said reporter gene when said marker gene is a down-regulated marker gene selected from the group consisting of the genes listed in Table 5, as compared to the expression level or activity detected in the absence of the test compound.

Suitable reporter genes and host cells are well known in the art. A reporter construct suitable for the screening method of the present invention can be prepared by using the transcriptional regulatory region of a marker gene. When the transcriptional regulatory region of the marker gene is known to those skilled in the art, a reporter construct can be prepared by using the previous sequence information. When the transcriptional regulatory region of the marker gene remains unidentified, a nucleotide segment containing the transcriptional regulatory region can be isolated from a genome library based on the nucleotide sequence information of the marker gene.

Using the C2093, B5860Ns or C6055s gene and/or proteins encoded by the genes or transcriptional regulatory region of the genes, compounds can be screened that alter the expression of the gene or the biological activity of a polypeptide encoded by the gene. Such compounds are used as pharmaceuticals for treating or preventing bladder cancer.

Therefore, the present invention provides a method of screening for a compound for treating or preventing bladder cancer using the polypeptide of the present invention. An embodiment of this screening method comprises the steps of: (a) contacting a test compound with a polypeptide encoded by C2093, B5860Ns or C6055s, or an equivalent thereof; (b) detecting the binding activity between the polypeptide and the test compound; and (c) selecting the compound that binds to the polypeptide. In the present invention the polypeptide encoded by C2093, B5860Ns or C6055s, or equivalent thereof may be selected from the group consisting of:
(1) a polypeptide comprising the amino acid sequence of selected from the group consisting of SEQ ID NOs: 2, 4, 6, 130, 132, 134 and 136;
(2) a polypeptide that comprises the amino acid sequence selected from the group consisting of SEQ ID NOs: 2, 4, 6, 130, 132, 134 and 136 or a sequence having at least about 80% homology to said sequence; and
(3) a polypeptide encoded by a polynucleotide that hybridizes under stringent conditions to a polynucleotide consisting of the nucleotide sequence selected from the group consisting of SEQ ID NOs:1, 3, 5, 129, 131, 133 and 135, wherein the polypeptide has a biological activity equivalent to a polypeptide consisting of the amino acid sequence selected from the group consisting of SEQ ID NOs: 2, 4, 6, 130, 132, 134 and 136;

The polypeptide of the present invention to be used for screening may be a recombinant polypeptide or a protein derived from the nature or a partial peptide thereof. The polypeptide of the present invention to be contacted with a test compound can be, for example, a purified polypeptide, a soluble protein, a form bound to a carrier or a fusion protein fused with other polypeptides.

As a method of screening for proteins, for example, that bind to the polypeptide of the present invention using the polypeptide encoded by C2093, B5860Ns or C6055s of the present invention, many methods well known by a person skilled in the art can be used. Such a screening can be conducted by, for example, immunoprecipation method, specifically, in the following manner. The C2093, B5860Ns or C6055s gene encoding the polypeptide of the present invention is expressed in host (e.g., animal) cells and so on by inserting the gene to an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), (1982) Genetic Engineering, vol. 3. Academic Press, London, 83-141), the EF-α promoter (Kim et al., Gene 91: 217-23 (1990)), the CAG promoter (Niwa et al., (1991) Gene 108:193-9), the RSV LTR promoter (Cullen, (1987) Methods in Enzymology 152: 684-704) the SRα promoter (Takebe et al., (1988) Mol Cell Biol 8: 466-72), the CMV immediate early promoter (Seed and Aruffo, (1987) Proc Natl Acad Sci USA 84: 3365-9), the SV40 late promoter (Gheysen and Fiers, (1982) J Mol Appl Genet 1: 385-94), the Adenovirus late promoter (Kaufman et al., (1989) Mol Cell Biol 9: 946-58), the HSV TK promoter and so on. The introduction of the gene into host cells to express a foreign gene can be performed according to any methods, for example, the electroporation method (Chu et al., (1987) Nucleic Acids Res 15: 1311-26), the calcium phosphate method (Chen and Okayama, (1987) Mol Cell Biol 7: 2745-52), the DEAE dextran method (Lopata et al., (1984) Nucleic Acids Res 12: 5707-17; Sussman and Milman, (1984) Mol Cell Biol 4: 1641-3), the Lipofectin method (Derijard B, et al., (1994) Cell 76: 1025-37; Lamb et al., (1993) Nature Genetics 5: 22-30: Rabindran et al., (1993) Science 259: 230-4) and so on. The polypeptide to be used for screening of the present invention can be expressed as a fusion protein comprising a recognition site (epitope) of a monoclonal antibody by introducing the epitope of the monoclonal antibody, whose specificity has been revealed, to the N- or C-terminus of the polypeptide of the present invention. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the polypeptide to be used for screening of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the polypeptide to be used for screening of the present invention (Experimental Medicine 13: 85-90 (1995)).

In immunoprecipitation, an immune complex is formed by adding these antibodies to cell lysate prepared using an appropriate detergent. The immune complex consists of the polypeptide to be used for screening of the present invention, a polypeptide comprising the binding ability with the polypeptide, and an antibody. Immunoprecipitation can be also conducted using antibodies against the polypeptide to be used for screening of the present invention, besides using antibodies against the above epitopes, which antibodies can be prepared as described above.

An immune complex can be precipitated, for example by Protein A sepharose or Protein G sepharose when the antibody is a mouse IgG antibody. If the polypeptide to be used for screening of the present invention is prepared as a fusion protein with an epitope, such as GST, an immune complex can be formed in the same manner as in the use of the antibody against the polypeptide to be used for screening of the present invention, using a substance specifically binding to these epitopes, such as glutathione-Sepharose 4B. Immunoprecipitation can be performed by following or according to, for example, the methods in the literature (Harlow and Lane, (1988) Antibodies, 511-52, Cold Spring Harbor Laboratory publications, New York).

SDS-PAGE is commonly used for analysis of immunoprecipitated proteins and the bound protein can be analyzed by the molecular weight of the protein using gels with an appropriate concentration. Since the protein bound to the polypeptide to be used for screening of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for screening for proteins that bind to a polypeptide of the present invention using the polypeptide, for example, West-Western blotting analysis (Skolnik et al., (1991) Cell 65: 83-90) can be used. Specifically, a protein binding to the polypeptide to be used for screening of the present invention can be obtained by preparing a cDNA library from cells, tissues, organs (for example, tissues such as testis), or cultured cells (e.g., HT1197, UMUC3, J82, HT1376, SW780, RT4 PC3, DU145, or HT1376) expected to express a protein binding to the polypeptide of the present invention using a phage vector (e.g., ZAP), expressing the protein on LB-agarose, fixing the protein expressed on a filter, reacting the purified and labeled polypeptide of the present invention with the above filter, and detecting the plaques expressing proteins bound to the polypeptide of the present invention according to the label. The polypeptide to be used for screening of the invention may be labeled by utilizing the binding between biotin and avidin, or by utilizing an antibody that specifically binds to the polypeptide to be used for screening of the present invention, or a peptide or polypeptide (for example, GST) that is fused to the polypeptide of the present invention. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, (1992) Cell 68: 597-612", "Fields and Sternglanz, (1994) Trends Genet 10: 286-92").

In the two-hybrid system, the polypeptide to be used for screening of the invention is fused to the SRF-binding region or GAL4-binding region and expressed in yeast cells. A cDNA library is prepared from cells expected to express a protein binding to the polypeptide to be used for screening of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide to be used for screening of the invention is expressed in yeast cells, the binding of the two activates a reporter gene, making positive clones detectable). A protein encoded by the cDNA can be prepared by introducing the cDNA isolated above to *E. coli* and expressing the protein.

As a reporter gene, for example, Ade2 gene, lacZ gene, CAT gene, luciferase gene and such can be used in addition to the HIS3 gene.

A compound binding to the polypeptide to be used for screening of the invention can also be screened using affinity chromatography. For example, the polypeptide to be used for screening of the invention may be immobilized on a carrier of an affinity column, and a test compound, containing a protein capable of binding to the polypeptide to be used for screening of the invention, is applied to the column. A test compound herein may be, for example, cell extracts, cell lysates, etc. After loading the test compound, the column is washed, and compounds bound to the polypeptide to be used for screening of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein. A biosensor using the surface plasmon resonance phenomenon may be used as a mean for detecting or quantifying the bound compound in the present invention. When such a biosensor is used, the interaction between the polypeptide to be used for screening of the invention and a test compound can be observed real-time as a surface plasmon resonance signal, using only a minute amount of polypeptide and without labeling (for example, BIAcore, Pharmacia). Therefore, it is possible to evaluate the binding between the polypeptide to be used for screening of the invention and a test compound using a biosensor such as BIAcore.

The methods of screening for molecules that bind when the immobilized polypeptide to be used for screening of the invention is exposed to synthetic chemical compounds, or natural substance banks or a random phage peptide display library, and the methods of screening using high-throughput based on combinatorial chemistry techniques (Wrighton et al., (1996) Science 273: 458-64; Verdine, (1996) Nature 384: 11-13; Hogan, (1996) Nature 384: 17-9) to isolate not only proteins but chemical compounds that bind to the protein to be used for screening of the invention (including agonist and antagonist) are well known to one skilled in the art.

Alternatively, the present invention provides a method of screening for a compound for treating or preventing bladder cancer using the polypeptide of the present invention encoded by C2093, B5860Ns or C6055s, or an equivalent thereof, comprising the steps as follows:
(a) contacting a test compound with the polypeptide or equivalent thereof;
(b) detecting the biological activity of the polypeptide or equivalent thereof of step (a); and
(c) selecting a compound that suppresses the biological activity of the polypeptide or equivalent thereof in comparison with the biological activity detected in the absence of the test compound.

Since the C2093, B5860Ns and C6055s proteins of the present invention have the activity of promoting cell proliferation of bladder cancer cells, a compound which inhibits this activity can be screened using this activity as an index. Any polypeptides can be used for screening, so long as they comprise the biological activity of the C2093, B5860Ns or C6055s protein. Such biological activities include the cell-proliferating activity of the human C2093, B5860Ns or C6055s protein. For example, a human C2093, B5860Ns or C6055s protein can be used and polypeptides functionally equivalent to these proteins can also be used. Such polypeptides may be expressed endogenously or exogenously by cells.

The compound isolated by this screening is a candidate for agonists or antagonists of the C2093, B5860Ns or C6055s polypeptide of the present invention. The term "agonist" refers to molecules that activate the function of the polypeptide of the present invention by binding thereto. Likewise, the term "antagonist" refers to molecules that inhibit the function of the polypeptide of the present invention by binding thereto. Moreover, a compound isolated by this screening as "antagonist" is a candidate for compounds which inhibit the in vivo interaction of the polypeptide to be used for screening of the present invention with molecules (including DNAs and proteins).

When the biological activity to be detected in the present method is cell proliferation, it can be detected, for example, by preparing cells which express the polypeptide to be used for screening of the present invention, culturing the cells in the presence of a test compound, and determining the speed of cell proliferation, measuring the cell cycle and such, as well as by measuring the colony forming activity as described in the Examples.

In a further embodiment, the present invention provides methods for screening compounds for treating or preventing bladder cancer. As discussed in detail above, by controlling the expression levels of the C2093, B5860Ns and/or C6055s genes, one can control the onset and progression of bladder cancer. Thus, compounds that may be used in the treatment or prevention of bladder cancer can be identified through screenings that use the expression levels of C2093, B5860Ns or C6055s as indices. In the context of the present invention, such screening may comprise, for example, the following steps:
a) contacting a test compound with a cell expressing one or more of the C2093, B5860Ns or C6055s gene; and
b) selecting a compound that reduces the expression level of one or more of the C2093, B5860Ns or C6055s gene in comparison with the expression level detected in the absence of the test compound.

Cells expressing at least one of the one or more of the C2093, B5860Ns or C6055s gene include, for example, cell lines established from bladder cancers; such cells can be used for the above screening of the present invention (e.g., HT1197, UMUC3, J82, HT1376, SW780, RT4 and HT1376). The expression level can be estimated by methods well known to one skilled in the art. In the method of screening, a compound that reduces the expression level of the C2093, B5860N or C6055 genes can be selected as candidate agents to be used for the treatment or prevention of bladder cancer.

Alternatively, the screening method of the present invention may comprise the following steps:
a) contacting a test compound with a cell into which a vector comprising the transcriptional regulatory region of one or more marker genes and a reporter gene that is expressed under the control of the transcriptional regulatory region has been introduced, wherein the one or more marker genes are C2093, B5860Ns or C6055s,
b) measuring the expression level or activity of said reporter gene; and
c) selecting a compound that reduces the expression level or activity of said reporter gene as compared to the expression level or activity detected in the absence of the test compound.

Suitable reporter genes and host cells are well known in the art. The reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

Examples of supports that may be used for binding proteins include insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they may be filled into a column.

The binding of a protein to a support may be conducted according to routine methods, such as chemical bonding and physical adsorption. Alternatively, a protein may be bound to a support via antibodies specifically recognizing the protein. Moreover, binding of a protein to a support can be also conducted by means of avidin and biotin. The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore, Pharmacia).

Alternatively, a C2093, B5860N or C6055 polypeptides may be labeled, and the label of the bound protein may be used to detect or measure the bound protein. Specifically, after prelabeling one of the proteins, the labeled protein is contacted with the other protein in the presence of a test compound, and then bound proteins are detected or measured according to the label after washing.

Labeling substances such as radioisotope (e.g., $^3$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiosyanete (FITC), rhodamine) and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

In case of using an antibody in the present screening, the antibody is preferably labeled with one of the labeling substances mentioned above, and detected or measured based on the labeling substance. Alternatively, the antibody against the C2093, B5860Ns or C6055s polypeptide may be used as a primary antibody to be detected with a secondary antibody that is labeled with a labeling substance. Furthermore, the antibody bound to the protein in the screening of the present invention may be detected or measured using protein G or protein A column.

Any test compound, including but not limited to, cell extracts, cell culture supernatant, products of fermenting microorganism, extracts from marine organism, plant extracts, purified or crude proteins, peptides, non-peptide compounds, syntheticmicromolecular compounds and natural compounds, can be used in the screening methods of the present invention. The test compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam (1997) Anticancer Drug Des. 12: 145-67). Examples of methods for the synthesis of molecular libraries can be found in the art (DeWitt et al. (1993) Proc. Natl. Acad. Sci. USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). Libraries of compounds may be presented in solution (see Houghten (1992) Bio/Techniques 13: 412-21) or on beads (Lam (1991) Nature 354: 82-4), chips (Fodor (1993) Nature 364: 555-6), bacteria (U.S. Pat. No. 5,223,409), spores (U.S. Pat. Nos. 5,571,698; 5,403,484, and 5,223,409), plasmids (Cull et al. (1992) Proc. Natl. Acad. Sci. USA 89: 1865-9) or phage (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US Pat. Application 2002103360).

A compound isolated by the screening serves as a candidate for the development of drugs that inhibit the expression of the marker gene or the activity of the protein encoded by the marker gene and can be applied to the treatment or prevention of bladder cancer.

Moreover, compounds in which a part of the structure of the compound inhibiting the activity of proteins encoded by marker genes is converted by addition, deletion and/or replacement are also included as the compounds obtainable by the screening method of the present invention.

When administrating a compound isolated by the method of the present invention as a pharmaceutical for humans and other mammals, including, but not limited to, mice, rats, guinea-pigs, rabbits, cats, dogs, sheep, pigs, cattle, monkeys, baboons, and chimpanzees, the isolated compound can be directly administered or can be formulated into a dosage form using known pharmaceutical preparation methods. Pharmaceutical compositions and preparations contemplated by the present invention, as well as methods of making and using same, are described in detail below.

Assessing the Prognosis of a Subject with Bladder Cancer:

The present invention also provides a method of assessing the prognosis of a subject with BLC, including the step of comparing the expression of one or more BLC-associated genes in a test cell population to the expression of the same BLC-associated genes in a reference cell population derived from patients over a spectrum of disease stages. By comparing the gene expression of one or more BLC-associated genes in the test cell population and the reference cell population(s), or by comparing the pattern of gene expression over time in test cell populations derived from the subject, the prognosis of the subject can be assessed.

For example, an increase in the expression of one or more of up-regulated BLC-associated genes, such as those listed in Table 4, as compared to a normal control or a decrease in the expression of one or more of down-regulated BLC-associated genes, such as those listed in Table 5, as compared to a normal control indicates less favorable prognosis. Conversely, a similarity in the expression of one or more of BLC-associated genes listed in Tables 4-5 as compared to normal control indicates a more favorable prognosis for the subject. Preferably, the prognosis of a subject can be assessed by comparing the expression profile of the one or more genes selected from the group consisting of genes listed in Table 4 and 5.

Kits:

The present invention also includes a BLC-detection reagent, e.g., a nucleic acid that specifically binds to or identifies one or more BLC nucleic acids, such as oligonucleotide sequences which are complementary to a portion of a BLC nucleic acid, or an antibody that bind to one or more proteins encoded by a BLC nucleic acid. The detection reagents may be packaged together in the form of a kit. For example, the detection reagents may be packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay may also be included in the kit. The assay format of the kit may be a Northern hybridization or a sandwich ELISA, both of which are known in the art.

For example, a BLC detection reagent may be immobilized on a solid matrix, such as a porous strip, to form at least one BLC detection site. The measurement or detection region of the porous strip may include a plurality of sites, each containing a nucleic acid. A test strip may also contain sites for negative and/or positive controls. Alternatively, control sites may be located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of BLC present in the sample. The detection sites may be configured in any suitably detectable shape and are typically in the shape of a bar or dot spanning the width of a test strip.

Alternatively, the kit may contain a nucleic acid substrate array comprising one or more nucleic acids. The nucleic acids on the array specifically identify one or more nucleic acid sequences represented by the BLC-associated genes listed in Tables 4-5. The expression of 2, 3, 4, 5, 6, 7, 8, 9, 10, 15, 20, 25, 40 or 50 or more of the nucleic acids represented by the BLC-associated genes listed in Tables 4-5 may be identified by virtue of the level of binding to an array test strip or chip. The substrate array can be on, e.g., a solid substrate, such as a "chip" described in U.S. Pat. No. 5,744,305, the contents of which are incorporated by reference herein in its entirety.

Arrays and Pluralities:

The present invention also includes a nucleic acid substrate array comprising one or more nucleic acids. The nucleic acids on the array specifically correspond to one or more nucleic acid sequences represented by the BLC-associated genes listed in Tables 4-5. The level of expression of 2, 3, 4, 5, 6, 7, 8, 9, 10, 15, 20, 25, 40 or 50 or more of the nucleic acids represented by the BLC-associated genes listed in Tables 4-5 may be identified by detecting nucleic acid binding to the array.

The present invention also includes an isolated plurality (i.e., a mixture of two or more nucleic acids) of nucleic acids. The nucleic acids may be in a liquid phase or a solid phase, e.g., immobilized on a solid support such as a nitrocellulose membrane. The plurality includes one or more of the nucleic acids represented by the BLC-associated genes listed in Tables 4-5. In various embodiments, the plurality includes 2, 3, 4, 5, 6, 7, 8, 9, 10, 15, 20, 25, 40 or 50 or more of the nucleic acids represented by the BLC-associated genes listed in Tables 4-5.

Methods of Inhibiting Bladder Cancer:

The present invention further provides a method for treating or alleviating a symptom of BLC in a subject by decreasing the expression of one or more of the up-regulated BLC-associated genes listed in Table 4 (or the activity of its gene product) or increasing the expression of one or more of the down-regulated BLC-associated genes listed in Table 5 (or the activity of its gene product). Suitable therapeutic compounds can be administered prophylactically or therapeutically to a subject suffering from or at risk of (or susceptible to) developing BLC. Such subjects can be identified using standard clinical methods or by detecting an aberrant level of expression of one or more of the BLC-associated genes listed in Tables 4-5 or aberrant activity of its gene product. In the context of the present invention, suitable therapeutic agents include, for example, inhibitors of cell cycle regulation, and cell proliferation.

The therapeutic method of the present invention includes the step of increasing the expression, activity, or both of one or more genes or gene products whose expression is decreased ("down-regulated" or "under-expressed" genes) in a BLC cell relative to normal cells of the same tissue type from which the BLC cells are derived. In these methods, the subject is treated with an effective amount of a compound that increases the amount of one or more of the under-expressed (down-regulated) genes in the subject. Administration can be systemic or local. Suitable therapeutic compounds include a polypeptide product of an under-expressed gene, a biologically active fragment thereof, and a nucleic acid encoding an under-expressed gene and having expression control elements permitting expression in the BLC cells; for example, an agent that increases the level of expression of such a gene endogenous to the BLC cells (i.e., which up-regulates the expression of the under-expressed gene or genes). Administration of such compounds counters the effects of aberrantly under-expressed gene or genes in the subject's bladder cancer cells and improves the clinical condition of the subject.

Alternatively, the therapeutic method of the present invention may include the step of decreasing the expression, activity, or both, of one or more genes or gene products whose expression is aberrantly increased ("up-regulated" or "over-expressed" gene) in bladder cancer cells. Expression may be inhibited in any of several ways known in the art. For example, expression can be inhibited by administering to the subject a nucleic acid that inhibits, or antagonizes the expression of the over-expressed gene or genes, e.g., an antisense oligonucleotide or small interfering RNA which disrupts expression of the over-expressed gene or genes.

In yet another embodiment, the therapeutic method includes the step of decreasing the expression or function of the C2093, B5860Ns or C6055s gene. In these methods, the subject is treated with an effective amount of a compound, which decreases the expression and/or activity of one or more of the over-expressed genes (i.e., the C2093, B5860Ns or C6055s gene) in the subject. Administration can be systemic or local. Therapeutic compounds include compounds that decrease the expression level of such gene endogenously existing in the bladder cancerous cells (i.e., compounds that down-regulate the expression of the over-expressed gene(s)). Administration of such therapeutic compounds counter the effects of aberrantly-over expressed gene(s) in the subject's cells and are expected to improve the clinical condition of the subject. Such compounds can be obtained by the screening method of the present invention described above.

The expression of the C2093, B5860Ns or C6055s gene may be also inhibited in any of several ways known in the art including administering to the subject a nucleic acid that inhibits or antagonizes the expression of the gene(s). Antisense oligonucleotides, siRNA or ribozymes which disrupts expression of the gene(s) can be used for inhibiting the expression of the genes.

As noted above, antisense-oligonucleotides corresponding to the nucleotide sequence of the C2093, B5860Ns or C6055s gene can be used to reduce the expression level of the C2093, B5860Ns or C6055s gene. Specifically, the antisense-oligonucleotides of the present invention may act by binding to any of the polypeptides encoded by the C2093, B5860Ns or C6055s gene, or mRNAs corresponding thereto, thereby inhibiting the transcription or translation of the genes, promoting the degradation of the mRNAs, and/or inhibiting the expression of proteins encoded by the genes, and finally inhibiting the function of the C2093, B5860Ns or C6055s proteins.

An antisense-oligonucleotides and derivatives thereof can be made into an external preparation, such as a liniment or a poultice, by mixing with a suitable base material which is inactive against the derivative and used in the method for treating or preventing bladder cancer of the present invention.

The nucleic acids that inhibit one or more gene products of over-expressed genes also include small interfering RNAs (siRNA) comprising a combination of a sense strand nucleic acid and an antisense strand nucleic acid of the nucleotide sequence encoding the C2093, B5860Ns or C6055s gene. Standard techniques of introducing siRNA into the cell can be used in the treatment or prevention of the present invention, including those in which DNA is a template from which RNA is transcribed. The siRNA is constructed such that a single transcript has both the sense and complementary antisense sequences from the target gene, e.g., a hairpin.

Antisense Polynucleotides, Small Interfering RNAs and Ribozymes

As noted above, antisense nucleic acids corresponding to the nucleotide sequence of the BLC-associated genes listed in Table 4 can be used to reduce the expression level of the genes. Antisense nucleic acids corresponding to the BLC-associated genes listed in Table 4 that are up-regulated in bladder cancer are useful for the treatment of bladder cancer. Specifically, the antisense nucleic acids of the present invention may act by binding to the BLC-associated genes listed in Table 4, or mRNAs corresponding thereto, thereby inhibiting the transcription or translation of the genes, promoting the degradation of the mRNAs, and/or inhibiting the expression of proteins encoded by the BLC-associated genes listed in Table 4, thereby, inhibiting the function of the proteins.

The present invention includes an antisense oligonucleotide that hybridizes with any site within the nucleotide sequence of SEQ ID NO: 3. Specifically, the present invention provides an antisense polynucleotide that hybridizes with nucleic acid comprising the nucleotide sequence from 988 to 1842 of SEQ ID NO: 3, i.e., the region that is specific to the B5860NV1 sequence. This antisense oligonucleotide is preferably against at least about 15 continuous nucleotides of the nucleotide sequence of SEQ ID NO: 3. The above-mentioned antisense oligonucleotide, which contains an initiation codon in the above-mentioned at least 15 continuous nucleotides, is even more preferred.

Derivatives or modified products of antisense oligonucleotides can also be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term "antisense nucleic acids" as used herein encompasses both nucleotides that are entirely complementary to the target sequence and those having a mismatch of one or more nucleotides, so long as the antisense nucleic acids can specifically hybridize to the target sequences. For example, the antisense nucleic acids of the present invention include polynucleotides that have a homology of at least about 70% or higher, preferably at least about 80% or higher, more preferably at least about 90% or higher, even more preferably at least about 95% or higher over a span of at least 15 continuous nucleotides. Algorithms known in the art can be used to determine the homology. Furthermore, derivatives or modified products of the antisense-oligonucleotides can also be used as antisense-oligonucleotides in the present invention. Examples of such modified products include, but are not limited to, lower alkyl phosphonate modifications such as methyl-phosphonate-type or ethyl-phosphonate-type, phosphorothioate modifications and phosphoroamidate modifications.

Such antisense polynucleotides are useful as probes for the isolation or detection of DNA encoding the polypeptide of the invention or as a primer used for amplifications.

The antisense nucleic acids of the present invention act on cells producing the proteins encoded by BLC-associated marker genes by binding to the DNAs or mRNAs encoding the proteins, inhibiting their transcription or translation, promoting the degradation of the mRNAs, and inhibiting the expression of the proteins, thereby resulting in the inhibition of the protein function.

An antisense nucleic acid of the present invention can be made into an external preparation, such as a liniment or a poultice, by admixing it with a suitable base material which is inactive against the nucleic acid.

Also, as needed, the antisense nucleic acids of the present invention can be formulated into, for example, tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following known methods.

The antisense nucleic acids of the present invention can be given to the patient by direct application onto the ailing site or by injection into a blood vessel so that it will reach the site of ailment. An antisense-mounting medium can also be used to increase durability and membrane-permeability. Examples include, but are not limited to, liposomes, poly-L-lysine, lipids, cholesterol, lipofectin or derivatives of these.

The dosage of the antisense nucleic acid derivative of the present invention can be adjusted suitably according to the patient's condition and used in desired amounts. For example, a dose range of 0.1 to 100 mg/kg, preferably 0.1 to 50 mg/kg can be administered.

The antisense nucleic acids of the present invention inhibit the expression of a protein of the present invention and are thereby useful for suppressing the biological activity of the protein of the invention. In addition, expression-inhibitors, comprising antisense nucleic acids of the present invention, are useful in that they can inhibit the biological activity of a protein of the present invention.

The method of the present invention can be used to alter the expression in a cell of an up-regulated BLC-associated gene, e.g., up-regulation resulting from the malignant transformation of the cells. Binding of the siRNA to a transcript corresponding to one of the BLC-associated genes listed in Table 4 in the target cell results in a reduction in the protein production by the cell. The length of the oligonucleotide is at least 10 nucleotides and may be as long as the naturally-occurring transcript. Preferably, the oligonucleotide is 75, 50, or 25 nucleotides or less in length. Most preferably, the oligonucleotide is about 19 to 25 nucleotides in length.

The antisense nucleic acids of present invention include modified oligonucleotides. For example, thioated oligonucleotides may be used to confer nuclease resistance to an oligonucleotide.

Also, an siRNA against a marker gene can be used to reduce the expression level of the marker gene. Herein, term "siRNA" refers to a double stranded RNA molecule which prevents translation of a target mRNA. Standard techniques for introducing siRNA into the cell may be used, including those in which DNA is a template from which RNA is transcribed. In the context of the present invention, the siRNA comprises a sense nucleic acid sequence and an anti-sense nucleic acid sequence against an up-regulated marker-gene, such as a BLC-associated gene listed in Table 4. The siRNA is constructed such that a single transcript has both the sense and complementary antisense sequences from the target gene, e.g., a hairpin.

An siRNA of a BLC-associated gene, such as listed in Table 4, hybridizes to target mRNA and thereby decreases or inhibits production of the polypeptides encoded by the BLC-associated gene listed in Table 4 by associating with the normally single-stranded mRNA transcript, thereby interfering with translation and thus, expression of the protein. Thus, siRNA molecules of the invention can be defined by their ability to hybridize specifically to mRNA or cDNA listed in Table 4 under stringent conditions. For the purposes of this invention the terms "hybridize" or "hybridize specifically" are used interchangeably to refer the ability of two nucleic acid molecules to hybridize under "stringent hybridization conditions." The phrase "stringent hybridization conditions" is discussed above and refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 50° C.

In the context of the present invention, an siRNA is preferably 500, 200, 100, 50, or 25 nucleotides or less in length. More preferably an siRNA is about 19 to about 25 nucleotides in length. In order to enhance the inhibition activity of the siRNA, nucleotide "U" can be added to 3' end of the antisense strand of the target sequence. The number of "u"s to be added is at least about 2, generally about 2 to about 10, preferably about 2 to about 5. The added "u"s form single strand at the 3'end of the antisense strand of the siRNA.

An siRNA of a BLC-associated gene, such as listed in Table 4, can be directly introduced into the cells in a form that is capable of binding to the mRNA transcripts. In these embodiments, the siRNA molecules of the invention are typically modified as described above for antisense molecules. Other modifications are also possible, for example, cholesterol-conjugated siRNAs have shown improved pharmacological properties. Song et al. *Nature Med* 9:347-51 (2003): Alternatively, a DNA encoding the siRNA may be carried in a vector.

Vectors may be produced, for example, by cloning a BLC-associated gene target sequence into an expression vector having operatively-linked regulatory sequences flanking the sequence in a manner that allows for expression (by transcription of the DNA molecule) of both strands (Lee, N. S., et al., (2002) Nature Biotechnology 20: 500-5.). An RNA molecule that is antisense strand for mRNA of a BLC-associated gene is transcribed by a first promoter (e.g., a promoter sequence 3' of the cloned DNA) and an RNA molecule that is the sense strand for the mRNA of a BLC-associated gene is transcribed by a second promoter (e.g., a promoter sequence 5' of the cloned DNA). The sense and antisense strands hybridize in vivo to generate siRNA constructs for silencing of the BLC-associated gene. Alternatively, the two constructs can be utilized to create the sense and antisense strands of an siRNA construct. Cloned BLC-associated genes can encode a construct having secondary structure, e.g., hairpins, wherein a single transcript has both the sense and complementary antisense sequences from the target gene.

A loop sequence, consisting of an arbitrary nucleotide sequence, can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence that specifically hybridizes to an mRNA or a cDNA listed in Table 4. In preferred embodiments, [A] is a ribonucleotide sequence corresponding a sequence of gene selected from Table 4,

[B] is a ribonucleotide sequence consisting of about 3 to about 23 nucleotides, and

[A'] is a ribonucleotide sequence consisting of the complementary sequence of [A]. The region [A] hybridizes to [A'], and then a loop consisting of region [B] is formed. The loop sequence may be preferably 3 to 23 nucleotide in length. The loop sequence, for example, can be selected from group consisting of following sequences (http://www.ambion.com/techlib/tb/tb_506.html). Furthermore, loop sequence consisting of 23 nucleotides also provides active siRNA (Jacque, J.-M., et al., (2002) Nature 418: 435-8.).

CCC, CCACC or CCACACC: Jacque, J. M, et al., (2002) Nature, 418: 435-8.

UUCG: Lee, N. S., et al., (2002) Nature Biotechnology 20: 500-5. Fruscoloni, P., et al., (2003) Proc. Natl. Acad. Sci. USA 100(4): 1639-44.

UUCAAGAGA: Dykxhoorn, D. M., et al., (2002) Nature Reviews Molecular Cell

Biology 4: 457-67.

For example, preferable siRNAs having hairpin structure of the present invention are shown below. In the following structure, the loop sequence can be selected from group consisting of, CCC, UUCG, CCACC, CCACACC, and UUCAAGAGA. Preferable loop sequence is UUCAAGAGA ("ttcaagaga" in DNA).

The nucleotide sequence of suitable siRNAs can be designed using an siRNA design computer program available from the Ambion website (http://www.ambion.com/techlib/ misc/siRNA_finder.html). The computer program selects nucleotide sequences for siRNA synthesis based on the following protocol.

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. (1999) *Genes Dev* 13(24): 3191-7, don't recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with binding of the siRNA endonuclease complex.
2. Compare the potential target sites to the human genome database and eliminate from consideration any target sequences with significant homology to other coding sequences. The homology search can be performed using BLAST, which can be found on the NCBI server at: www.ncbi.nlm.nih.gov/BLAST/.
3. Select qualifying target sequences for synthesis. At Ambion, preferably several target sequences can be selected along the length of the gene to evaluate.

The regulatory sequences flanking the BLC-associated gene sequences can be identical or different, such that their expression can be modulated independently, or in a temporal or spatial manner. siRNAs are transcribed intracellularly by cloning the BLC-associated gene templates, respectively, into a vector containing, e.g., a RNA polymerase III transcription unit from the small nuclear RNA (snRNA) U6 or the human Hi RNA promoter. For introducing the vector into the cell, transfection-enhancing agent can be used. FuGENE (Rochediagnostices), Lipofectamine 2000 (Invitrogen), Oligofectamine (Invitrogen), and Nucleofector (Wako pure Chemical) are useful as the transfection-enhancing agent.

Oligonucleotides and oligonucleotides complementary to various portions of C2093, B5860Ns, or C6055s mRNA were tested in vitro for their ability to decrease production of C2093, B5860Ns, or C6055s in tumor cells (e.g., using the HT1197, UMUC3, J82, HT1376, SW780, RT4 or HT1376 bladder cancer cell line) according to standard methods. A reduction in product of C2093, B5860Ns, or C6055s transcript in cells contacted with the candidate siRNA composition compared to cells cultured in the absence of the candidate composition is detected using C2093, B5860Ns, or C6055s-specific antibodies or other detection strategies. Sequences which decrease production of C2093, B5860Ns, or C6055s in in vitro cell-based or cell-free assays are then tested for there inhibitory effects on cell growth. Sequences which inhibit cell growth in in vitro cell-based assay are test in in vivo in rats or mice to confirm decreased C2093, B5860Ns, or C6055s production and decreased tumor cell growth in animals with malignant neoplasms.

Also included in the invention are double-stranded molecules that include the nucleic acid sequence of target sequences, for example, nucleotides 2543-2561 (SEQ ID NO: 21) of SEQ ID NO: 1, nucleotides 2491-2509 of SEQ ID NO: 3 or nucleotides 1639-1657 of SEQ ID NO: 5 (SEQ ID NO: 25), or nucleotides 1905-1923 of SEQ ID NO: 129, nucleotides 1873-1891 of SEQ ID NO: 131, nucleotides 1921-1939 of SEQ ID NO: 133 or nucleotides 2001-2019 of SEQ ID NO: 135 (SEQ ID NO: 144). In the present invention, the double-stranded molecule comprising a sense strand and an antisense strand, wherein the sense strand comprises a ribonucleotide sequence corresponding to SEQ ID NO: 21, 25 or 144, and wherein the antisense strand comprises a ribonucleotide sequence which is complementary to said sense strand, wherein said sense strand and said antisense strand hybridize to each other to form said double-stranded molecule, and wherein said double-stranded molecule, when introduced into a cell expressing the C2093, B5860Ns, or C6055s gene, inhibits expression of said gene. In the present invention, when the isolated nucleic acid is RNA or derivatives thereof, base "t" should be replaced with "u" in the nucleotide sequences. As used herein, the term "complementary" refers to Watson Crick or Hoogsteen base pairing between nucleotides units of a nucleic acid molecule, and the term "binding" means the physical or chemical interaction between two nucleic acids or compounds or associated nucleic acids or compounds or combinations thereof.

Complementary nucleic acid sequences hybridize under appropriate conditions to form stable duplexes containing few or no mismatches. Furthermore, the sense strand and antisense strand of the isolated nucleotide of the present invention, can form double stranded nucleotide or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches. The nucleic acid molecule is less than 6319 nucleotides (for SEQ ID NO: 1), 5318 nucleotides (for SEQ ID NO: 3), 3851 nucleotides (for SEQ ID NO: 129), 3819 nucleotides (for SEQ ID NO: 131), 3851 nucleotides (for SEQ ID NO: 133) or 3819 nucleotides (for SEQ ID NO: 135) in length. For example, the nucleic acid molecule is 500, 200, or 75 nucleotides or less in length. Also included in the invention is a vector containing one or more of the nucleic acids described herein, and a cell containing the vectors. The isolated nucleic acids of the present invention are useful for siRNA against C2093, B5860Ns, or C6055s or DNA encoding the siRNA. When the nucleic acids are used for siRNA or coding DNA thereof, the sense strand is preferably longer than about 19 nucleotides, and more preferably longer than about 21 nucleotides.

The antisense oligonucleotide or siRNA of the present invention inhibits the expression of a polypeptide of the present invention and is thereby useful for suppressing the biological activity of a polypeptide of the invention. Also, expression-inhibitors, comprising the antisense oligonucleotide or siRNA of the invention, are useful in the point that they can inhibit the biological activity of the polypeptide of the invention.

Therefore, a composition comprising an antisense oligonucleotide or siRNA of the present invention is useful for treating a bladder cancer. Furthermore, in order to enhance the inhibition activity of the siRNA, nucleotide "u" can be added to 3' end of the antisense strand of the target sequence. The number of "u"s to be added is at least about 2, generally about 2 to about 10, preferably about 2 to about 5. The added "u"s form single strand at the 3' end of the antisense strand of the siRNA.

Also, expression-inhibitors, comprising the antisense oligonucleotide or siRNA of the invention, are useful in the point that they can inhibit the biological activity of the polypeptide of the invention. Therefore, a composition comprising the antisense oligonucleotide or siRNA of the present invention is useful in treating a cell proliferative disease such as bladder cancer.

Furthermore, the present invention provides ribozymes that inhibit the expression of the C2093, B5860Ns, or C6055spolypeptide of the present invention.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi et al., (1988) FEBS Lett 228: 228-30) and hairpin type ribozymes (Buzayan, (1986) Nature 323: 349-53; Kikuchi and Sasaki, (1991) Nucleic Acids Res 19: 6751-5) are included in the small ribozymes. Methods for designing and constructing ribozymes are known in the art (see Koizumi et al., (1988) FEBS Lett 228: 228-30; Koizumi et al., (1989) Nucleic Acids Res 17: 7059-71; Kikuchi and Sasaki, (1991) Nucleic Acids Res 19: 6751-5). Thus, ribozymes inhibiting the expression of the polypeptides of the present invention can also be constructed based on their sequence information (SEQ ID NO:1, 3, 5, 129, 131, 133 or 135) and these conventional methods.

Ribozymes against the C2093, B5860Ns, or C6055s transcript inhibit the expression of the over-expressed C2093, B5860Ns, or C6055s protein and can suppress the biological activity of the protein. Therefore, the ribozymes are useful in treating or preventing bladder cancer.

Antibodies:

Alternatively, function of one or more gene products of the genes over-expressed in BLC can be inhibited by administering a compound that binds to or otherwise inhibits the function of the gene products. For example, the compound is an antibody which binds to the over-expressed gene product or gene products.

The present invention refers to the use of antibodies, particularly antibodies against a protein encoded by an up-regulated marker gene, or a fragment of such an antibody. As used herein, the term "antibody" refers to an immunoglobulin molecule having a specific structure, that interacts (i.e., binds) only with the antigen that was used for synthesizing the antibody (i.e., the gene product of an up-regulated marker) or with an antigen closely related thereto.

The present invention provides an antibody that binds to the polypeptide of the invention. Specifically, the present invention provides an antibody which binds to antigenic determinant comprising the amino acid sequence from 304 to 588 of SEQ ID NO:4, which is the B5860NV1 specific sequence. The antibody of the invention can be used in any form, such as monoclonal or polyclonal antibodies, and includes antiserum obtained by immunizing an animal such as a rabbit with the polypeptide of the invention, all classes of polyclonal and monoclonal antibodies, human antibodies and humanized antibodies produced by genetic recombination.

A polypeptide of the invention used as an antigen to obtain an antibody may be derived from any animal species, but preferably is derived from a mammal such as a human, mouse, or rat, more preferably from a human. A human-derived polypeptide may be obtained from the nucleotide or amino acid sequences disclosed herein.

According to the present invention, the polypeptide to be used as an immunization antigen may be a complete protein or a partial peptide of the protein. A partial peptide may comprise, for example, the partial amino acid sequence selected from the B5860NV1 specific sequence (positions from 304 to 588 of SEQ ID NO:4).

Herein, an antibody is defined as a protein that reacts with either the full length or a fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates or a chemically synthesized polypeptide may be used as the antigen.

Any mammalian animal may be immunized with the antigen, but preferably the compatibility with parental cells used for cell fusion is taken into account. In general, animals of Rodentia, Lagomorpha or Primates are used. Animals of Rodentia include, for example, mouse, rat and hamster. Animals of Lagomorpha include, for example, rabbit. Animals of Primates include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, (1981) Methods Enzymol 73: 346).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells or their lysates in vitro. Then, the immunized lymphocytes are fused with human-derived myeloma cells that are capable of indefinitely dividing, such as U266, to yield a hybridoma producing a desired human antibody that is able to bind to the polypeptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the polypeptide of the present invention is coupled. The antibody of the present invention can be used not only for purification and detection of the polypeptide of the present invention, but also as a candidate for agonists and antagonists of the polypeptide of the present invention. In addition, this antibody can be applied to the antibody treatment for diseases related to the polypeptide of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a polypeptide, polypeptide expressing cells or their lysates. Antibody producing cells are then collected from the animals and fused with myeloma cells to obtain hybridoma, from which human antibodies against the polypeptide can be prepared (see WO92-03918, WO94-02602, WO94-25585, WO96-33735 and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, (1990) Therapeutic Monoclonal Antibodies, published in the United Kingdom by MacMillan Publishers LTD). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, F(ab')2, Fv or single chain Fv (scFv), in which Fv fragments from H and L chains are ligated by an appropriate linker (Huston et al., (1988) Proc Natl Acad Sci USA 85: 5879-83). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., (1994) J Immunol 152: 2968-76; Better and Horwitz, (1989) Methods Enzymol 178: 476-96; Pluckthun and Skerra, (1989) Methods Enzymol 178: 497-515; Lamoyi, (1986) Methods Enzymol 121: 652-63; Rousseaux et al., (1986) Methods Enzynol 121: 663-9; Bird and Walker, (1991) Trends Biotechnol 9: 132-7).

An antibody may be modified by conjugation with a variety of molecules, such as, for example, polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from a nonhuman antibody and the constant region derived from human antibody, or as a humanized antibody, comprising the complementarity determining region (CDR) derived from a nonhuman antibody, the frame work region (FR) and the constant region derived from a human antibody. Such antibodies can be prepared according to known technology. Humanization can be performed by substituting rodent CDRs or CDR sequences for the corresponding sequences of a human antibody (see e.g., Verhoeyen et al., (1988) Science 239:1534-6). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, (1992) J. Mol. Biol. 227:381-8, Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, (1988) Cold Spring Harbor Laboratory), but are not limited thereto. A protein A column and protein G column can be used as the affinity column. Exemplary protein A columns to be used include, for example, Hyper D, POROS and Sepharose F. F. (Pharmacia).

Exemplary chromatography, with the exception of affinity includes, for example, ion-exchange chromatography, hydrophobic chromatography, gel filtration, reverse-phase chromatography, adsorption chromatography and the like (Strategies for Protein Purification and Characterization: A Laboratory Course Manual. Ed Daniel R. Marshak et al., (1996) Cold Spring Harbor Laboratory Press). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of a polypeptide of the invention, by exposing the antibody of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

Cancer therapies directed at specific molecular alterations that occur in cancer cells have been validated through clinical development and regulatory approval of anti-cancer drugs such as trastuzumab (Herceptin) for the treatment of advanced breast cancer, imatinib methylate (Gleevec) for chronic myeloid leukemia, gefitinib (Iressa) for non-small cell lung cancer (NSCLC), and rituximab (anti-CD20 mAb) for B-cell lymphoma and mantle cell lymphoma (Ciardiello F and Tortora G. (2001) Clin Cancer Res.; 7(10):2958-70. Review; Slamon D J, et al., (2001) N Engl J Med.; 344(11): 783-92.; Rehwald U, et al., (2003) Blood; 101(2):420-4.; Fang G, et al., (2000). Blood, 96, 2246-53.). These drugs are clinically effective and better tolerated than traditional anti-cancer agents because they target only transformed cells. Hence, such drugs not only improve survival and quality of life for cancer patients, but also validate the concept of molecularly targeted cancer therapy. Furthermore, targeted drugs can enhance the efficacy of standard chemotherapy when used in combination with it (Gianni L. (2002). Oncology, 63 Suppl 1, 47-56.; Klejman A, et al., (2002). Oncogene, 21, 5868-76.). Therefore, future cancer treatments will probably involve combining conventional drugs with target-specific agents aimed at different characteristics of tumor cells such as angiogenesis and invasiveness.

These modulatory methods can be performed ex vivo or in vitro (e.g., by culturing the cell with the agent) or, alternatively, in vivo (e.g., by administering the agent to a subject). The methods involve administering a protein, or combination of proteins, or a nucleic acid molecule, or combination of nucleic acid molecules, as therapy to counteract aberrant expression of the differentially expressed genes or aberrant activity of their gene products.

Diseases and disorders that are characterized by increased (relative to a subject not suffering from the disease or disorder) expression levels or biological activities of genes and gene products, respectively, may be treated with therapeutics that antagonize (i.e., reduce or inhibit) activity of the over-expressed gene or genes. Therapeutics that antagonize activity can be administered therapeutically or prophylactically.

Accordingly, therapeutics that may be utilized in the context of the present invention include, e.g., (i) a polypeptide of the over-expressed or under-expressed gene or genes, or analogs, derivatives, fragments or homologs thereof; (ii) antibodies to the over-expressed gene or gene products; (iii) nucleic acids encoding the over-expressed or under-expressed gene or genes; (iv) antisense nucleic acids or nucleic acids that are "dysfunctional" (i.e., due to a heterologous insertion within the nucleic acids of one or more over-expressed gene or genes); (v) small interfering RNA (siRNA); or (vi) modulators (i.e., inhibitors, agonists and antagonists that alter the interaction between an over-expressed or under-expressed polypeptide and its binding partner). The dysfunctional antisense molecules are utilized to "knockout" endogenous function of a polypeptide by homologous recombination (see, e.g., Capecchi, (1989) Science 244: 1288-92).

Diseases and disorders that are characterized by decreased (relative to a subject not suffering from the disease or disorder) biological activity may be treated with therapeutics that increase (i.e., are agonists to) activity. Therapeutics that up-regulate activity may be administered in a therapeutic or prophylactic manner. Therapeutics that may be utilized include, but are not limited to, a polypeptide (or analogs, derivatives, fragments or homologs thereof) or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic administration occurs prior to the manifestation of overt clinical symptoms of disease, such that a disease or disorder is prevented or, alternatively, delayed in its progression. Therapeutic methods of the present invention may include the step of contacting a cell with an agent that modulates one or more of the activities of the gene products of the differentially expressed genes. Examples of agents that modulate protein activity include, but are not limited to, nucleic acids, proteins, naturally-occurring cognate ligands of such proteins, peptides, peptidomimetics, and other small molecule. For example, a suitable agent may stimulate one or more protein activities of one or more differentially under-expressed genes.

Vaccinating Against Bladder Cancer:

The present invention also relates to a method of treating or preventing bladder cancer in a subject comprising the step of administering to said subject a vaccine comprising a polypeptide encoded by a nucleic acid selected from the group consisting of the BLC-associated genes listed in Table 4 (i.e., up-regulated genes), an immunologically active fragment of said polypeptide, or a polynucleotide encoding such a polypeptide or fragment thereof. Administration of the polypeptide induces an anti-tumor immunity in a subject. To induce anti-tumor immunity, a polypeptide encoded by a nucleic acid selected from the group consisting of the BLC-associated genes listed in Table 4, an immunologically active fragment of said polypeptide, or a polynucleotide encoding such a polypeptide or fragment thereof is administered to subject in need thereof. The polypeptide or the immunologically active fragment thereof are useful as vaccines against BLC. In some cases, the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the present invention, a vaccine against BLC refers to a substance that has the ability to induce anti-tumor immunity upon inoculation into animals. According to the present invention, polypeptides encoded by the BLC-associated genes listed in Table 4, or fragments thereof, were suggested to be HLA-A24 or HLA-A*0201 restricted epitopes peptides that may induce potent and specific immune response against BLC cells expressing the BLC-associated genes listed in Table 4. Thus, the present invention also encompasses a method of inducing anti-tumor immunity using the polypeptides. In general, anti-tumor immunity includes immune responses such as follows:

induction of cytotoxic lymphocytes against tumors,
induction of antibodies that recognize tumors, and
induction of anti-tumor cytokine production.

Therefore, when a certain protein induces any one of these immune responses upon inoculation into an animal, the protein is determined to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. Specifically, a foreign substance that enters the living body is presented to T cells and B cells by the action of antigen presenting cells (APCs). T cells that respond to the antigen presented by the APCs in an antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell via an APC, and detecting the induction of CTLs. Furthermore, APCs have the effect of activating CD4+ T cells, CD8+ T cells, macrophages, eosinophils, and NK cells. Since CD4+ T cells and CD8+ T cells are also important in anti-tumor immunity, the anti-tumor immunity-inducing action of the peptide can be evaluated using the activation effect of these cells as indicators.

A method for evaluating the inducing action of CTLs using dendritic cells (DCs) as the APC is well known in the art. DCs are a representative APCs having the strongest CTL-inducing action among APCs. In this method, the test polypeptide is initially contacted with DCs, and then the DCs are contacted with T cells. Detection of T cells having cytotoxic effects against the cells of interest after the contact with DC shows that the test polypeptide has an activity of inducing the cytotoxic T cells. Activity of CTLs against tumors can be detected, for example, using the lysis of $^{51}$Cr-labeled tumor cells as the indicator. Alternatively, the method of evaluating the degree of tumor cell damage using $^{3}$H-thymidine uptake activity or LDH (lactose dehydrogenase)-release as the indicator is also well known.

Apart from DCs, peripheral blood mononuclear cells (PB-MCs) may also be used as the APC. The induction of CTLs has been reported to be enhanced by culturing PBMCs in the presence of GM-CSF and IL-4. Similarly, CTLs have been shown to be induced by culturing PBMCs in the presence of keyhole limpet hemocyanin (KLH) and IL-7.

Test polypeptides confused to possess CTL-inducing activity by these methods are deemed to be polypeptides having DC activation effect and subsequent CTL-inducing activity. Therefore, polypeptides that induce CTLs against tumor cells are useful as vaccines against tumors. Furthermore, APCs that have acquired the ability to induce CTLs against tumors through contact with the polypeptides are also useful as vaccines against tumors. Furthermore, CTLs that have acquired cytotoxicity due to presentation of the polypeptide antigens by APCs can be also used as vaccines against tumors. Such therapeutic methods for tumors, using antitumor immunity due to APCs and CTLs, are referred to as cellular immunotherapy.

Generally, when using a polypeptide for cellular immunotherapy, efficiency of the CTL-induction is known to be increased by combining a plurality of polypeptides having different structures and contacting them with DCs. Therefore, when stimulating DCs with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide is deemed to have the ability to induce anti-tumor immunity.

Anti-tumor immunity is induced by administering the vaccine of this invention, and the induction of anti-tumor immunity enables treatment and prevention of BLC. Therapy against cancer or prevention of the onset of cancer includes any of the following steps, such as inhibition of the growth of cancerous cells, involution of cancer, and suppression of the occurrence of cancer. A decrease in mortality and morbidity of individuals having cancer, decrease in the levels of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA may be used for statistical analysis.

The above-mentioned proteins having immunological activity or a vector encoding such a protein may be combined with an adjuvant. An adjuvant refers to a compound that enhances the immune response against the protein when administered together (or successively) with the protein having immunological activity. Exemplary adjuvants include, but are not limited to, cholera toxin, *salmonella* toxin, alum, and such, but are not limited thereto. Furthermore, the vaccine of this invention may be combined appropriately with a pharmaceutically acceptable carrier. Examples of such carriers include, but are not limited to, sterilized water, physiological saline, phosphate buffer, culture fluid, and such. Furthermore, the vaccine may contain as necessary, stabilizers, suspensions, preservatives, surfactants, and such. The vaccine can be administered systemically or locally. Vaccine administration can be performed by single administration, or boosted by multiple administrations.

When using an APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APCs or CTLs, the cells may be administered to the subject. APCs can be also induced by introducing a vector encoding the polypeptide into PBMCs ex vivo. APCs or CTLs induced in vitro can be cloned prior to administration. By cloning and growing cells having high activity of damaging target cells, cellular immunotherapy can be performed more effectively. Furthermore, APCs and CTLs isolated in this manner may be used for cellular immunotherapy not only against individuals from whom the cells are derived, but also against similar types of tumors from other individuals.

Furthermore, a pharmaceutical composition for treating or preventing a cell proliferative disease, such as cancer, comprising a pharmaceutically effective amount of a polypeptide of the present invention is provided. The pharmaceutical composition may be used for raising anti-tumor immunity.

The normal expression of C2093, B5860Ns or C6055s is restricted to testis. Therefore, suppression of this gene may not adversely affect other organs. Thus, the C2093, B5860Ns or C6055s polypeptides are preferable for treating cell proliferative disease, especially bladder cancers. Furthermore, since peptide fragments of proteins specifically expressed in cancerous cells were revealed to induce immune response against the cancer, peptide fragments of C2093, B5860Ns or C6055s can also be used in a pharmaceutical composition for treating or preventing cell proliferative diseases such as bladder cancers. In the present invention, the polypeptide or fragment thereof is administered at a dosage sufficient to induce anti-tumor immunity, which is in the range of 0.1 mg to 10 mg, preferably 0.3 mg to 5 mg, more preferably 0.8 mg to 1.5 mg. The administrations are repeated. For example, 1 mg of the peptide or fragment thereof may be administered 4 times in every two weeks for inducing the anti-tumor immunity.

In addition, polynucleotides encoding C2093, B5860Ns or C6055s, or fragments thereof may be used for raising anti tumor immunity. Such polynucleotides may be incorporated in an expression vector to express C2093, B5860Ns or C6055s, or fragments thereof in a subject to be treated. Thus, the present invention encompasses method for inducing anti tumor immunity wherein the polynucleotides encoding C2093, B5860Ns or C6055s, or fragments thereof are administered to a subject suffering or being at risk of developing cell proliferative diseases such as bladder cancer.

Pharmaceutical Compositions for Inhibiting BLC or Malignant BLC:

The present invention provides compositions for treating or preventing bladder cancer comprising any of the compounds selected by the screening methods of the present invention.

When administrating a compound isolated by the screening methods of the present invention as a pharmaceutical for humans or other mammals, including, but not limited to, mice, rats, guinea-pigs, rabbits, cats, dogs, sheep, pigs, cattle, monkeys, baboons, chimpanzees, for treating a cell proliferative disease (e.g., bladder cancer) the isolated compound can be directly administered or can be formulated into a dosage form using known pharmaceutical preparation methods. For example, according to the need, the drugs can be taken orally, as sugar-coated tablets, capsules, elixirs and microcapsules; or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules include, but are not limited to, binders, such as gelatin, corn starch, tragacanth gum and arabic gum; excipients, such as crystalline cellulose; swelling agents, such as corn starch, gelatin and alginic acid; lubricants, such as magnesium stearate; sweeteners, such as sucrose, lactose or saccharin; and flavoring agents, such as peppermint, *Gaultheria adenothrix* oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol and sodium chloride, can be used as aqueous solutions for injections. These can be used in conjunction with suitable solubilizers, such as alcohol, specifically ethanol, polyalcohols such as propylene glycol and polyethylene glycol, nonionic surfactants, such as Polysorbate 80™ and HCO-50. Sesame oil or soy-bean oil are examples of oleaginous liquids that may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampoule.

Methods well known to one skilled in the art may be used to administer the inventive pharmaceutical compound to patients, for example as intraarterial, intravenous, percutaneous injections and also as intranasal, intramuscular or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient; however, the selection and optimization of these parameters is within the purview of one skilled in the art.

In the context of the present invention, suitable pharmaceutical formulations include those suitable for oral, rectal, nasal, topical (including buccal and sub-lingual), vaginal or parenteral (including intramuscular, sub-cutaneous and intravenous) administration, or for administration by inhalation or insufflation. Preferably, administration is intravenous. The formulations are optionally packaged in discrete dosage units.

Pharmaceutical formulations suitable for oral administration include capsules, cachets or tablets, each containing a predetermined amount of active ingredient. Suitable formulations also include powders, granules, solutions, suspensions and emulsions. The active ingredient is optionally administered as a bolus electuary or paste. Tablets and capsules for oral administration may contain conventional excipients, such as binding agents, fillers, lubricants, disintegrant and/or wetting agents. A tablet may be made by compression or molding, optionally with one or more formulational ingredients. Compressed tablets may be prepared by compressing in a suitable machine the active ingredients in a free-flowing form, such as a powder or granules, optionally mixed with a binder, lubricant, inert diluent, lubricating, surface active and/or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives, such as suspending agents, emulsifying agents, non-aqueous vehicles (which may include edible oils), and/or preservatives. The tablets may optionally be formulated so as to provide slow or controlled release of the active ingredient therein. A package of tablets may contain one tablet to be taken on each of the month.

Formulations suitable for parenteral administration include aqueous and non-aqueous sterile injection solutions, optionally contain anti-oxidants, buffers, bacteriostats and solutes which render the formulation isotonic with the blood of the intended recipient; as well as aqueous and non-aqueous sterile suspensions including suspending agents and/or thickening agents. The formulations may be presented in unit dose or multi-dose containers, for example as sealed ampoules and vials, and may be stored in a freeze-dried (lyophilized) condition, to requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations suitable for rectal administration include suppositories with standard carriers such as cocoa butter or polyethylene glycol. Formulations suitable for topical administration in the mouth, for example, buccally or sublingually, include lozenges, containing the active ingredient in a flavored base such as sucrose and acacia or tragacanth, and pastilles, comprising the active ingredient in a base such as gelatin and glycerin or sucrose and acacia. For intra-nasal administration, the compounds of the invention may be used as a liquid spray, a dispersible powder, or in the form of drops. Drops may be formulated with an aqueous or non-aqueous base also comprising one or more dispersing agents, solubilizing agents and/or suspending agents.

For administration by inhalation the compounds can be conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base, such as lactose or starch. The powder composition may be presented in unit dosage form, for example, as capsules, cartridges, gelatin or blister packs, from which the powder may be administered with the aid of an inhalator or insufflators.

Other formulations include implantable devices and adhesive patches which release a therapeutic agent.

When desired, the above described formulations, adapted to give sustained release of the active ingredient, may be employed. The pharmaceutical compositions may also contain other active ingredients, such as antimicrobial agents, immunosuppressants and/or preservatives.

It should be understood that in addition to the ingredients particularly mentioned above, the formulations of this invention may include other agents conventional in the art with regard to the type of formulation in question. For example, formulations suitable for oral administration may include flavoring agents.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kg of body-weight.

Preferred unit dosage formulations contain an effective dose, as recited below, or an appropriate fraction thereof, of the active ingredient.

For each of the aforementioned conditions, the compositions, e.g., polypeptides and organic compounds, can be administered orally or via injection at a dose ranging from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, more typically from about 100 mg to about 500 mg.

The dose employed will depend upon a number of factors, including the age and sex of the subject, the precise disorder being treated, and its severity. Also the route of administration may vary depending upon the condition and its severity. In any event, appropriate and optimum dosages may be routinely calculated by those skilled in the art, taking into consideration the above-mentioned factors.

Furthermore, the present invention provides pharmaceutical compositions for treating or preventing bladder cancer comprising active ingredients that inhibits the expression of the C2093, B5860Ns or C6055s gene. Such active ingredients include antisense polynucleotides, siRNAs or ribozymes against the C2093, B5860Ns or C6055s gene or derivatives, such as expression vector, of the antisense polynucleotides, siRNAs or ribozymes.

The nucleotide sequence of siRNAs may also be designed in the same manner as mentioned above. Furthermore, oligonucleotides and oligonucleotides complementary to various portions of the C2093, B5860Ns or C6055s mRNA may also be selected in the same manner as mentioned above. Examples of C2093, B5860Ns or C6055s siRNA oligonucleotides which inhibit the expression in mammalian cells include the target sequence containing SEQ ID NO: 21, 25 and 144, respectively. The target sequence of SEQ ID NO: 25 is shared between the two B5860N transcripts, B5860NV1 and B5860NV2. Thus, siRNA comprising SEQ ID NO:25 as sense strand may inhibit the expression of both the B5860NV1 and B5860NV2 transcripts. The target sequence of SEQ ID NO: 144 is shared between the four C6055 transcripts, MGC34032, Genbank Accession NO.AK128063, C6055V1 and 6055V2. Thus, siRNA comprising SEQ ID NO:144 as sense strand may inhibit the expression of all the MGC34032, Genbank Accession NO.AK128063, C6055V1 and 6055V2 transcripts. In the present invention, when the nucleic sequence is RNA or derivatives thereof, base "t" should be replaced with "u" in the nucleotide sequences.

The siRNA is directly introduced into the cells in a form that is capable of binding to the mRNA transcripts. Alternatively, the DNA encoding the siRNA is in a vector in the same manner as in the use of the siRNA against the C2093, B5860N or C6055. Furthermore, a loop sequence consisting of an arbitrary nucleotide sequence can be located between the sense and antisense sequence in order to form the hairpin loop structure. Thus, the present invention also provides siRNA having the general formula 5'-[A]-[B]-[A']-3'. As mentioned above, in this formula, wherein

[A] is a ribonucleotide sequence corresponding to a sequence that specifically hybridizes to an mRNA or a cDNA of C2093, B5860N or C6055,

[B] is a ribonucleotide sequence consisting of about 3 to about 23 nucleotides, and

[A'] is a ribonucleotide sequence consisting of the complementary sequence of [A].

In the present invention, the siRNA, nucleotide "u" can be added to the 3' end of [A'], in order to enhance the inhibiting activity of the siRNA. The number of "u"s to be added is at least about 2, generally about 2 to about 10, preferably about 2 to about 5. Furthermore, loop sequence consisting of 23 nucleotides also provides active siRNA (Jacque, J.-M., et. al., (2002) Nature 418: 435-438.). For example, preferable siRNAs having hairpin structure of the present invention are shown below. In the following structure, the loop sequence can be selected from the group consisting of CCC, UUCG, CCACC, CCACACC, and UUCAAGAGA. Preferable loop sequence is UUCAAGAGA ("ttcaagaga" in DNA) Exemplary hairpin siRNA suitable for use in the context of the present invention include: for C2093-siRNA (for target sequence of GTGAAGAAGTGCGACCGAA/SEQ ID NO: 21) 5'-gugaagaagugcgaccgaa-[B]-uucggucgcacuucuucac-3' (SEQ ID NO: 24), for B5860N-siRNA (for target sequence of CCAAAGTTCCGTAGTCTAA/SEQ ID NO: 25) 5'-ccaaag-uuccguagucuaa-[B]-uuagacuacggaacuuugg-3' (SEQ ID NO: 28) and for C6055-siRNA (for target sequence of GTTG-CAGTTACAGATGAAG/SEQ ID NO: 144) 5'-gttgcagttaca-gatgaag-[B]-cttcatctgtaactgcaac-3' (SEQ ID NO: 147)

These active ingredients can be made into an external preparation, such as a liniment or a poultice, by mixing with a suitable base material which is inactive against the derivatives. Also, as needed, they can be formulated into, for example, tablets, powders, granules, capsules, liposome capsules, injections, solutions, nose-drops and freeze-drying agents by adding excipients, isotonic agents, solubilizers, stabilizers, preservatives, pain-killers and such. These can be prepared according to conventional methods.

The active ingredient is given to the patient by directly applying onto the ailing site or by injecting into a blood vessel so that it will reach the site of ailment. A mounting medium can also be used to increase durability and membrane-permeability. Examples of mounting medium includes liposome, poly-L-lysine, lipid, cholesterol, lipofectin or derivatives of these.

The dosage of such compositions of the present invention can be adjusted suitably according to the patient's condition and used in desired amounts. For example, a dose range of 0.1 to 100 mg/kg, preferably 0.1 to 50 mg/kg can be administered. Another embodiment of the present invention is a composition for treating or preventing bladder cancer comprising an antibody against a polypeptide encoded by the C2093, B5860Ns or C6055s gene or fragments of the antibody that bind to the polypeptide.

Although there are some differences according to the symptoms, the dose of an antibody or fragments thereof for treating or preventing bladder cancer is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the condition of the patient, symptoms of the disease and method of administration, it is convenient to intravenously inject a dose of about 0.01 mg to about 30 mg per day, preferably about 0.1 to about 20 mg per day and more preferably about 0.1 to about 10 mg per day. Also in the case of other animals too, it is possible to administer an amount converted to 60 kg of body-weight.

Aspects of the present invention are described in the following examples, which are not intended to limit the scope of the invention described in the claims. The following examples illustrate the identification and characterization of genes differentially expressed in BLC cells. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications cited herein are incorporated by reference.

EXAMPLES

Materials and Methods

Patients, Cell Line, Tissue Samples and Neoadjuvant Chemotherapy.

Human-bladder cancer cell lines HT1197, UMUC3, J82, HT1376, SW780 and RT4 were obtained from ATCC. All cells were cultured in appropriate media; i.e. EMEM (Sigma, St. Louis, Mo.) with 0.1 mM essential amino acid (Roche), 1 mM sodium pyruvate (Roche), 0.01 mg/ml Insulin (Sigma) for HT1197, UMUC3, J82 and HT1376; Dulbecco's modified Eagle's medium (Invitrogen, Carlsbad, Calif.) for HBL100, COS7; McCoy's 5a (Sigma) for RT-4; L-15 for SW 780. Each medium was supplemented with 10% fetal bovine serum (Cansera) and 1% antibiotic/antimycotic solution (Sigma). SW 780 cells were maintained at 37° C. an atmosphere of humidified air without CO2. Other cell lines were maintained at 37° C. an atmosphere of humidified air with 5% CO2.

Tissue samples from surgically resected bladder cancers and corresponding clinical information were obtained after each patient had provided written informed consent. A total of 33 cancer samples (9 females, 24 males; median age 66.5 in a range of 53-77 years, except one case with unknown years (BC01025)) (Table 1) that had been confirmed histologically as transitional cell carcinoma of the bladder were selected for this study. Clinical stage was judged according to the UICC TNM classification; we enrolled only patients without node metastasis, T2aN0M0 to T3bN0M0, who were expected to undergo radical cystectomy without prior radiation therapy. Participants were required to have no serious abnormality in renal, hepatic, or hematological function, with ECOG performance status (PS) judged to be ≦2.

TABLE 1

Patients Examined

| No. | ID | Sex | Age | Stage | Grade |
|---|---|---|---|---|---|
| 1 | BC01001 | M | 62 | T3b | G3 |
| 2 | BC01004 | M | 54 | T3b | G3 |
| 3 | BC01007 | M | 75 | T2b | G2 > G3 |

TABLE 1-continued

Patients Examined

| No. | ID | Sex | Age | Stage | Grade |
|---|---|---|---|---|---|
| 4 | BC01009 | M | 66 | T3b | G2 |
| 5 | BC01010 | M | 77 | T2b | G1 |
| 6 | BC01011 | M | 64 | T3b | G2 > G3 |
| 7 | BC01012 | M | 72 | T2b | G2 > G3 |
| 8 | BC01013 | F | 57 | T3b | G2 |
| 9 | BC01014 | M | 64 | T3b | G2 |
| 10 | BC01015 | M | 57 | T3b | G3 |
| 11 | BC01016 | M | 70 | T3b | G2 |
| 12 | BC01017 | M | 65 | T2b | G2 |
| 13 | BC01018 | M | 71 | T3b | G2 |
| 14 | BC01019 | M | 59 | T2b | G2 |
| 15 | BC01020 | M | 72 | T3b | G2 |
| 16 | BC01021 | F | 68 | T2b | G2 |
| 17 | BC01022 | M | 73 | T3b | G1 > G2 |
| 18 | BC01023 | F | 74 | T3b | G3 |
| 19 | BC01024 | M | 66 | T3b | G3 |
| 20 | BC01025 | M | unknown | T2b | G2 |
| 21 | BC01026 | M | 58 | T3b | G3 |
| 22 | BC01027 | M | 72 | T2b | G2 |
| 23 | BC01028 | M | 69 | T3a | G2 |
| 24 | BC01029 | F | 67 | T3a | G3 |
| 25 | BC01031 | M | 74 | T3b | G2 |
| 26 | BC01032 | F | 64 | T3b | G3 >> G2 |
| 27 | BC01033 | F | 68 | T3b | G2 |
| 28 | BC02003 | F | 53 | T3a | G2 |
| 29 | BC02014 | M | 56 | T3b | G2 |
| 30 | BC03001 | M | 53 | T3b | G3 |
| 31 | BC04001 | F | 70 | T3b | G3 |
| 32 | BC05001 | F | 73 | T3a | G1 = G2 |
| 33 | BC05002 | M | 60 | T3b | G2 |

Three to five pieces of cancer tissue were taken from each patient at the time of biopsy prior to neoadjuvant chemotherapy. These samples were immediately embedded in TissueTek OCT medium (Sakura, Tokyo, Japan), frozen, and stored at −80° C. The frozen tissues were sliced into 8-μm sections using a cryostat (Sakura, Tokyo, Japan) and then stained with hematoxylin and eosin for histological examination. Bladder-cancer cells were selectively enriched for our experiments using the EZ-cut system with a pulsed ultraviolet narrow beam-focus laser (SL Microtest GmbH, Germany) according to the manufacturer's protocols. All patients were examined by chest X-ray, computed tomography (CT) and magnetic resonance imaging (MRI) of the abdomen and pelvis, and conformed to have neither lymph node nor distant metastases.

Extraction of RNA and T7-Based RNA Amplification.

Total RNAs were extracted from each population of microdissected cancer cells, as described previously (Kitahara O, et al., (2001) Cancer Res; 61:3544-9). To guarantee the quality of RNAS, total RNA extracted from the residual tissue of each case were electrophoresed on a denaturing agarose gel, and quality was confirmed by the presence of ribosomal RNA bands. Extraction of total RNA and T7-based RNA amplification were performed as described previously (Okabe H, et al., (2001) Cancer Res; 61:2129-37), except that we used RNeasy Micro Kits (QIAGEN, Valencia, Calif., USA). After two rounds of RNA amplification, we obtained 30-100 μg of amplified RNA (aRNA) for each sample. As a control, normal human bladder poly $(A)^+$ RNA (BD Bioscience, Palo Alto, Calif.), was amplified in the same way. RNA amplified by this method accurately reflects the proportions in the original RNA source, as we had confirmed earlier by semi-quantitative RT-PCR experiments (Kitahara O, et al., (2001) Cancer Res; 61:3544-9), where data from the microarrays were consistent with results from RT-PCR regardless of whether total RNAs or aRNAs were used as templates.

cDNA microarray.

To obtain cDNAs for spotting on the glass slides, we performed RT-PCR for each gene, as described previously (Kitahara O, et al., (2001) Cancer Res; 61:3544-9). The PCR products were spotted on type VII glass slides (GE Healthcare, Amersham Biosciences, Buckinghamshire UK) with a high-density Microarray Spotter Lucidea (GE Healthcare, Amersham Biosciences); 9,216 genes were spotted in duplicate on a single slide. Three different sets of slides (a total of 27,648 gene spots) were prepared, on each of which the same 52 housekeeping genes and two negative control genes were spotted as well. The cDNA probes were prepared from aRNA in the manner described previously (Okabe H, et al., (2001) Cancer Res; 61:2129-37). For hybridization experiments, 9.0 μg of amplified RNAs (aRNAs) from each cancerous tissue and from the control were reversely transcribed in the presence of Cy5-dCTP and Cy3-dCTP (GE Healthcare, Amersham Biosciences) respectively. Hybridization, washing and detection of signals were carried out as described previously (Okabe H, et al., (2001) Cancer Res; 61:2129-37).

Quantification of Signals.

The signal intensities of Cy3 and Cy5 were quantified from the 27,648 spots and analyzed the signals by substituting backgrounds, using Arrayvision software (Imaging Research, Inc., St. Catharines, Ontario, Canada). Subsequently, the fluorescence intensities of Cy5 (tumor) and Cy3 (control) for each target spot were adjusted so that the mean Cy5/Cy3 ratio of the 52 housekeeping genes became one. Because data derived from low signal intensities are less reliable, we determined a cutoff value on each slide as described previously (Ono K, et al., (2000) Cancer Res; 60:5007-11), and excluded genes from further analysis when both Cy3 and Cy5 dyes yielded signal intensities lower than the cutoff (Saito-Hisaminato A, et al., (2002) DNA Res; 9:35-45). For other genes, the previous method that calculated Cy5/Cy3 as a relative expression ratio using the raw data of each sample was modified, because if either Cy3 or Cy5 signal intensity was lower than the cutoff value the Cy5/Cy3 ratio might provide an extremely high or low reading and lead to selection of false-prediction genes. To reduce that bias, if either Cy3 or Cy5 signal intensity was less than the cutoff value, the Cy5/Cy3 ratios were calculated using half of each cut-off value plus the Cy5 and Cy3 signal intensities of each sample.

Identification of Up- or Down-Regulated Genes in Bladder Cancers.

Up- or down-regulated genes common to bladder cancers were identified and analyzed according to the following criteria. Initially, genes were selected whose relative expression ratio was able to calculate of more than 50% cases and whose expression were up- or down-regulated in more than 50% of cases. Moreover, if the relative expression ratio was able to calculate of 30 to 50% cases, the genes were also evaluated that 80% of cases were up- or down-regulated. The relative expression ratio of each gene (Cy5/Cy3 intensity ratio) was classified into one of four categories as follows: (1) up-regulated (expression ratio was more than 5.0); (2) down-regulated (expression ratio less than 0.2); (3) unchanged expression (expression ratio between 0.2 and 5.0); and (4) not expressed (or slight expression but under the cut-off level for detection). These categories were used to detect a set of genes whose changes in expression ratios were common among samples as well as specific to a certain subgroup. To detect candidate genes that were commonly up- or down-regulated in bladder cancer cell, the overall expression patterns of 27,648 genes were screened to select genes with expression ratios of more than 5.0 or less than 0.2. Among the total of 394 genes that appeared to up-regulated in tumor cells, attention was focused on the ones with in-house identification numbers C2093, B5860N and C6055 because their expression ratios were greater than 5.0 in more than 50% of the informative bladder cancer cases, and showed low expression in normal organs including heart, lung liver and kidney through the expression profiles of normal human tissues.

Semi-quantitative RT-PCR

The 44 up-regulated genes were selected and examined their expression levels by applying the semi-quantitative RT-PCR experiments. A 3-μg aliquot of aRNA from each sample was reverse-transcribed for single-stranded cDNAs using random primer (Roche) and Superscript II (Invitrogen). Each cDNA mixture was diluted for subsequent PCR amplification with the same primer sets that were prepared for the target DNA- or GAPDH-specific reactions. The primer sequences using RT-PCR in FIG. 1a are listed in Table 2. The PCR primer sequences using RT-PCR in FIGS. 1b and 1c are as follows; 5'-TGCTGG TTCAGAACGAACTATG-3' (SEQ ID NO.9) and 5'-TCCTCGTGGCTAATGAAAGC-3' (SEQ ID NO.10) for C2093, 5'-GCTACAAGTAAAGAGGGGATGG-3' (SEQ ID NO.11) and 5'-GGACAGAAAGGTAAGT-CAGTGGG-3' (SEQ ID NO.12) for the common sequence of B5860N V1 and V2. Expression of GAPDH served as an internal control. PCR reactions were optimized for the number of cycles to ensure product intensity within the linear phase of amplification (Table 2).

TABLE 2

Primer Sequence for RT-PCR in FIG. 1a

| LMMID | Forward Primer | SEQ ID No | Reverse Primer | SEQ ID No. | PCR |
|---|---|---|---|---|---|
| B5860N | 5'-ATTGTGGGAATGCACAGG TT-3' | 37 | 5'-GGACAGAAAGGTAAG TCAGTGGG-3' | 12 | 56d 25cy |
| B0811 | 5'-GATGTACATATGAGGATT TCCCG-3' | 38 | 5'-GTCAGTGCACATAAT TCCAATAGC-3' | 39 | 56d 25cy |
| C2093 | 5'-TTCTAGCTCCTCAACCAA ATCCT-3' | 40 | 5'-CCGGGAAAGTAAACT GACTCAC-3' | 41 | 56d 25cy |
| F6022 | 5'-TTCTCTTGAGGGCTGCTT TGT-3' | 42 | 5'-TCATCCACTGAAATA CCTGGCTT-3' | 43 | 56d 25cy |
| F7562 | 5'-TGGCCATATCAGTTCCAA CA-3' | 44 | 5'-CTTTGGCATAGCAGC CTGAACT-3' | 45 | 56d 25cy |
| F4976 | 5'-GGAGAATGAGCTGGATCA GG-3' | 46 | 5'-ATGCTGCAATTCCCA AATCTCT-3' | 47 | 56d 25cy |
| F6193 | 5'-AACTCATTGTGTGGCTGT GC-3' | 48 | 5'-CATCACAATCCTGGG AATTCAG-3' | 49 | 56d 25cy |
| F7409 | 5'-TCCTGAGGGCCATrTACT CA-3' | 50 | 5'-TGCATCCAGTAGCTA TTCAGCAA-3' | 51 | 56d 25cy |
| C6055 | 5'-TCCAGTTGGTTACTCAGT GTTTG-3' | 52 | 5'-CTGTCATGTGCTCAT GTGAGTTT-3' | 53 | 56d 25cy |
| D5491 | 5'-CGTCGACAATATAAACAG GGACT-3' | 54 | 5'-CGAGCACAAGATAAT TTTTCCC-3' | 55 | 56d 25cy |
| C5088 | 5'-GCAAGTCAGTGCCTAGAT GGATA-3' | 56 | 5'-AAAAATTGAGTGTGT CTCGGTG-3' | 57 | 56d 25cy |
| D7746 | 5'-TACAGAGAGGATGGGATT GTGTT-3' | 58 | 5'-CCTAGCAGTTGTTAG AGGCAGAA-3' | 59 | 56d 25cy |
| A0303 | 5'-GGGCTTTTAATTTGTGAA CTTCTG-3' | 60 | 5'-TGAAATAGTCTGGCC ATTTGAC-3' | 61 | 56d 25cy |
| C6865 | 5'-GTCCCAGACAACAGAAGT TACCA-3' | 62 | 5'-AATTTCCTCAGAGCT CACATACG-3' | 63 | 56d 25cy |
| F0411 | 5'-TTTATATTGTGCCATGCA GTCC-3' | 64 | 5'-ACCAGGATCACAGAG AGCTTGA-3' | 65 | 56d 25cy |
| A8295 | 5'-TCAGAGTGAGGACTCATT TATCATTT-3' | 66 | 5'-CACAGGGCAGGTTTT GATTTAT-3' | 67 | 56d 25cy |
| F4025 | 5'-CCCCTTCAGTGAGCCTCA TA-3' | 68 | 5'-TGAAATTGACCTGGT AGAGCCTT-3' | 69 | 56d 30cy |
| B2879N | 5'-TGTGTTTTCTTTTGGCAC CAT-3' | 70 | 5'-TTACTCCTGGCAAGC TGTGAG-3' | 71 | 56d 30cy |
| A0576N | 5'-ATATCAGCATCACGGCAC AA-3' | 72 | 5'-GTATGATGTAGCTGA GGTCCGTG-3' | 73 | 56d 30cy |

TABLE 2-continued

Primer Sequence for RT-PCR in FIG. 1a

| LMMID | Forward Primer | SEQ ID No | Reverse Primer | SEQ ID No. | PCR |
|---|---|---|---|---|---|
| F6507 | 5'-TGCTGGCTAACTAAAGAAGATGC-3' | 74 | 5'-AAATGAGGCCATTCTGTTGAGA-3' | 75 | 56d 30cy |
| F1653 | 5'-TGAGATTCTGGAGAGTGAATGC-3' | 76 | 5'-TCAGATGTTGTAGCAGGGACTTT-3' | 77 | 56d 30cy |
| C2210 | 5'-CATTTCTTTATAGTTGCCTCCCC-3' | 78 | 5'-TTTTGGGTCAGCACTGACAAT-3' | 79 | 56d 30cy |
| C7757 | 5'-GTCTTGGAGGAGCAGATTCCA-3' | 80 | 5'-CTACAATTTATTTCCGAGTCCCC-3' | 81 | 56d 30cy |
| F5981 | 5'-CCTCAAGGCCATTGATGTAAA-3' | 82 | 5'-ATGGTAACCCACATGACCCACTG-3' | 83 | 56d 25cy |
| B9838 | 5'-AGATAAATCATGACAAGGTCCCC3' | 84 | 5'-GCCTTTTGCTTCTTCTGTCTTCT-3' | 85 | 56d 28cy |
| F6910 | 5'-TTGGTGTAGCACCACACTGG-3' | 86 | 5'-GCATGACTCAGGGAAGGGTATT-3' | 87 | 56d 30cy |
| D7443 | 5'-AATGGCATGATCTTGTGTGAAG-3' | 88 | 5'-AGATCACTGTGGGTCTTAAGCAA-3' | 89 | 56d 25cy |
| C5509 | 5'-TCTACACCACAGAAAGCAAGTCA-3' | 90 | 5'-TACCTGAGGAAATTCCCGTTACT-3' | 91 | 56d 25cy |
| A8407 | 5'-ATAGGGATAATGGCCTCCAATTC-3' | 92 | 5'-CTCGCACCTAATAATCTGGTCTC-3' | 93 | 56d 28cy |
| B6283 | 5'-TGTGTCTCATCTGTGAACTGCTT-3' | 94 | 5'-TTCGTGTTACGGTATATCCTGCT-3' | 95 | 56d 25cy |
| D9407 | 5'-CCCTAAAGAGTGAGTTTTCCACA-3' | 96 | 5'-AAAGGTATTTTCCTGCAGTAGCC-3' | 97 | 56d 25cy |
| B2426 | 5'-GGGCCAGTATGTGTAACTGACAT-3' | 98 | 5'-TCAGACATCTGCTGACTACAGGA-3' | 99 | 56d 25cy |
| C1898 | 5'-CAACGAGAGCAAAACTCCAATAC-3' | 100 | 5'-ATAGGGTTTTGCAGTAGGGAGAG-3' | 101 | 56d 25cy |
| A7343N | 5'-CACATGGTGACCACAGTGCAT-3' | 102 | 5'-AGAGGGTGAGGGCTTTCATCT-3' | 103 | 56d 25cy |
| D8150 | 5'-CTTGCTATTGTCAGGTTTTGGTG-3' | 104 | 5'-CACTGCATTTACTGCTTTTGGA-3' | 105 | 56d 25cy |
| C7747 | 5'-AGGAGAGGGAGAAATCTTAGCAA-3' | 106 | 5'-CCAGTTGTATGCCAACATACTCA-3' | 107 | 56d 27cy |
| F7016 | 5'-CAGGATTCCAAATGTCAGTGAG-3' | 108 | 5'-CCTGCCATTGTCTTTCAGGTTT-3' | 109 | 56d 25cy |
| A8317N | 5'-CCTATCACAGACGGAAATCCC-3' | 110 | 5'-TAGGGCAGTTTCCTGGGTTCCT-3' | 111 | 56d 25cy |
| F6225 | 5'-TGCTCTGTACATGCCTCTGC | 112 | 5'-GCACCCAGAAGGACTTGCTATT-3' | 113 | 56d 25cy |
| D6311 | 5'-CTTCAGAGTGGGTTGGAAAAAT-3' | 114 | 5'-TAGTGTGTAATGCGATCCTGTGA-3' | 115 | 56d 30cy |
| C6902 | 5'-CACTGTGGCAAGATTGCTCT-3' | 116 | 5'-TACATCACAGCCTTGTTCTTTCC-3' | 117 | 56d 25cy |

TABLE 2-continued

Primer Sequence for RT-PCR in FIG. 1a

| LMMID | Forward Primer | SEQ ID No | Reverse Primer | SEQ ID No. | PCR |
|---|---|---|---|---|---|
| F6333 | 5'-AAGCGGTCCACAGTCCAA TA-3' | 118 | 5'-TCACATTGGAG-GATAG CTGGAA-3' | 119 | 56d 30cy |
| F7636 | 5'-GAAGTTTCCTGAGGCTCC AA-3' | 120 | 5'-GCCCACAA-GAGAAGGT AGAGGA-3' | 121 | 56d 25cy |
| F2376 | 5'-TCCTCTGTCGGTAGCTGT CA-3' | 122 | 5'-ACCCTTCAT-GTTTCTA GGGCTG-3' | 123 | 56d 25cy |
| GAPDH | 5'-CGACCACTTTGTCAAGCT CA-3' | 7 | 5'-GGTTGAGCA-CAGGGTA CTTTATT-3' | 8 | 56d 20cy |

Northern-blot Analysis

Northern blots were hybridized with [$\alpha^{32}$P]-dCTP-labeled amplification products of A0576N, C2093, C5509, B5860N, F1653, B9838 and C6055 prepared by RT-PCR, respectively (Table 3). Specific probes for C6055 were prepared by PCR using a primer set as follows; 5'-CCCCAGT-TGAGAGTTTGCTC-3' (SEQ ID. NO: 137) and 5'-CTGT-CATGT GCTCATGTGAGTTT-3' (SEQ ID NO: 53) for the microarray probe of C6055, 5'-TGACA TCGGGATTCA-GACTAA-3' (SEQ ID NO: 138) and 5'-AAAGATGCTG-GTCCTTGTGC-3' (SEQ ID NO: 139) for the common region among four transcripts of C6055. Total RNAs were extracted from all bladder cancer cell lines and frozen surgical specimens using TRIzol reagent (Invitrogen) according to the manufacturer's instructions. After treatment with DNase I (Nippon Gene, Osaka, Japan), mRNA was isolated with Micro-FastTrack (Invitrogen) following the manufacturer's instructions. A 1-µg aliquot of each mRNA, along with polyA (+) RNAs isolated from normal adult human heart, lung, liver, kidney, brain, pancreas, testis and bladder (Clontech, Palo Alto, Calif.), were separated on 1% denaturing agarose gels and transferred to nylon membranes. Pre-hybridization, hybridization and washing were performed according to the supplier's recommendations. The blots were autoradiographed with intensifying screens at −80° C. for 14 days.

TABLE 3

Primer Sequence for production of Northern probe by RT-PCR

| | Sequence | SEQ ID NO. |
|---|---|---|
| C2093_F2 | 5'-TGCTGGTTCAGAACGAACTATG-3' | 9 |
| C2093_R2 | 5'-TCCTCGTGGCTAATGAAAGC-3' | 10 |
| B5860N_F2 | 5'-AGGCAGGCAACTTTCATTTG-3' | 13 |
| B5860N_RT | 5'-GGACAGAAAGGTAAGTCAGTGGG-3' | 12 |
| A0576N_FT | 5'-GTCCCTCATGCCATCACAGTAT-3' | 124 |
| A0576N_RT | 5'-GTATGATGTAGCTGAGGTCCGTG-3' | 73 |
| F1653_F1 | 5'-AGCAGAGGCTGAGCAAAGAG-3' | 125 |
| F1653_R1 | 5'-CCCCAGTTTCTGGAATGCTA-3' | 126 |
| C5509_F1 | 5'-AGCGGAGTTCATAAGCCAAA-3' | 127 |
| C5509_R1 (RT) | 5'-TACCTGAGGAAATTCCCGTTACT-3' | 91 |
| B9838_F2-RT | 5'-TCAAGGGACAATGGTGTGAC-3' | 128 |
| B9838_RT | 5'-GCCTTTTGCTTCTTCTGTCTTCT-3' | 85 |
| C6055_F1 | 5'-CCCCAGTTGAGAGTTTGCTC-3' | 137 |
| C6055_R1 | 5'-CTGTCATGTGCTCATGTGAGTTT-3' | 53 |
| C6055_F2 | 5'-TGACATCGGGATTCAGACTAA-3' | 138 |
| C6055_R2 | 5'-AAAGATGCTGGTCCTTGTGC-3' | 139 |

5'RACE and 3'RACE

The sequence of 5' end and 3' end of B5860N and C6055 was determined by performing 5' rapid amplification of cDNA ends (5'RACE) and 3' rapid amplification of cDNA ends (3'RACE) using SMART™ RACE cDNA Amplification Kit (Clontech). The cDNA template was synthesized from bladder cancer cell line, SW780 cells, for amplification and the PCR was carried out using B5860N-specific reverse primer (5'-CATTT TCTGATCCCCACCTCCCTTTG-3' (SEQ ID NO.14)), C6055-specific reverse primer (C6055_GSP1; 5'-GATCCAAATGCTAGGGATCCTGT-GTG-3' (SEQ ID NO: 140) and C6055_NGSP1; 5'-CCTGT-GTGATATCGTATGGCTCGTCCA-3' (SEQ ID NO: 141)) for 5'RACE and B5860N-specific forward primer (5'-AGAGGGGATGGGGAAGGTGTTGC-3' (SEQ ID NO. 15)) for 3'RACE and the AP1 primer supplied in the kit.

Construction of Expression Vectors

The entire coding sequence of C2093, B5860Ns and C6055s cDNA was amplified by PCR using KOD-Plus DNA polymerase (Toyobo, Osaka, Japan) with primers as follows; C2093-forward, 5'-ATAAGAATGCGGCCGCAATG-GAATCTAATTTTTAATCAAGAGG-3' (SEQ ID NO. 16) (the underline indicates NotI site) and C2093-reverse, 5'-ATAAGAATGCGGCCGCTTTGGCT-GTTTTTTGTTCGA-3' (SEQ ID NO:17) (the underline indicates NotI site), B5860NV1-forward, 5'-ATAAGAATGCGGCCGCTATG-GAGAGTCAGGGTGTGC-3' (SEQ ID NO. 18) (the underline indicates NotI site) and B5860NV1-reverse, 5'-CCGCTCGAGTCTTAGACTACG-GAACTTTGGT-3' (SEQ ID NO. 19) (the underline indicates XhoI site), B5860NV2-forward, 5'-GGAATTCATGGAGAGT-CAGGGTGTG-3' (SEQ ID NO. 20) (the underline indicates EcoRI site) and B5860NV2-reverse, 5'-CCGCTCGAGTCTTAGACTACG-GAACTTTGGT-3' (SEQ ID NO. 19) (the underline indicates XhoI site), C6055-forward, 5'-AGAATTCATGATCTTCCTACTGTG-TATTATTGGC-3' (SEQ ID NO: 142) (the underline indicates EcoRI site) and C6055-reverse, 5'-TATCTCGAGCTGCTTC-CTAGTTTGTGGATTTTC-3'; (SEQ ID NO: 143) (the underline indicates XhoI site). The PCR products were inserted into the EcoRI and XhoI, and NotI sites of pCAGGSnHA expression vectors, respectively. These constructs were confirmed by DNA sequencing.

Western Blotting Analysis

COS7 cells were transiently transfected with 1 µg of pCAGGS-C2093-HA, pCAGGS-B5860NV1-HA, pCAGGS-B5860NV2-HA, or pCAGGS-C6055-HA using FuGENE 6 transfection reagent (Roche) according to the manufacturer's instructions, respectively. Cell lysates were separated on 10% SDS-polyacrylamide gels (for pCAGGS-C2093-HA, pCAGGS-B5860NV1-HA, pCAGGS-B5860NV2-HA transfected cells) or 7.5% SDS-polyacrylamide gels (for pCAGGS-C6055-HA transfected cells) and transferred to nitrocellulose membranes, then incubated with a mouse anti-HA antibody (Roche) as primary antibody at 1:1000 dilution. After incubation with sheep anti-mouse IgG-HRP as secondary antibody (Amersham Biosciences), signals were visualized with an ECL kit (Amersham Biosciences).

Immunocytochemical Staining to Detect Exogenous C2093, B5860N and C6055 Proteins in Bladder Cancer Cells To examine the sub-cellular localization of exogenous C2093, B5860NV1 and B5860NV2, or C6055, COS7 cells were seeded at $1 \times 10^5$ cells per well for all three constructs. After 24 hours, we transiently transfected with 1 µg of pCAGGS-C2093-HA, pCAGGS-B5860NV1-HA, pCAGGS-B5860NV2-HA or pCAGGS-C6055-HA into COS7 cells using FuGENE 6 transfection reagent (Roche) according to the manufacturer's instructions, respectively. Then, cells were fixed with PBS containing 4% paraformaldehyde for 15 min, and rendered permeable with PBS containing 0.1% Triton X-100 for 2.5 min at 4° C. Subsequently the cells were covered with 3% BSA in PBS for 12 hours at 4° C. to block non-specific hybridization. Next, each construct-transfected COS7 cells were incubated with a mouse anti-HA antibody (Roche) at 1:1000 dilution. After washing with PBS, both transfected-cells were stained by an Alexa488-conjugated anti-mouse secondary antibody (Molecular Probe) at 1:3000 dilution. Nuclei were counter-stained with 4',6-diamidino-2-phenylindole dihydrochloride (DAPI). Fluorescent images were obtained under a TCS SP2 AOBS microscope (Leica, Tokyo, Japan).

Synchronization and Flow Cytometry Analysis

HeLa cells ($1 \times 10^6$) are transfected with 8 µg of pCAGGS-C2093-HA, or pCAGGS-B5860NV1-HA, pCAGGS-B5860NV2-HA using FuGENE 6 (Roche) according to supplier's protocol. Cells are arrested in G1 phase 24 hours after transfection with aphidicolin (1 ng/ml) for further 16 hours. Cell cycle is released by washing three times with fresh medium and cells are collected at indicated time points. To arrest cells at mitotic phase, cells are incubated with Nocodazole (250 ng/ml) 16 hours before harvest.

For FACS analysis, 400 ml aliquot of synchronized adherent and detached cells were combined and fixed with 70% ethanol at 4° C. After washing with PBS (−) twice, cells were incubated for 30 min with 1 ml of PBS containing 1 mg of RNase I at 37° C. Cells were then stained in 1 ml of PBS containing 50 mg of propidium iodide (PI). The percentages of each fraction of cell cycle phases were determined from at least 10000 cells in a flow cytometer (FACScalibur; Becton Dickinson, San Diego, Calif.).

Construction of C2093, B5860N and C6055 Specific-siRNA Expression Vector Using psiU6X3.0

A vector-based RNAi system was established using psiU6BX siRNA expression vector according to the previous report (WO2004/076623). siRNA expression vector against C2093 (psiU6BX-C2093), B5860N (psiU6BX-B5860N), C6055 (psiU6BX-C6055) and control plasmids, psiU6BX-EGFP, —SCR were prepared by cloning of double-stranded oligonucleotides into the BbsI site in the psiU6BX vector. Nucleotide sequences of the double-stranded oligonucleotides are shown below.

C2093si#3 for the target sequence of GTGAAGAAGT-GCGACCGAA (SEQ ID NO: 21)

Sense
(SEQ ID NO: 22)
5'-CACCGTGAAGAAGTGCGACGAATTCAAGAGATTCGGTCGCACTTCTT
CAC-3'

Antisense
(SEQ ID NO: 23)
5'-AAAAGTGAAGAAGTGCGACCGAATCTCTTGAATTCGGTCGCACTTCT
TCAC-3'

B5860Nsi#3 for the target sequence of CCAAAGTTCCG-TAGTCTAA (SEQ ID NO: 25)

Sense
(SEQ ID NO: 26)
5'-CACCCCAAAGTTCCGTAGTCTAATTCAAGAGATTAGACTACGGAACT
TTGG-3'

Antisense
(SEQ ID NO: 27)
5'-AAAACCAAAGTTCCGTAGTCTAATCTCTTGAATTAGACTACGGAACT
TTGG-3'

C6055si-08 for the target sequence of GTTGCAGTTACA-GATGAAG (SEQ ID NO: 144)

Sense
(SEQ ID NO: 145)
5'-CACCGTTGCAGTTACAGATGAAGTTCAAGAGACTTCATCTGTAACTG
CAAC-3'

Antisense
(SEQ ID NO: 146)
5'-AAAAGTTGCAGTTACAGATGAAGTCTCTTGAACTTCATCTGTAACTG
CAAC-3' siRNA control (SiEGFP) for the target sequence of GAAGCAGCACGACTTCTTC (SEQ ID NO: 29)

Sense
(SEQ ID NO: 30)
5'-CACCGAAGCAGCACGACTTCTTCTTCAAGAGAGAAGAAGTCGTGCTG
CTTC-3'

-continued

Antisense
(SEQ ID NO: 31)
5'-AAAAGAAGCAGCACGACTTCTTCTCTCTTGAAGAAGAAGTCGTGCTG
CTTC-3' siRNA control (SiSCR) for the target sequence of GCGCGCTTTGTAGGATTCG (SEQ ID NO: 33)

Sense
(SEQ ID NO: 34)
5'-CACCGCGCGCTTTGTAGGATTCGTTCAAGAGACGAATCCTACAAAGC
GCGC-3'

Antisense
(SEQ ID NO: 35)
5'-AAAAGCGCGCTTTGTAGGATTCGTCTCTTGAACGAATCCTACAAAGC
GCGC-3'

These siRNA expression vectors express siRNA having hairpin structure consisting of nucleotide sequence of as follows:

C2093 si#3;
(SEQ ID NO: 24)
GTGAAGAAGTGCGACCGAATTCAAGAGATTCGGTCGCACTTCTTCAC,

B5860N si#3:
(SEQ ID NO: 28)
CCAAAGTTCCGTAGTCTAATTCAAGAGATTAGACTACGGAACTTTGG,

C6055 si-08
(SEQ ID NO: 147)
GTTGCAGTTACAGATGAAGTTCAAGAGACTTCATCTGTAACTGCAAC

EGFP control:
(SEQ ID NO: 32)
GAAGCAGCACGACTTCTTCTTCAAGAGAGAAGAAGTCGTGCTGCTTC,
and SCR control:
(SEQ ID NO: 36)
GCGCGCTTTGTAGGATTCGTTCAAGAGACGAATCCTACAAAGCGCGC Gene-Silencing Effect of C2093, B5860N and C6055

Human bladder cancer cells lines, UMUC3 and J82 for C2093 and B5860N, or SW780 for C6055, were plated onto 10-cm dishes (1×10⁶ cells/dish) and transfected with psiU6BX-EGFP and psiU6BX-SCR as negative controls, psiU6BX-C2093, psiU6BX-B5860N or psiU6BX-C6055 using FuGENE6 (Roche) and Lipofectamine-2000 (Invitrogen) reagents for C2093 and B5860N, or using Nucleofector (Amaxa) regent for C6055 according to the supplier's recommendations, respectively. Total RNAs were extracted from the cells at 6 days after the transfection of each construct, and then the knockdown effect of siRNAs was confirmed by semi-quantitative RT-PCR using specific primers for common regions of C2093, B5860N and C6055 as above mentioned. The primers for GAPDH and ACTB as internal control is as follows;

GAPDH
5'-CGACCACTTTGTCAAGCTCA-3' (SEQ ID NO.7)
and

5'-GGTTGAGCACAGGGTACTTTATT-3'. (SEQ ID NO.8)

ACTB
5'-CATCCACGAAACTACCTTCAACT-3' (SEQ ID NO: 148)

5'-TCTCCTTAGAGAGAAGTGGGGTG-3' (SEQ ID NO: 149)

Moreover, transfectants expressing siRNAs using UMUC3, J82 and SW780 cell lines were grown for 21, 28 and 24 days in selective media containing 0.6, 1.0 and 0.3 mg/mil of neomycin, respectively. After fixation with 4% paraformaldehyde, transfected cells were stained with Giemsa solution to assess colony formation. MTT assays were performed to quantify cell viability. After 21 and 28 days of culture in the neomycin-containing medium, respectively, MTT solution (3-(4,5-dimethylthiazol-2-yl)-2,5-diphenyltetrazolium bromide) (Sigma) was added at a concentration of 0.5 mg/ml. Following incubation at 37° C. for 2.5 or 1.5 hours, acid-SDS (0.01N HCl/10% SDS) was added; the suspension was mixed vigorously and then incubated overnight at 37° C. to dissolve the dark blue crystals. Absorbance at 570 nm was measured with a Microplate Reader 550 (BioRad).

Observation of Multi-Nucleated Cells by C2093-siRNA

After UMUC3 cells were transfected with si-EGFP as negative controls, and si-C2093 using FuGENE6 (Roche), they were cultured and their cellular morphology were observed by microscopy on 7 days after transfection. To further confirm suppression of C2093 protein expression, Western blotting was carried out with anti-C2093 antibody according to the standard protocol.

Anti-C2093 and Anti-B5860N Antibodies

Plasmids expressing partial fragments of C2093 (1612-1780 a.a.) (SEQ ID NO: 150) and B5860NV2 (337-527 a.a) or B5860NV1 (621-811a.a) (SEQ ID NO: 151) that contained His-tag at their COOH-terminals were prepared using pET21 vector, respectively. The recombinant proteins were expressed in *Escherichia coli*, BL21 codon-plus strain (Stratagene, La Jolla, Calif.), and purified using Ni-NTA resin and TALON according to the supplier's protocols. The proteins were inoculated into rabbits; the immune sera were purified on affinity columns according to standard protocols. Affinity-purified anti-C2093 and anti-B5860N antibodies were used for Western blotting, immunoprecipitation, and immunostaining.

Immunocytochemical Staining to Detect Endogenous C2093 and B5860N Proteins in Bladder Cancer Cells To examine the subcellular localization of endogenous C2093 or B5860N, we seeded UMUC3 cells that expressed C2093 or B5860N endogenously at 1×05 cells per well, respectively. After 24 hours, cells were fixed with PBS containing 4% paraformaldehyde for 15 min, and rendered permeable with PBS containing 0.1% Triton X-100 for 2 min at 4° C. Subsequently the cells were covered with 3% BSA in PBS for 12 hours at 4° C. to block non-specific hybridization. Next, UMUC3 cells were incubated with affinity-purified anti-C2093 antibody or anti-B5860N antibody at 1:100 dilution. Nuclei were counter-stained with 4',6'-diamidine-2'-phenylindole dihydrochloride (DAPI). After washing with PBS, UMUC3 cells were stained by an Alexa488-conjugated anti-rabbit secondary antibody (Molecular Probe) at 1:1000 dilution. Fluorescent images were obtained under a confocal microscope (Leica, Tokyo, Japan).

Immunohistochemical Staining to Detect Endogenous C2093 and B5860N Proteins in Normal or Bladder Cancer Tissues Slides of paraffin-embedded normal adult human tissues (BioChain, Hayward, Calif.) and surgical bladder cancer specimens were stained using ENVISION+Kit/HRP (DakoCytomation, Glostrup, Denmark) after the sections were deparaffinized and warmed with the microwave oven for 5 minutes at 80° C. in antigen retrieval solution with high pH (DAKO) using anti-C2093 antibody, or the sections were deparaffinized and autocraved for 15 minutes at 108° C. in antigen retrieval solution with high pH (DAKO) using anti-B5860N antibody, respectively. After blocking of endogenous peroxidase and proteins, these sections were incubated with affinity-purified anti-C2093 or anti-B5860N antibodies at 1:20 dilution. Immunodetection was done with peroxidase-labeled anti-rabbit immunoglobulin (Envision kit, Dako Cytomation, Carpinteria, Calif.). Finally, the reactants were developed with 3,3 V-diaminobenzidine (Dako) and the cells were counterstained with hematoxylin.

Results

To obtain precise expression profiles of bladder cancers, only bladder cancer cells with LMM were collected. The proportion of cancer cells selected by this procedure was estimated to be nearly 100%, as determined by microscopic visualization (data not shown).

394 up-regulated genes whose expression ratio was more than 5.0 were identified (Table 4). Of these genes, the 288 functionally characterized genes that were over-expressed in bladder cancer cells were included, and the other 106 (including 51 ESTs) were currently unknown. These up-regulated elements included significant genes involved in signal transduction pathway, oncogenes, cell cycle, and cell adhesion and cytoskeleton. On the other hand, 1272 down-regulated genes whose expression ratio was less than 0.2 were identified (Table 5). Of these down-regulated genes, the 1026 functionally characterized genes that were down-regulated in bladder cancer cells were included, and the other 246 (including 119 ESTs) were unknown.

To confirm the expression pattern of these up-regulated genes in bladder cancers, semi-quantitative RT-PCR analysis was performed using bladder cancer cell lines and normal human tissues including normal bladder and normal transitional cells. Comparing the ratios of the expression levels of the 44 up-regulated genes whose expression were over-expressed in almost of all informative cases, the results were highly similar to those of the microarray analysis in the great majority of the tested cases (FIG. 1). Particularly, B5860N, B0811, C2093, F6022, F4976, D5491, F0411, D7746, A0576N, F1653, C2210, C7757 and D7443 also showed no expression in normal vital organs. These data verified the reliability of our strategy to identify commonly up-regulated genes in bladder cancer cells.

To further examine the expression pattern of these up-regulated genes, A0576N, C2093, C5509, B5860N, F1653, B9838 and C6055, Northern blot analyses were performed with bladder cancer cell lines using each $[\alpha^{32}P]$-dCTP-labeled amplification products of A0576N, C2093, C5509, B5860N, F1653, B9838 and C6055 prepared by RT-PCR using each primer set as shown in Table 3 as each probe (FIG. 2). All of them also showed much higher expression in bladder cancer cell lines than that in normal bladder. Particularly, A0576N, C2093, B5860N, B9838 and C6055 were specifically over-expressed in bladder cancer cell lines, but were not expressed in normal human tissues including normal bladder. These suggest that these specifically over-expressed genes might be good candidate for molecular target-therapy.

TABLE 4

Up-regulated gene in bladder cancer

| BLC assignment | LMMID | ACCESSION | GENE | TITLE |
|---|---|---|---|---|
| 1 | C3760 | BC008718 | BIRC5 | Baculoviral IAP repeat-containing 5 (survivin) |
| 2 | D9621 | NM_178229 | IQGAP3 | IQ motif containing GTPase activating protein 3 |
| 3 | F1653 | BC011621 | HOOK1 | Hook homolog 1 (*Drosophila*) |
| 4 | C8776 | AA766028 | AF15Q14 | AF15q14 protein |
| 5 | F6507 | AL046246 | PGAP1 | GPI deacylase |
| 6 | F3374 | AF195765 | RAMP | RA-regulated nuclear matrix-associated protein |
| 7 | A3555 | K02581 | TK1 | Thymidine kinase 1, soluble |
| 8 | C5005 | BX648571 | FLJ38736 | Hypothetical protein FLJ38736 |
| 9 | D0006 | NM_145697 | CDCA1 | Cell division cycle associated 1 |
| 10 | B8706 | R52614 | CDK5R1 | Cyclin-dependent kinase 5, regulatory subunit 1 (p35) |
| 11 | A4693 | U42408 | LAD1 | Ladinin 1 |
| 12 | E0388 | BC033193 | MGC30208 | Hypothetical protein MGC30208 |
| 13 | B8882 | BC005832 | KIAA0101 | KIAA0101 |
| 14 | D4920 | AI247180 | GUCY1B2 | Guanylate cyclase 1, soluble, beta 2 |
| 15 | F2861 | CR598555 | KIF20A | Kinesin family member 20A |
| 16 | E1412 | AI989840 | | |
| 17 | E1349 | BC041395 | | *Homo sapiens*, Similar to diaphanous homolog 3 (*Drosophila*), clone IMAGE: 5277415, mRNA |
| 18 | A3243 | CR624652 | TTK | TTK protein kinase |
| 19 | E1138 | AF318349 | LEMD2 | LEM domain containing 2 |
| 20 | B0259 | AA234962 | PKP3 | Plakophilin 3 |
| 21 | A2921 | NM_002391 | MDK | Midkine (neurite growth-promoting factor 2) |
| 22 | A3058 | NM_202002 | FOXM1 | Forkhead box M1 |
| 23 | B5904 | BC008947 | C10orf3 | Chromosome 10 open reading frame 3 |
| 24 | D6767 | BM312795 | | Transcribed locus |
| 25 | A4388 | NM_001988 | EVPL | Envoplakin |
| 26 | D4636 | AF370395 | EPS8L1 | EPS8-like 1 |
| 27 | B4587 | AB096683 | MGC57827 | Similar to RIKEN cDNA 2700049P18 gene |
| 28 | A1618 | X70683 | SOX4 | SRY (sex determining region Y)-box 4 |
| 29 | F6022 | AK022479 | HDHD1A | Haloacid dehalogenase-like hydrolase domain containing 1A |
| 30 | A0061 | AF053306 | BUB1B | BUB1 budding uninhibited by benzimidazoles 1 homolog beta (yeast) |

TABLE 4-continued

Up-regulated gene in bladder cancer

| BLC assignment | LMMID | ACCESSION | GENE | TITLE |
|---|---|---|---|---|
| 31 | E2104 | CN280172 | | CDNA clone IMAGE: 4734740, partial cds |
| 32 | A2254 | NM_006845 | KIF2C | Kinesin family member 2C |
| 33 | B8870 | NM_018685 | ANLN | Anillin, actin binding protein (scraps homolog, *Drosophila*) |
| 34 | A3896 | BC015050 | OIP5 | Opa-interacting protein 5 |
| 35 | A8287 | R87657 | DKFZp762E1312 | Hypothetical protein DKFZp762E1312 |
| 36 | A1835 | U18018 | ETV4 | Ets variant gene 4 (E1A enhancer binding protein, E1AF) |
| 37 | D2882 | AA777954 | | |
| 38 | A2282 | BC014039 | MELK | Maternal embryonic leucine zipper kinase |
| 39 | C7457 | W44613 | LY6K | CDNA for differentially expressed CO16 gene |
| 40 | E1774 | AK022881 | KIAA1272 | KIAA1272 protein |
| 41 | E0785 | BC039269 | NALP2 | NACHT, leucine rich repeat and PYD containing 2 |
| 42 | F1332 | CR592757 | BRRN1 | Barren homolog (*Drosophila*) |
| 43 | F7562 | AI146812 | | |
| 44 | C2093 | H93085 | MPHOSPH1 | M-phase phosphoprotein 1 |
| 45 | F7083 | AL044366 | RUNX1 | Runt-related transcription factor 1 (acute myeloid leukemia 1; aml1 oncogene) |
| 46 | F6312 | AW977404 | SLC15A2 | Solute carrier family 15 (H+/peptide transporter), member 2 |
| 47 | E0954 | BC021290 | IMP-2 | IGF-II mRNA-binding protein 2 |
| 48 | A5657 | BQ219156 | HSPC150 | HSPC150 protein similar to ubiquitin-conjugating enzyme |
| 49 | F7407 | AF095288 | PTTG2 | Pituitary tumor-transforming 2 |
| 50 | B2909 | CR625760 | TOP2A | Topoisomerase (DNA) II alpha 170 kDa |
| 51 | F2445 | AK022644 | MGC3101 | Hypothetical protein MGC3101 |
| 52 | B9303 | AK129960 | LOC92558 | Hypothetical protein LOC92558 |
| 53 | C6902 | BC007608 | HMGB3 | High-mobility group box 3 |
| 54 | A0499 | BM912233 | CKS2 | CDC28 protein kinase regulatory subunit 2 |
| 55 | A9518N | AA570186 | | Hypothetical gene supported by AK096951; BC066547 |
| 56 | A2728 | AK126687 | LLGL2 | Lethal giant larvae homolog 2 (*Drosophila*) |
| 57 | A5623 | AF044588 | PRC1 | Protein regulator of cytokinesis 1 |
| 58 | B6283 | AY257469 | CIT | Citron (rho-interacting, serine/threonine kinase 21) |
| 59 | C8054 | NM_001445 | FABP6 | Fatty acid binding protein 6, ileal (gastrotropin) |
| 60 | E0465 | BC010044 | CDC20 | CDC20 cell division cycle 20 homolog (*S. cerevisiae*) |
| 61 | B0811 | AW183154 | KIF14 | Kinesin family member 14 |
| 62 | E1010 | CN341726 | 2'-PDE | 2'-phosphodiesterase |
| 63 | F4976 | AF165527 | DGCR8 | DiGeorge syndrome critical region gene 8 |
| 64 | F2376 | AK021714 | | CDNA FLJ11652 fis, clone HEMBA1004461 |
| 65 | C0234 | NM_020639 | RIPK4 | Receptor-interacting serine-threonine kinase 4 |
| 66 | A5953 | N24235 | KIAA0789 | KIAA0789 gene product |
| 67 | B7725 | NM_031966 | CCNB1 | Cyclin B1 |
| 68 | A0576N | NM_138555 | KIF23 | Kinesin family member 23 |
| 69 | B7480 | AF407165 | PPP1R14C | Protein phosphatase 1, regulatory (inhibitor) subunit 14C |
| 70 | B4218 | BQ052480 | IFI27 | Interferon, alpha-inducible protein 27 |
| 71 | F1655 | AL137343 | NSE1 | NSE1 |
| 72 | C9468 | AA885242 | KIFC2 | Kinesin family member C2 |
| 73 | A1787 | NM_016343 | CENPF | Centromere protein F, 350/400ka (mitosin) |
| 74 | D6683 | NM_003106 | SOX2 | SRY (sex determining region Y)-box 2 |
| 75 | A0024 | AF017790 | KNTC2 | Kinetochore associated 2 |
| 76 | D9407 | CR749484 | LOC152519 | Hypothetical protein LOC152519 |
| 77 | F6910 | BF940192 | KIAA0776 | KIAA0776 |
| 78 | A1367 | D14520 | KLF5 | Kruppel-like factor 5 (intestinal) |
| 79 | C2210 | AI755171 | MRCL3 | Myosin regulatory light chain MRCL3 |

TABLE 4-continued

Up-regulated gene in bladder cancer

| BLC assignment | LMMID | ACCESSION | GENE | TITLE |
|---|---|---|---|---|
| 80 | C5088 | R62589 | SEMA3C | Sema domain, immunoglobulin domain (Ig), short basic domain, secreted, (semaphorin) 3C |
| 81 | F1242 | AB020713 | NUP210 | Nucleoporin 210 |
| 82 | C7747 | CA314541 | | Transcribed locus |
| 83 | D5753 | AA971042 | RHPN1 | Rhophilin, Rho GTPase binding protein 1 |
| 84 | E1801 | AW971869 | SORL1 | Sortilin-related receptor, L(DLR class) A repeats-containing |
| 85 | A1063 | BU600928 | SPRR1B | Small proline-rich protein 1B (cornifin) |
| 86 | A8317N | BQ013695 | FLJ10420 | Hypothetical protein FLJ10420 |
| 87 | B5860N | BM683578 | DEPDC1 | DEP domain containing 1 |
| 88 | F3847 | AK027006 | TNRC9 | Trinucleotide repeat containing 9 |
| 89 | A0018 | NM_198433 | STK6 | Serine/threonine kinase 6 |
| 90 | A4356 | Y00503 | KRT19 | Keratin 19 |
| 91 | A0004 | AB003698 | CDC7 | CDC7 cell division cycle 7 (*S. cerevisiae*) |
| 92 | D7212 | AA132702 | XTP2 | HBxAg transactivated protein 2 |
| 93 | F4584 | XM_049695 | VANGL2 | Vang-like 2 (van gogh, *Drosophila*) |
| 94 | E1619 | BU620217 | NS | Nucleostemin |
| 95 | B6905 | BU675191 | CGI-72 | CGI-72 protein |
| 96 | C6486 | X83618 | HMGCS2 | 3-hydroxy-3-methylglutaryl-Coenzyme A synthase 2 (mitochondrial) |
| 97 | A3298 | M91670 | UBE2S | Ubiquitin-conjugating enzyme E2S |
| 98 | C0488 | AA781195 | PRAME | Preferentially expressed antigen in melanoma |
| 99 | A2691N | BC041846 | CDH3 | Cadherin 3, type 1, P-cadherin (placental) |
| 100 | F0757 | AK023834 | CDCP1 | CUB domain-containing protein 1 |
| 101 | F6193 | AK026280 | | Transcribed locus, weakly similar to XP_375099.1 hypothetical protein LOC283585 [*Homo sapiens*] |
| 102 | A0303 | U79240 | PASK | PAS domain containing serine/threonine kinase |
| 103 | C7757 | AK024506 | C14orf80 | Chromosome 14 open reading frame 80 |
| 104 | F2228 | X51688 | CCNA2 | Cyclin A2 |
| 105 | D9210 | CA844321 | MGC3196 | Hypothetical protein MGC3196 |
| 106 | F6225 | AW970636 | FOXP1 | Forkhead box P1 |
| 107 | C7353 | AK122903 | EPS8L2 | EPS8-like 2 |
| 108 | E1776 | AI138333 | MAP4K3 | Mitogen-activated protein kinase kinase kinase kinase 3 |
| 109 | D5491 | AA947258 | | Transcribed locus |
| 110 | E0885 | NM_183047 | PRKCBP1 | Protein kinase C binding protein 1 |
| 111 | B4479 | AF258572 | GSDML | Gasdermin-like |
| 112 | C6719 | BC013892 | PVRL4 | Poliovirus receptor-related 4 |
| 113 | A2796 | NM_006681 | NMU | Neuromedin U |
| 114 | D8458 | AA830668 | | |
| 115 | F6333 | AW590215 | SLC4A8 | Solute carrier family 4, sodium bicarbonate cotransporter, member 8 |
| 116 | D4789 | AW070371 | SIMP | Source of immunodominant MHC-associated peptides |
| 117 | A4875 | NM_000336 | SCNN1B | Sodium channel, nonvoltage-gated 1, beta (Liddle syndrome) |
| 118 | A0143N | AJ606319 | MYB | V-myb myeloblastosis viral oncogene homolog (avian) |
| 119 | B2426 | CB116740 | POGK | Pogo transposable element with KRAB domain |
| 120 | F7685 | AV699624 | | Transcribed locus |
| 121 | C5020 | BC004352 | KIF22 | Kinesin family member 22 |
| 122 | C7114 | BU738386 | LOC284352 | Hypothetical protein LOC284352 |
| 123 | F7399 | AI928242 | TFCP2L1 | Transcription factor CP2-like 1 |
| 124 | A6002 | AA179812 | FLJ21918 | Hypothetical protein FLJ21918 |
| 125 | A2439 | AF053305 | BUB1 | BUB1 budding uninhibited by benzimidazoles 1 homolog (yeast) |
| 126 | A1591 | NM_002534 | OAS1 | 2',5'-oligoadenylate synthetase 1, 40/46 kDa |
| 127 | F6689 | AK021848 | | |
| 128 | C7737 | AA969163 | | Transcribed locus |
| 129 | F0411 | AW898615 | | |
| 130 | B6548 | R61700 | | |
| 131 | A5136N | AF133086 | ST14 | Suppression of tumorigenicity 14 (colon carcinoma, matriptase, epithin) |

TABLE 4-continued

Up-regulated gene in bladder cancer

| BLC assignment | LMMID | ACCESSION | GENE | TITLE |
|---|---|---|---|---|
| 132 | D6877 | AI002358 | | |
| 133 | B4478 | AA910946 | AP1M2 | Adaptor-related protein complex 1, mu 2 subunit |
| 134 | C9858 | NM_006892 | DNMT3B | DNA (cytosine-5-)-methyltransferase 3 beta |
| 135 | B1194 | AK090897 | GPATC2 | G patch domain containing 2 |
| 136 | A4438 | AF055015 | EYA2 | Eyes absent homolog 2 (*Drosophila*) |
| 137 | A7602 | CD359557 | DAZAP2 | DAZ associated protein 2 |
| 138 | D7746 | AI024928 | C13orf24 | Chromosome 13 open reading frame 24 |
| 139 | C1901 | AA649063 | FLJ21865 | Endo-beta-N-acetylglucosaminidase |
| 140 | E0639 | AK023937 | THEA | Thioesterase, adipose associated |
| 141 | A7322 | CA314912 | LOC202451 | Hypothetical protein LOC202451 |
| 142 | B2879N | AA173525 | | Similar to Zinc finger protein Rlf (Rearranged L-myc fusion gene protein) (Zn-15 related protein) |
| 143 | B7367 | CR616479 | AMACR | Alpha-methylacyl-CoA racemase |
| 144 | F4070 | NM_020897 | HCN3 | Hyperpolarization activated cyclic nucleotide-gated potassium channel 3 |
| 145 | C4658 | AF132541 | GMIP | GEM interacting protein |
| 146 | B8739 | AA992910 | VSIG2 | V-set and immunoglobulin domain containing 2 |
| 147 | F7003 | AW291323 | | |
| 148 | B2454 | AL833191 | SMC2L1 | SMC2 structural maintenance of chromosomes 2-like 1 (yeast) |
| 149 | A1223 | X73502 | KRT20 | Keratin 20 |
| 150 | F0969 | AK026201 | RAB3IP | RAB3A interacting protein (rabin3) |
| 151 | F3726 | AF098668 | LYPLA2 | Lysophospholipase II |
| 152 | A1209 | NM_001071 | TYMS | Thymidylate synthetase |
| 153 | C3759 | NM_003072 | SMARCA4 | SWI/SNF related, matrix associated, actin dependent regulator of chromatin, subfamily a, member 4 |
| 154 | C0328 | CR592555 | | Full-length cDNA clone CS0DE011YI04 of Placenta of *Homo sapiens* (human) |
| 155 | B6353 | R19310 | RELN | Reelin |
| 156 | C1555 | AK094156 | | Similar to KIAA0454 protein |
| 157 | D7443 | AI017753 | AHI1 | Abelson helper integration site |
| 158 | D8001 | AW976634 | | Transcribed locus |
| 159 | F7409 | AI739486 | MFAP3 | Microfibrillar-associated protein 3 |
| 160 | F6200 | AK023542 | | |
| 161 | B4626 | BC052574 | FLJ20171 | Hypothetical protein FLJ20171 |
| 162 | F7636 | AI651388 | | |
| 163 | A2310 | AF261758 | DHCR24 | 24-dehydrocholesterol reductase |
| 164 | C9450 | AI338875 | CDK3 | Cyclin-dependent kinase 3 |
| 165 | F3973 | AL157504 | | MRNA; cDNA DKFZp586O0724 (from clone DKFZp586O0724) |
| 166 | C7681 | AA151182 | ZNF339 | Zinc finger protein 339 |
| 167 | D9500 | AI361654 | | |
| 168 | C9098 | AY376439 | ECT2 | Epithelial cell transforming sequence 2 oncogene |
| 169 | B5152N | CR618521 | CSNK1E | Casein kinase 1, epsilon |
| 170 | D4223 | AK095136 | RASGEF1A | RasGEF domain family, member 1A |
| 171 | F2073 | NM_020990 | CKMT1 | Creatine kinase, mitochondrial 1 (ubiquitous) |
| 172 | B7466 | AA128378 | KIAA0303 | KIAA0303 protein |
| 173 | A7083 | CR608243 | ARHGAP8 | Rho GTPase activating protein 8 |
| 174 | D5363 | AI419859 | GALNT7 | UDP-N-acetyl-alpha-D-galactosamine:polypeptide N-acetylgalactosaminyltransferase 7 (GalNAc-T7) |
| 175 | A9044 | BC003186 | Pfs2 | DNA replication complex GINS protein PSF2 |
| 176 | C8682 | NM_005329 | HAS3 | Hyaluronan synthase 3 |
| 177 | A1605 | NM_203401 | STMN1 | Stathmin 1/oncoprotein 18 |
| 178 | A4045N | BE538546 | PMCH | Pro-melanin-concentrating hormone |
| 179 | A0042 | AF029082 | SFN | Stratifin |
| 180 | A1524 | U29344 | FASN | Fatty acid synthase |
| 181 | F3821 | AL117612 | MAL2 | Mal, T-cell differentiation protein 2 |
| 182 | C4276 | NM_001407 | CELSR3 | Cadherin, EGF LAG seven-pass G-type receptor 3 (flamingo homolog, *Drosophila*) |

TABLE 4-continued

Up-regulated gene in bladder cancer

| BLC assignment | LMMID | ACCESSION | GENE | TITLE |
|---|---|---|---|---|
| 183 | D7936 | BQ022849 | TEX27 | Testis expressed sequence 27 |
| 184 | A5159 | BC080193 | ERBB2 | V-erb-b2 erythroblastic leukemia viral oncogene homolog 2, neuro/glioblastoma derived oncogene homolog (avian) |
| 185 | A4542 | NM_001305 | CLDN4 | Claudin 4 |
| 186 | F8586 | AA579871 | SMARCC1 | SWI/SNF related, matrix associated, actin dependent regulator of chromatin, subfamily c, member 1 |
| 187 | A7870 | NM_018492 | TOPK | T-LAK cell-originated protein kinase |
| 188 | B7330N | BM726315 | GALNT6 | UDP-N-acetyl-alpha-D-galactosamine:polypeptide N-acetylgalactosaminyltransferase 6 (GalNAc-T6) |
| 189 | A1054 | M13755 | G1P2 | Interferon, alpha-inducible protein clone (IFI-15K) |
| 190 | A6139 | BU730831 | PAFAH1B3 | Platelet-activating factor acetylhydrolase, isoform Ib, gamma subunit 29 kDa |
| 191 | A6127 | AI356291 | GPT2 | Glutamic pyruvate transaminase (alanine aminotransferase) 2 |
| 192 | C8580 | CR611223 | CLDN7 | Claudin 7 |
| 193 | C6055 | AA001450 | MGC34032 | Hypothetical protein MGC34032 |
| 194 | F8392 | AI432199 | LMO4 | LIM domain only 4 |
| 195 | A1970 | BC000356 | MAD2L1 | MAD2 mitotic arrest deficient-like 1 (yeast) |
| 196 | D8466 | AI619500 | | Transcribed locus |
| 197 | C9305 | AI080640 | AGR2 | Anterior gradient 2 homolog (*Xenopus laevis*) |
| 198 | E0170 | BQ417235 | | Transcribed locus |
| 199 | F7497 | AW973864 | SYNJ2BP | Synaptojanin 2 binding protein |
| 200 | D7200 | BC069011 | TRA2A | Transformer-2 alpha |
| 201 | F4522 | AK023400 | DCL-1 | Type I transmembrane C-type lectin receptor DCL-1 |
| 202 | B8930 | AA513445 | RBM21 | RNA binding motif protein 21 |
| 203 | A4643 | J05428 | UGT2B7 | UDP glycosyltransferase 2 family, polypeptide B7 |
| 204 | F8409 | BC041096 | CLCA2 | Chloride channel, calcium activated, family member 2 |
| 205 | A2603N | Z46629 | SOX9 | SRY (sex determining region Y)-box 9 (campomelic dysplasia, autosomal sex-reversal) |
| 206 | A6979 | AI357616 | LOC90133 | Hypothetical protein LOC90133 |
| 207 | E1348 | BX640908 | EVI1 | Ecotropic viral integration site 1 |
| 208 | F5885 | AK023050 | | |
| 209 | A3644 | NM_006949 | STXBP2 | Syntaxin binding protein 2 |
| 210 | C5509 | NM_201269 | Zep-2 | Zinc finger motif enhancer binding protein 2 |
| 211 | B2579N | N70341 | ELAC2 | ElaC homolog 2 (*E. coli*) |
| 212 | D4039 | CB142087 | MARVELD2 | MARVEL domain containing 2 |
| 213 | A1800 | NM_052987 | CDK10 | Cyclin-dependent kinase (CDC2-like) 10 |
| 214 | F3387 | AK126185 | PPFIA4 | Protein tyrosine phosphatase, receptor type, f polypeptide (PTPRF), interacting protein (liprin), alpha 4 |
| 215 | A2735 | BC036811 | PTHR2 | Parathyroid hormone receptor 2 |
| 216 | C9937 | BC013048 | C8orf20 | Chromosome 8 open reading frame 20 |
| 217 | F7614 | AI114655 | LOC284058 | Hypothetical protein LOC284058 |
| 218 | B1561 | AK074562 | QKI | Quaking homolog, KH domain RNA binding (mouse) |
| 219 | B4400 | BX647949 | FRAS1 | Fraser syndrome 1 |
| 220 | C4588 | AA016977 | | MRNA; cDNA DKFZp686F1844 (from clone DKFZp686F1844) |
| 221 | D3205 | AY024361 | MLL3 | B melanoma antigen family, member 4 |
| 222 | B7272 | BQ268701 | | |
| 223 | B7706 | R22536 | FLJ13052 | NAD kinase |
| 224 | G0074 | AK127891 | MGC10744 | Hypothetical protein MGC10744 |
| 225 | C0909 | U38276 | SEMA3F | Sema domain, immunoglobulin domain (Ig), short basic domain, secreted, (semaphorin) 3F |
| 226 | A8777 | BM990713 | IL28RA | Interleukin 28 receptor, alpha (interferon, lambda receptor) |

TABLE 4-continued

Up-regulated gene in bladder cancer

| BLC assignment | LMMID | ACCESSION | GENE | TITLE |
|---|---|---|---|---|
| 227 | E1497 | BU625507 | SLC16A3 | Solute carrier family 16 (monocarboxylic acid transporters), member 3 |
| 228 | C6865 | BC041417 | | Transcribed locus, moderately similar to NP_955751.1 potassium channel regulator [Homo sapiens] |
| 229 | A0327N | NM_002421 | MMP1 | Matrix metalloproteinase 1 (interstitial collagenase) |
| 230 | C8624 | NM_005858 | AKAP8 | A kinase (PRKA) anchor protein 8 |
| 231 | B9838 | AA018510 | MGC33382 | Hypothetical protein MGC33382 |
| 232 | B4649 | BM996064 | TJP3 | Tight junction protein 3 (zona occludens 3) |
| 233 | F7985 | AA682421 | | |
| 234 | B5490 | AB014555 | HIP1R | Huntingtin interacting protein-1-related |
| 235 | A0959 | NM_001034 | RRM2 | Ribonucleotide reductase M2 polypeptide |
| 236 | A5644 | BC015582 | MGC23280 | Hypothetical protein MGC23280 |
| 237 | B7163 | AA262462 | NT5C2 | 5'-nucleotidase, cytosolic II |
| 238 | F5981 | AL050119 | TMEM1 | Transmembrane protein 1 |
| 239 | F7087 | AL043093 | FAM47B | Family with sequence similarity 47, member B |
| 240 | C6634 | AA398740 | | CDNA FLJ41168fis, clone BRACE 2041095 |
| 241 | C0285 | AK093343 | FLJ23231 | Hypothetical protein FLJ23231 |
| 242 | C0417 | AF311320 | SLC37A1 | Solute carrier family 37 (glycerol-3-phosphate transporter), member 1 |
| 243 | F3641 | AY099469 | SLAC2-B | SLAC2-B |
| 244 | C1730 | BU682808 | GNAS | GNAS complex locus |
| 245 | F2351 | AL162042 | | |
| 246 | C3640 | NM_182641 | FALZ | Fetal Alzheimer antigen |
| 247 | B7032N | AA398096 | PFKFB4 | 6-phosphofructo-2-kinase/fructose-2,6-biphosphatase 4 |
| 248 | D8837 | NM_012189 | CABYR | Calcium-binding tyrosine-(Y)-phosphorylation regulated (fibrousheathin 2) |
| 249 | F6161 | BF056203 | ABHD7 | Abhydrolase domain containing 7 |
| 250 | B5458N | AA889610 | CARHSP1 | Calcium regulated heat stable protein 1, 24 kDa |
| 251 | D3452 | BX482647 | PARP14 | Poly (ADP-ribose) polymerase family, member 14 |
| 252 | B6562 | CA306079 | PLEKHJ1 | Pleckstrin homology domain containing, family J member 1 |
| 253 | C6789 | AK125177 | LOC149134 | Hypothetical protein LOC149134 |
| 254 | C0485 | BC064568 | LOC150223 | Hypothetical protein LOC150223 |
| 255 | A7343N | N68578 | LIPC | Lipase, hepatic |
| 256 | A6349 | AK095197 | PAQR6 | Progestin and adipoQ receptor family member VI |
| 257 | A1865 | U60808 | CDS1 | CDP-diacylglycerol synthase (phosphatidate cytidylyltransferase) 1 |
| 258 | A7352 | AJ421269 | TD-60 | RCC1-like |
| 259 | F0534 | NM_004360 | CDH1 | Cadherin 1, type 1, E-cadherin (epithelial) |
| 260 | F3919 | AK025341 | FARP1 | FERM, RhoGEF (ARHGEF) and pleckstrin domain protein 1 (chondrocyte-derived) |
| 261 | F7374 | AI656728 | ARIH1 | Ariadne homolog, ubiquitin-conjugating enzyme E2 binding protein, 1 (Drosophila) |
| 262 | A2822 | BQ015859 | CSTA | Cystatin A (stefin A) |
| 263 | E1344 | BC064421 | C2orf29 | Chromosome 2 open reading frame 29 |
| 264 | A1604 | X52186 | ITGB4 | Integrin, beta 4 |
| 265 | D8789 | AI025912 | GLCCI1 | Glucocorticoid induced transcript 1 |
| 266 | D3350 | R45979 | | |
| 267 | F7016 | BE179023 | FLJ11142 | Hypothetical protein FLJ11142 |
| 268 | A0636 | Z29066 | NEK2 | NIMA (never in mitosis gene a)-related kinase 2 |
| 269 | A5223 | BC007379 | MGC16207 | Hypothetical protein MGC16207 |
| 270 | G0445 | AK000981 | | |
| 271 | B0869N | AF274048 | UHRF1 | Ubiquitin-like, containing PHD and RING finger domains, 1 |
| 272 | C7864 | D84454 | SLC35A2 | Solute carrier family 35 (UDP-galactose transporter), member A2 |

TABLE 4-continued

Up-regulated gene in bladder cancer

| BLC assignment | LMMID | ACCESSION | GENE | TITLE |
|---|---|---|---|---|
| 273 | A2837 | BU618918 | CDKN3 | Cyclin-dependent kinase inhibitor 3 (CDK2-associated dual specificity phosphatase) |
| 274 | C7435 | BC029267 | MUC20 | Mucin 20 |
| 275 | A4383 | Z97029 | RNASEH2A | Ribonuclease H2, large subunit |
| 276 | F7162 | AK000364 | CHD7 | Chromodomain helicase DNA binding protein 7 |
| 277 | B1819 | AY165122 | MYH14 | Myosin, heavy polypeptide 14 |
| 278 | A0207 | M73812 | CCNE1 | Cyclin E1 |
| 279 | D8150 | BF965334 | PRKRA | Protein kinase, interferon-inducible double stranded RNA dependent activator |
| 280 | C8051 | BM685415 | C10orf116 | Chromosome 10 open reading frame 116 |
| 281 | A5601 | H19339 | | MRNA; cDNA DKFZp5470036 (from clone DKFZp547G036) |
| 282 | B7365 | BC025755 | C6orf134 | Chromosome 6 open reading frame 134 |
| 283 | A1957 | U20979 | CHAF1A | Chromatin assembly factor 1, subunit A (p150) |
| 284 | B5103N | AI091425 | VGLL1 | Vestigial like 1 (*Drosophila*) |
| 285 | F2779 | BC001226 | PLEK2 | Pleckstrin 2 |
| 286 | C6110 | W67193 | GFPT1 | Glutamine-fructose-6-phosphate transaminase 1 |
| 287 | A4616 | AJ007669 | FANCG | Fanconi anemia, complementation group G |
| 288 | A1859N | NM_001002295 | GATA3 | GATA binding protein 3 |
| 289 | A0333 | NM_002466 | MYBL2 | V-myb myeloblastosis viral oncogene homolog (avian)-like 2 |
| 290 | A6869 | BC011665 | TCF3 | Transcription factor 3 (E2A immunoglobulin enhancer binding factors E12/E47) |
| 291 | C7801 | AI299827 | TFCP2L3 | Transcription factor CP2-like 3 |
| 292 | F8081 | BF433219 | | |
| 293 | A3587 | NM_003088 | FSCN1 | Fascin homolog 1, actin-bundling protein (*Strongylocentrotus purpuratus*) |
| 294 | A6935 | AA523117 | DC-TM4F2 | Tetraspanin similar to TM4SF9 |
| 295 | F3642 | CR619487 | DKFZP564C103 | DKFZP564C103 protein |
| 296 | F3549 | AK025185 | | |
| 297 | F6831 | AK024988 | | Similar to KIAA0160 gene product is novel. |
| 298 | E0499 | BM906554 | COX6B1 | Cytochrome c oxidase subunit Vib polypeptide 1 (ubiquitous) |
| 299 | A7770 | R55185 | IRX3 | Iroquois homeobox protein 3 |
| 300 | A2865 | AJ297436 | PSCA | Prostate stem cell antigen |
| 301 | B3762 | BC035311 | ZD52F10 | Dermokine |
| 302 | F8140 | AW976457 | MBNL1 | Muscleblind-like (*Drosophila*) |
| 303 | A8295 | AA430571 | | Transcribed locus |
| 304 | F8687 | AW081894 | | |
| 305 | A1166 | S62028 | RCV1 | Recoverin |
| 306 | B8658 | CA429220 | SKP2 | S-phase kinase-associated protein 2 (p45) |
| 307 | B6813 | BX092653 | | Transcribed locus |
| 308 | E0909 | BU726646 | | Transcribed locus |
| 309 | D1287 | BC012136 | ISL2 | ISL2 transcription factor, LIM/homeodomain, (islet-2) |
| 310 | A6151 | BU620959 | RAPGEFL1 | Rap guanine nucleotide exchange factor (GEF)-like 1 |
| 311 | A6486 | W67936 | RAI | RelA-associated inhibitor |
| 312 | G0008 | AK026743 | C21orf96 | Chromosome 21 open reading frame 96 |
| 313 | F3089 | AB046838 | KIAA1618 | KIAA1618 |
| 314 | F3293 | AL389951 | NUP50 | Nucleoporin 50 kDa |
| 315 | B5870 | AI312573 | CPNE3 | Copine III |
| 316 | A9334 | BC039343 | HN1 | Hematological and neurological expressed 1 |
| 317 | B9951 | NM_005556 | KRT7 | Keratin 7 |
| 318 | B8627 | R39044 | RAB27B | RAB27B, member RAS oncogene family |
| 319 | D2335 | BQ018544 | | Hypothetical LOC389908 |
| 320 | B4097 | CR596974 | MLP | MARCKS-like protein |
| 321 | F7332 | AI936859 | RTKN | Rhotekin |
| 322 | B8205 | AL133100 | FLJ20531 | Hypothetical protein FLJ20531 |
| 323 | C2132 | AW134658 | MSI2 | Musashi homolog 2 (*Drosophila*) |

TABLE 4-continued

Up-regulated gene in bladder cancer

| BLC assignment | LMMID | ACCESSION | GENE | TITLE |
|---|---|---|---|---|
| 324 | E0491 | BC062785 | | CDNA clone IMAGE: 4734740, partial cds |
| 325 | A4959 | AF042282 | EXO1 | Exonuclease 1 |
| 326 | A1824 | NM_002224 | ITPR3 | Inositol 1,4,5-triphosphate receptor, type 3 |
| 327 | A1007 | Z29093 | DDR1 | Discoidin domain receptor family, member 1 |
| 328 | C4330 | BC006000 | CAPNS2 | Calpain, small subunit 2 |
| 329 | D6311 | BI771102 | PHYHIPL | Family with sequence similarity 13, member C1 |
| 330 | B5994 | T81301 | AFURS1 | ATPase family homolog up-regulated in senescence cells |
| 331 | C6374 | AA493372 | LOC55971 | Insulin receptor tyrosine kinase substrate |
| 332 | F7512 | AW978905 | HNRPK | Heterogeneous nuclear ribonucleoprotein K |
| 333 | F0864 | AK025277 | TNRC6 | Trinucleotide repeat containing 6 |
| 334 | A9568 | BC022217 | C6orf85 | Chromosome 6 open reading frame 85 |
| 335 | F2807 | AL080146 | CCNB2 | Cyclin B2 |
| 336 | A0587 | NM_006739 | MCM5 | MCM5 minichromosome maintenance deficient 5, cell division cycle 46 (*S. cerevisiae*) |
| 337 | B1119 | AI215478 | HMMR | Hyaluronan-mediated motility receptor (RHAMM) |
| 338 | B7060 | BC067795 | MGC11308 | Hypothetical protein MGC11308 |
| 339 | B8276 | BC009831 | RAB25 | RAB25, member RAS oncogene family |
| 340 | A8043 | W72411 | TP73L | Tumor protein p73-like |
| 341 | B9340 | T78186 | DNMT3A | DNA (cytosine-5-)-methyltransferase 3 alpha |
| 342 | B4456 | BX537652 | FLJ12892 | Hypothetical protein FLJ12892 |
| 343 | B3796 | AA116022 | USP18 | Ubiquitin specific protease 18 |
| 344 | E0950 | BF740209 | PYGB | Phosphorylase, glycogen; brain |
| 345 | B4409 | XM_371116 | MYO5B | Myosin VB |
| 346 | C1898 | AL713801 | SLAMF7 | SLAM family member 7 |
| 347 | F4025 | AK021428 | C6orf210 | Chromosome 6 open reading frame 210 |
| 348 | F0983 | AL832106 | MLR2 | Ligand-dependent corepressor |
| 349 | A3256 | L07597 | RPS6KA1 | Ribosomal protein S6 kinase, 90 kDa, polypeptide 1 |
| 350 | A1715 | M74178 | MST1 | Macrophage stimulating 1 (hepatocyte growth factor-like) |
| 351 | A8407 | CB988759 | C2orf33 | Chromosome 2 open reading frame 33 |
| 352 | A6363 | CR621577 | | *Homo sapiens*, clone IMAGE: 5301514, mRNA |
| 353 | B4618 | BM014054 | LOC339229 | Hypothetical protein LOC339229 |
| 354 | D9773 | BC039118 | STX6 | Syntaxin 6 |
| 355 | A0309 | U85658 | TFAP2C | Transcription factor AP-2 gamma (activating enhancer binding protein 2 gamma) |
| 356 | F4885 | NM_003681 | PDXK | Pyridoxal (pyridoxine, vitamin B6) kinase |
| 357 | A0516 | BC064662 | TRAF2 | TNF receptor-associated factor 2 |
| 358 | B2664 | AA682861 | PARD6B | Par-6 partitioning defective 6 homolog beta (*C. elegans*) |
| 359 | A1874 | CR617220 | KRT8 | Keratin 8 |
| 360 | A2608 | NM_002230 | JUP | Junction plakoglobin |
| 361 | A5157 | AF027153 | | |
| 362 | A1767 | M93107 | BDH | 3-hydroxybutyrate dehydrogenase (heart, mitochondrial) |
| 363 | B4853N | CD013889 | CHRNA1 | Cholinergic receptor, nicotinic, alpha polypeptide 1 (muscle) |
| 364 | A5044 | AK127479 | SPINT2 | Serine protease inhibitor, Kunitz type, 2 |
| 365 | A4467 | AF038961 | MPDU1 | Mannose-P-dolichol utilization defect 1 |
| 366 | B3995 | BC073757 | KRT18 | Keratin 18 |
| 367 | D5376 | BQ946404 | CALM2 | Calmodulin 2 (phosphorylase kinase, delta) |
| 368 | A2620 | NM_001649 | APXL | Apical protein-like (*Xenopus laevis*) |
| 369 | A0437 | NM_005782 | THOC4 | THO complex 4 |
| 370 | B5141 | NM_194463 | RNF128 | Ring finger protein 128 |
| 371 | B9661 | BF764924 | WSB1 | WD repeat and SOCS box-containing 1 |
| 372 | C8847 | AA232990 | | Transcribed locus |
| 373 | C0023 | NM_002744 | PRKCZ | Protein kinase C, zeta |

TABLE 4-continued

Up-regulated gene in bladder cancer

| BLC assignment | LMMID | ACCESSION | GENE | TITLE |
|---|---|---|---|---|
| 374 | D6248 | AW295407 | FLJ25078 | Hypothetical protein FLJ25078 |
| 375 | A2088 | BF131641 | S100A11 | S100 calcium binding protein A11 (calgizzarin) |
| 376 | D8834 | BM729250 | GTF3A | General transcription factor IIIA |
| 377 | A1139 | AF230388 | TRIM29 | Tripartite motif-containing 29 |
| 378 | C9024 | AI678218 | AE2 | Hypothetical protein AE2 |
| 379 | E0571 | BG115155 | FLJ10726 | Hypothetical protein FLJ10726 |
| 380 | C4878 | BC040176 | LOC130576 | Hypothetical protein LOC130576 |
| 381 | E0516 | AK075185 | KDELR1 | KDEL (Lys-Asp-Glu-Leu) endoplasmic reticulum protein retention receptor 1 |
| 382 | B6529 | CA314443 | PLXNA3 | Plexin A3 |
| 383 | A2111 | BC062996 | DBI | Diazepam binding inhibitor (GABA receptor modulator, acyl-Coenzyme A binding protein) |
| 384 | A6657 | BX451670 | FLJ30525 | Hypothetical protein FLJ30525 |
| 385 | F5784 | AK022067 | KIAA1217 | KIAA1217 |
| 386 | A7182 | NM_003731 | SSNA1 | Sjogren's syndrome nuclear autoantigen 1 |
| 387 | A4144 | BC004376 | ANXA8 | Annexin A8 |
| 388 | A2382 | NM_004456 | EZH2 | Enhancer of zeste homolog 2 (*Drosophila*) |
| 389 | A9467 | BC045658 | LOC57228 | Hypothetical protein from clone 643 |
| 390 | F6419 | AW978490 | SSH2 | Slingshot homolog 2 (*Drosophila*) |
| 391 | B3971 | AF290612 | NUSAP1 | Nucleolar and spindle associated protein 1 |
| 392 | B4325 | BC053605 | | LOC440448 |
| 393 | A6441 | AI279896 | CGI-69 | CGI-69 protein |
| 394 | C7625 | BU684240 | EHF | Ets homologous factor |

TABLE 5

Down-regulated gene in bladder cancer

| BLC assignment | LMMID | ACCESSION | GENE | TITLE |
|---|---|---|---|---|
| 395 | A0898 | BC011393 | CHN1 | Chimerin (chimaerin) 1 |
| 396 | A0944 | Z24725 | PLEKHC1 | Pleckstrin homology domain containing, family C (with FERM domain) member 1 |
| 397 | A1750 | D31716 | BTEB1 | Basic transcription element binding protein 1 |
| 398 | A1852 | M19713 | TPM1 | Tropomyosin 1 (alpha) |
| 399 | A2460 | AF000959 | CLDN5 | Claudin 5 (transmembrane protein deleted in velocardiofacial syndrome) |
| 400 | A2701 | NM_003028 | SHB | SHB (Src homology 2 domain containing) adaptor protein B |
| 401 | A6184 | NM_133268 | OSBPL1A | Oxysterol binding protein-like 1A |
| 402 | A3188 | M27110 | PLP1 | Proteolipid protein 1 (Pelizaeus-Merzbacher disease, spastic paraplegia 2, uncomplicated) |
| 403 | A3340 | M93284 | PNLIPRP2 | Pancreatic lipase-related protein 2 |
| 404 | A4189 | AA922716 | PRKACB | Protein kinase, cAMP-dependent, catalytic, beta |
| 405 | A4472 | AF042081 | SH3BGRL | SH3 domain binding glutamic acid-rich protein like |
| 406 | A5084 | CR614015 | CD14 | CD14 antigen |
| 407 | A5498 | BX093242 | | Transcribed locus |
| 408 | A5356 | NM_001002260 | C9orf58 | Chromosome 9 open reading frame 58 |
| 409 | A5795 | BQ775444 | CORO1C | Coronin, actin binding protein, 1C |
| 410 | A5704 | AB018254 | KIAA0711 | KIAA0711 gene product |
| 411 | A0100 | NM_002006 | FGF2 | Fibroblast growth factor 2 (basic) |
| 412 | A6111 | NM_018105 | THAP1 | THAP domain containing, apoptosis associated protein 1 |
| 413 | A1365 | D10653 | TM4SF2 | Transmembrane 4 superfamily member 2 |
| 414 | A1764 | NM_002526 | NT5E | 5'-nucleotidase, ecto (CD73) |
| 415 | A2964 | BQ219660 | GNG11 | Guanine nucleotide binding protein (G protein), gamma 11 |

TABLE 5-continued

Down-regulated gene in bladder cancer

| BLC assignment | LMMID | ACCESSION | GENE | TITLE |
|---|---|---|---|---|
| 416 | A3203 | NM_002436 | MPP1 | Membrane protein, palmitoylated 1, 55 kDa |
| 417 | A3322 | M80899 | AHNAK | AHNAK nucleoprotein (desmoyokin) |
| 418 | A3739 | NM_000090 | COL3A1 | Collagen, type III, alpha 1 (Ehlers-Danlos syndrome type IV, autosomal dominant) |
| 419 | A3748 | X51593 | MYH3 | Myosin, heavy polypeptide 3, skeletal muscle, embryonic |
| 420 | A4630 | U89281 | RODH | 3-hydroxysteroid epimerase |
| 421 | A4972 | NM_002487 | NDN | Necdin homolog (mouse) |
| 422 | A5807 | W80773 | | CDNA FLJ13601 fis, clone PLACE1010069 |
| 423 | A5937 | BC028315 | GABARAPL1 | GABA(A) receptor-associated protein like 1 |
| 424 | A5785 | CR627469 | PSMB7 | Proteasome (prosome, macropain) subunit, beta type, 7 |
| 425 | A1572 | NM_015833 | ADARB1 | Adenosine deaminase, RNA-specific, B1 (RED1 homolog rat) |
| 426 | A1847 | U31525 | GYG | Glycogenin |
| 427 | A1879 | U45955 | GPM6B | Glycoprotein M6B |
| 428 | A2452 | BX537488 | CSRP1 | Cysteine and glycine-rich protein 1 |
| 429 | A2978 | X04741 | UCHL1 | Ubiquitin carboxyl-terminal esterase L1 (ubiquitin thiolesterase) |
| 430 | A3946 | NM_021738 | SVIL | Supervillin |
| 431 | A4579 | L29394 | HP | Haptoglobin |
| 432 | A4473 | BX648582 | SPRY2 | Sprouty homolog 2 (*Drosophila*) |
| 433 | A4611 | S79851 | TXNRD1 | Thioredoxin reductase 1 |
| 434 | A5118 | X17576 | NCK1 | NCK adaptor protein 1 |
| 435 | A5888 | U56417 | AGPAT1 | 1-acylglycerol-3-phosphate O-acyltransferase 1 (lysophosphatidic acid acyltransferase, alpha) |
| 436 | A6099 | W60630 | JAM3 | Junctional adhesion molecule 3 |
| 437 | A1083 | BX510904 | MYH2 | Myosin, heavy polypeptide 2, skeletal muscle, adult |
| 438 | A2610 | NM_020546 | ADCY2 | Adenylate cyclase 2 (brain) |
| 439 | A2972 | X72475 | | Amyloid immunoglobulin light chain protein BRE |
| 440 | A3214 | X17042 | PRG1 | Proteoglycan 1, secretory granule |
| 441 | A5485 | NM_018357 | FLJ11196 | Acheron |
| 442 | A0260 | U47413 | CCNG1 | Cyclin G1 |
| 443 | A0232 | NM_006219 | PIK3CB | Phosphoinositide-3-kinase, catalytic, beta polypeptide |
| 444 | A0946 | U62961 | OXCT1 | 3-oxoacid CoA transferase 1 |
| 445 | A1617 | NM_133378 | TTN | Titin |
| 446 | A1855 | X73114 | MYBPC1 | Myosin binding protein C, slow type |
| 447 | A1891 | BC038984 | GAS6 | Growth arrest-specific 6 |
| 448 | A2372 | AF458589 | PPP1R12A | Protein phosphatase 1, regulatory (inhibitor) subunit 12A |
| 449 | A2739 | AF073920 | RGS6 | Regulator of G-protein signalling 6 |
| 450 | A3733 | X04665 | THBS1 | Thrombospondin 1 |
| 451 | A5211 | R55332 | LRIG1 | Leucine-rich repeats and immunoglobulin-like domains 1 |
| 452 | A5251 | NM_025164 | KIAA0999 | KIAA0999 protein |
| 453 | A5694 | BM996053 | C10orf9 | Chromosome 10 open reading frame 9 |
| 454 | A0094 | NM_002293 | LAMC1 | Laminin, gamma 1 (formerly LAMB2) |
| 455 | A0383 | M13690 | SERPING1 | Serine (or cysteine) proteinase inhibitor, clade G (C1 inhibitor), member 1, (angioedema, hereditary) |
| 456 | A0791 | X63556 | FBN1 | Fibrillin 1 (Marfan syndrome) |
| 457 | A1064 | NM_024164 | TPSB2 | Tryptase, alpha |
| 458 | A0960 | U60115 | FHL1 | Four and a half LIM domains 1 |
| 459 | A1736 | NM_001456 | FLNA | Filamin A, alpha (actin binding protein 280) |
| 460 | A2031 | NM_003040 | SLC4A2 | Solute carrier family 4, anion exchanger, member 2 (erythrocyte membrane protein band 3-like 1) |
| 461 | A2388 | BC000574 | PCOLCE | Procollagen C-endopeptidase enhancer |
| 462 | A2860 | BC002436 | STX4A | Syntaxin 4A (placental) |
| 463 | A4328 | NM_000573 | CR1 | Complement component (3b/4b) receptor 1, including Knops blood group system |

TABLE 5-continued

Down-regulated gene in bladder cancer

| BLC assignment | LMMID | ACCESSION | GENE | TITLE |
|---|---|---|---|---|
| 464 | A4602 | X63679 | TRAM1 | Translocation associated membrane protein 1 |
| 465 | A4974 | NM_006063 | KBTBD10 | Kelch repeat and BTB (POZ) domain containing 10 |
| 466 | A5015 | NM_001451 | FOXF1 | Forkhead box F1 |
| 467 | A0941 | S59049 | RGS1 | Regulator of G-protein signalling 1 |
| 468 | A1753 | BC063289 | C4A | Complement component 4B |
| 469 | A1882 | AF018081 | COL18A1 | Collagen, type XVIII, alpha 1 |
| 470 | A2595 | BC010839 | RPN1 | Ribophorin I |
| 471 | A2224 | NM_004469 | FIGF | C-fos induced growth factor (vascular endothelial growth factor D) |
| 472 | A2740 | CR607883 | CDO1 | Cysteine dioxygenase, type I |
| 473 | A3089 | AK091961 | UMOD | Uromodulin (uromucoid, Tamm-Horsfall glycoprotein) |
| 474 | A4193 | BU737730 | RBP1 | Retinol binding protein 1, cellular |
| 475 | A4841 | AF037261 | SCAM-1 | Vinexin beta (SH3-containing adaptor molecule-1) |
| 476 | A5514 | AA669799 | ASMTL | Acetylserotonin O-methyltransferase-like |
| 477 | A1085 | BQ073704 | LGALS1 | Lectin, galactoside-binding, soluble, 1 (galectin 1) |
| 478 | A0837 | L02950 | CRYM | Crystallin, mu |
| 479 | A0961 | NM_001482 | GATM | Glycine amidinotransferase (L-arginine:glycine amidinotransferase) |
| 480 | A1592 | NM_000177 | GSN | Gelsolin (amyloidosis, Finnish type) |
| 481 | A2043 | BC005330 | TFPI2 | Tissue factor pathway inhibitor 2 |
| 482 | A2272 | AF195530 | XPNPEP1 | X-prolyl aminopeptidase (aminopeptidase P) 1, soluble |
| 483 | A6080 | N99340 | CLIPR-59 | CLIP-170-related protein |
| 484 | A0357 | X15606 | ICAM2 | Intercellular adhesion molecule 2 |
| 485 | A0775 | L12579 | CUTL1 | Cut-like 1, CCAAT displacement protein (Drosophila) |
| 486 | A1074 | D90228 | ACAT1 | Acetyl-Coenzyme A acetyltransferase 1 (acetoacetyl Coenzyme A thiolase) |
| 487 | A1610 | NM_002084 | GPX3 | Glutathione peroxidase 3 (plasma) |
| 488 | A1452 | CD013947 | ITGB6 | Integrin, beta 6 |
| 489 | A1754 | AB119995 | CES1 | Carboxylesterase 1 (monocyte/macrophage serine esterase 1) |
| 490 | A3061 | U07643 | LTF | Lactotransferrin |
| 491 | A2715 | BC035802 | GZMK | Granzyme K (serine protease, granzyme 3; tryptase II) |
| 492 | A2751 | M68874 | PLA2G4A | Phospholipase A2, group IVA (cytosolic, calcium-dependent) |
| 493 | A3563 | NM_021136 | RTN1 | Reticulon 1 |
| 494 | A4201 | CR592913 | RRAS2 | Related RAS viral (r-ras) oncogene homolog 2 |
| 495 | A4237 | BC058074 | WISP2 | WNT1 inducible signaling pathway protein 2 |
| 496 | A4709 | BC016952 | CYR61 | Cysteine-rich, angiogenic inducer, 61 |
| 497 | A4871 | Z19002 | ZBTB16 | Zinc finger and BTB domain containing 16 |
| 498 | A6057 | BC035939 | MRAS | Muscle RAS oncogene homolog |
| 499 | A5773 | N72174 | EGFL5 | EGF-like-domain, multiple 5 |
| 500 | A0533 | NM_003932 | ST13 | Suppression of tumorigenicity 13 (colon carcinoma) (Hsp70 interacting protein) |
| 501 | A1748 | U29089 | PRELP | Proline arginine-rich end leucine-rich repeat protein |
| 502 | A2478 | Y13647 | SCD | Stearoyl-CoA desaturase (delta-9-desaturase) |
| 503 | A6225 | AJ420439 | | MRNA full length insert cDNA clone EUROIMAGE 1585492 |
| 504 | A3965 | AF078695 | REV3L | REV3-like, catalytic subunit of DNA polymerase zeta (yeast) |
| 505 | A6264 | BC022522 | CD200 | CD200 antigen |
| 506 | A4365 | U68494 | SLC30A1 | Solute carrier family 30 (zinc transporter), member 1 |
| 507 | A4491 | L15388 | GRK5 | G protein-coupled receptor kinase 5 |
| 508 | A4983 | X12830 | IL6R | Interleukin 6 receptor |
| 509 | A4769 | AF004563 | STXBP1 | Syntaxin binding protein 1 |
| 510 | A4887 | NM_001173 | ARHGAP5 | Rho GTPase activating protein 5 |

TABLE 5-continued

Down-regulated gene in bladder cancer

| BLC assignment | LMMID | ACCESSION | GENE | TITLE |
|---|---|---|---|---|
| 511 | A6081 | AK023172 | C2orf23 | Chromosome 2 open reading frame 23 |
| 512 | A0090 | BC040499 | TGFBR2 | Transforming growth factor, beta receptor II (70/80 kDa) |
| 513 | A0905 | X14723 | CLU | Clusterin (complement lysis inhibitor, SP-40,40, sulfated glycoprotein 2, testosterone-repressed prostate message 2, apolipoprotein J) |
| 514 | A0635 | NM_004329 | BMPR1A | Bone morphogenetic protein receptor, type IA |
| 515 | A1474 | M86406 | ACTN2 | Actinin, alpha 2 |
| 516 | A1453 | M37721 | PAM | Peptidylglycine alpha-amidating monooxygenase |
| 517 | A1886 | BC029261 | MYOC | Myocilin, trabecular meshwork inducible glucocorticoid response |
| 518 | A1995 | M14745 | BCL2 | B-cell CLL/lymphoma 2 |
| 519 | A3435 | CR623240 | PSG9 | Pregnancy specific beta-1-glycoprotein 9 |
| 520 | A3866 | AF080157 | CHUK | Conserved helix-loop-helix ubiquitous kinase |
| 521 | A4111 | BC033040 | SLC1A1 | Solute carrier family 1 (neuronal/epithelial high affinity glutamate transporter, system Xag), member 1 |
| 522 | A3834 | AB010419 | CBFA2T3 | Core-binding factor, runt domain, alpha subunit 2; translocated to, 3 |
| 523 | A3959 | AF055081 | DES | Desmin |
| 524 | A4076 | BC008837 | AKR1B10 | Aldo-keto reductase family 1, member B10 (aldose reductase) |
| 525 | A3738 | NM_002332 | LRP1 | Low density lipoprotein-related protein 1 (alpha-2-macroglobulin receptor) |
| 526 | A4586 | D86977 | DHX38 | DEAH (Asp-Glu-Ala-His) box polypeptide 38 |
| 527 | A5806 | BC042960 | | Transcribed locus, moderately similar to NP_787073.2 hypothetical protein MGC35023 [*Homo sapiens*] |
| 528 | A0386 | K02215 | AGT | Angiotensinogen (serine (or cysteine) proteinase inhibitor, clade A (alpha-1 antiproteinase, antitrypsin), member 8) |
| 529 | A0415 | M77349 | TGFBI | Transforming growth factor, beta-induced, 68 kDa |
| 530 | A0922 | NM_004394 | DAP | Death-associated protein |
| 531 | A1594 | NM_002422 | MMP3 | Matrix metalloproteinase 3 (stromelysin 1, progelatinase) |
| 532 | A2471 | NM_001155 | ANXA6 | Annexin A6 |
| 533 | A3114 | M95585 | HLF | Hepatic leukemia factor |
| 534 | A4742 | AF019214 | HBP1 | HMG-box transcription factor 1 |
| 535 | A5262 | NM_020182 | TMEPAI | Transmembrane, prostate androgen induced RNA |
| 536 | A5911 | AK125888 | FBXO32 | F-box protein 32 |
| 537 | A6082 | N66336 | ALS2CR15 | Amyotrophic lateral sclerosis 2 (juvenile) chromosome region, candidate 14 |
| 538 | A0159 | BC028049 | PPP3CB | Protein phosphatase 3 (formerly 2B), catalytic subunit, beta isoform (calcineurin A beta) |
| 539 | A0423 | NM_006744 | RBP4 | Retinol binding protein 4, plasma |
| 540 | A0192 | M62829 | EGR1 | Early growth response 1 |
| 541 | A1378 | NM_000362 | TIMP3 | Tissue inhibitor of metalloproteinase 3 (Sorsby fundus dystrophy, pseudoinflammatory) |
| 542 | A2275 | L80005 | SNRPN | SNRPN upstream reading frame |
| 543 | A2508 | X03350 | ADH1B | Alcohol dehydrogenase IB (class I), beta polypeptide |
| 544 | A2188 | J02770 | IF | I factor (complement) |
| 545 | A2542 | J02874 | FABP4 | Fatty acid binding protein 4, adipocyte |
| 546 | A3037 | BC030975 | IL1RL1 | Interleukin 1 receptor-like 1 |
| 547 | A6208 | NM_004264 | SURB7 | SRB7 suppressor of RNA polymerase B homolog (yeast) |
| 548 | A4040 | NM_181425 | FXN | Frataxin |
| 549 | A4254 | NM_001848 | COL6A1 | Collagen, type VI, alpha 1 |

TABLE 5-continued

Down-regulated gene in bladder cancer

| BLC assignment | LMMID | ACCESSION | GENE | TITLE |
|---|---|---|---|---|
| 550 | A4407 | AF055872 | TNFSF13 | Tumor necrosis factor (ligand) superfamily, member 12 |
| 551 | A5853 | N72866 | MITF | Microphthalmia-associated transcription factor |
| 552 | A5740 | AI304392 | PTGFRN | Prostaglandin F2 receptor negative regulator |
| 553 | A1150 | NM_000560 | CD53 | CD53 antigen |
| 554 | A6221 | N67054 | RANBP5 | RAN binding protein 5 |
| 555 | A3680 | U79751 | BLZF1 | Basic leucine zipper nuclear factor 1 (JEM-1) |
| 556 | A3778 | BC050277 | PELO | Integrin, alpha 1 |
| 557 | A4024 | AK091336 | STMN2 | Stathmin-like 2 |
| 558 | A4394 | AF039701 | MBD2 | Methyl-CpG binding domain protein 2 |
| 559 | A4823 | D50370 | NAP1L3 | Nucleosome assembly protein 1-like 3 |
| 560 | A6003 | BC042605 | FKBP5 | FK506 binding protein 5 |
| 561 | A0152 | M19154 | TGFB2 | Transforming growth factor, beta 2 |
| 562 | A6102 | R71596 | | Transcribed locus |
| 563 | A0735 | NM_001847 | COL4A6 | Collagen, type IV, alpha 6 |
| 564 | A1010 | D28475 | CLCN6 | Chloride channel 6 |
| 565 | A1387 | BC038588 | AEBP1 | AE binding protein 1 |
| 566 | A1516 | U24488 | TNXB | Tenascin XB |
| 567 | A1414 | NM_001855 | COL15A1 | Collagen, type XV, alpha 1 |
| 568 | A1815 | NM_002664 | PLEK | Pleckstrin |
| 569 | A1951 | AL833268 | MEF2C | MADS box transcription enhancer factor 2, polypeptide C (myocyte enhancer factor 2C) |
| 570 | A2158 | NM_005410 | SEPP1 | Selenoprotein P, plasma, 1 |
| 571 | A2189 | NM_000112 | SLC26A2 | Solute carrier family 26 (sulfate transporter), member 2 |
| 572 | A2536 | U48707 | PPP1R1A | Protein phosphatase 1, regulatory (inhibitor) subunit 1A |
| 573 | A2518 | BM557396 | IGFBP6 | Insulin-like growth factor binding protein 6 |
| 574 | A2543 | NM_213674 | TPM2 | Tropomyosin 2 (beta) |
| 575 | A2625 | L26081 | SEMA3A | Sema domain, immunoglobulin domain (Ig), short basic domain, secreted, (semaphorin) 3A |
| 576 | A3360 | NM_031850 | AGTR1 | Angiotensin II receptor, type 1 |
| 577 | A3631 | NM_005908 | MANBA | Mannosidase, beta A, lysosomal |
| 578 | A4641 | J02854 | MYL9 | Myosin, light polypeptide 9, regulatory |
| 579 | A5991 | BX537522 | FLJ34077 | Weakly similar to zinc finger protein 195 |
| 580 | A1032 | M87790 | IGLC2 | Immunoglobulin lambda constant 2 (Kern-Oz-marker) |
| 581 | A2074 | CR594071 | SERPINA1 | Serine (or cysteine) proteinase inhibitor, clade A (alpha-1 antiproteinase, antitrypsin), member 1 |
| 582 | A2291 | AF003341 | ALDH1A1 | Aldehyde dehydrogenase 1 family, member A1 |
| 583 | A2202 | AJ001016 | RAMP3 | Receptor (calcitonin) activity modifying protein 3 |
| 584 | A2319 | AK126978 | VCL | Vinculin |
| 585 | A2182 | CR749540 | FAHD1 | Hydroxyacylglutathione hydrolase |
| 586 | A2530 | CA310505 | APOD | Apolipoprotein D |
| 587 | A2444 | AY366508 | LOH11CR2A | Loss of heterozygosity, 11, chromosomal region 2, gene A |
| 588 | A2644 | BC062476 | ADH1C | Alcohol dehydrogenase 1C (class I), gamma polypeptide |
| 589 | A3044 | BC075840 | IGHG1 | Immunoglobulin heavy constant gamma 1 (G1m marker) |
| 590 | A2693 | NM_002742 | PRKCM | Protein kinase C, mu |
| 591 | A3382 | AF004021 | PTGFR | Prostaglandin F receptor (FP) |
| 592 | A3296 | M24122 | MYL3 | Myosin, light polypeptide 3, alkali; ventricular, skeletal, slow |
| 593 | A3412 | NM_000552 | VWF | Von Willebrand factor |
| 594 | A4267 | BU689993 | NDUFA6 | NADH dehydrogenase (ubiquinone) 1 alpha subcomplex, 6, 14 kDa |
| 595 | A0593 | NM_002290 | LAMA4 | Laminin, alpha 4 |
| 596 | A1959 | U10550 | GEM | GTP binding protein overexpressed in skeletal muscle |
| 597 | A2159 | L10340 | EEF1A2 | Eukaryotic translation elongation factor 1 alpha 2 |

TABLE 5-continued

Down-regulated gene in bladder cancer

| BLC assignment | LMMID | ACCESSION | GENE | TITLE |
|---|---|---|---|---|
| 598 | A2626 | NM_004137 | KCNMB1 | Potassium large conductance calcium-activated channel, subfamily M, beta member 1 |
| 599 | A3499 | NM_005406 | ROCK1 | Rho-associated, coiled-coil containing protein kinase 1 |
| 600 | A3390 | BC001093 | PDLIM7 | PDZ and LIM domain 7 (enigma) |
| 601 | A6234 | NM_000667 | ADH1A | Alcohol dehydrogenase 1A (class I), alpha polypeptide |
| 602 | A4545 | BC056898 | PLS3 | Plastin 3 (T isoform) |
| 603 | A4680 | NM_004517 | ILK | Integrin-linked kinase |
| 604 | A5306 | AB046764 | NBEA | Neurobeachin |
| 605 | A5720 | BQ787632 | SPON1 | Spondin 1, extracellular matrix protein |
| 606 | A0460 | X55656 | HBG2 | Hemoglobin, gamma G |
| 607 | A0994 | BC016928 | OAT | Ornithine aminotransferase (gyrateatrophy) |
| 608 | A1154 | NM_000784 | CYP27A1 | Cytochrome P450, family 27, subfamily A, polypeptide 1 |
| 609 | A1423 | L38486 | MFAP4 | Microfibrillar-associated protein 4 |
| 610 | A1301 | AF039018 | PDLIM3 | PDZ and LIM domain 3 |
| 611 | A1431 | L43821 | NEDD9 | Neural precursor cell expressed, developmentally down-regulated 9 |
| 612 | A1966 | X81438 | AMPH | Amphiphysin (Stiff-Man syndrome with breast cancer 128 kDa autoantigen) |
| 613 | A2075 | L02321 | GSTM5 | Glutathione S-transferase M5 |
| 614 | A2175 | J03075 | PRKCSH | Protein kinase C substrate 80K-H |
| 615 | A6159 | T17385 | | Hypothetical LOC399951 |
| 616 | A2557 | NM_001928 | DF | D component of complement (adipsin) |
| 617 | A3019 | J00068 | ACTA1 | Actin, alpha 1, skeletal muscle |
| 618 | A3511 | NM_006200 | PCSK5 | Proprotein convertase subtilisin/kexin type 5 |
| 619 | A3291 | BM805032 | PRSS2 | Protease, serine, 2 (trypsin 2) |
| 620 | A3903 | AF026692 | SFRP4 | Secreted frizzled-related protein 4 |
| 621 | A4297 | NM_012205 | HAAO | 3-hydroxyanthranilate 3,4-dioxygenase |
| 622 | A4403 | NM_001856 | COL16A1 | Collagen, type XVI, alpha 1 |
| 623 | A4695 | NM_001003395 | TPD52L1 | Tumor protein D52-like 1 |
| 624 | A5457 | AF038193 | ARL3 | ADP-ribosylation factor-like 3 |
| 625 | A5849 | NM_024095 | ASB8 | Ankyrin repeat and SOCS box-containing 8 |
| 626 | A0971 | AY034086 | DSCR1L1 | Down syndrome critical region gene 1-like 1 |
| 627 | A0707 | NM_000677 | ADORA3 | Adenosine A3 receptor |
| 628 | A0745 | NM_004024 | ATF3 | Activating transcription factor 3 |
| 629 | A1510 | NM_004385 | CSPG2 | Chondroitin sulfate proteoglycan 2 (versican) |
| 630 | A1693 | X94991 | ZYX | Zyxin |
| 631 | A3032 | NM_000055 | BCHE | Butyrylcholinesterase |
| 632 | A2904 | BM727781 | PCP4 | Purkinje cell protein 4 |
| 633 | A4043 | NM_000304 | PMP22 | Peripheral myelin protein 22 |
| 634 | A4136 | BC035128 | MXI1 | MAX interactor 1 |
| 635 | A4263 | BX647780 | ITGA5 | Integrin, alpha 5 (fibronectin receptor, alpha polypeptide) |
| 636 | A4390 | AB007836 | TGFB1I1 | Transforming growth factor beta 1 induced transcript 1 |
| 637 | A5442 | AF105036 | KLF4 | Kruppel-like factor 4 (gut) |
| 638 | A5422 | W91908 | GALNAC4S-6ST | B cell RAG associated protein |
| 639 | A5834 | AK025773 | LMAN1 | Lectin, mannose-binding, 1 |
| 640 | A1432 | L47738 | CYFIP2 | Cytoplasmic FMR1 interacting protein 2 |
| 641 | A6243 | BM564532 | OPN1SW | Opsin 1 (cone pigments), short-wave-sensitive (color blindness, tritan) |
| 642 | A4702 | NM_014890 | DOC1 | Downregulated in ovarian cancer 1 |
| 643 | A5428 | H05313 | | Transcribed locus |
| 644 | A5556 | BC071586 | TIMP2 | Tissue inhibitor of metalloproteinase 2 |
| 645 | A6008 | NM_005504 | BCAT1 | Branched chain aminotransferase 1, cytosolic |
| 646 | A1553 | BC023505 | ECM1 | Extracellular matrix protein 1 |
| 647 | A2063 | U47025 | PYGB | Phosphorylase, glycogen; brain |
| 648 | A3015 | NM_201442 | C1S | Complement component 1, s subcomponent |

TABLE 5-continued

Down-regulated gene in bladder cancer

| BLC assignment | LMMID | ACCESSION | GENE | TITLE |
|---|---|---|---|---|
| 649 | A3119 | J04621 | SDC2 | Syndecan 2 (heparan sulfate proteoglycan 1, cell surface-associated, fibroglycan) |
| 650 | A3501 | BC051748 | TOP3A | Topoisomerase (DNA) III alpha |
| 651 | A3151 | M83712 | CHRNA5 | Cholinergic receptor, nicotinic, alpha polypeptide 5 |
| 652 | A3373 | L13858 | SOS2 | Son of sevenless homolog 2 (*Drosophila*) |
| 653 | A4547 | NM_004586 | RPS6KA3 | Ribosomal protein S6 kinase, 90 kDa, polypeptide 3 |
| 654 | A5868 | BC037733 | SLC40A1 | Solute carrier family 40 (iron-regulated transporter), member 1 |
| 655 | A0578 | NM_004417 | DUSP1 | Dual specificity phosphatase 1 |
| 656 | A6152 | XM_376018 | KIAA1644 | KIAA1644 protein |
| 657 | A3054 | U01839 | FY | Duffy blood group |
| 658 | A3550 | NM_000702 | ATP1A2 | ATPase, Na+/K+ transporting, alpha 2 (+) polypeptide |
| 659 | A3299 | BM696587 | CRYAB | Crystallin, alpha B |
| 660 | A3783 | X70991 | NAB2 | NGFI-A binding protein 2 (EGR1 binding protein 2) |
| 661 | A4819 | D17408 | CNN1 | Calponin 1, basic, smooth muscle |
| 662 | A4917 | X83688 | P2RX1 | Purinergic receptor P2X, ligand-gated ion channel, 1 |
| 663 | A5597 | BC012347 | FGF13 | Fibroblast growth factor 13 |
| 664 | A6010 | U79271 | AKT3 | V-akt murine thymoma viral oncogene homolog 3 (protein kinase B, gamma) |
| 665 | A6089 | CR749654 | PHLDB2 | Pleckstrin homology-like domain, family B, member 2 |
| 666 | A0975 | NM_002037 | FYN | FYN oncogene related to SRC, FGR, YES |
| 667 | A0875 | L13740 | NR4A1 | Nuclear receptor subfamily 4, group A, member 1 |
| 668 | A0597 | X72760 | LAMB2 | Laminin, beta 2 (laminin S) |
| 669 | A1023 | X05610 | COL4A2 | Collagen, type IV, alpha 2 |
| 670 | A1147 | NM_000129 | F13A1 | Coagulation factor XIII, A1 polypeptide |
| 671 | A1956 | NM_004010 | DMD | Dystrophin (muscular dystrophy, Duchenne and Becker types) |
| 672 | A2404 | M15395 | ITGB2 | Integrin, beta 2 (antigen CD18 (p95), lymphocyte function-associated antigen 1; macrophage antigen 1 (mac-1) beta subunit) |
| 673 | A2675 | NM_005907 | MAN1A1 | Mannosidase, alpha, class 1A, member 1 |
| 674 | A2641 | X69090 | MYOM1 | Myomesin 1 (skelemin) 185 kDa |
| 675 | A4175 | CR594469 | RHOQ | Ras homolog gene family, member Q |
| 676 | A4807 | AJ001515 | RYR3 | Ryanodine receptor 3 |
| 677 | A5152 | AK129891 | CASQ2 | Calsequestrin 2 (cardiac muscle) |
| 678 | A0184 | NM_000426 | LAMA2 | Laminin, alpha 2 (merosin, congenital muscular dystrophy) |
| 679 | A6115 | NM_175709 | CBX7 | Chromobox homolog 7 |
| 680 | A2415 | M15856 | LPL | Lipoprotein lipase |
| 681 | A2442 | AK074668 | ISLR | Immunoglobulin superfamily containing leucine-rich repeat |
| 682 | A2450 | NM_001740 | CALB2 | Calbindin 2, 29 kDa (calretinin) |
| 683 | A3055 | AK095384 | PDE4C | Phosphodiesterase 4C, cAMP-specific (phosphodiesterase E1 dunce homolog, *Drosophila*) |
| 684 | A3380 | L20977 | ATP2B2 | ATPase, Ca++ transporting, plasma membrane 2 |
| 685 | A3181 | NM_002193 | INHBB | Inhibin, beta B (activin AB beta polypeptide) |
| 686 | A4053 | AB005293 | PLIN | Perilipin |
| 687 | A4794 | AF064493 | LDB2 | LIM domain binding 2 |
| 688 | A4830 | NM_004557 | NOTCH4 | Notch homolog 4 (*Drosophila*) |
| 689 | A5436 | BQ009281 | ELL2 | Elongation factor, RNA polymerase II, 2 |
| 690 | A5690 | AB028952 | SYNPO | Synaptopodin |
| 691 | A6510 | AI215810 | CAPN7 | Calpain 7 |
| 692 | B1689 | AL359062 | COL8A1 | Collagen, type VIII, alpha 1 |
| 693 | B2439 | U04735 | STCH | Stress 70 protein chaperone, microsome-associated, 60 kDa |
| 694 | B6764 | M14338 | PROS1 | Protein S (alpha) |
| 695 | B8155 | NM_006873 | SBLF | TFIIA-alpha/beta-like factor |

TABLE 5-continued

Down-regulated gene in bladder cancer

| BLC assignment | LMMID | ACCESSION | GENE | TITLE |
|---|---|---|---|---|
| 696 | A6427 | BC004995 | MARVELD1 | MARVEL domain containing 1 |
| 697 | A6436 | AB014609 | MRC2 | Mannose receptor, C type 2 |
| 698 | A7576 | AI640497 | C9orf103 | Chromosome 9 open reading frame 103 |
| 699 | A8863 | BM678420 | | Transcribed locus |
| 700 | B1851 | AA032154 | FLJ22655 | Hypothetical protein FLJ22655 |
| 701 | B3746 | AF311912 | SFRP2 | Secreted frizzled-related protein 2 |
| 702 | B3759 | AF067420 | MGC27165 | Hypothetical protein MGC27165 |
| 703 | B4090 | M34175 | AP2B1 | Adaptor-related protein complex 2, beta 1 subunit |
| 704 | A6545 | NM_004613 | TGM2 | Transglutaminase 2 (C polypeptide, protein-glutamine-gamma-glutamyltransferase) |
| 705 | A6949 | AB014733 | SMAP-5 | Golgi membrane protein SB140 |
| 706 | A6923 | AA677283 | KIRREL | Kin of IRRE like (*Drosophila*) |
| 707 | A9130 | AF001436 | CDC42EP2 | CDC42 effector protein (Rho GTPase binding) 2 |
| 708 | A9161 | BC051700 | PHF10 | PHD finger protein 10 |
| 709 | B0149 | AF052090 | NNT | Nicotinamide nucleotide transhydrogenase |
| 710 | B1400 | BX538213 | CPEB4 | Cytoplasmic polyadenylation element binding protein 4 |
| 711 | B2148 | M61900 | | |
| 712 | B2723 | AA018259 | | Full-length cDNA clone CS0DF027YN23 of Fetal brain of *Homo sapiens* (human) |
| 713 | A6778 | M36172 | MYL4 | Myosin, light polypeptide 4, alkali; atrial, embryonic |
| 714 | A7349 | BX647178 | FILIP1 | Filamin A interacting protein 1 |
| 715 | B2829 | AA121865 | FLJ10081 | Hypothetical protein FLJ10081 |
| 716 | B2547 | BM725055 | | Transcribed locus |
| 717 | A9341 | BG576897 | MSRB | Methionine sulfoxide reductase B |
| 718 | B0275 | AK092204 | DNAJB9 | DnaJ (Hsp40) homolog, subfamily B, member 9 |
| 719 | B2490 | BX112650 | RYR2 | Ryanodine receptor 2 (cardiac) |
| 720 | B2456 | AL550901 | CCNI | Cyclin I |
| 721 | B3649 | AI199480 | WASF2 | WAS protein family, member 2 |
| 722 | B4064 | NM_000047 | ARSE | Arylsulfatase E (chondrodysplasia punctata 1) |
| 723 | A6385 | AA663484 | PPP2R2B | Protein phosphatase 2 (formerly 2A), regulatory subunit B (PR 52), beta isoform |
| 724 | A8114 | AL832154 | CAP2 | CAP, adenylate cyclase-associated protein, 2 (yeast) |
| 725 | B0739 | AK074209 | PLEKHA3 | Pleckstrin homology domain containing, family A (phosphoinositide binding specific) member 3 |
| 726 | B0268 | AK123393 | CCDC3 | Coiled-coil domain containing 3 |
| 727 | B1032 | NM_172127 | CAMK2D | Calcium/calmodulin-dependent protein kinase (CaM kinase) II delta |
| 728 | B4077 | NM_004099 | STOM | Stomatin |
| 729 | B0283 | AL832993 | NDFIP1 | Nedd4 family interacting protein 1 |
| 730 | B2130 | NM_000448 | RAG1 | Recombination activating gene 1 |
| 731 | B2457 | NM_007353 | GNA12 | Guanine nucleotide binding protein (G protein) alpha 12 |
| 732 | B4085 | NM_198098 | AQP1 | Aquaporin 1 (channel-forming integral protein, 28 kDa) |
| 733 | B4092 | AB011126 | FNBP1 | Formin binding protein 1 |
| 734 | B6287 | U66680 | | |
| 735 | A7286 | NM_021201 | MS4A7 | Membrane-spanning 4-domains, subfamily A, member 7 |
| 736 | A8203 | AK026966 | AK3 | Adenylate kinase 3 |
| 737 | A7795 | BC044582 | UBL3 | Ubiquitin-like 3 |
| 738 | A8531 | BX537531 | FBLN5 | Fibulin 5 |
| 739 | B1081 | AK096303 | FLJ38984 | Hypothetical protein FLJ38984 |
| 740 | B1985 | AI052390 | FLJ20071 | Dymeclin |
| 741 | B4230 | AK054596 | IGBP1 | Immunoglobulin (CD79A) binding protein 1 |
| 742 | B4078 | AK093049 | SERPINA3 | Serine (or cysteine) proteinase inhibitor, clade A (alpha-1 antiproteinase, antitrypsin), member 3 |
| 743 | C0670 | AK093067 | CHPT1 | Choline phosphotransferase 1 |
| 744 | A6409 | AK091288 | C9orf19 | Chromosome 9 open reading frame 19 |

TABLE 5-continued

Down-regulated gene in bladder cancer

| BLC assignment | LMMID | ACCESSION | GENE | TITLE |
|---|---|---|---|---|
| 745 | A6664 | H19830 | DKFZP434G156 | Hypothetical protein DKFZp434G156 |
| 746 | A7411 | BC035028 | SERPIND1 | Serine (or cysteine) proteinase inhibitor, clade D (heparin cofactor), member 1 |
| 747 | A7145 | X52005 | | |
| 748 | A7963 | AK024964 | NFIA | KIAA0485 protein |
| 749 | A7972 | NM_170677 | MEIS2 | Meis1, myeloid ecotropic viral integration site 1 homolog 2 (mouse) |
| 750 | A8433 | NM_005843 | STAM2 | Signal transducing adaptor molecule (SH3 domain and ITAM motif) 2 |
| 751 | B2609 | AL833069 | KIAA1434 | Hypothetical protein KIAA1434 |
| 752 | A9305 | BC035417 | | Transcribed locus, weakly similar to NP_650255.1 *Drosophila melanogaster* CG11670 gene |
| 753 | A9187 | BC034222 | HRLP5 | H-rev107-like protein 5 |
| 754 | A9801 | AI350750 | PDGFD | DNA-damage inducible protein 1 |
| 755 | B1288 | H73979 | CACNB2 | Calcium channel, voltage-dependent, beta 2 subunit |
| 756 | B2506 | AL834231 | MTPN | Myotrophin |
| 757 | B4086 | NM_006206 | PDGFRA | Platelet-derived growth factor receptor, alpha polypeptide |
| 758 | A6672 | H27000 | WBSCR17 | Williams-Beuren syndrome chromosome region 17 |
| 759 | A6683 | AB088477 | PER1 | Period homolog 1 (*Drosophila*) |
| 760 | A8568 | BQ071428 | CUEDC2 | CUE domain containing 2 |
| 761 | A9468 | BX110596 | | *Homo sapiens*, clone IMAGE: 4799216, mRNA |
| 762 | B8113 | BC020848 | RNASE6 | Ribonuclease, RNase A family, k6 |
| 763 | B6773 | BC077077 | DPYSL3 | Dihydropyrimidinase-like 3 |
| 764 | A6781 | CB529051 | G0S2 | Putative lymphocyte G0/G1 switch gene |
| 765 | A6410 | XM_496907 | PEG10 | Paternally expressed 10 |
| 766 | A6665 | AW450890 | LMO3 | LIM domain only 3 (rhombotin-like 2) |
| 767 | A6936 | AI766077 | FLJ13456 | Hypothetical protein FLJ13456 |
| 768 | A9993 | AB007903 | GPRASP1 | G protein-coupled receptor associated sorting protein 1 |
| 769 | B0327 | NM_144658 | DOCK11 | Dedicator of cytokinesis 11 |
| 770 | B4288 | AK092766 | OLFML3 | Olfactomedin-like 3 |
| 771 | A6776 | BM726594 | COX7A1 | Cytochrome c oxidase subunit VIIa polypeptide 1 (muscle) |
| 772 | A7599 | AK095147 | | CDNA FLJ37828 fis, clone BRSSN2006575 |
| 773 | A7330 | NM_018434 | RNF130 | Ring finger protein 130 |
| 774 | A9462 | BM474898 | SLIT2 | Slit homolog 2 (*Drosophila*) |
| 775 | A9042 | NM_022349 | MS4A6A | Membrane-spanning 4-domains, subfamily A, member 6A |
| 776 | A6522 | BC045177 | FLJ30046 | Hypothetical protein FLJ30046 |
| 777 | A6530 | NM_006988 | ADAMTS1 | A disintegrin-like and metalloprotease (reprolysin type) with thrombospondin type 1 motif, 1 |
| 778 | A6567 | AK096428 | PDK4 | Pyruvate dehydrogenase kinase, isoenzyme 4 |
| 779 | A7663 | BX647421 | FSTL1 | Follistatin-like 1 |
| 780 | B2584 | CR620669 | PBX3 | Pre-B-cell leukemia transcription factor 3 |
| 781 | A8129 | AB067468 | KIAA1881 | KIAA1881 |
| 782 | A8552 | AK056721 | LOC56181 | Hypothetical protein RP1-317E23 |
| 783 | A8591 | BC078139 | EIF2C2 | Eukaryotic translation initiation factor 2C, 2 |
| 784 | A8744 | NM_001233 | CAV2 | Caveolin 2 |
| 785 | B0328 | AK094236 | DDIT4L | DNA-damage-inducible transcript 4-like |
| 786 | B4847 | AA490011 | LTBP1 | Latent transforming growth factor beta binding protein 1 |
| 787 | A6611 | N58556 | DKFZp547K1113 | Hypothetical protein DKFZp547K1113 |
| 788 | A6317 | AI205684 | HSPA2 | Heat shock 70 kDa protein 2 |
| 789 | A7191 | BC007655 | PPP1R2 | Protein phosphatase 1, regulatory (inhibitor) subunit 2 |
| 790 | A8600 | CR749355 | hIAN2 | Human immune associated nucleotide 2 |
| 791 | B1649 | AA244092 | | Chromosome 9 pericentromeric mRNA sequence |

TABLE 5-continued

Down-regulated gene in bladder cancer

| BLC assignment | LMMID | ACCESSION | GENE | TITLE |
|---|---|---|---|---|
| 792 | B4691 | NM_024605 | ARHGAP10 | Rho GTPase activating protein 10 |
| 793 | B6518 | CA419435 | GNPDA2 | Glucosamine-6-phosphate deaminase 2 |
| 794 | B9201 | BX647427 | WIF1 | WNT inhibitory factor 1 |
| 795 | A6458 | AK127289 | SLCO2B1 | Solute carrier organic anion transporter family, member 2B1 |
| 796 | A6602 | W87690 | ITGA9 | Integrin, alpha 9 |
| 797 | A6863 | AK027199 | MGC48972 | Hypothetical protein MGC48972 |
| 798 | A6906 | BC050423 | TMEM22 | Transmembrane protein 22 |
| 799 | A8147 | AY422170 | TP53INP2 | Tumor protein p53 inducible nuclear protein 2 |
| 800 | B4154 | D87074 | RIMS3 | Regulating synaptic membrane exocytosis 3 |
| 801 | B6579 | AK126500 | APEG1 | Aortic preferentially expressed protein 1 |
| 802 | A6712 | NM_182643 | DLC1 | Deleted in liver cancer 1 |
| 803 | A6993 | H10356 | | CDNA FLJ36544 fis, clone TRACH2006378 |
| 804 | A7225 | NM_002729 | HHEX | Hematopoietically expressed homeobox |
| 805 | A6837 | BX412783 | LOC283140 | Hypothetical protein LOC283140 |
| 806 | A7425 | NM_003250 | THRA | Thyroid hormone receptor, alpha (erythroblastic leukemia viral (v-erb-a) oncogene homolog, avian) |
| 807 | A8162 | AL832955 | TNFAIP9 | Tumor necrosis factor, alpha-induced protein 9 |
| 808 | A7679 | M97675 | ROR1 | Receptor tyrosine kinase-like orphan receptor 1 |
| 809 | B2084 | S45018 | CHAT | Choline acetyltransferase |
| 810 | A6593 | AF007150 | ANGPTL2 | Angiopoietin-like 2 |
| 811 | A7075 | NM_004982 | KCNJ8 | Potassium inwardly-rectifying channel, subfamily J, member 8 |
| 812 | A7710 | AK125609 | CKIP-1 | CK2 interacting protein 1; HQ0024c protein |
| 813 | A7772 | BC028314 | SURF1 | Surfeit 1 |
| 814 | A9120 | AF332010 | CDV-1 | Carnitine deficiency-associated gene expressed in ventricle 1 |
| 815 | B0202 | NM_021914 | CFL2 | Cofilin 2 (muscle) |
| 816 | B0240 | AA081184 | TCF4 | Transcription factor 4 |
| 817 | B5402 | XM_375377 | KIAA0513 | KIAA0513 |
| 818 | B8811 | D86962 | GRB10 | Growth factor receptor-bound protein 10 |
| 819 | A6613 | AB018278 | SV2B | Synaptic vesicle glycoprotein 2B |
| 820 | A6583 | XM_371114 | FHOD3 | Formin homology 2 domain containing 3 |
| 821 | A6876 | AA705804 | DPT | Dermatopontin |
| 822 | A7426 | BG617617 | SAA2 | Serum amyloid A2 |
| 823 | A7689 | X00457 | HLA-DPA1 | Major histocompatibility complex, class II, DP alpha 1 |
| 824 | A8605 | AK025205 | DKFZP564O0823 | DKFZP564O0823 protein |
| 825 | A8639 | AI368204 | ENPP3 | Ectonucleotide pyrophosphatase/phosphodiesterase 3 |
| 826 | A8647 | XM_290734 | | Similar to ataxin 2-binding protein 1 isoform 4; hexaribonucleotide binding protein 1 |
| 827 | A9250 | BC062575 | RHOJ | Ras homolog gene family, member J |
| 828 | B3940 | K02765 | C3 | Complement component 3 |
| 829 | B3977 | AI056268 | PARVA | Parvin, alpha |
| 830 | B4699 | NM_003450 | ZNF174 | Zinc finger protein 174 |
| 831 | B8782 | AK022926 | CTNNAL1 | Catenin (cadherin-associated protein), alpha-like 1 |
| 832 | A6719 | AI302184 | SQRDL | Sulfide quinone reductase-like (yeast) |
| 833 | A7464 | AF081287 | CTDP1 | CTD (carboxy-terminal domain, RNA polymerase II, polypeptide A) phosphatase, subunit 1 |
| 834 | A7246 | N75862 | EYA4 | Eyes absent homolog 4 (*Drosophila*) |
| 835 | A7773 | NM_002504 | NFX1 | Nuclear transcription factor, X-box binding 1 |
| 836 | A8155 | CD242398 | LOC51255 | Hypothetical protein LOC51255 |
| 837 | B2641 | BX094063 | PIN4 | Protein (peptidyl-prolyl cis/trans isomerase) NIMA-interacting, 4 (parvulin) |
| 838 | A9121 | AB002388 | ZNF536 | Zinc finger protein 536 |
| 839 | A9280 | AW136599 | HUNK | Hormonally upregulated Neu-associated kinase |

TABLE 5-continued

Down-regulated gene in bladder cancer

| BLC assignment | LMMID | ACCESSION | GENE | TITLE |
|---|---|---|---|---|
| 840 | B0241 | BC056414 | PLVAP | Plasmalemma vesicle associated protein |
| 841 | B1531 | BC063304 | NPR1 | Natriuretic peptide receptor A/guanylate cyclase A (atrionatriuretic peptide receptor A) |
| 842 | B2663 | BC009978 | ACTC | Actin, alpha, cardiac muscle |
| 843 | B4213 | NM_001001937 | ATP5A1 | ATP synthase, H+ transporting, mitochondrial F1 complex, alpha subunit, isoform 1, cardiac muscle |
| 844 | A6348 | AK026653 | C14orf168 | Chromosome 14 open reading frame 168 |
| 845 | A6842 | AB043585 | RPRM | Reprimo, TP53 dependant G2 arrest mediator candidate |
| 846 | A8761 | BM984852 | C6orf166 | Hypothetical protein PRO2266 |
| 847 | B0337 | R28608 | MAPRE2 | Microtubule-associated protein, RP/EB family, member 2 |
| 848 | B5155 | W84893 | AGTRL1 | Angiotensin II receptor-like 1 |
| 849 | B7659 | AF541281 | LPPR4 | Plasticity related gene 1 |
| 850 | B6542 | NM_014819 | PJA2 | Praja 2, RING-H2 motif containing |
| 851 | A7775 | BC033820 | FGL2 | Fibrinogen-like 2 |
| 852 | A8156 | BQ010373 | HEG | HEG homolog |
| 853 | B2659 | AI025259 | | Transcribed locus |
| 854 | A9282 | AF086912 | OGN | Osteoglycin (osteoinductive factor, mimecan) |
| 855 | B0845 | H68305 | PRKAB2 | Protein kinase, AMP-activated, beta 2 non-catalytic subunit |
| 856 | B3924 | AK075151 | HSPB7 | Heat shock 27 kDa protein family, member 7 (cardiovascular) |
| 857 | B4008 | XM_167709 | C10orf38 | Chromosome 10 open reading frame 38 |
| 858 | C4095 | NM_002122 | HLA-DQA1 | Major histocompatibility complex, class II, DQ alpha 1 |
| 859 | B9009 | XM_039796 | TNIK, | TRAF2 and NCK interacting kinase |
| 860 | A6475 | BC032508 | FLJ10781 | Hypothetical protein FLJ10781 |
| 861 | A6358 | AK056079 | JAM2 | Junctional adhesion molecule 2 |
| 862 | A7230 | NM_001845 | COL4A1 | Collagen, type IV, alpha 1 |
| 863 | A9373 | AK128695 | COL6A2 | Collagen, type VI, alpha 2 |
| 864 | A9103 | AK091635 | FLJ11200 | Hypothetical protein FLJ11200 |
| 865 | A9081 | BC000693 | ACTR1A | ARP1 actin-related protein 1 homolog A, centractin alpha (yeast) |
| 866 | A9381 | AL117605 | | CDNA: FLJ21418 fis, clone COL04072 |
| 867 | A9719 | XM_294521 | FLJ43950 | FLJ43950 protein |
| 868 | B1004 | NM_004530 | MMP2 | Matrix metalloproteinase 2 (gelatinase A, 72 kDa gelatinase, 72 kDa type IV collagenase) |
| 869 | B4674 | AA149429 | ATP10D | ATPase, Class V, type 10D |
| 870 | A6856 | XM_051081 | TBC1D12 | TBC1 domain family, member 12 |
| 871 | A7467 | BC034989 | P2RY14 | Purinergic receptor P2Y, G-protein coupled, 14 |
| 872 | A7088 | AB031046 | TCF7L1 | Transcription factor 7-like 1 (T-cell specific, HMG-box) |
| 873 | A7222 | NM_001911 | CTSG | Cathepsin G |
| 874 | A7893 | AA417560 | | Transcribed locus |
| 875 | A8030 | AL137734 | DKFZp586C0721 | Hypothetical protein DKFZp586C0721 |
| 876 | A8514 | AL110212 | H2AFV | H2A histone family, member V |
| 877 | A9870 | AB040938 | KIAA1505 | KIAA1505 protein |
| 878 | B1676 | BC025985 | IGHG4 | Immunoglobulin heavy constant gamma 4 (G4m marker) |
| 879 | A6447 | AK127088 | EPB41L2 | Erythrocyte membrane protein band 4.1-like 2 |
| 880 | A6457 | AJ318805 | | CDNA FLJ44429 fis, clone UTERU2015653 |
| 881 | A6360 | AL390127 | KLF13 | Kruppel-like factor 13 |
| 882 | A7000 | XM_496727 | DKFZP564J102 | DKFZP564J102 protein |
| 883 | A6844 | AL831898 | LOC285812 | Hypothetical protein LOC285812 |
| 884 | A7239 | AA523541 | DSIPI | Delta sleep inducing peptide, immunoreactor |
| 885 | A8482 | BC047492 | ADHFE1 | Alcohol dehydrogenase, iron containing, 1 |
| 886 | A8493 | AA780301 | CTSF | Cathepsin F |
| 887 | A9564 | NM_000076 | CDKN1C | Cyclin-dependent kinase inhibitor 1C (p57, Kip2) |

TABLE 5-continued

Down-regulated gene in bladder cancer

| BLC assignment | LMMID | ACCESSION | GENE | TITLE |
|---|---|---|---|---|
| 888 | B2874 | AA883488 | KIAA0408 | KIAA0408 |
| 889 | B6561 | AB014544 | KIAA0644 | KIAA0644 gene product |
| 890 | B7552 | NM_016143 | NSFL1C | NSFL1 (p97) cofactor (p47) |
| 891 | A6751 | NM_002258 | KLRB1 | Killer cell lectin-like receptor subfamily B, member 1 |
| 892 | A8186 | BM551020 | SCAMP2 | Secretory carrier membrane protein 2 |
| 893 | A8159 | BX537904 | APG5L | APG5 autophagy 5-like (*S. cerevisiae*) |
| 894 | A8823 | N26005 | PPP1R3C | Protein phosphatase 1, regulatory (inhibitor) subunit 3C |
| 895 | B4810 | BM701072 | KIAA0103 | KIAA0103 |
| 896 | B9056 | AF433662 | ARHGEF3 | Rho guanine nucleotide exchange factor (GEF) 3 |
| 897 | B2978 | AA442090 | FLJ10292 | Hypothetical protein FLJ10292 |
| 898 | B3794N | BC033829 | AKAP12 | A kinase (PRKA) anchor protein (gravin) 12 |
| 899 | B3766 | NM_000933 | PLCB4 | Phospholipase C, beta 4 |
| 900 | B4194N | BG292094 | FLJ11000 | Hypothetical protein FLJ11000 |
| 901 | B6051 | R32860 | MOBKL2B | MOB1, Mps One Binder kinase activator-like 2B (yeast) |
| 902 | B6511 | AK124739 | | CDNA FLJ36725 fis, clone UTERU2012230 |
| 903 | B6358 | AL161983 | MGC39820 | Hypothetical protein MGC39820 |
| 904 | B7880N | AK125119 | C6orf68 | Chromosome 6 open reading frame 68 |
| 905 | B9198 | AK123132 | MSRA | Methionine sulfoxide reductase A |
| 906 | B8754 | AL833264 | FEM1B | Fem-1 homolog b (*C. elegans*) |
| 907 | B9564 | CR609948 | KPNB1 | Karyopherin (importin) beta 1 |
| 908 | B9394 | AL117521 | C20orf77 | Chromosome 20 open reading frame 77 |
| 909 | A1871N | NM_198235 | RNASE1 | Ribonuclease, RNase A family, 1 (pancreatic) |
| 910 | A3439N | BM994174 | HBB | Hemoglobin, beta |
| 911 | A7605 | R15801 | NRN1 | Neuritin 1 |
| 912 | B4394 | N46424 | RAI14 | Retinoic acid induced 14 |
| 913 | B3827 | N20989 | ANTXR1 | Anthrax toxin receptor 1 |
| 914 | B4574 | AK160376 | FLJ12895 | Hypothetical protein FLJ12895 |
| 915 | B6373 | BX423161 | LHPP | Phospholysine phosphohistidine inorganic pyrophosphate phosphatase |
| 916 | B7122 | AA480009 | | CDNA FLJ13569 fis, clone PLACE1008369 |
| 917 | B7310 | R72837 | DKFZP434F2021 | DKFZP434F2021 protein |
| 918 | B8308 | NM_001001936 | KIAA1914 | KIAA1914 |
| 919 | B7903 | N49237 | | *Homo sapiens*, clone IMAGE: 5312516, mRNA |
| 920 | B8141 | BC042478 | DKFZP434F0318 | Hypothetical protein DKFZp434F0318 |
| 921 | B9647 | AK125651 | FLJ43663 | Hypothetical protein FLJ43663 |
| 922 | A0925N | L42374 | PPP2R5B | Protein phosphatase 2, regulatory subunit B (B56), beta isoform |
| 923 | A6533N | AL833076 | FLJ14281 | Hypothetical protein FLJ14281 |
| 924 | A6272 | NM_139346 | BIN1 | Bridging integrator 1 |
| 925 | B4133 | BC039740 | LOC84549 | RNA binding protein |
| 926 | B4694 | AK074046 | ZNF521 | Zinc finger protein 521 |
| 927 | B5489 | NM_003916 | AP1S2 | Adaptor-related protein complex 1, sigma 2 subunit |
| 928 | B6306 | AF107454 | C7orf2 | Chromosome 7 open reading frame 2 |
| 929 | B7500 | H14059 | LOC197336 | Similar to RIKEN cDNA 3230401M21 [*Mus musculus*] |
| 930 | B8069 | NM_013366 | ANAPC2 | Anaphase promoting complex subunit 2 |
| 931 | B8422 | CA310622 | ACTR3 | ARP3 actin-related protein 3 homolog (yeast) |
| 932 | B8679 | NM_030569 | ITIH5 | Inter-alpha (globulin) inhibitor H5 |
| 933 | B9427 | BC047114 | | CDNA clone IMAGE: 5313062, partial cds |
| 934 | B9435 | Z39318 | SP2 | Sp2 transcription factor |
| 935 | A4798N | NM_174953 | ATP2A3 | ATPase, Ca++ transporting, ubiquitous |
| 936 | A0774N | BC012613 | CPA3 | Carboxypeptidase A3 (mast cell) |
| 937 | A6640N | BC001816 | RAP1GDS1 | RAP1, GTP-GDP dissociation stimulator 1 |
| 938 | A8783N | AA621565 | ENPP1 | Ectonucleotide pyrophosphatase/phosphodiesterase 1 |

TABLE 5-continued

Down-regulated gene in bladder cancer

| BLC assignment | LMMID | ACCESSION | GENE | TITLE |
|---|---|---|---|---|
| 939 | B0870N | CR610395 | ASF1A | ASF1 anti-silencing function 1 homolog A (S. cerevisiae) |
| 940 | B5768 | BX647147 | | Transcribed locus, weakly similar to XP_375099.1 hypothetical protein LOC283585 [Homo sapiens] |
| 941 | B6365 | AK091292 | FATJ | Fat-like cadherin FATJ |
| 942 | B6571 | BC039332 | LOC285086 | Hypothetical protein LOC285086 |
| 943 | B7170N | NM_019035 | PCDH18 | Protocadherin 18 |
| 944 | B9172 | AK092542 | C2orf32 | Chromosome 2 open reading frame 32 |
| 945 | B9634 | BX110180 | | Transcribed locus |
| 946 | B9317 | N24737 | | Transcribed locus |
| 947 | B9419 | BM996307 | LNX | Ligand of numb-protein X |
| 948 | A2660N | NM_021023 | CFHL3 | Complement factor H-related 3 |
| 949 | A0881N | Z21707 | ZNF197 | Zinc finger protein 197 |
| 950 | A1816N | BC075800 | PRKAR2B | Protein kinase, cAMP-dependent, regulatory, type II, beta |
| 951 | A0702N | BQ189297 | FLT1 | Fms-related tyrosine kinase 1 (vascular endothelial growth factor/vascular permeability factor receptor) |
| 952 | A0936N | M86852 | PXMP3 | Peroxisomal membrane protein 3, 35 kDa (Zellweger syndrome) |
| 953 | B4137 | NM_053025 | MYLK | Myosin, light polypeptide kinase |
| 954 | B4949 | R26358 | SLMAP | Sarcolemma associated protein |
| 955 | B5172N | NM_001289 | CLIC2 | Chloride intracellular channel 2 |
| 956 | B6700 | AL133579 | STARD9 | START domain containing 9 |
| 957 | B6104N | BM987057 | KIAA0563 | KIAA0563 gene product |
| 958 | B7105 | AK055782 | PDLIM2 | PDZ and LIM domain 2 (mystique) |
| 959 | B7930 | N21096 | | |
| 960 | B7887 | BU580616 | FLJ10159 | Hypothetical protein FLJ10159 |
| 961 | B8081 | BM981462 | FLJ13710 | Hypothetical protein FLJ13710 |
| 962 | B8438 | AA403307 | UBE4B | Ubiquitination factor E4B (UFD2 homolog, yeast) |
| 963 | B9300 | CA446432 | C6orf66 | Chromosome 6 open reading frame 66 |
| 964 | A6448N | AK127801 | FLJ46603 | FLJ46603 protein |
| 965 | A9346N | AY358379 | PP2135 | PP2135 protein |
| 966 | B3779 | BF966783 | | |
| 967 | B4396 | W58589 | DDR2 | Discoidin domain receptor family, member 2 |
| 968 | B4568 | AK021950 | PRTFDC1 | Phosphoribosyl transferase domain containing 1 |
| 969 | B4956 | NM_005737 | ARL7 | ADP-ribosylation factor-like 7 |
| 970 | B4577 | AY081219 | ABCC4 | ATP-binding cassette, sub-family C (CFTR/MRP), member 4 |
| 971 | B5199 | AK098381 | ADCY5 | Adenylate cyclase 5 |
| 972 | B5399 | XM_056455 | D2S448 | Melanoma associated gene |
| 973 | B6366 | AK130263 | KIAA1430 | KIAA1430 |
| 974 | B7304N | AA777308 | C6orf60 | Chromosome 6 open reading frame 60 |
| 975 | B7312 | BU738244 | | Hypothetical gene supported by AK094796 |
| 976 | B7171 | H75419 | CYBRD1 | Cytochrome b reductase 1 |
| 977 | B7708 | AA938297 | FLJ20716 | Hypothetical protein FLJ20716 |
| 978 | B8098 | R42864 | PAPOLA | Poly(A) polymerase alpha |
| 979 | B7768 | BC017032 | GCNT3 | Glucosaminyl (N-acetyl) transferase 3, mucin type |
| 980 | B8770 | J04605 | PEPD | Peptidase D |
| 981 | B9603 | BM679454 | ASAM | Adipocyte-specific adhesion molecule |
| 982 | B9803 | AF414088 | COL21A1 | Collagen, type XXI, alpha 1 |
| 983 | A4655N | NM_001164 | APBB1 | Amyloid beta (A4) precursor protein-binding, family B, member 1 (Fe65) |
| 984 | A1818N | NM_033138 | CALD1 | Caldesmon 1 |
| 985 | A3200N | AK122763 | COL5A1 | Collagen, type V, alpha 1 |
| 986 | B2864 | AI088622 | PRKCDBP | Protein kinase C, delta binding protein |
| 987 | B4348 | AK055071 | PIGK | Phosphatidylinositol glycan, class K |
| 988 | B8670 | NM_021038 | MBNL1 | Muscleblind-like (Drosophila) |
| 989 | B9836 | R79561 | ARRDC3 | Arrestin domain containing 3 |
| 990 | A1779N | AF025534 | LILRB5 | Leukocyte immunoglobulin-like receptor, subfamily B (with TM and ITIM domains), member 5 |

TABLE 5-continued

Down-regulated gene in bladder cancer

| BLC assignment | LMMID | ACCESSION | GENE | TITLE |
|---|---|---|---|---|
| 991 | A3034N | BC027913 | PPP3R1 | Protein phosphatase 3 (formerly 2B), regulatory subunit B, 19 kDa, alpha isoform (calcineurin B, type I) |
| 992 | A3147N | U20938 | DPYD | Dihydropyrimidine dehydrogenase |
| 993 | A1963N | BC047756 | QPCT | Glutaminyl-peptide cyclotransferase (glutaminyl cyclase) |
| 994 | B3829 | AF091434 | PDGFC | Platelet derived growth factor C |
| 995 | B4578 | AI290343 | STC2 | Stanniocalcin 2 |
| 996 | B5151 | BU627644 | 7h3 | Hypothetical protein FLJ13511 |
| 997 | B4614 | AL833852 | TAZ | Transcriptional co-activator with PDZ-binding motif (TAZ) |
| 998 | B4971 | NM_020443 | NAV1 | Neuron navigator 1 |
| 999 | B6319 | BX414085 | ICSBP1 | Interferon consensus sequence binding protein 1 |
| 1000 | B7526 | R40594 | CYP2U1 | Cytochrome P450, family 2, subfamily U, polypeptide 1 |
| 1001 | B9790 | BC067746 | CLEC1 | C-type lectin-like receptor-1 |
| 1002 | B9341 | BC012984 | ALS2CR19 | Amyotrophic lateral sclerosis 2 (juvenile) chromosome region, candidate 19 |
| 1003 | A0907N | NM_016083 | CNR1 | Cannabinoid receptor 1 (brain) |
| 1004 | A5065 | BC036661 | CMKOR1 | Chemokine orphan receptor 1 |
| 1005 | A3369N | L13283 | MUC7 | Mucin 7, salivary |
| 1006 | A8391N | AA482082 | FOXK1 | Forkhead box K1 |
| 1007 | B4364 | CD365397 | TRPV2 | Transient receptor potential cation channel, subfamily V, member 2 |
| 1008 | B3958 | AF145713 | SCHIP1 | Schwannomin interacting protein 1 |
| 1009 | B5164 | R37342 | PARVG | Parvin, gamma |
| 1010 | B6108 | AW409897 | LOC91461 | Hypothetical protein BC007901 |
| 1011 | B6565N | BC007997 | RERG | RAS-like, estrogen-regulated, growth inhibitor |
| 1012 | B7875 | H17818 | | Transcribed locus |
| 1013 | B9007 | BQ028161 | hSyn | Brain synembryn |
| 1014 | A1780N | CR606785 | ENPP2 | Ectonucleotide pyrophosphatase/phosphodiesterase 2 (autotaxin) |
| 1015 | A1151N | M55618 | TNC | Tenascin C (hexabrachion) |
| 1016 | A6369N | NM_013374 | PDCD6IP | Programmed cell death 6 interacting protein |
| 1017 | B3930 | XM_290629 | C14orf78 | Chromosome 14 open reading frame 78 |
| 1018 | B4217 | BU608626 | WFDC2 | WAP four-disulfide core domain 2 |
| 1019 | B4447 | NM_032287 | LDOC1L | Leucine zipper, down-regulated in cancer 1-like |
| 1020 | B5721N | AK024116 | FLJ14054 | Hypothetical protein FLJ14054 |
| 1021 | B5949 | NM_016293 | BIN2 | Bridging integrator 2 |
| 1022 | B6719 | BX537713 | | *Homo sapiens*, clone IMAGE: 4150640, mRNA |
| 1023 | B6738 | BX640757 | DRCTNNB1A | Down-regulated by Ctnnb1, a |
| 1024 | A1669 | M95787 | TAGLN | Transgelin |
| 1025 | A0919N | J05550 | MRC1 | Mannose receptor, C type 1 |
| 1026 | A2753N | BC009924 | NPTX2 | Neuronal pentraxin II |
| 1027 | A0969N | NM_001873 | CPE | Carboxypeptidase E |
| 1028 | B3911 | BC038457 | DKFZP586H2123 | Regeneration associated muscle protease |
| 1029 | B4953 | AB007960 | SH3GLB1 | SH3-domain GRB2-like endophilin B1 |
| 1030 | B5382N | AK125194 | MAP1B | Microtubule-associated protein 1B |
| 1031 | B6568 | AK091271 | GPR161 | G protein-coupled receptor 161 |
| 1032 | B7877 | AB029033 | IQSEC3 | IQ motif and Sec7 domain 3 |
| 1033 | B9777 | NM_030781 | COLEC12 | Collectin sub-family member 12 |
| 1034 | A3079 | J04599 | BGN | Biglycan |
| 1035 | A3160N | NM_000125 | ESR1 | Estrogen receptor 1 |
| 1036 | A1981 | U58514 | CHI3L2 | Chitinase 3-like 2 |
| 1037 | A6696 | NM_012072 | C1QR1 | Complement component 1, q subcomponent, receptor 1 |
| 1038 | A8809N | NM_000755 | CRAT | Carnitine acetyltransferase |
| 1039 | B1090N | AF361473 | ROBO4 | Roundabout homolog 4, magic roundabout (*Drosophila*) |
| 1040 | B3933 | AY358360 | ELTD1 | EGF, latrophilin and seven transmembrane domain containing 1 |
| 1041 | B3966 | BC047724 | C10orf128 | Chromosome 10 open reading frame 128 |
| 1042 | B3831 | AK125356 | KLHL13 | Kelch-like 13 (*Drosophila*) |
| 1043 | B4450 | BC048969 | TSPYL1 | TSPY-like 1 |

TABLE 5-continued

Down-regulated gene in bladder cancer

| BLC assignment | LMMID | ACCESSION | GENE | TITLE |
|---|---|---|---|---|
| 1044 | B5396 | AF208863 | C6orf209 | Chromosome 6 open reading frame 209 |
| 1045 | B5410 | BC033183 | CHST3 | Carbohydrate (chondroitin 6) sulfotransferase 3 |
| 1046 | B6082 | BX537781 | FNDC5 | Fibronectin type III domain containing 5 |
| 1047 | B7003N | AF045584 | SLC43A1 | Solute carrier family 43, member 1 |
| 1048 | B7922 | NM_181844 | BCL6B | B-cell CLL/lymphoma 6, member B (zinc finger protein) |
| 1049 | B8790 | AK123915 | ZBED3 | Zinc finger, BED domain containing 3 |
| 1050 | A0055N | AF058925 | JAK2 | Janus kinase 2 (a protein tyrosine kinase) |
| 1051 | A7633 | AL136578 | MGC3040 | Hypothetical protein MGC3040 |
| 1052 | B5842N | AF545852 | MK2S4 | Protein kinase substrate MK2S4 |
| 1053 | B7363 | AL832469 | | Hypothetical gene supported by BX647608 |
| 1054 | B9053 | AB023158 | RAB11FIP2 | RAB11 family interacting protein 2 (class I) |
| 1055 | A0560N | NM_000618 | IGF1 | Insulin-like growth factor 1 (somatomedin C) |
| 1056 | A1624N | NM_003034 | SIAT8A | Sialyltransferase 8A (alpha-N-acetylneuraminate: alpha-2,8-sialyltransferase, GD3 synthase) |
| 1057 | A7760N | BC047390 | ARID5A | AT rich interactive domain 5A (MRF1-like) |
| 1058 | A8879N | CR597401 | HCA112 | Hepatocellular carcinoma-associated antigen 112 |
| 1059 | A5504N | AK056479 | SPRED2 | Sprouty-related, EVH1 domain containing 2 |
| 1060 | B2957 | CR599541 | TFIP11 | Tuftelin interacting protein 11 |
| 1061 | B3586 | AA748009 | PPP2R5E | Protein phosphatase 2, regulatory subunit B (B56), epsilon isoform |
| 1062 | B4320 | N56931 | C5orf4 | Chromosome 5 open reading frame 4 |
| 1063 | B4277 | AJ420529 | STX7 | Syntaxin 7 |
| 1064 | B3893 | AY549722 | ITLN1 | Intelectin 1 (galactofuranose binding) |
| 1065 | B7204N | AK074765 | CA14 | Carbonic anhydrase XIV |
| 1066 | B7444 | AW452608 | C9orf87 | Chromosome 9 open reading frame 87 |
| 1067 | B8593 | BU624282 | KIAA0779 | KIAA0779 protein |
| 1068 | B9132 | AA455877 | MRVI1 | Murine retrovirus integration site 1 homolog |
| 1069 | B9504 | AA521163 | PTEN | Phosphatase and tensin homolog (mutated in multiple advanced cancers 1) |
| 1070 | A8864N | N93511 | FLJ10853 | Hypothetical protein FLJ10853 |
| 1071 | B2559 | CA426475 | HBE1 | Hemoglobin, epsilon 1 |
| 1072 | B4235N | AK095908 | MFGE8 | Milk fat globule-EGF factor 8 protein |
| 1073 | B4291 | AK025198 | XIST | X (inactive)-specific transcript |
| 1074 | B4245 | AF034176 | NUDT3 | Nudix (nucleoside diphosphate linked moiety X)-type motif 3 |
| 1075 | B7559 | AB073386 | SGEF | Src homology 3 domain-containing guanine nucleotide exchange factor |
| 1076 | B8203 | NM_018325 | C9orf72 | Chromosome 9 open reading frame 72 |
| 1077 | B8035 | AL834240 | KIAA1576 | KIAA1576 protein |
| 1078 | B8212 | AK023159 | LSM11 | LSM11, U7 small nuclear RNA associated |
| 1079 | A0085N | D37965 | PDGFRL | Platelet-derived growth factor receptor-like |
| 1080 | A4391N | NM_003155 | STC1 | Stanniocalcin 1 |
| 1081 | A1437N | NM_002210 | ITGAV | Integrin, alpha V (vitronectin receptor, alpha polypeptide, antigen CD51) |
| 1082 | A7247N | AL133118 | EMCN | Endomucin |
| 1083 | A8289N | AK127420 | | Transcribed locus, weakly similar to XP_375268.2 similar to FLJ43276 protein [Homo sapiens] |
| 1084 | B3883 | BC027937 | RAI2 | Retinoic acid induced 2 |
| 1085 | B4321 | BX648583 | EDIL3 | EGF-like repeats and discoidin I-like domains 3 |
| 1086 | B4684 | BC036485 | | Homo sapiens, clone IMAGE: 5261213, mRNA |
| 1087 | B5442 | AK124604 | LOC283537 | Hypothetical protein LOC283537 |

TABLE 5-continued

Down-regulated gene in bladder cancer

| BLC assignment | LMMID | ACCESSION | GENE | TITLE |
|---|---|---|---|---|
| 1088 | B6492 | AK057151 | | CDNA FLJ32589 fis, clone SPLEN2000443 |
| 1089 | B7082 | AK055323 | | CDNA clone IMAGE: 5263177, partial cds |
| 1090 | B9505 | NM_004796 | NRXN3 | Neurexin 3 |
| 1091 | A3538 | J03464 | COL1A2 | Collagen, type I, alpha 2 |
| 1092 | A7704N | NM_003749 | IRS2 | Insulin receptor substrate 2 |
| 1093 | B3059 | NM_004755 | RPS6KA5 | Ribosomal protein S6 kinase, 90 kDa, polypeptide 5 |
| 1094 | B3834 | AB033040 | RNF150 | Ring finger protein 150 |
| 1095 | B4237 | XM_290941 | PRNPIP | Prion protein interacting protein |
| 1096 | B4498N | BX648979 | SLC41A1 | Solute carrier family 41, member 1 |
| 1097 | B4661 | AI765053 | PTPRD | Protein tyrosine phosphatase, receptor type, D |
| 1098 | B4633 | AL162008 | CLIC4 | Chloride intracellular channel 4 |
| 1099 | B5019 | BQ574410 | | Full-length cDNA clone CS0DI014YH21 of Placenta Cot 25-normalized of Homo sapiens (human) |
| 1100 | B7429 | BM723215 | SMARCE1 | SWI/SNF related, matrix associated, actin dependent regulator of chromatin, subfamily e, member 1 |
| 1101 | B8028 | AK057742 | C10orf46 | Chromosome 10 open reading frame 46 |
| 1102 | B8036 | R20340 | ATP5S | ATP synthase, H+ transporting, mitochondrial F0 complex, subunit s (factor B) |
| 1103 | B8213 | AA729769 | LOC112476 | Similar to lymphocyte antigen 6 complex, locus G5B; G5b protein; open reading frame 31 |
| 1104 | B9470 | N29574 | RRAGD | Ras-related GTP binding D |
| 1105 | A2632N | NM_003816 | ADAM9 | A disintegrin and metalloproteinase domain 9 (meltrin gamma) |
| 1106 | B0081N | AB040962 | KIAA1529 | KIAA1529 |
| 1107 | B3699 | NM_006617 | NES | Nestin |
| 1108 | B8411 | BX412247 | EFHD1 | EF hand domain containing 1 |
| 1109 | A2019N | AA442410 | EMP1 | Epithelial membrane protein 1 |
| 1110 | B4240 | BC018652 | FXYD6 | FXYD domain containing ion transport regulator 6 |
| 1111 | B4249 | BC070071 | RBM16 | RNA binding motif protein 16 |
| 1112 | B3721 | AB023177 | KIAA0960 | KIAA0960 protein |
| 1113 | B5418 | BQ573990 | ZNF148 | Zinc finger protein 148 (pHZ-52) |
| 1114 | B5464 | AK127355 | SEC23A | Sec23 homolog A (S. cerevisiae) |
| 1115 | B7185 | W61217 | RAB23 | RAB23, member RAS oncogene family |
| 1116 | B7996N | BQ445850 | | CDNA clone IMAGE: 5561426, partial cds |
| 1117 | B8341 | BC043003 | NEK7 | NIMA (never in mitosis gene a)-related kinase 7 |
| 1118 | B8547 | BC033746 | PNCK | Pregnancy upregulated non-ubiquitously expressed CaM kinase |
| 1119 | B8351 | R26919 | DSCR1L2 | Down syndrome critical region gene 1-like 2 |
| 1120 | B8389 | AK095203 | PDE3A | Phosphodiesterase 3A, cGMP-inhibited |
| 1121 | B9722 | BQ773658 | | Hypothetical LOC402560 |
| 1122 | A1600N | NM_001844 | COL2A1 | Collagen, type II, alpha 1 (primary osteoarthritis, spondyloepiphyseal dysplasia, congenital) |
| 1123 | A1471N | M83772 | FMO3 | Flavin containing monooxygenase 3 |
| 1124 | A1634N | BC026324 | MMD | Monocyte to macrophage differentiation-associated |
| 1125 | A2633N | BX648814 | ANGPT1 | Angiopoietin 1 |
| 1126 | B4030 | AK055793 | C20orf129 | Chromosome 20 open reading frame 129 |
| 1127 | B4339 | W73738 | TMEM25 | Transmembrane protein 25 |
| 1128 | B4891 | W19216 | PKIG | Protein kinase (cAMP-dependent, catalytic) inhibitor gamma |
| 1129 | B5059N | T88953 | | Transcribed locus |
| 1130 | B6284 | AK096240 | | Similar to protein of fungal metazoan origin like (11.1 kD) (2C514) |
| 1131 | B7814 | BC039414 | | Homo sapiens, clone IMAGE: 5302158, mRNA |
| 1132 | B8234 | AF070632 | | Clone 24405 mRNA sequence |

TABLE 5-continued

Down-regulated gene in bladder cancer

| BLC assignment | LMMID | ACCESSION | GENE | TITLE |
|---|---|---|---|---|
| 1133 | B8924 | AI357442 | SPARC | Secreted protein, acidic, cysteine-rich (osteonectin) |
| 1134 | A0038N | W73825 | TCF21 | Transcription factor 21 |
| 1135 | B3584 | AA917358 | | Transcribed locus |
| 1136 | B6250 | N30317 | LOC91526 | Hypothetical protein DKFZp434D2328 |
| 1137 | B7018 | R00826 | RAB3GAP | RAB3 GTPase-ACTIVATING PROTEIN |
| 1138 | B7435 | AK093246 | RPL13 | Ribosomal protein L13 |
| 1139 | B8344 | AB019210 | PGM2L1 | Phosphoglucomutase 2-like 1 |
| 1140 | B8850 | Z30256 | KIF1B | Kinesin family member 1B |
| 1141 | A2087N | BC012617 | ACTG2 | Actin, gamma 2, smooth muscle, enteric |
| 1142 | A4459N | BC013188 | TPST1 | Tyrosylprotein sulfotransferase 1 |
| 1143 | A7346N | N70296 | ANK3 | Ankyrin 3, node of Ranvier (ankyrin G) |
| 1144 | B3695 | BC017312 | MGC3047 | Hypothetical protein MGC3047 |
| 1145 | B3889 | BC013042 | MGC7036 | Hypothetical protein MGC7036 |
| 1146 | B4032 | AF545571 | SULF1 | Sulfatase 1 |
| 1147 | B5618 | AA502764 | RKHD1 | Ring finger and KH domain containing 1 |
| 1148 | B6405 | AA045332 | ME1 | Malic enzyme 1, NADP(+)-dependent, cytosolic |
| 1149 | B6035N | AF205632 | SH3BP3 | SH3-domain binding protein 3 |
| 1150 | B7441 | AA994299 | C16orf30 | Chromosome 16 open reading frame 30 |
| 1151 | B7274 | BM671249 | BAZ2A | Bromodomain adjacent to zinc finger domain, 2A |
| 1152 | B8865 | N66810 | | *Homo sapiens*, clone IMAGE: 4690669, mRNA |
| 1153 | B8404 | AF173389 | EEA1 | Early endosome antigen 1, 162 kD |
| 1154 | A4381N | U81523 | EBAF | Endometrial bleeding associated factor (left-right determination, factor A; transforming growth factor beta superfamily) |
| 1155 | A6909 | NM_018667 | SMPD3 | Sphingomyelin phosphodiesterase 3, neutral membrane (neutral sphingomyelinase II) |
| 1156 | A7232N | BX648421 | IGJ | Immunoglobulin J polypeptide, linker protein for immunoglobulin alpha and mu polypeptides |
| 1157 | B4665N | AA045171 | | |
| 1158 | B4638 | BX648635 | LIFR | Leukemia inhibitory factor receptor |
| 1159 | B5081N | AL832416 | C9orf13 | Chromosome 9 open reading frame 13 |
| 1160 | B5460 | BX537492 | FLJ23091 | Putative NFkB activating protein 373 |
| 1161 | B5427 | CR600360 | DNAJA2 | DnaJ (Hsp40) homolog, subfamily A, member 2 |
| 1162 | B5292 | BQ574739 | SMAP | Small acidic protein |
| 1163 | B7193N | BX109986 | | Transcribed locus |
| 1164 | B7424 | CA503060 | FLJ21069 | Hypothetical protein FLJ21069 |
| 1165 | B8040 | AJ420553 | ID4 | Inhibitor of DNA binding 4, dominant negative helix-loop-helix protein |
| 1166 | B8354 | NM_003387 | WASPIP | Wiskott-Aldrich syndrome protein interacting protein |
| 1167 | B8628 | AA658236 | HECTD2 | HECT domain containing 2 |
| 1168 | B9368 | AF504647 | | Cilia-associated protein (CYS1) |
| 1169 | B9749 | BQ575959 | HTRA3 | Serine protease HTRA3 |
| 1170 | A1397N | AK091875 | PPP2CB | Protein phosphatase 2 (formerly 2A), catalytic subunit, beta isoform |
| 1171 | A1485N | BC050283 | WASF3 | WAS protein family, member 3 |
| 1172 | A6126N | H11384 | CDC42EP3 | CDC42 effector protein (Rho GTPase binding) 3 |
| 1173 | B4330 | AB020637 | KIAA0830 | KIAA0830 protein |
| 1174 | B4491 | BX537444 | ATP2B4 | ATPase, Ca++ transporting, plasma membrane 4 |
| 1175 | B5815 | T72611 | | Transcribed locus |
| 1176 | B6819N | AL542335 | EEF1A1 | Eukaryotic translation elongation factor 1 alpha 1 |
| 1177 | B7058 | BX094037 | | Transcribed locus |
| 1178 | B8051 | AK094950 | | CDNA FLJ37631 fis, clone BRCOC2015944 |

TABLE 5-continued

Down-regulated gene in bladder cancer

| BLC assignment | LMMID | ACCESSION | GENE | TITLE |
|---|---|---|---|---|
| 1179 | B8866 | CR749586 | FLJ11088 | GGA binding partner |
| 1180 | B8599 | R37079 | PDZRN4 | PDZ domain containing RING finger 4 |
| 1181 | B9502 | AL050227 | PTGER3 | Prostaglandin E receptor 3 (subtype EP3) |
| 1182 | C0213 | BX110085 | | Transcribed locus |
| 1183 | C0226 | AK074924 | KIAA0853 | KIAA0853 |
| 1184 | C3653 | BC066956 | VIM | Vimentin |
| 1185 | C4908 | BX118828 | | Transcribed locus |
| 1186 | C6830 | R49122 | FLJ14800 | Hypothetical protein FLJ14800 |
| 1187 | C7111 | T15991 | | Transcribed locus |
| 1188 | C8074 | X79204 | ATXN1 | Ataxin 1 |
| 1189 | C9718 | W94051 | DTNA | Dystrobrevin, alpha |
| 1190 | C0685 | H27764 | SLC18A2 | Solute carrier family 18 (vesicular monoamine), member 2 |
| 1191 | C3767 | BC018128 | FGFR1 | Fibroblast growth factor receptor 1 (fms-related tyrosine kinase 2, Pfeiffer syndrome) |
| 1192 | C4060 | N35250 | | |
| 1193 | C7466 | NM_003480 | MFAP5 | Microfibrillar associated protein 5 |
| 1194 | C8953 | AL136678 | DEPDC6 | DEP domain containing 6 |
| 1195 | C9351 | AA195210 | DKFZP761M1511 | Hypothetical protein DKFZP761M1511 |
| 1196 | C3791 | BU170801 | PAI-RBP1 | PAI-1 mRNA-binding protein |
| 1197 | C4729 | N70455 | FBXO31 | F-box protein 31 |
| 1198 | C6623 | AA102332 | MLSTD1 | Male sterility domain containing 1 |
| 1199 | C8039 | Z22970 | CD163 | CD163 antigen |
| 1200 | C8442 | AB011151 | ZCCHC14 | Zinc finger, CCHC domain containing 14 |
| 1201 | C8606 | BC063430 | CPXM | Carboxypeptidase X (M14 family) |
| 1202 | C9730 | BQ448187 | | Transcribed locus |
| 1203 | C0791 | BC051340 | CD164L1 | CD164 sialomucin-like 1 |
| 1204 | C0830 | AA012832 | IRS1 | Insulin receptor substrate 1 |
| 1205 | C3778 | NM_003617 | RGS5 | Regulator of G-protein signalling 5 |
| 1206 | C4735 | AL136805 | ZNF537 | Zinc finger protein 537 |
| 1207 | C4765 | CR626993 | | MRNA; cDNA DKFZp686N07104 (from clone DKFZp686N07104) |
| 1208 | C4743 | AL137554 | CDADC1 | Cytidine and dCMP deaminase domain containing 1 |
| 1209 | C6116 | W67536 | FLJ31204 | Hypothetical protein FLJ31204 |
| 1210 | C7126 | NM_020871 | LRCH2 | Leucine-rich repeats and calponin homology (CH) domain containing 2 |
| 1211 | C7172 | AF377960 | CTTNBP2 | Cortactin binding protein 2 |
| 1212 | C8260 | BM981111 | MEF2D | MADS box transcription enhancer factor 2, polypeptide D (myocyte enhancer factor 2D) |
| 1213 | C2020 | CA420307 | SF3B1 | Splicing factor 3b, subunit 1, 155 kDa |
| 1214 | C2324 | BQ182775 | ECRG4 | Esophageal cancer related gene 4 protein |
| 1215 | C3763 | AF480883 | PPAP2B | Phosphatidic acid phosphatase type 2B |
| 1216 | C4549 | N64370 | TMOD2 | Tropomodulin 2 (neuronal) |
| 1217 | C6059 | AK096344 | FLJ35220 | Hypothetical protein FLJ35220 |
| 1218 | C6234 | AI247176 | TARSH | Target of Nesh-SH3 |
| 1219 | C7503 | N90724 | IGSF4 | Immunoglobulin superfamily, member 4 |
| 1220 | C7652 | AA142913 | ARGBP2 | Arg/Abl-interacting protein ArgBP2 |
| 1221 | C7256 | NM_021963 | NAP1L2 | Nucleosome assembly protein 1-like 2 |
| 1222 | C8088 | D87465 | SPOCK2 | Sparc/osteonectin, cwcv and kazal-like domains proteoglycan (testican) 2 |
| 1223 | C8286 | AY369207 | RBPMS2 | RNA-binding protein with multiple splicing 2 |
| 1224 | C8659 | BF673156 | MYL1 | Myosin, light polypeptide 1, alkali; skeletal, fast |
| 1225 | D0785 | AA936292 | | Transcribed locus |
| 1226 | C0678 | AI796508 | | Transcribed locus |
| 1227 | C0274 | NM_005157 | ABL1 | V-abl Abelson murine leukemia viral oncogene homolog 1 |
| 1228 | C4258 | AK092045 | C3orf6 | Chromosome 3 open reading frame 6 |
| 1229 | C6974 | AK124567 | HIBCH | 3-hydroxyisobutyryl-Coenzyme A hydrolase |
| 1230 | C7876 | AW023627 | | Transcribed locus |
| 1231 | C8066 | NM_014279 | OLFM1 | Olfactomedin 1 |

TABLE 5-continued

Down-regulated gene in bladder cancer

| BLC assignment | LMMID | ACCESSION | GENE | TITLE |
|---|---|---|---|---|
| 1232 | C9569 | H18926 | | Full-length cDNA clone CS0DK010YA20 of HeLa cells Cot 25-normalized of *Homo sapiens* (human) |
| 1233 | D1322 | BX647857 | ASB5 | Ankyrin repeat and SOCS box-containing 5 |
| 1234 | C0219 | AJ303079 | PALM2-AKAP2 | PALM2-AKAP2 protein |
| 1235 | C1520 | BC014640 | COL14A1 | Collagen, type XIV, alpha 1 (undulin) |
| 1236 | C2029 | H14510 | LOC286191 | Hypothetical protein LOC286191 |
| 1237 | C7654 | BC060868 | BMPER | BMP-binding endothelial regulator precursor protein |
| 1238 | C8228 | AK124641 | CXCL12 | Chemokine (C—X—C motif) ligand 12 (stromal cell-derived factor 1) |
| 1239 | C8438 | NM_002827 | PTPN1 | Protein tyrosine phosphatase, non-receptor type 1 |
| 1240 | C8274 | AK056736 | MBTPS2 | Membrane-bound transcription factor protease, site 2 |
| 1241 | D0735 | AA740582 | | Transcribed locus |
| 1242 | D1185 | AA451886 | CYP1B1 | Cytochrome P450, family 1, subfamily B, polypeptide 1 |
| 1243 | D1161 | BX537988 | ST7L | Suppression of tumorigenicity 7 like |
| 1244 | C0787 | AL832207 | PLEKHH2 | Pleckstrin homology domain containing, family H (with MyTH4 domain) member 2 |
| 1245 | C3772 | U70063 | ASAH1 | N-acylsphingosine amidohydrolase (acid ceramidase) 1 |
| 1246 | C3780 | AK055619 | GNAQ | Guanine nucleotide binding protein (G protein), q polypeptide |
| 1247 | C4232 | AI668702 | | Transcribed locus |
| 1248 | C4884 | AA036952 | Gup1 | GRINL1A complex upstream protein |
| 1249 | C6084 | W60379 | | Transcribed locus |
| 1250 | C7138 | BM678096 | TNA | Tetranectin (plasminogen binding protein) |
| 1251 | C7919 | X79981 | CDH5 | Cadherin 5, type 2, VE-cadherin (vascular epithelium) |
| 1252 | C8117 | BE905862 | SPAG9 | Sperm associated antigen 9 |
| 1253 | C9367 | AL558594 | PRKAG2 | Protein kinase, AMP-activated, gamma 2 non-catalytic subunit |
| 1254 | C1466 | H03229 | GAB1 | GRB2-associated binding protein 1 |
| 1255 | C4732 | CR595618 | BRMS1L | Breast cancer metastasis-suppressor 1-like |
| 1256 | C5118 | AL137572 | C1orf24 | Chromosome 1 open reading frame 24 |
| 1257 | C6476 | AA001390 | KIAA1463 | KIAA1463 protein |
| 1258 | C8044 | NM_004430 | EGR3 | Early growth response 3 |
| 1259 | C7793 | BX648935 | TBL1XR1 | Transducin (beta)-like 1X-linked receptor 1 |
| 1260 | C8090 | NM_032088 | PCDHGC3 | Protocadherin gamma subfamily C, 3 |
| 1261 | C4066 | AF303058 | NP25 | Neuronal protein |
| 1262 | C3648 | AK023450 | ANTXR2 | Anthrax toxin receptor 2 |
| 1263 | C8253 | BC017021 | MEOX2 | Mesenchyme homeo box 2 (growth arrest-specific homeo box) |
| 1264 | C8456 | AB032954 | KIAA1128 | KIAA1128 |
| 1265 | C7882 | NM_013261 | PPARGC1A | Peroxisome proliferative activated receptor, gamma, coactivator 1, alpha |
| 1266 | C8636 | CR607734 | DKK3 | Dickkopf homolog 3 (*Xenopus laevis*) |
| 1267 | C0671 | NM_007197 | FZD10 | Frizzled homolog 10 (*Drosophila*) |
| 1268 | C1984 | W92438 | | Hypothetical gene supported by BX647608 |
| 1269 | C2154 | AF007144 | DIO2 | Deiodinase, iodothyronine, type II |
| 1270 | C4105 | XM_376503 | ENPP4 | Ectonucleotide pyrophosphatase/phosphodiesterase 4 (putative function) |
| 1271 | C4755 | Z30137 | LDB3 | LIM domain binding 3 |
| 1272 | C4873 | BX537721 | CMYA5 | Cardiomyopathy associated 5 |
| 1273 | C7657 | AI219521 | AP1G1 | Adaptor-related protein complex 1, gamma 1 subunit |
| 1274 | C8046 | NM_002864 | PZP | Pregnancy-zone protein |
| 1275 | C9503 | AA621124 | LOC338773 | Hypothetical protein LOC338773 |
| 1276 | C3775 | BQ003524 | KCTD12 | Potassium channel tetramerisation domain containing 12 |
| 1277 | C4082 | BC041798 | POLK | Polymerase (DNA directed) kappa |

TABLE 5-continued

Down-regulated gene in bladder cancer

| BLC assignment | LMMID | ACCESSION | GENE | TITLE |
|---|---|---|---|---|
| 1278 | C4778 | N67331 | SEC63 | SEC63-like (S. cerevisiae) |
| 1279 | C6278 | BC039245 | SART2 | Squamous cell carcinoma antigen recognized by T cells 2 |
| 1280 | C6460 | W96022 | | Transcribed locus |
| 1281 | C8119 | NM_002775 | PRSS11 | Protease, serine, 11 (IGF binding) |
| 1282 | C9118 | BX114286 | CD99 | CD99 antigen |
| 1283 | C8687 | NM_006166 | NFYB | Nuclear transcription factor Y, beta |
| 1284 | C9565 | AK129819 | LHFP | Lipoma HMGIC fusion partner |
| 1285 | C0284 | AK123940 | MGC34648 | Hypothetical protein MGC34648 |
| 1286 | C0728 | AK095472 | DKFZp762C1112 | Hypothetical protein DKFZp762C1112 |
| 1287 | B9925 | BC039242 | TM4SF10 | Transmembrane 4 superfamily member 10 |
| 1288 | C0579 | BX648468 | DKFZP564J0863 | DKFZP564J0863 protein |
| 1289 | C1100 | BG257592 | FAIM | Fas apoptotic inhibitory molecule |
| 1290 | C7731 | AF245505 | DKFZp564I1922 | Adlican |
| 1291 | C7977 | AL833463 | LOC283658 | Hypothetical protein LOC283658 |
| 1292 | C7992 | AL833291 | CMYA3 | Cardiomyopathy associated 3 |
| 1293 | C9580 | AK057189 | NOX4 | NADPH oxidase 4 |
| 1294 | C9221 | CR613361 | RNF24 | Ring finger protein 24 |
| 1295 | B9888 | AB023155 | NAV3 | Neuron navigator 3 |
| 1296 | C4526 | N63752 | MPHOSPH1 | M-phase phosphoprotein 1 |
| 1297 | C4850 | BC040502 | BVES | Blood vessel epicardial substance |
| 1298 | C8203 | NM_012180 | FBXO8 | F-box protein 8 |
| 1299 | D1419 | NM_018328 | MBD5 | Methyl-CpG binding domain protein 5 |
| 1300 | C0544 | BX640884 | C14orf24 | Chromosome 14 open reading frame 24 |
| 1301 | C1403 | N49231 | KIAA1345 | KIAA1345 protein |
| 1302 | C6728 | AK000337 | GFOD1 | Glucose-fructose oxidoreductase domain containing 1 |
| 1303 | C7585 | AK095271 | LOC128977 | Hypothetical protein LOC128977 |
| 1304 | C7687 | CB119523 | IL6ST | Interleukin 6 signal transducer (gp130, oncostatin M receptor) |
| 1305 | C9008 | D82786 | TA-PP2C | T-cell activation protein phosphatase 2C |
| 1306 | C0893 | BC052210 | GARP | Glycoprotein A repetitions predominant |
| 1307 | C2259 | CA436350 | | Transcribed locus |
| 1308 | C3895 | BC035090 | KPNA3 | Karyopherin alpha 3 (importin alpha 4) |
| 1309 | C4350 | BX089823 | FRMD3 | FERM domain containing 3 |
| 1310 | C7057 | H22566 | DACH1 | Dachshund homolog 1 (Drosophila) |
| 1311 | C7574 | AB028993 | NLGN1 | Neuroligin 1 |
| 1312 | C0371 | CA431042 | | Transcribed locus |
| 1313 | C0844 | BC009951 | COLEC11 | Collectin sub-family member 11 |
| 1314 | C1091 | AI263903 | SIAT10 | Sialyltransferase 10 (alpha-2,3-sialyltransferase VI) |
| 1315 | C0922 | AF378757 | PLXDC2 | Plexin domain containing 2 |
| 1316 | C4175 | BM683457 | EPHA7 | EphA7 |
| 1317 | C4681 | XM_071793 | C14orf28 | Chromosome 14 open reading frame 28 |
| 1318 | C6523 | NM_198968 | DZIP1 | DAZ interacting protein 1 |
| 1319 | C6706 | BC033034 | DIXDC1 | DIX domain containing 1 |
| 1320 | C6572 | NM_005197 | CHES1 | Checkpoint suppressor 1 |
| 1321 | C8146 | BF697545 | MGP | Matrix Gla protein |
| 1322 | C7994 | NM_016150 | ASB2 | Ankyrin repeat and SOCS box-containing 2 |
| 1323 | C8744 | NM_152309 | PIK3AP1 | Phosphoinositide-3-kinase adaptor protein 1 |
| 1324 | D0018 | BX091065 | | Transcribed locus |
| 1325 | D1273 | AJ001015 | RAMP2 | Receptor (calcitonin) activity modifying protein 2 |
| 1326 | B9880 | CR749402 | NFASC | Neurofascin |
| 1327 | C2088 | AF161423 | COMMD10 | COMM domain containing 10 |
| 1328 | C4351 | CN430728 | | Transcribed locus |
| 1329 | C6723 | AA028127 | CD209 | CD209 antigen |
| 1330 | C7059 | XM_059702 | FLJ36748 | Hypothetical protein FLJ36748 |
| 1331 | C7375 | CA312122 | PSMC2 | Proteasome (prosome, macropain) 26S subunit, ATPase, 2 |
| 1332 | D0007 | CR596214 | HNRPA0 | Heterogeneous nuclear ribonucleoprotein A0 |
| 1333 | C0318 | M16451 | CKB | Creatine kinase, brain |
| 1334 | C0912 | BQ071673 | RAMP1 | Receptor (calcitonin) activity modifying protein 1 |
| 1335 | C1412 | BX648776 | LOC253827 | Hypothetical protein LOC253827 |

TABLE 5-continued

Down-regulated gene in bladder cancer

| BLC assignment | LMMID | ACCESSION | GENE | TITLE |
|---|---|---|---|---|
| 1336 | C1603 | BQ446275 | HBD | Hemoglobin, delta |
| 1337 | C4170 | AB007884 | ARHGEF9 | Cdc42 guanine nucleotide exchange factor (GEF) 9 |
| 1338 | C4318 | AI275068 | | Transcribed locus |
| 1339 | C5860 | BU683028 | | CDNA FLJ10151 fis, clone HEMBA1003402 |
| 1340 | C5950 | CF146489 | NKX3-1 | NK3 transcription factor related, locus 1 (*Drosophila*) |
| 1341 | C6708 | BQ003734 | | Mesenchymal stem cell protein DSC96 |
| 1342 | C7078 | AK130067 | ADAMTS15 | A disintegrin-like and metalloprotease (reprolysin type) with thrombospondin type 1 motif, 15 |
| 1343 | C9587 | H17302 | LRRC3B | Leucine rich repeat containing 3B |
| 1344 | D1274 | BF435815 | | MRNA; cDNA DKFZp564O0862 (from clone DKFZp564O0862) |
| 1345 | B9884 | BX641069 | FLJ20481 | Hypothetical protein FLJ20481 |
| 1346 | C1622 | AK074184 | FLJ34922 | Hypothetical protein FLJ34922 |
| 1347 | C1902 | CR591938 | WDR33 | WD repeat domain 33 |
| 1348 | C4861 | BX647931 | | Similar to ENSANGP00000004103 |
| 1349 | C6042 | H25761 | | |
| 1350 | C6718 | AK124339 | GJA7 | Gap junction protein, alpha 7, 45 kDa (connexin 45) |
| 1351 | C7105 | R50993 | | |
| 1352 | C7439 | AA102033 | BMPR2 | Bone morphogenetic protein receptor, type II (serine/threonine kinase) |
| 1353 | D1423 | AK055040 | | MRNA; cDNA DKFZp313C0240 (from clone DKFZp313C0240) |
| 1354 | C0357 | BC035779 | SLC9A9 | Solute carrier family 9 (sodium/hydrogen exchanger), isoform 9 |
| 1355 | C1604 | AA044381 | | |
| 1356 | C1422 | AA095034 | GK001 | GK001 protein |
| 1357 | C2068 | XM_375527 | LOC339290 | Hypothetical protein LOC339290 |
| 1358 | C3978 | BC030112 | HIPK3 | Homeodomain interacting protein kinase 3 |
| 1359 | C4287 | CR621395 | BAG2 | BCL2-associated athanogene 2 |
| 1360 | C6143 | NM_001496 | GFRA3 | GDNF family receptor alpha 3 |
| 1361 | C5014 | AI185804 | FN1 | Fibronectin 1 |
| 1362 | C6748 | AF487514 | GEFT | RAC/CDC42 exchange factor |
| 1363 | C7089 | H14263 | GAS1 | Growth arrest-specific 1 |
| 1364 | C8384 | X98834 | SALL2 | Sal-like 2 (*Drosophila*) |
| 1365 | C7744 | AF196185 | PARD3 | Par-3 partitioning defective 3 homolog (*C. elegans*) |
| 1366 | D0657 | AB058780 | ST6GalII | Beta-galactoside alpha-2,6-sialyltransferase II |
| 1367 | D0995 | BC040983 | PCDH7 | BH-protocadherin (brain-heart) |
| 1368 | C0335 | CR590615 | ACTA2 | Actin, alpha 2, smooth muscle, aorta |
| 1369 | C2131 | BQ014434 | PIAS1 | Protein inhibitor of activated STAT, 1 |
| 1370 | C3746 | NM_199511 | URB | Steroid sensitive gene 1 |
| 1371 | C4184 | NM_020482 | FHL5 | Four and a half LIM domains 5 |
| 1372 | C4700 | AA934589 | MGC45780 | Hypothetical protein MGC45780 |
| 1373 | C7603 | AA292234 | | CDNA FLJ14942 fis, A-PLACE1011185 |
| 1374 | D1435 | T15727 | DNCI1 | Dynein, cytoplasmic, intermediate polypeptide 1 |
| 1375 | C2085 | AA400893 | PDE1A | Phosphodiesterase 1A, calmodulin-dependent |
| 1376 | C4971 | BC000234 | NNMT | Nicotinamide N-methyltransferase |
| 1377 | C7050 | AA084479 | DNAJC9 | DnaJ (Hsp40) homolog, subfamily C, member 9 |
| 1378 | C9868 | AL136646 | ARHGAP24 | Rho GTPase activating protein 24 |
| 1379 | B9970 | AB014540 | SWAP70 | SWAP-70 protein |
| 1380 | C4998 | CR591834 | DSTN | Destrin (actin depolymerizing factor) |
| 1381 | C5058 | N62595 | KBTBD7 | Kelch repeat and BTB (POZ) domain containing 7 |
| 1382 | C6217 | NM_001448 | GPC4 | Glypican 4 |
| 1383 | C8023 | M81141 | HLA-DQB1 | Major histocompatibility complex, class II, DQ beta 1 |
| 1384 | D0533 | AF180681 | ARHGEF12 | Rho guanine nucleotide exchange factor (GEF) 12 |

TABLE 5-continued

Down-regulated gene in bladder cancer

| BLC assignment | LMMID | ACCESSION | GENE | TITLE |
|---|---|---|---|---|
| 1385 | D2960 | NM_033281 | MRPS36 | Mitochondrial ribosomal protein S36 |
| 1386 | D4169 | AK128510 | GOLPH3 | Golgi phosphoprotein 3 (coat-protein) |
| 1387 | E0537 | BX647115 | DPYSL2 | Dihydropyrimidinase-like 2 |
| 1388 | E0690 | AI743134 | SERPINE2 | Serine (or cysteine) proteinase inhibitor, clade E (nexin, plasminogen activator inhibitor type 1), member 2 |
| 1389 | D4142 | AK091311 | JAZF1 | Juxtaposed with another zinc finger gene 1 |
| 1390 | D4211 | BC069830 | LETM2 | Leucine zipper-EF-hand containing transmembrane protein 2 |
| 1391 | D4328 | AK021601 | FLJ11539 | Hypothetical protein FLJ11539 |
| 1392 | E1219 | AB011175 | TBC1D4 | TBC1 domain family, member 4 |
| 1393 | E0783 | NM_139033 | MAPK7 | Mitogen-activated protein kinase 7 |
| 1394 | D3166 | AK097340 | RPESP | RPE-spondin |
| 1395 | D3356 | NM_014829 | DDX46 | DEAD (Asp-Glu-Ala-Asp) box polypeptide 46 |
| 1396 | D7420 | AK124757 | SHPRH | SNF2 histone linker PHD RING helicase |
| 1397 | D6809 | AA927082 | | Transcribed locus |
| 1398 | D4165 | AK123831 | LOC149832 | Hypothetical protein LOC149832 |
| 1399 | D4020 | AA858162 | C18orf4 | Chromosome 18 open reading frame 4 |
| 1400 | D8933 | BX538309 | MAMDC2 | MAM domain containing 2 |
| 1401 | E0644 | NM_000610 | CD44 | CD44 antigen (homing function and Indian blood group system) |
| 1402 | D4215 | AB096175 | SP5 | Sp5 transcription factor |
| 1403 | D5074 | AA044778 | | CDNA FLJ38215 fis, clone FCBBF2000291 |
| 1404 | D7205 | AI040887 | ARHGEF7 | Rho guanine nucleotide exchange factor (GEF) 7 |
| 1405 | D8143 | AK075059 | GLIS3 | GLIS family zinc finger 3 |
| 1406 | E1492 | AY326464 | TXNDC5 | Thioredoxin domain containing 5 |
| 1407 | D4128 | NM_173060 | CAST | Calpastatin |
| 1408 | D4739 | BC022957 | C9orf102 | Chromosome 9 open reading frame 102 |
| 1409 | E0358 | AK021543 | DNM3 | Dynamin 3 |
| 1410 | E1300 | BC040974 | PDE2A | Phosphodiesterase 2A, cGMP-stimulated |
| 1411 | D9372 | AI034385 | SORBS1 | Sorbin and SH3 domain containing 1 |
| 1412 | E0240 | NM_020433 | JPH2 | Junctophilin 2 |
| 1413 | E0721 | AW024176 | FBLN1 | Fibulin 1 |
| 1414 | D7305 | BX092512 | SCNN1A | Sodium channel, nonvoltage-gated 1 alpha |
| 1415 | E0139 | AL390147 | FAM20C | Family with sequence similarity 20, member C |
| 1416 | D1798 | AK074734 | FCGRT | Fc fragment of IgG, receptor, transporter, alpha |
| 1417 | D3702 | AL096748 | ARMC8 | Armadillo repeat containing 8 |
| 1418 | D4501 | CA447839 | FAM49A | Family with sequence similarity 49, member A |
| 1419 | D5553 | AA031882 | | Transcribed locus |
| 1420 | D9082 | NM_052954 | CYYR1 | Cysteine and tyrosine-rich 1 |
| 1421 | E0475 | CR627373 | EIF4EBP2 | Eukaryotic translation initiation factor 4E binding protein 2 |
| 1422 | D6213 | AK123531 | | CDNA FLJ41537 fis, clone BRTHA2017985 |
| 1423 | D9915 | BM463727 | MEIS4 | Meis1, myeloid ecotropic viral integration site 1 homolog 4 (mouse) |
| 1424 | E0985 | NM_001343 | DAB2 | Disabled homolog 2, mitogen-responsive phosphoprotein (*Drosophila*) |
| 1425 | D1810 | NM_002373 | MAP1A | Microtubule-associated protein 1A |
| 1426 | D4231 | C05897 | ARL5 | ADP-ribosylation factor-like 5 |
| 1427 | D8491 | NM_001122 | ADFP | Adipose differentiation-related protein |
| 1428 | D9934 | CA450275 | FREQ | Frequenin homolog (*Drosophila*) |
| 1429 | E0476 | AF000984 | DDX3Y | DEAD (Asp-Glu-Ala-Asp) box polypeptide 3, Y-linked |
| 1430 | E0733 | NM_004684 | SPARCL1 | SPARC-like 1 (mast9, hevin) |
| 1431 | E0861 | BX648282 | ATP2A2 | ATPase, Ca++ transporting, cardiac muscle, slow twitch 2 |
| 1432 | D1811 | AK128814 | | CDNA FLJ25106 fis, clone CBR01467 |
| 1433 | D4059 | BF512606 | | Transcribed locus |

TABLE 5-continued

Down-regulated gene in bladder cancer

| BLC assignment | LMMID | ACCESSION | GENE | TITLE |
|---|---|---|---|---|
| 1434 | D5243 | AK074301 | FAM8A1 | Family with sequence similarity 8, member A1 |
| 1435 | D6180 | AK096674 | C14orf32 | Chromosome 14 open reading frame 32 |
| 1436 | D7516 | AI074524 | DKFZp434H2111 | Hypothetical protein DKFZp434H2111 |
| 1437 | E0726 | AB023199 | WDR37 | WD repeat domain 37 |
| 1438 | E1622 | NM_001753 | CAV1 | Caveolin 1, caveolae protein, 22 kDa |
| 1439 | E1419 | AL833496 | TAF10 | TAF10 RNA polymerase II, TATA box binding protein (TBP)-associated factor, 30 kDa |
| 1440 | D7796 | CR613362 | ALDH6A1 | Aldehyde dehydrogenase 6 family, member A1 |
| 1441 | D8862 | NM_032105 | PPP1R12B | Protein phosphatase 1, regulatory (inhibitor) subunit 12B |
| 1442 | E0880 | AK000617 | LOC92912 | Hypothetical protein LOC92912 |
| 1443 | D5244 | BF510155 | GPR155 | G protein-coupled receptor 155 |
| 1444 | D7997 | AW152624 | AKAP13 | A kinase (PRKA) anchor protein 13 |
| 1445 | D8515 | CR591759 | LUM | Lumican |
| 1446 | E0237 | AI093257 | | Transcribed locus |
| 1447 | E0764 | AF087902 | TDE2 | Tumor differentially expressed 2 |
| 1448 | E0896 | BC045606 | NID | Nidogen (enactin) |
| 1449 | D1767 | BC014357 | CCND2 | Cyclin D2 |
| 1450 | D4996 | NM_001001927 | MTUS1 | Mitochondrial tumor suppressor 1 |
| 1451 | D9075 | AL832156 | CPEB1 | Cytoplasmic polyadenylation element binding protein 1 |
| 1452 | E0623 | AL162079 | SLC16A1 | Solute carrier family 16 (monocarboxylic acid transporters), member 1 |
| 1453 | D6606 | AI733562 | | Transcribed locus |
| 1454 | E0082 | AI082254 | | Transcribed locus |
| 1455 | E1421 | BC044777 | DJ971N18.2 | Hypothetical protein DJ971N18.2 |
| 1456 | D5395 | BX094351 | | Transcribed locus |
| 1457 | F0968 | AK025758 | NFATC2 | Nuclear factor of activated T-cells, cytoplasmic, calcineurin-dependent 2 |
| 1458 | F1046 | NM_014583 | LMCD1 | LIM and cysteine-rich domains 1 |
| 1459 | F1770 | AK025713 | DHX40 | DEAH (Asp-Glu-Ala-His) box polypeptide 40 |
| 1460 | F3132 | AL133095 | C14orf103 | Chromosome 14 open reading frame 103 |
| 1461 | F3574 | NM_016377 | AKAP7 | A kinase (PRKA) anchor protein 7 |
| 1462 | F3080 | NM_006633 | IQGAP2 | IQ motif containing GTPase activating protein 2 |
| 1463 | F9005 | D50406 | RECK | Reversion-inducing-cysteine-rich protein with kazal mtifs |
| 1464 | F2203 | AK024352 | EPHA3 | EphA3 |
| 1465 | A7714 | AB002351 | DMN | Desmuslin |
| 1466 | C6534 | AI057000 | | Transcribed locus |
| 1467 | F1119 | U27460 | UGP2 | UDP-glucose pyrophosphorylase 2 |
| 1468 | F1176 | AY368150 | KIAA1228 | KIAA1228 protein |
| 1469 | F5819 | BQ671518 | EEF2K | Similar to NAD(P) dependent steroid dehydrogenase-like |
| 1470 | F6592 | AY358353 | STK32B | Serine/threonine kinase 32B |
| 1471 | A6371 | BU681010 | | Full length insert cDNA clone YT94E02 |
| 1472 | F0018 | NM_000963 | PTGS2 | Prostaglandin-endoperoxide synthase 2 (prostaglandin G/H synthase and cyclooxygenase) |
| 1473 | C0081 | NM_182485 | CPEB2 | Cytoplasmic polyadenylation element binding protein 2 |
| 1474 | F3496 | AB023148 | KIAA0931 | KIAA0931 protein |
| 1475 | F4227 | AK001050 | C10orf118 | Chromosome 10 open reading frame 118 |
| 1476 | F8898 | BE841307 | HRMT1L1 | HMT1 hnRNP methyltransferase-like 1 (S. cerevisiae) |
| 1477 | F3184 | NM_033380 | COL4A5 | Collagen, type IV, alpha 5 (Alport syndrome) |
| 1478 | A1331N | NM_199072 | HIC | I-mfa domain-containing protein |
| 1479 | A2869 | AF054839 | TSPAN-2 | Tetraspan 2 |
| 1480 | B4350N | AF037364 | PNMA1 | Paraneoplastic antigen MA1 |
| 1481 | F1120 | L13463 | RGS2 | Regulator of G-protein signalling 2, 24 kDa |
| 1482 | F4886 | AK026403 | TLN2 | Talin 2 |
| 1483 | F6054 | AA905353 | NCBP1 | Nuclear cap binding protein subunit 1, 80 kDa |

TABLE 5-continued

Down-regulated gene in bladder cancer

| BLC assignment | LMMID | ACCESSION | GENE | TITLE |
|---|---|---|---|---|
| 1484 | F6595 | AW938336 |  | CDNA FLJ26188 fis, clone ADG04821 |
| 1485 | F6738 | AK022173 | LAF4 | Lymphoid nuclear protein related to AF4 |
| 1486 | B2123 | NM_005912 | MC4R | Melanocortin 4 receptor |
| 1487 | C8826 | AI091545 | SYNCRIP | Synaptotagmin binding, cytoplasmic RNA interacting protein |
| 1488 | F0480 | NM_015635 | DKFZP434C212 | DKFZP434C212 protein |
| 1489 | F2307 | AF010236 | SGCD | Sarcoglycan, delta (35 kDa dystrophin-associated glycoprotein) |
| 1490 | F2424 | AF111783 | MYH4 | Myosin, heavy polypeptide 4, skeletal muscle |
| 1491 | F4281 | AF199023 | PLSCR4 | Phospholipid scramblase 4 |
| 1492 | F4410 | AK026500 | HPCAL1 | Hippocalcin-like 1 |
| 1493 | F7115 | AF230201 | C20orf17 | Chromosome 20 open reading frame 17 |
| 1494 | F0344 | AL049957 | CD59 | CD59 antigen p18-20 (antigen identified by monoclonal antibodies 16.3A5, EJ16, EJ30, EL32 and G344) |
| 1495 | A7732 | BC017984 | ARG99 | ARG99 protein |
| 1496 | A3113 | M60445 | HDC | Histidine decarboxylase |
| 1497 | B8326 | AK125533 | BNIP2 | BCL2/adenovirus E1B 19 kDa interacting protein 2 |
| 1498 | B7331 | H45412 | EHD2 | EH-domain containing 2 |
| 1499 | F0196 | AL050224 | PTRF | Polymerase I and transcript release factor |
| 1500 | F0299 | NM_145693 | LPIN1 | Lipin 1 |
| 1501 | F0211 | BC032379 | TMEM18 | Transmembrane protein 18 |
| 1502 | F0307 | D86425 | NID2 | Nidogen 2 (osteonidogen) |
| 1503 | F3849 | AF302502 | PELI2 | Pellino homolog 2 (Drosophila) |
| 1504 | F5852 | AL137573 |  |  |
| 1505 | F9522 | AB011141 | ZFHX1B | Zinc finger homeobox 1b |
| 1506 | A0029N | BC063856 | SPRY1 | Sprouty homolog 1, antagonist of FGF signaling (Drosophila) |
| 1507 | B6193N | NM_030806 | C1orf21 | Chromosome 1 open reading frame 21 |
| 1508 | C9234 | AK093732 |  | CDNA FLJ36413 fis, clone THYMU2010816 |
| 1509 | F0121 | AF089854 | TU3A | TU3A protein |
| 1510 | F0862 | AK023375 |  | CDNA FLJ13313 fis, clone OVARC1001489 |
| 1511 | F1093 | AY029191 | ASPN | Asporin (LRR class 1) |
| 1512 | F3501 | AK021708 | PDZRN3 | PDZ domain containing RING finger 3 |
| 1513 | F8152 | AI022632 | RAB7 | RAB7, member RAS oncogene family |
| 1514 | A3817N | AB000114 | OMD | Osteomodulin |
| 1515 | B3754 | BC011561 | HEPH | Hephaestin |
| 1516 | C6614 | AK074076 | USP47 | Ubiquitin specific protease 47 |
| 1517 | F0343 | AK025548 | TLOC1 | Translocation protein 1 |
| 1518 | F0615 | NM_007173 | PRSS23 | Protease, serine, 23 |
| 1519 | F2076 | AL162032 | GPR133 | G protein-coupled receptor 133 |
| 1520 | F3313 | AK025164 | FLJ21511 | Hypothetical protein FLJ21511 |
| 1521 | A6689 | BU741863 | SPOCK | Sparc/osteonectin, cwcv and kazal-like domains proteoglycan (testican) |
| 1522 | B6462 | NM_032515 | BOK | BCL2-related ovarian killer |
| 1523 | C9237 | XM_211958 |  |  |
| 1524 | C0484 | NM_005472 | KCNE3 | Potassium voltage-gated channel, Isk-related family, member 3 |
| 1525 | F0482 | AK000008 | BHMT2 | Betaine-homocysteine methyltransferase 2 |
| 1526 | F0528 | AK025661 | LIMS1 | LIM and senescent cell antigen-like domains 1 |
| 1527 | F0920 | AF098269 | PCOLCE2 | Procollagen C-endopeptidase enhancer 2 |
| 1528 | F2225 | AF188700 | AFAP | Hypothetical protein LOC254848 |
| 1529 | F1525 | M24736 | SELE | Selectin E (endothelial adhesion molecule 1) |
| 1530 | F2310 | AB002367 | DCAMKL1 | Doublecortin and CaM kinase-like 1 |
| 1531 | F3502 | X05409 | ALDH2 | Aldehyde dehydrogenase 2 family (mitochondrial) |
| 1532 | F5279 | L76566 | HLA-DRB6 | Major histocompatibility complex, class II, DR beta 6 (pseudogene) |

TABLE 5-continued

Down-regulated gene in bladder cancer

| BLC assignment | LMMID | ACCESSION | GENE | TITLE |
|---|---|---|---|---|
| 1533 | F6175 | AV700633 | FLJ10404 | Hypothetical protein FLJ10404 |
| 1534 | F6365 | AL080114 | C10orf72 | Chromosome 10 open reading frame 72 |
| 1535 | F3573 | NM_172171 | CAMK2G | Calcium/calmodulin-dependent protein kinase (CaM kinase) II gamma |
| 1536 | D8979 | AA740585 | | |
| 1537 | F1289 | CR623543 | SC4MOL | Sterol-C4-methyl oxidase-like |
| 1538 | F1221 | AL109700 | | CDNA FLJ37610 fis, clone BRCOC2011398 |
| 1539 | F3457 | AB020630 | PPP1R16B | Protein phosphatase 1, regulatory (inhibitor) subunit 16B |
| 1540 | F6060 | AK023814 | FLJ41603 | FLJ41603 protein |
| 1541 | A1022N | M98399 | CD36 | CD36 antigen (collagen type I receptor, thrombospondin receptor) |
| 1542 | B6200N | M79123 | NAP1L5 | Nucleosome assembly protein 1-like 5 |
| 1543 | F0927 | AK021823 | TRIM44 | Tripartite motif-containing 44 |
| 1544 | A1403 | J05401 | CKMT2 | Creatine kinase, mitochondrial 2 (sarcomeric) |
| 1545 | B4088N | NM_000311 | PRNP | Prion protein (p27-30) (Creutzfeld-Jakob disease, Gerstmann-Strausler-Scheinker syndrome, fatal familial insomnia) |
| 1546 | F0304 | NM_002510 | GPNMB | Glycoprotein (transmembrane) nmb |
| 1547 | F1405 | AF131837 | SIAT7E | Sialyltransferase 7 ((alpha-N-acetylneuraminyl-2,3-beta-galactosyl-1,3)-N-acetylgalactosaminide alpha-2,6-sialyltransferase) E |
| 1548 | F1225 | AF118108 | XLKD1 | Extracellular link domain containing 1 |
| 1549 | F4131 | AF389429 | SEMA6D | Sema domain, transmembrane domain (TM), and cytoplasmic domain, (semaphorin) 6D |
| 1550 | C8476 | R59552 | CHRDL1 | Chordin-like 1 |
| 1551 | C1827 | BC008703 | TCEAL3 | Transcription elongation factor A (SII)-like 3 |
| 1552 | D6878 | AI002365 | PDGFRB | Platelet-derived growth factor receptor, beta polypeptide |
| 1553 | D7732 | CB242274 | | Transcribed locus |
| 1554 | F2379 | AB002365 | KIAA0367 | KIAA0367 |
| 1555 | F1446 | AJ277587 | SPIRE1 | Spire homolog 1 (*Drosophila*) |
| 1556 | F3692 | NM_004673 | ANGPTL1 | Angiopoietin-like 1 |
| 1557 | A1101N | NM_022977 | ACSL4 | Acyl-CoA synthetase long-chain family member 4 |
| 1558 | B7430N | AA522674 | LIMS2 | LIM and senescent cell antigen-like domains 2 |
| 1559 | B7571N | BU619137 | TGFBR3 | Transforming growth factor, beta receptor III (betaglycan, 300 kDa) |
| 1560 | F1143 | AF070543 | ODZ2 | Odz, odd Oz/ten-m homolog 2 (*Drosophila*) |
| 1561 | F1241 | AF114263 | HH114 | Hypothetical protein HH114 |
| 1562 | F2686 | CR616854 | EVI2B | Ecotropic viral integration site 2B |
| 1563 | F2462 | NM_182734 | PLCB1 | Phospholipase C, beta 1 (phosphoinositide-specific) |
| 1564 | F2715 | BC035776 | CILP | Cartilage intermediate layer protein, nucleotide pyrophosphohydrolase |
| 1565 | F4824 | U82319 | YDD19 | YDD19 protein |
| 1566 | A0203N | NM_000043 | TNFRSF6 | Tumor necrosis factor receptor superfamily, member 6 |
| 1567 | A5933 | XM_059689 | | Similar to CG4502-PA |
| 1568 | C0524 | BM724780 | | Transcribed locus, weakly similar to XP_375099.1 hypothetical protein LOC283585 [*Homo sapiens*] |
| 1569 | C8150 | NM_014335 | CRI1 | CREBBP/EP300 inhibitor 1 |
| 1570 | C9677 | AL832661 | LOC143381 | Hypothetical protein LOC143381 |
| 1571 | E2113 | BC005248 | EIE1AY | Eukaryotic translation initiation factor 1A, Y-linked |
| 1572 | F0821 | AL050030 | | |
| 1573 | F2190 | AK021985 | FBXL7 | F-box and leucine-rich repeat protein 7 |
| 1574 | F1447 | NM_014629 | ARHGEF10 | Rho guanine nucleotide exchange factor (GEF) 10 |
| 1575 | F2205 | AF052181 | EPIM | Epimorphin |
| 1576 | F0092 | AK001789 | SMUG1 | Single-strand selective monofunctional uracil DNA glycosylase |

TABLE 5-continued

Down-regulated gene in bladder cancer

| BLC assignment | LMMID | ACCESSION | GENE | TITLE |
|---|---|---|---|---|
| 1577 | A3258 | U19487 | PTGER2 | Prostaglandin E receptor 2 (subtype EP2), 53 kDa |
| 1578 | B4152N | W89185 | SET7 | SET domain-containing protein 7 |
| 1579 | B8840 | BX648004 | SPG20 | Spastic paraplegia 20, spartin (Troyer syndrome) |
| 1580 | F1146 | AK025893 | RBPMS | RNA binding protein with multiple splicing |
| 1581 | F0597 | AK000146 | CGI-30 | CGI-30 protein |
| 1582 | F2464 | AK027243 | BBS1 | Bardet-Biedl syndrome 1 |
| 1583 | F2803 | AF170562 | USP25 | Ubiquitin specific protease 25 |
| 1584 | F4063 | AL109779 | HDGFRP3 | Hepatoma-derived growth factor, related protein 3 |
| 1585 | F4950 | NM_194430 | RNASE4 | Angiogenin, ribonuclease, RNase A family, 5 |
| 1586 | F7716 | BE178490 | | Hypothetical gene supported by AK093334; AL833330; BC020871; BC032492 |
| 1587 | A0095 | J03241 | TGFB3 | Transforming growth factor, beta 3 |
| 1588 | A0217 | M83233 | TCF12 | Transcription factor 12 (HTF4, helix-loop-helix transcription factors 4) |
| 1589 | F0001N | NM_153831 | PTK2 | PTK2 protein tyrosine kinase 2 |
| 1590 | A0375N | BC057815 | RRAD | Ras-related associated with diabetes |
| 1591 | A0911N | M63256 | CDR2 | Cerebellar degeneration-related protein 2, 62 kDa |
| 1592 | C1400 | BC007632 | KIAA0318 | RIM binding protein 2 |
| 1593 | C0661 | H18687 | CLDN11 | Claudin 11 (oligodendrocyte transmembrane protein) |
| 1594 | C8718 | AA206141 | PRICKLE1 | Prickle-like 1 (*Drosophila*) |
| 1595 | D6726 | AA897762 | PPM1A | Protein phosphatase 1A (formerly 2C), magnesium-dependent, alpha isoform |
| 1596 | F3564 | CR749667 | PDE4B | Phosphodiesterase 4B, cAMP-specific (phosphodiesterase E4 dunce homolog, *Drosophila*) |
| 1597 | F4186 | AB023168 | NLGN4Y | Neuroligin 4, Y-linked |
| 1598 | F6116 | BC030244 | TNNC1 | Troponin C, slow |
| 1599 | F7080 | AW973637 | GGTA1 | Glycoprotein, alpha-galactosyltransferase 1 |
| 1600 | F7477 | AW868740 | SYNPO2 | Synaptopodin 2 |
| 1601 | F0520 | BC041337 | RHOBTB3 | Rho-related BTB domain containing 3 |
| 1602 | B4181 | AK021510 | KCNMB3 | Potassium large conductance calcium-activated channel, subfamily M beta member 3 |
| 1603 | B5089N | AA828067 | C1QB | Complement component 1, q subcomponent, beta polypeptide |
| 1604 | B7158N | XM_085175 | TTC7B | Tetratricopeptide repeat domain 7B |
| 1605 | E1632 | BU633335 | SMAD4 | SMAD, mothers against DPP homolog 4 (*Drosophila*) |
| 1606 | F0174 | AK024029 | MOAP1 | Modulator of apoptosis 1 |
| 1607 | F1147 | AK125336 | LOC90167 | Hypothetical protein LOC90167 |
| 1608 | F4952 | AL080082 | | MRNA; cDNA DKFZp564G1162 (from clone DKFZp564G1162) |
| 1609 | B3745 | N92541 | | Transcribed locus |
| 1610 | A0270N | AF241831 | HABP4 | Hyaluronan binding protein 4 |
| 1611 | B6485 | BC009753 | ACACB | Acetyl-Coenzyme A carboxylase beta |
| 1612 | F0416 | AF082557 | TNKS | Tankyrase, TRF1-interacting ankyrin-related ADP-ribose polymerase |
| 1613 | F0470 | AJ250865 | TES | Testis derived transcript (3 LIM domains) |
| 1614 | F0911 | L08177 | EBI2 | Epstein-Barr virus induced gene 2 (lymphocyte-specific G protein-coupled receptor) |
| 1615 | F2392 | NM_001901 | CTGF | Connective tissue growth factor |
| 1616 | F3618 | AK172810 | SLC39A14 | Solute carrier family 39 (zinc transporter), member 14 |
| 1617 | F4440 | AB032773 | TU12B1-TY | TU12B1-TY protein |
| 1618 | F6326 | NM_015458 | MTMR9 | Myotubularin related protein 9 |
| 1619 | F7458 | AK123706 | ADAMTS8 | A disintegrin-like and metalloprotease (reprolysin type) with thrombospondin type 1 motif, 8 |

TABLE 5-continued

Down-regulated gene in bladder cancer

| BLC assignment | LMMID | ACCESSION | GENE | TITLE |
|---|---|---|---|---|
| 1620 | A1666N | NM_000176 | NR3C1 | Nuclear receptor subfamily 3, group C, member 1 (glucocorticoid receptor) |
| 1621 | A3471 | NM_006281 | STK3 | Serine/threonine kinase 3 (STE20 homolog, yeast) |
| 1622 | B7499 | BX641020 | ARID5B | AT rich interactive domain 5B (MRF1-like) |
| 1623 | B8216 | CR623023 | | Full-length cDNA clone CS0DC029YI23 of Neuroblastoma Cot 25-normalized of Homo sapiens (human) |
| 1624 | F0286 | NM_000132 | F8 | Coagulation factor VIII, procoagulant component (hemophilia A) |
| 1625 | F1338 | AF056195 | NAG | Neuroblastoma-amplified protein |
| 1626 | F2115 | AK021795 | BNC2 | Basonuclin 2 |
| 1627 | F2699 | AF022789 | USP12 | Ubiquitin specific protease 12 |
| 1628 | F5702 | AK024358 | MPEG1 | Macrophage expressed gene 1 |
| 1629 | A0279 | NM_005257 | GATA6 | GATA binding protein 6 |
| 1630 | A3940 | AF048722 | PITX2 | Paired-like homeodomain transcription factor 2 |
| 1631 | F0004 | NM_005252 | FOS | V-fos FBJ murine osteosarcoma viral oncogene homolog |
| 1632 | G2550 | NM_000962 | PTGS1 | Prostaglandin-endoperoxide synthase 1 (prostaglandin G/H synthase and cyclooxygenase) |
| 1633 | B2787 | CR619015 | MRGPRF | MAS-related GPR, member F |
| 1634 | B6424 | AL049313 | CLIC5 | Chloride intracellular channel 5 |
| 1635 | C0810 | AK123757 | EBF | Early B-cell factor |
| 1636 | F2322 | AL080213 | PDE4DIP | Phosphodiesterase 4D interacting protein (myomegalin) |
| 1637 | F1600 | AB038523 | MBIP | MAP3K12 binding inhibitory protein 1 |
| 1638 | F2393 | M14091 | SERPINA7 | Serine (or cysteine) proteinase inhibitor, clade A (alpha-1 antiproteinase, antitrypsin), member 7 |
| 1639 | F2908 | AK023821 | MACF1 | Microtubule-actin crosslinking factor 1 |
| 1640 | A8838 | AK075242 | MGC45438 | Hypothetical protein MGC45438 |
| 1641 | B4271 | AB011121 | ALS2CR3 | Amyotrophic lateral sclerosis 2 (juvenile) chromosome region, candidate 3 |
| 1642 | B7509 | CN268436 | | CDNA clone IMAGE: 5263177, partial cds |
| 1643 | B9025 | BU537728 | HSA9761 | Putative dimethyladenosine transferase |
| 1644 | F0288 | BC080187 | LMOD1 | Leiomodin 1 (smooth muscle) |
| 1645 | F0333 | AK026095 | SNTB1 | Syntrophin, beta 1 (dystrophin-associated protein A1, 59 kDa, basic component 1) |
| 1646 | F0728 | NM_021614 | KCNN2 | Potassium intermediate/small conductance calcium-activated channel, subfamily N, member 2 |
| 1647 | F1259 | AK000776 | | Full-length cDNA clone CS0DD009YB17 of Neuroblastoma Cot 50-normalized of Homo sapiens (human) |
| 1648 | F2702 | AL049990 | | MRNA; cDNA DKFZp564G112 (from clone DKFZp564G112) |
| 1649 | F4940 | BC035161 | CRY2 | Cryptochrome 2 (photolyase-like) |
| 1650 | A4080 | AF054992 | PKD2 | Polycystic kidney disease 2 (autosomal dominant) |
| 1651 | A9898 | BC010353 | PTPLA | Protein tyrosine phosphatase-like (proline instead of catalytic arginine), member a |
| 1652 | B1461N | CR744550 | MYO9A | Myosin IXA |
| 1653 | C0591 | AB014523 | ULK2 | Unc-51-like kinase 2 (C. elegans) |
| 1654 | C1450 | AB075828 | ZNF545 | Zinc finger protein 545 |
| 1655 | F0518 | AF035307 | PLXNC1 | Plexin C1 |
| 1656 | F2283 | AJ276316 | ZNF304 | Zinc finger protein 304 |
| 1657 | F2335 | AK001832 | FLJ10970 | Hypothetical protein FLJ10970 |
| 1658 | F5448 | AK023831 | FLJ13769 | Hypothetical protein FLJ13769 |
| 1659 | F2161 | AF116646 | GALNACT-2 | Chondroitin sulfate GalNAcT-2 |
| 1660 | A1157N | NM_002667 | PLN | Phospholamban |
| 1661 | B4276 | AK056725 | | CDNA FLJ32163 fis, clone PLACE6000371 |

TABLE 5-continued

Down-regulated gene in bladder cancer

| BLC assignment | LMMID | ACCESSION | GENE | TITLE |
|---|---|---|---|---|
| 1662 | B5186N | AK056963 | | Full length insert cDNA clone ZE03F06 |
| 1663 | C6412 | BX090035 | | Transcribed locus |
| 1664 | F0182 | BC009203 | LOC90355 | Hypothetical gene supported by AF038182; BC009203 |
| 1665 | F1343 | BC032404 | DKFZp434D0215 | SH3 domain protein D19 |
| 1666 | F4628 | AF119893 | | |

Identification of C2093, B5860N and C6055 as Up-regulated Genes in Bladder Cancer Cells When gene-expression profiles of cancer cells from 33 bladder cancer patients were analyzed using a cDNA microarray representing 27,648 human genes, 394 genes that were commonly up-regulated in bladder cancer cells were identified. Among them, attention was focused on the genes with the in-house codes C2093, which designated M-phase phosphoprotein 1 (MPHOSPH1) (Genebank Accession NM_016195 (SEQ ID NO.1, encoding SEQ ID NO.2)), B5860N, designated DEP domain containing 1 (DEPDC1) (SEQ ID NO.3, encoding SEQ ID NO.4), and C6055, designated MGC34032 hypothetical protein, (Genebank Accession NM_152697 SEQ ID NO: 133, encoding SEQ ID NO: 134). Expression of the C2093, B5860N and C6055 genes were elevated in 24 of 25, 17 of 20 and 21 of 32 bladder cancer cases which were able to obtain expression data, respectively. To confirm the expression of these up-regulated genes, semi-quantitative RT-PCR analysis was performed to compare the expression level between bladder cancer specimens and normal human tissues including normal bladder cancer cells. Firstly, it was discovered that C2093 showed the elevated expression in 17 of 21 clinical bladder cancer samples, as compared to normal bladder cells and normal human tissues including lung, heart liver and kidney (FIGS. 1a and b). In addition, this gene was overexpressed in all of six bladder cancer cell lines as well (FIG. 1b). Next, it was discovered that B5860N showed the elevated expression in 20 of 21 clinical bladder cancer specimens compared to normal human tissues, especially normal bladder mRNA (FIGS. 1a and c), and was overexpressed in all of six bladder cancer cell lines we examined (FIG. 1c).

To further examine the expression pattern of these genes, northern blot analyses were performed with multiple-human tissues and bladder cancer cell lines using cDNA fragments of C2093, B5860N and C6055 as probes (see Material and Method). Expression of C2093 was no or undetectable in normal human tissues except testis (FIG. 2e; the upper panel), while was surprisingly overexpressed in all of bladder cancer cell lines (FIG. 2e; the bottom panel). B5860N was also exclusively expressed in testis (FIG. 2f, the upper panel), while was significantly overexpressed in all of bladder cancer cell lines, compared to in other normal tissues, especially in normal human bladder (FIG. 2f, the bottom panel). C6055 was also no or undetectable in normal human tissues (FIG. 2g; the upper panel), while was overexpressed in three of six bladder cancer cell lines (FIG. 2g; the bottom panel). Thus, attention was focused the bladder cancer specifically expressed transcripts.

Genomic Structure of C2093, B5860N and C6055

To obtain the entire cDNA sequences of C2093, B5860N and C6055, RT-PCR was performed as EST-walking, and 5'RACE and 3'RACE experiments using bladder cancer cell line, SW780, as template (see Materials and Methods) because C2093 initially was not full length on database. C2093 consists of 31 exons, designated M-phase phosphoprotein 1 (MPHOSPH1), located on the chromosome 10q23.31. The full-length mRNA sequences of C2093 contained 6319 nucleotides, encoding 1780 amino acids. The ORF of this transcript starts at within each exon 1.

B5860N, designated DEP domain containing 1 (DEPDC1), located on the chromosome 1p31.2. This gene has also two different transcriptional variants consisting of 12 and 11 exons, corresponding to B5860N V1 (SEQ ID NO.3, encoding SEQ ID NO.4) and B5860N V2 (SEQ ID NO.5, encoding SEQ ID NO.6), respectively (FIG. 3b). There were alternative variations in exon 8 of V1, and the other remaining exons were common to both variants. V2 variant has no exon 8 of the V1, generating same stop codon within last exon. The full-length cDNA sequences of B5860NV1 and B5860NV2 variants consist of 5318 and 4466 nucleotides, respectively. The ORF of these variants start at within each exon 1. Eventually, V1 and V2 transcripts encode 811 and 527 amino acids, respectively; To further confirm the expression pattern of each variant in bladder cancer cell lines and normal human tissues including bladder, heart, lung, liver, kidney, brain, pancreas, northern blot analysis was performed. As a result, it was discovered that both variants were highly overexpressed in bladder cancer cells, but no or undetectable expression in normal human tissues (FIG. 2f, lower panel) except trestis. In particular, V2 transcript was expressed exclusively in testis. Therefore, functional analysis for both variants of B5860N were further performed.

According to the database from NCBI, C6055 consists of 24 exons, designated MGC34032, located on the chromosome 1p31.3. Because C6055 is not included within last exon (exon 24) of MGC34032 on database, we performed RT-PCR as EST-walking, and 5'RACE experiments using bladder cancer cell line, SW780, as a template to obtain the entire cDNA sequence of C6055 (see Materials and Methods). As a result; we found two novel transcripts, C6055V1 (SEQ ID NO: 129, encoding SEQ ID NO: 130) and C6055V2 (SEQ ID NO: 131, encoding SEQ ID NO: 132). Eventually, this gene has four different splicing variants consisting of 24, 25, 22 and 22 exons, corresponding to MGC34032, Genbank Accession No.AK128063, C6055V1 and C6055V2, respectively (FIG. 3c). There were alternative splicing in exon 1, 2, 3, 4 and 24 of MGC34032, and the other remaining exons were common among four transcripts. C6055V1 and C6055V2 transcripts have no exon 1, 2 and 3 of MGC34032, generating same stop codon within last exon. In particular, the ORF of C6055V1 and C6055V2 transcripts start at within each exon 4, indicating C6055V1 and C6055V2 transcripts have same ORF. The full-length cDNA sequences of MGC34032, Genbank Accession No.AK128063, C6055V1 and C6055V2 transcripts consist of 2302, 3947, 3851, and 3819 nucleotides, respectively.

Eventually, MGC34032, Genbank Accession No.AK128063, C6055V1V1 and C6055V2 transcripts encode 719, 587, 675 and 675 amino acids, respectively. To further confirm the expression pattern of each variant in bladder cancer cell lines and normal human tissues including bladder, heart, lung, liver, kidney, brain, testis, pancreas, we performed northern blot analysis using a cDNA fragment C6055 for microarray as a probe. As a result, approximately 3.9 kb transcripts were highly overexpressed in some bladder cancer cells (HT-1376, SW780 and RT4), but no or undetectable expression in normal human tissues (FIG. 2g upper panel). In addition, 7.5 kb transcript was specifically expressed only in HT1376 cells, but we have not yet identified the entire mRNA sequence of this transcript. Furthermore, when we performed northern blot analysis using the common region among these transcripts as a probe, we detected 2.3 kb transcript exclusively in normal testis, corresponding to MGC34032 (FIG. 2g middle and lower panel). Therefore, we further perform functional analysis for C6055V1 gene product.

Subcellular Localization of C2093, B5860N and C6055

Figure 4:
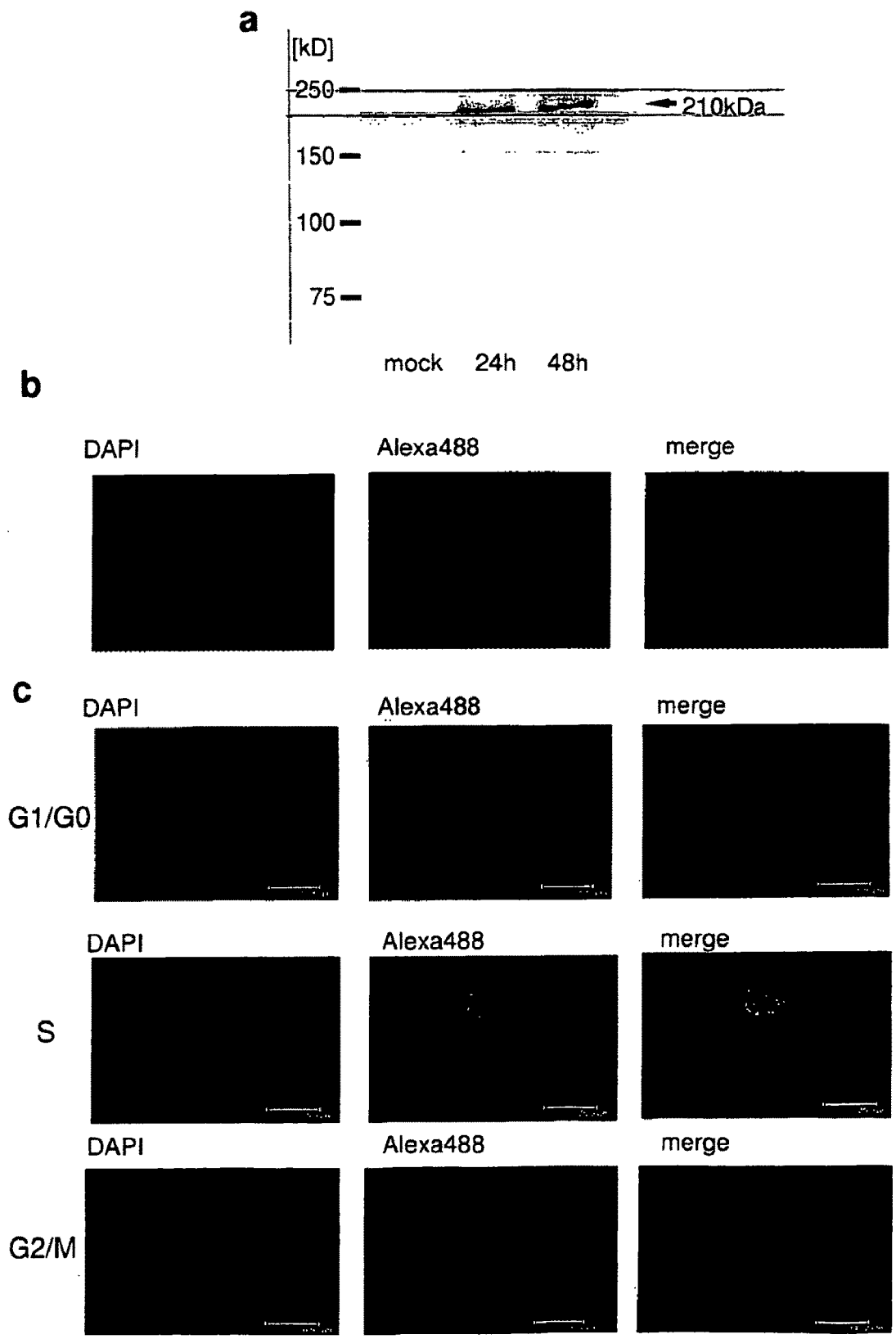
FIG. 4 depicts the exogenous expression and subcellular localization of C2093, B5860Ns and C6055s. (a) Exogenous expression of C2093 protein by Western blot at 24 and 48 hours after transfection, (b) Subcellular localization of C2093 protein, (c) Cell cycle dependent localization of C2093, (d) Exogenous expression of B5860N V1 (left panel) and B5860N V2 (right panel) proteins by Western blot analysis at 24 and 48 hours after transfection. Subcellular localization of (e) B5860N V1 and (f) B5860N V2 proteins, Cell cycle dependent localization of (g) B5860N V1 proteins, and (h) B5860N V2. (i) Co-transfection with B5860N V1 and B5860N V2 into COS7 cells. (j) Subcellular localization of C2093 during cell cycle progression. (k) Subcellular localization of B5860N during cell cycle progression. (l) Expression of C6055 protein by Western blot at 36 hours after transfection, (m) Post-translational modification of C6055 protein (n) Subcellular localization of exogenous C6055 protein.
Figure 4:
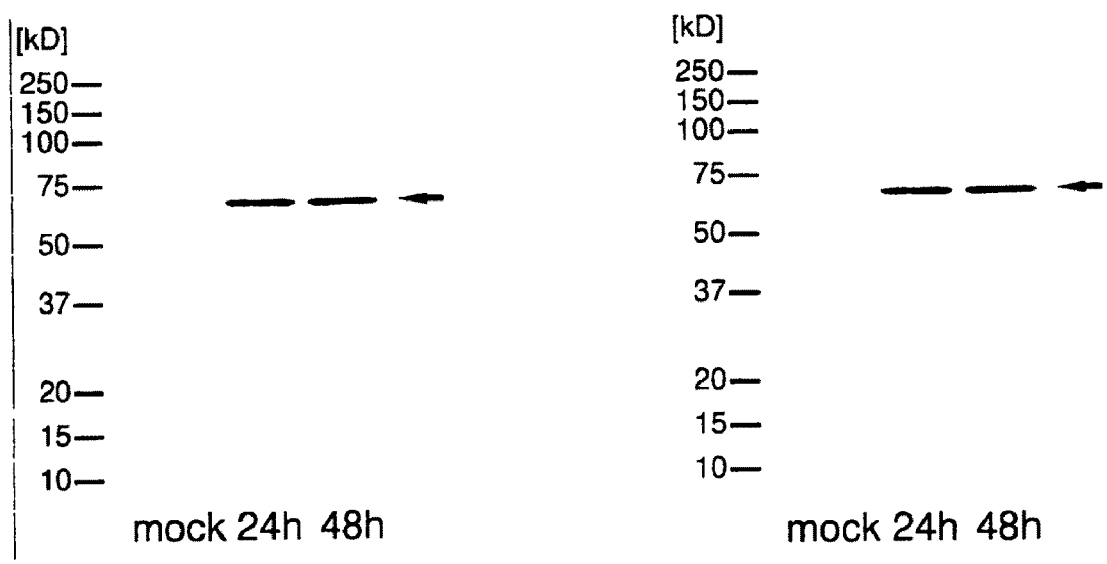
Figure 4:
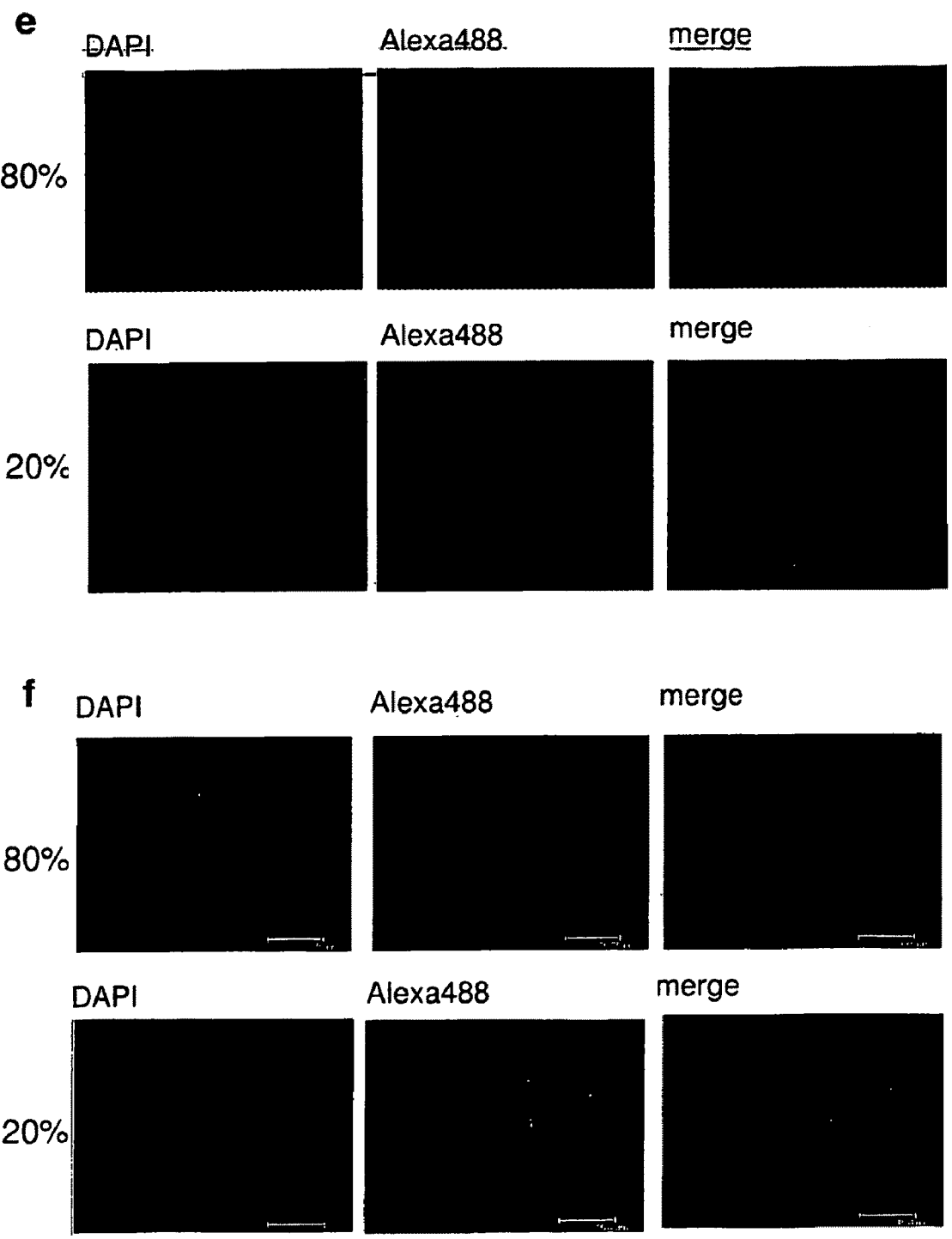
Figure 4:
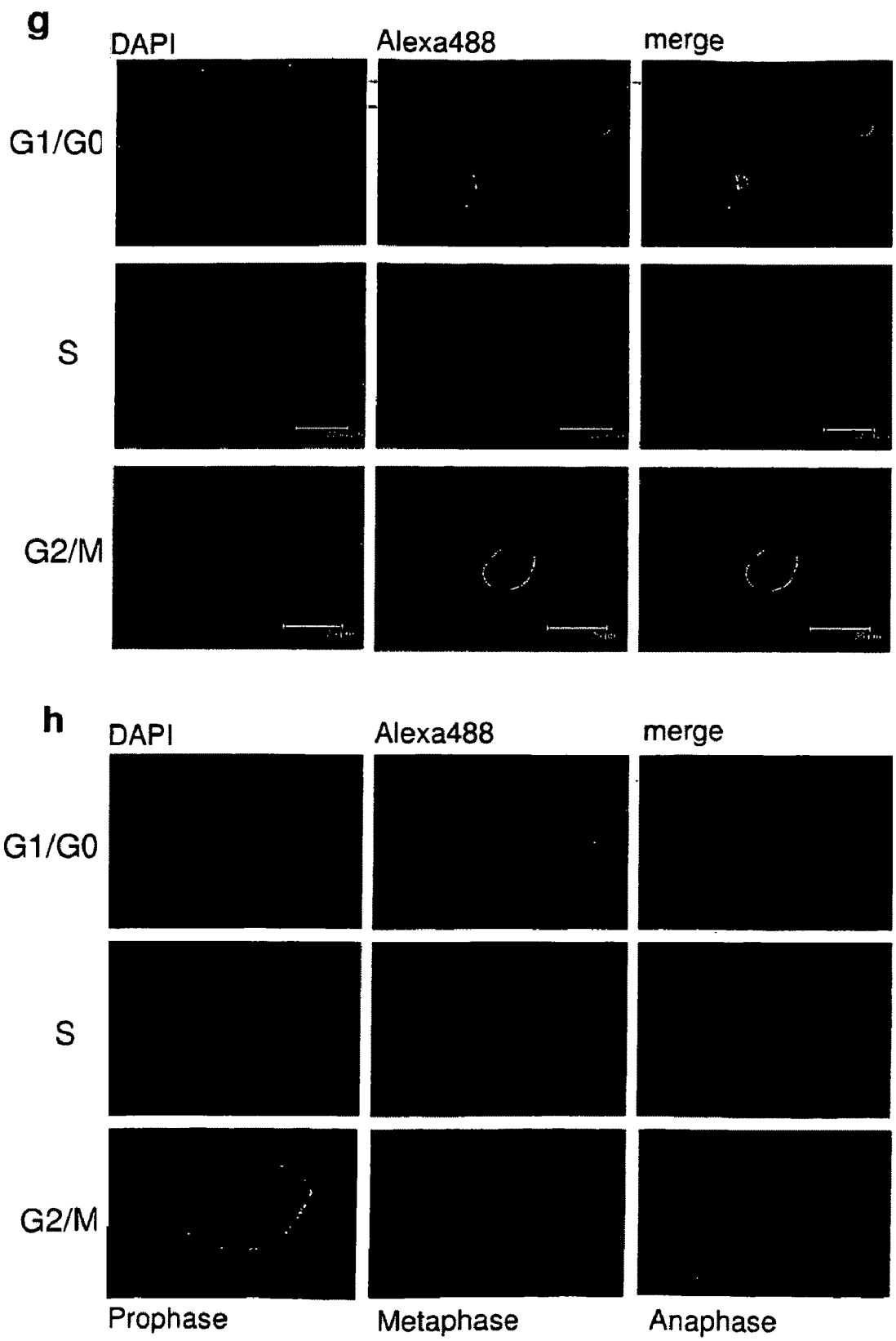
Figure 4:
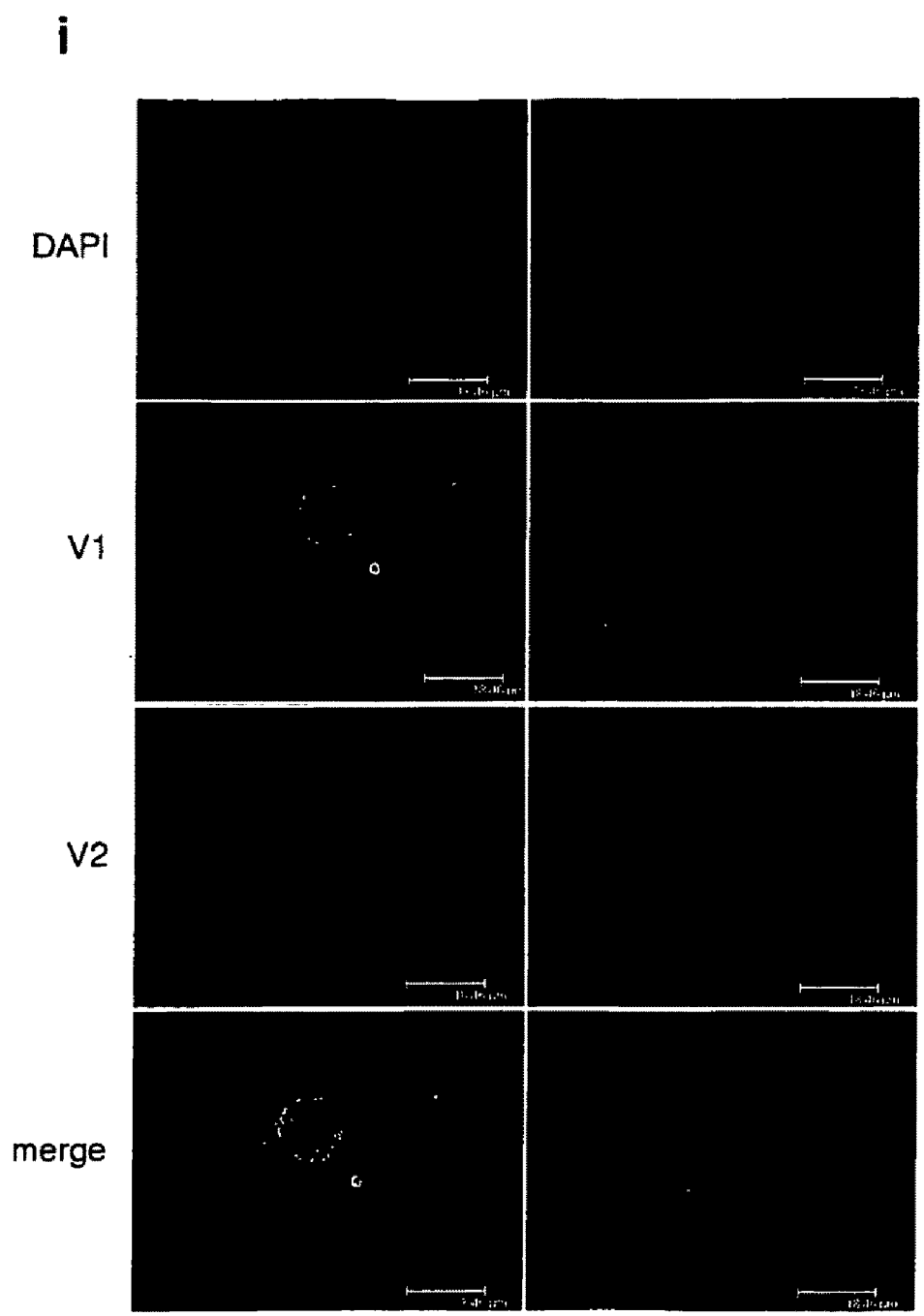
Figure 4:
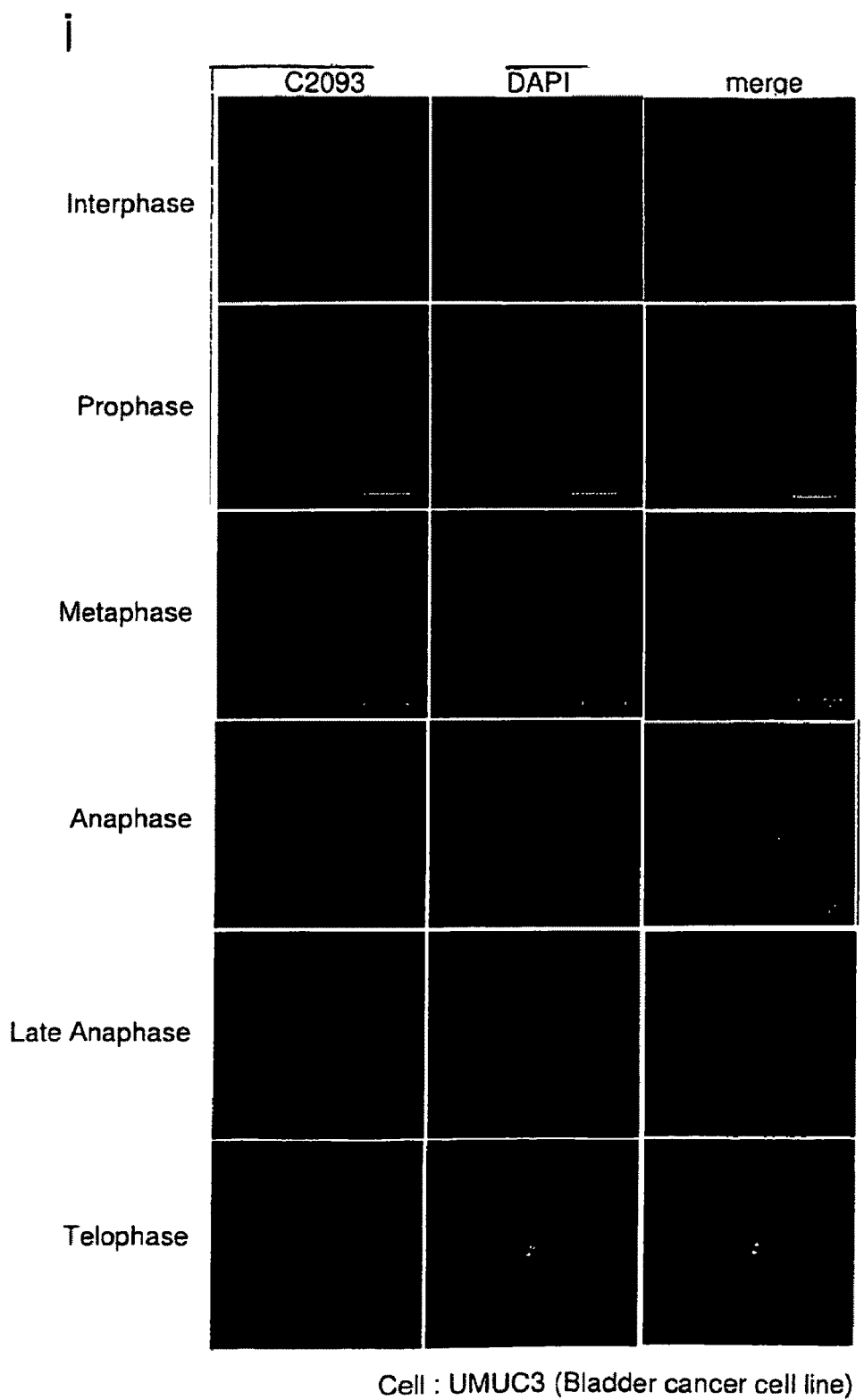
Figure 4:
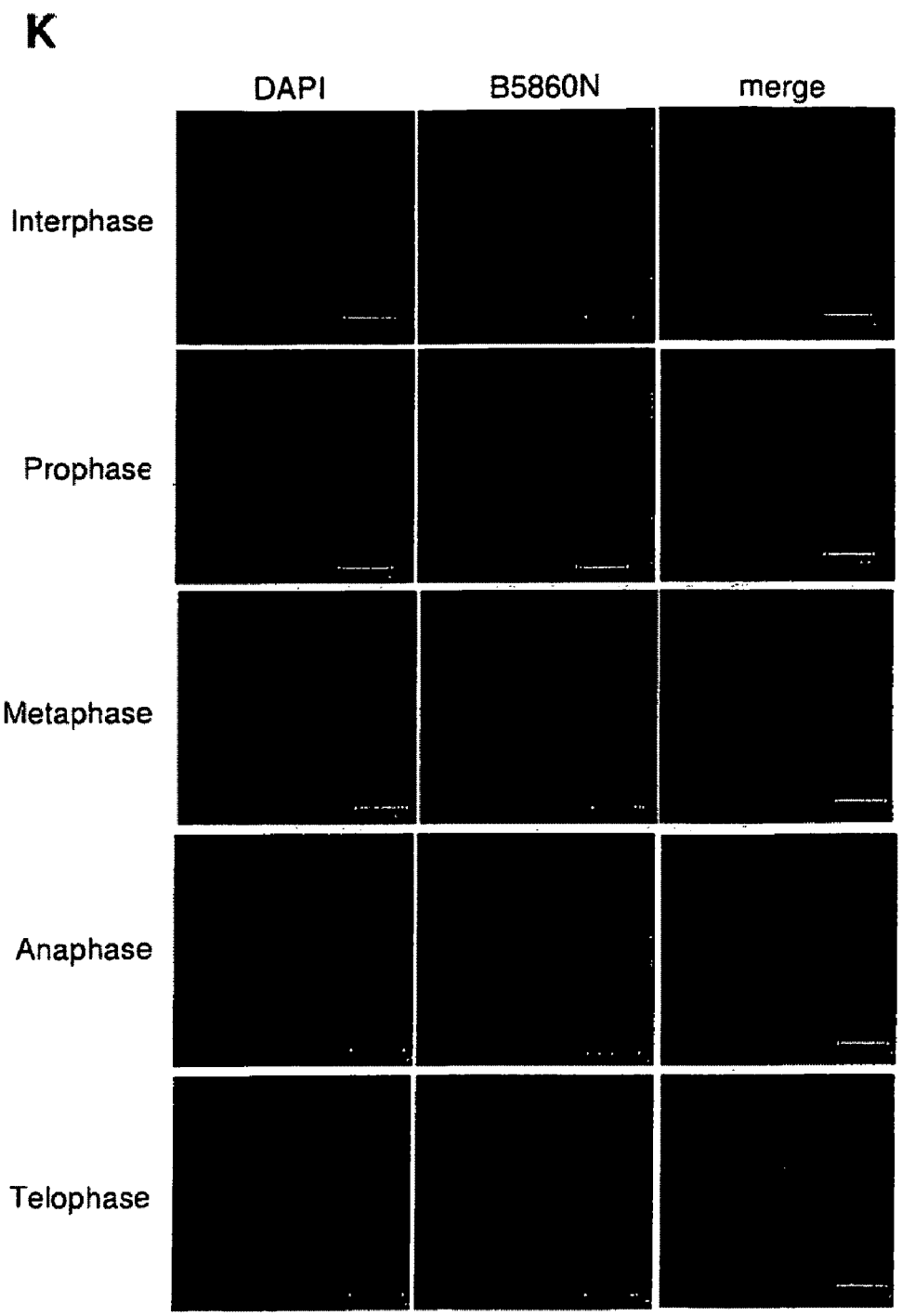
Figure 4:
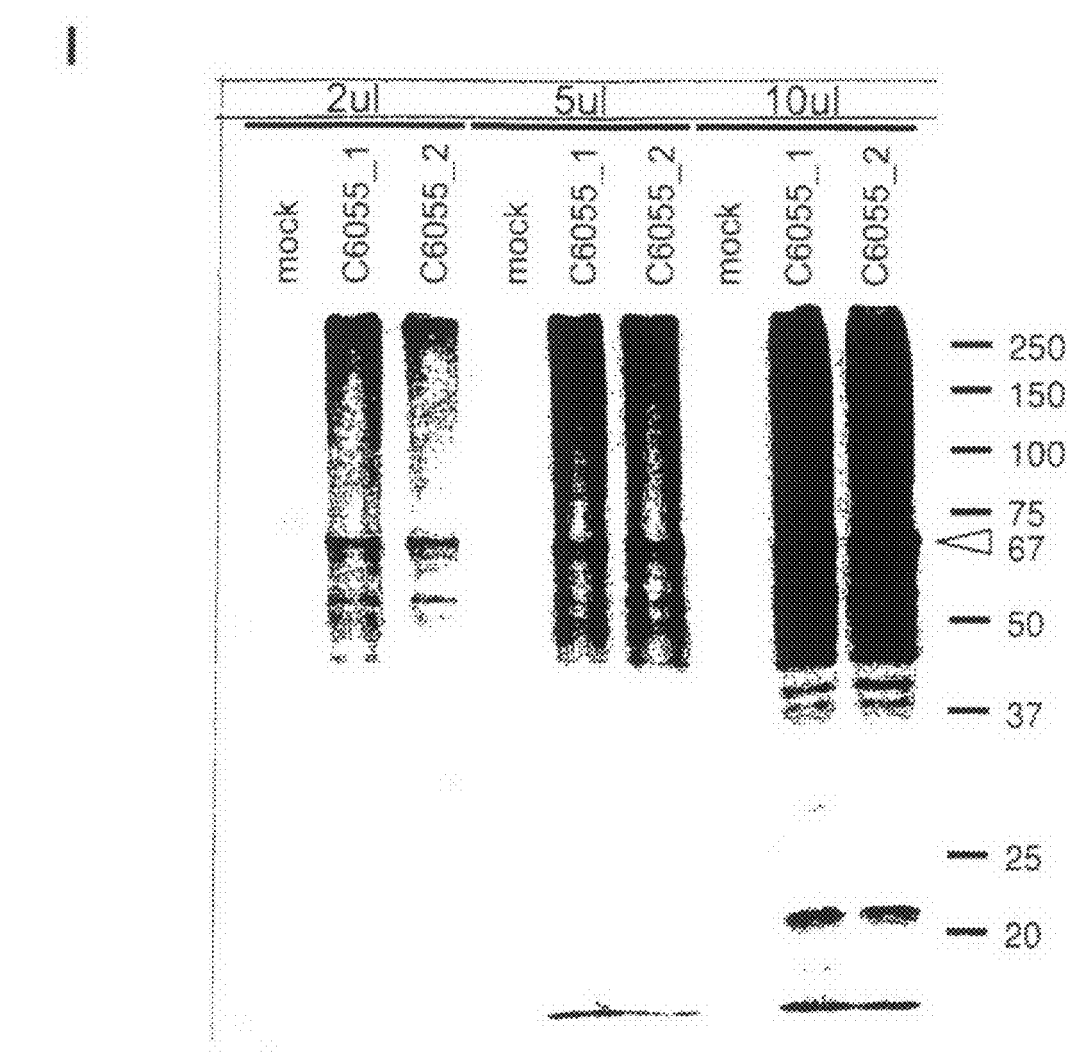

To further examine the characterization of C2093, B5860N and C6055, the sub-cellular localization of these gene products was examined in COS7 cells. Firstly, when plasmids expressing the C2093 protein (pCAGGS-C2093-HA) were transiently transfected into COS7 cells, the 210 KDa-C2093 protein was observed as an expected size by Western blot analysis (FIG. 4a). Immunocytochemical staining reveals exogenous C2093 mainly localized to the nucleus apparatus in COS7 cells, but in some cells was observed to be accumulated around chromosome (FIG. 4b). Therefore, the cells were synchronized using aphidicolin and examine C2093 protein localization during cell-cycle progression. Notably the protein was located in nuclei at G1/G00 and S phases, and, especially, accumulated around chromosome during G2/M phase (FIG. 4c).

Next, when plasmids expressing B5860NV1 or V2 proteins (pCAGGS-B5860NV-1 HA or pCAGGS-B5860NV2-HA) were transiently transfected into COS7, respectively, exogenous B5860NV1 and V2 proteins were observed as each expected size by Western blot analysis at 24 and 48 hours after transfection (FIG. 4d, V1; left panel, V2 right panel). Moreover, immunocytochemical staining reveals that B5860NV1 localized to the cytoplasm (FIG. 4e, upper panel), but some cells was also observed to be nuclei apparatus (FIG. 4e, bottom panel), ant that B5860NV2 mainly localized to the cytoplasm (FIG. 4f, upper panel), and some cells was also observed under cytoplasmic membrane (FIG. 4f, bottom panel). Therefore, the cells were synchronized using aphidicolin and examined B5860NV1 and V2 proteins localization during cell-cycle progression. B5860NV1 protein was located in nuclei at G1/G0 and S phases, but localized under cytoplasmic membrane during G2/M phases (FIG. 4g), but B5860NV2 protein was located under cytoplasmic membrane during G2/M phase (FIG. 4h). Furthermore, when both plasmids expressing B5860NV1 and V2 proteins were transiently co-transfected into COS7, it was observed that B5860NV1 protein located in nuclei and cytoplasm apparatus, and B5860NV2 located nuclei and translocated to under cytoplasmic membrane during G2/M phase (FIG. 4i).

To further determine the subcellular localization of endogenous C2093 localization during cell cycle progression by immunocytochemical analysis using affinity-purified anti-C2093 antibodies. Endogenous C2093 protein was localized in the nucleus during interphase, but in the cytoplasm during prophase, metaphase and early anaphase, especially located in the midbody in late anaphase, and then near the contractile ring in telophase (FIG. 4j). Therefore, C2093 may play an important role in the cytokinesis.

Next, we examined endogenous B5860N in bladder cancer cells during cell cycle progression as well as C2093, we performed immunocytochemical analysis using affinity-purified B5860N polyclonal antibodies. Endogenous B5860N protein was localized mainly in the nucleus during interphase, but in the cytoplasm during M-phase (FIG. 4k).

The SMART and SOSUI computer predictions revealed that the predicted C6055 protein contained 8th, 9th or 10th transmembrane domains. To confirm this prediction, we examined the sub-cellular localization of this gene product in COS7 cells at 36 and 60 hours after transfection. Firstly, when we transiently transfected plasmids expressing C6055 protein-(pCAGGS-C6055-HA) into COS7 cells, we performed Western blot analysis using an anti-HA tag antibody. The results showed a 67 KDa-band corresponding to the predicted size of the C6055 protein as well as an additional 75 KDa band (FIG. 4l). To verify whether the 75 KDa band represented a form of C6055 modified by phosphorylation or glycosylation, we treated the cellular extracts with λ-phosphatase, O-glycosidase or N-glycosydase and O-glycosidase before immunoblotting. Although the 75-kDa band did not disappear after phosphatase and O-glycosidase, it disappeared after O-glycosidase treatment, suggesting that C6055 protein was O-glycosylated only in living cells (FIG. 4m). To investigate the subcellular localization of C6055 protein, we performed fluorescent immunohistochemical staining in C6055-transfected COS7 cells. The results revealed exogenous C6055 mainly localized to cytoplasmic membrane in COS7 cells at 60 hours although we observed C6055 localization in cytoplasm at 36 hours (FIG. 4n).

Growth-inhibitory Effects of Small-interfering RNA (siRNA) Designed to Reduce Expression of C2093, B5860N and C6055

Figure 7:
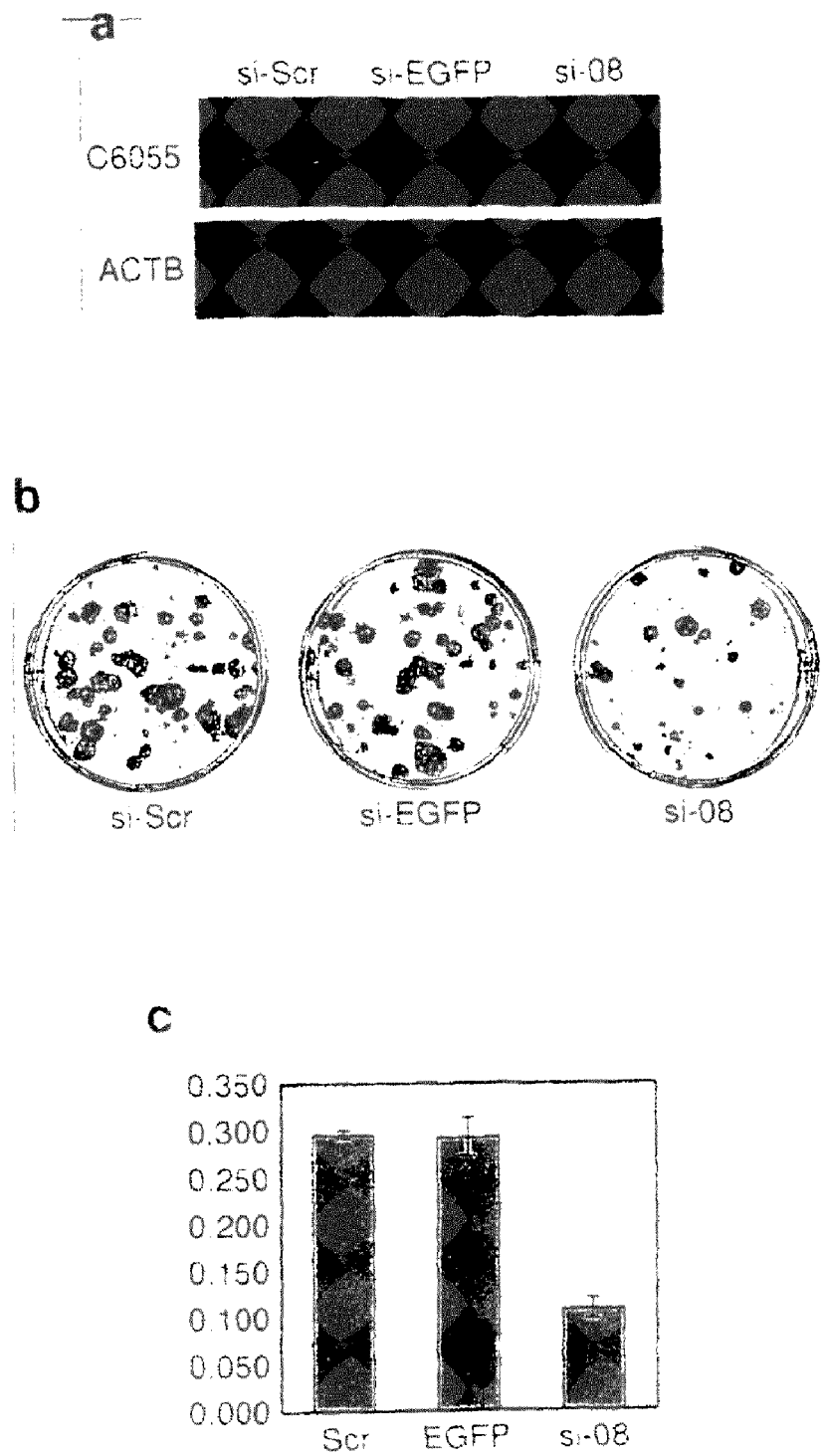
FIG. 7 depicts the growth-inhibitory effects of small-interfering RNAs (siRNAs) designed to reduce expression of C6055 in bladder cancer cells. (a) Semi-quantitative RT-PCR showing suppression of endogenous expression of C6055 in bladder cancer cell line, SW780 cells. ACTB was used as an internal control. SCR; scramble sequence as a control (see Materials and Methods) (b) Colony-formation assay demonstrating a decrease in the numbers of colonies by knockdown of C6055 in SW780 cells. (c) MTT assay demonstrating a decrease in the numbers of colonies by knockdown of C6055 in SW780 cells.

To assess the growth-promoting role of C2093, B5860N and C6055, the expression of endogenous C2093, B5860N and C6055 was knocked down in bladder cancer lines, J82, UMUC3 and SW780 that have shown the overexpression of C2093, B5860N and C6055, by means of the mammalian vector-based RNA interference (RNAi) technique (see Materials and Methods). Expression levels of C2093, B5860N and C6055 were examined by semi-quantitative RT-PCR experiments. As shown in FIG. 5 to 7 C2093, B5860N and C6055-specific siRNAs significantly suppressed expression of each gene, compared with control siRNA constructs (psiU6BX-EGFP and SCR) (FIG. 5a, 5d, 6a, 7a). To confirm the cell growth inhibition with C2093, B5860N and C6055-specific siRNAs, we performed colony-formation and MTT assays were performed, respectively. Introduction of C2093-si3 constructs suppressed growth of J82 and UMUC3 cells (FIG. 5 b, c, e, f), B5860N-si3 constructs suppressed growth of J82 cells (FIG. 6b, c) and C6055-si-08 constructs suppressed growth of SW780 cells (FIG. 7b,c), consisting with the result of above reduced expression. Each result was verified by three independent experiments. These findings suggest that C2093, B5860N and C6055 have a significant function in the cell growth of the bladder cancer.

Figure 8:
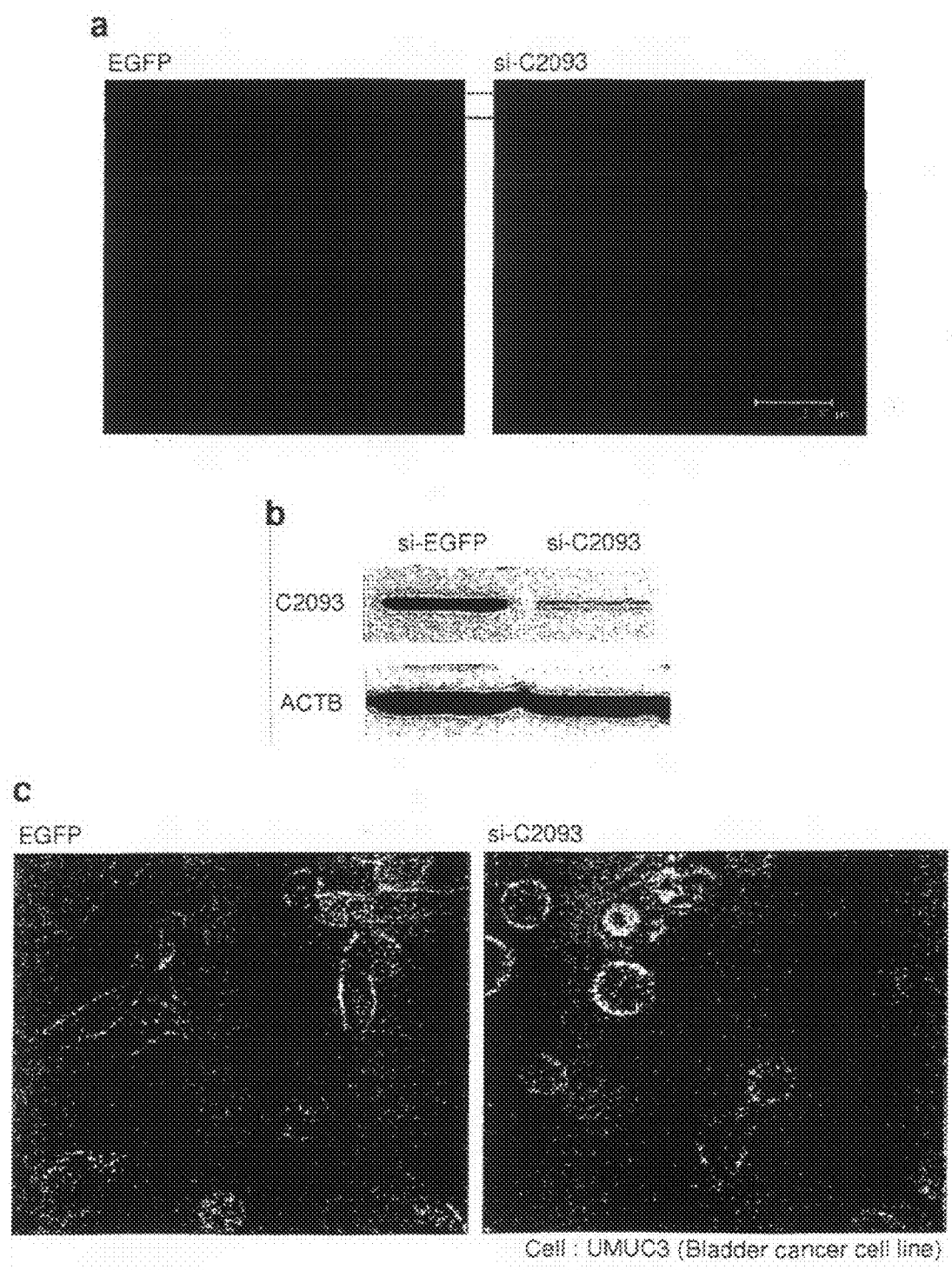
FIG. 8 (a) Multi-nucleated cells by treatment of C2093-siRNA. (b) western blotting analysis using anti-C2093 antibody. (c) cell morphology with microscopy.

In particular, to further elucidate the role of C2093 in cytokinesis, we transfected C2093-siRNA into bladder cancer cell line UMUC3 cells and then observed cell morphology by microscopy on 7 days after transfection. We confirmed expression of C2093 protein was knockdowned by C2093-siRNA (FIG. 8b), and observed multi-nucleated cells in siRNA-transfected cells (FIG. 8a, c), indicating si-C2093 knockdown cells failed in cytokinesis.

Expression of C2093 and B6850N Proteins in Clinical Samples.

We performed immunohistochemical analysis of C2093 or B5860N in surgically resected invasive bladder cancer tissue and normal bladder tissue sections and various normal tissues (kidney, heart, lung and liver), respectively. Strong staining against both proteins were observed only in bladder cancer tissues (FIG. 9a, b), and undetectable staining of C2093 was observed normal bladder tissue (FIG. 9a).

Discussion:

In this report, through the precise expression profiles of bladder cancer by means of genome wide cDNA microarray, novel genes, C2093, B5860N and C6055 that were significantly overexpressed in bladder cancer cells, as compared to normal human tissues, were isolated.

The B5860N protein was observed to localize in cytoplasm as intermediate filaments by immunochemical staining, suggesting that B5860N may play a key role of interaction of cell to cell.

Furthermore, it was demonstrated that treatment of bladder cancer cells with siRNA effectively inhibited expression of all three target genes, C2093, B5860N and C6055 and significantly suppressed cell/tumor growth of bladder cancer. These findings suggest that C2093, B5860N and C6055 might play key roles in tumor cell growth proliferation, and may be promising targets for development of anti-cancer drugs.

INDUSTRIAL APPLICABILITY

The gene-expression analysis of bladder cancer described herein, obtained through a combination of laser-capture dissection and genome-wide cDNA microarray, has identified specific genes as targets for cancer prevention and therapy. Based on the expression of a subset of these differentially expressed genes, the present invention provides molecular diagnostic markers for identifying and detecting bladder cancer.

The methods described herein are also useful in the identification of additional molecular targets for prevention, diagnosis and treatment of bladder cancer. The data reported herein add to a comprehensive understanding of bladder cancer, facilitate development of novel diagnostic strategies, and provide clues for identification of molecular targets for therapeutic drugs and preventative agents. Such information contributes to a more profound understanding of bladder tumorigenesis, and provide indicators for developing novel strategies for diagnosis, treatment, and ultimately prevention of bladder cancer.

The expression of human genes C2093, B5860Ns and C6055s are markedly elevated in bladder cancer as compared to non-cancerous bladder tissue. Accordingly, these genes are useful as a diagnostic marker of bladder cancer and the proteins encoded thereby are useful in diagnostic assays of bladder cancer.

The present inventors have also shown that the expression of the C2093, B5860Ns or C6055s proteins promote cell growth whereas cell growth is suppressed by small interfering RNAs corresponding to the C2093, B5860Ns or C6055s genes. These findings show that C2093, B5860Ns and C6055s proteins stimulates oncogenic activity. Thus, each of these oncoproteins is a useful target for the development of anti-cancer pharmaceuticals. For example, agents that block the expression of C2093, B5860Ns or C6055s, or prevent its activity find therapeutic utility as anti-cancer agents, particularly anti-cancer agents for the treatment of bladder cancers. Examples of such agents include antisense oligonucleotides, small interfering RNAs, and ribozymes against the C2093, B5860Ns or C6055s gene, and antibodies that recognize C2093, B5860Ns or C6055s.

All patents, patent applications, and publications cited herein are incorporated by reference in their entirety.

Furthermore, while the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. A method of diagnosing bladder cancer in a subject, comprising the steps of:
   (a) determining a level of expression of a gene encoding the amino acid sequence selected from the group consisting of SEQ ID NOs: 2, 4, and 6 in a patient-derived bladder tissue, and
   (b) diagnosing bladder cancer in the subject when there is an increase in said sample expression level, as compared to a normal control level of said gene.

2. The method of claim 1, wherein said sample expression level is at least 10% greater than said normal control level.

3. The method of claim 1, wherein gene expression level is determined by a method selected from the group consisting of:
   (a) detecting mRNA encoding the amino acid sequence selected from the group consisting of SEQ ID NOs: 2, 4, and 6, and
   (b) detecting a protein comprising the amino acid sequence selected from the group consisting of SEQ ID NOs: 2, 4, and 6.

4. The method of claim 3, wherein said detection is carried out on a DNA array.

5. The method of claim 1, wherein said patient-derived bladder tissue comprises an epithelial cell obtained from the bladder tissue.

6. The method of claim 1, wherein said gene is the gene encoding the amino acid sequence of SEQ ID NOs: 2 or 4.

* * * * *